US006933311B2

(12) United States Patent
Lee et al.

(10) Patent No.: US 6,933,311 B2
(45) Date of Patent: Aug. 23, 2005

(54) FUSED AZABICYCLIC COMPOUNDS THAT INHIBIT VANILLOID RECEPTOR SUBTYPE 1 (VR1) RECEPTOR

(75) Inventors: Chih-Hung Lee, Vernon Hills, IL (US); Erol K. Bayburt, Gurnee, IL (US); Stanley DiDomenico, Jr., Richmond, IL (US); Irene Drizin, Wadsworth, IL (US); Arthur R. Gomtsyan, Vernon Hills, IL (US); John R. Koenig, Chicago, IL (US); Richard J. Perner, Gurnee, IL (US); Robert G. Schmidt, Jr., Waukegan, IL (US); Sean C. Turner, Evanston, IL (US); Tammie K. White, Gurnee, IL (US); Guo Zhu Zheng, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/634,678

(22) Filed: Aug. 5, 2003

(65) Prior Publication Data

US 2004/0157849 A1 Aug. 12, 2004

Related U.S. Application Data

(63) Continuation-in-part of application No. 10/364,210, filed on Feb. 11, 2003.

(51) Int. Cl.[7] .................... A61K 31/415; C07D 231/56
(52) U.S. Cl. .................................... 514/406; 548/361.1
(58) Field of Search ....................... 514/406; 548/361.1

(56) References Cited

U.S. PATENT DOCUMENTS

| | | | | |
|---|---|---|---|---|
| 3,647,910 A | * | 3/1972 | Kirchner | |
| 3,711,610 A | * | 1/1973 | Kirchner | |
| 3,814,711 A | | 6/1974 | Eloy et al. | |
| 4,958,026 A | * | 9/1990 | Schoellkopf et al. | 538/259 |
| 5,362,878 A | * | 11/1994 | Chang et al. | 546/296 |
| 5,444,038 A | * | 8/1995 | James et al. | 504/253 |
| 5,646,140 A | * | 7/1997 | Sugg et al. | 517/221 |
| 5,656,634 A | * | 8/1997 | Chang et al. | 514/255 |
| 5,760,246 A | * | 6/1998 | Biller et al. | 548/309.7 |
| 6,291,476 B1 | * | 9/2001 | Kordik et al. | 514/310 |
| 6,472,414 B1 | * | 10/2002 | Biller et al. | 514/395 |
| 6,511,998 B2 | * | 1/2003 | Kordik et al. | 514/341 |
| 6,555,539 B2 | * | 4/2003 | Reich et al. | 514/252.02 |

FOREIGN PATENT DOCUMENTS

| | | |
|---|---|---|
| EP | 0 418 071 | 3/1991 |
| EP | 0 609 960 | 8/1994 |
| EP | 1403255 A1 * | 3/2004 |
| FR | 1 344 579 | 10/1963 |
| GB | 2 020 280 | 11/1979 |
| WO | 91/13874 | 9/1991 |
| WO | W O 97/26240 A1 * | 7/1997 |
| WO | 00/50387 | 8/2000 |
| WO | 02/08221 | 1/2002 |
| WO | 03/014064 | 2/2003 |
| WO | W O 03/22809 A2 * | 3/2003 |
| WO | 03/80578 | 10/2003 |

OTHER PUBLICATIONS

Lichtenthaler et al., "Nucleosides. 44. Benzo–separated Pyrazolopyrimidines: Expeditious Synthesis of [3,4–g] and [3,4–h]–linked Pyrazoloquinazolinones," *Tetrahedron Letters*, 22(44), 4397–4400 (1981).*

Nunn et al., "Semmler–Wolff Aromatization and Abnormal Beckmann and Schmidt Reactions of 3–Alkyl–4–oxo–1–phenyl–4,5,6,7–tetrahydroindazoles and Their Oximes in Polyphosphoric Acid," *J. Chem. Soc, Perkin Transactions I*, 1973, Issue No. 22, 2697–2703 (1973).*

Adams et al., "Dialkylaminoalkylquinolines," J. Chem. Soc. 3066–3071 (1957).

Berge, et al. "Pharmacutical Salts," *Journal of Pharmaceutical Sciences* 66:1 et seq. (1977) (Jan., 1977).

Cannon et al., "Synthesis of N–alkyl derivatives of 4–(2'–aminothyl)indole," J. Heterocyclic Chemistry 19:1195–1199 (1982) (Sep. Oct., 1982).

Caterina, et al., "Impaired Nociception and pain sensation in mice lacking the capsaicin receptor," Science 288:306–313 (2000) (Apr. 14, 2000).

Caterina, et al., "The capsaicin receptor: a heat–activated ion channel in the pain pathway," Nature 389:816–824 (1997) (Oct. 23, 1997).

Caterina, et al., "The Vanilloid Receptor: A Molecular gateway to the pain pathway," *Annual Review of Neuroscience* 24:487–517 (2001).

Collier, et al., Br. J. Pharmacol. Chemother. 32:295–310 (1968).

(Continued)

*Primary Examiner*—James O. Wilson
*Assistant Examiner*—L. E. Crane
(74) *Attorney, Agent, or Firm*—Michael J. Ward; Gabryleda Ferrari-Dileo

(57) ABSTRACT

Compounds of formula (I)

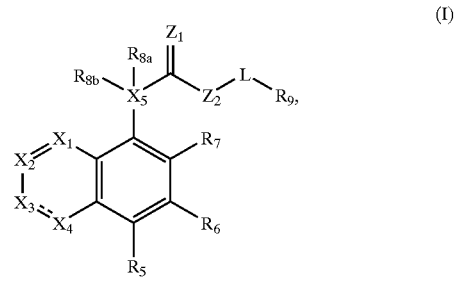

are novel VR1 antagonists that are useful in treating pain, inflammatory thermal hyperalgesia, urinary incontinence and bladder overactivity, wherein $X_1$, $X_2$, $X_3$, $X_4$, $X_5$, $R_5$, $R_6$, $R_7$, $R_{8a}$, $R_{8b}$, $R_9$, $Z_1$, $Z_2$ and L are as defined in the description.

23 Claims, No Drawings

OTHER PUBLICATIONS

Davies, "Indazole Derivatives: The synthesis of various amino– and hydroxy–indazoles and derived sulphonic acids," J. Chem. Soc. 2412–2423 (1955).

Davis, et al., "Vanilloid receptor–1 is essential for inflammatory thermal hyperalgesia," Nature 405:183–187 (2000) (May 11, 2000).

Fieser et al., "A comparison of heterocyclic systems with benzene. VI. Quinines of the quinoline and isoquinoline series," J. Amer. Chem. Soc. 57:1840–1844 (1935) (Oct., 1935).

Forbes et al., "N–(1–methyl–5–indolyl)–N'–(3–pyridyl)urea hydrochloride: the first selective $5-HT_{1c}$ receptor antagonist," J. Med. Chem. 36:1104–1107 (1993).

Fowler, "Intravesical treatment of overactive bladder," Urology 55(Supp 5A):60–64 (2000) (May, 2000).

Gall et al., "171. On a few derivatives of heterocyclic carbonic acids IV. Metal ions and biological action, $36^{th}$ report," Helv. Chim. Acta 38(171):1421–1423 (1955) with translation.

Giencke et al. "Desmethyl(trifluormethyl)actinomycine," Liebigs Ann. Chem. 6:569–579 (1990).

Hayes, et al., "Cloning and functional expression of a human orthologue of rat vanilloid receptor–1," Pain 88:205–215 (2000).

Honma et al., "Structure–based generation of a new class of potent Cdk4 inhibitors: New de Novo design strategy and library design," J. Med. Chem. 44:4615–4627 (2001) (WEB Published Dec. 13, 2001).

Kawasaki et al., "A new approach to 4–(2–aminoethyl)indoles via Claisen ortho–amide rearrangement of 3–hydroxy–2–methoxyindolines," J. Chem. Soc. Chem. Commun. 10:781–782 (1990).

Kumar et al. "Antiparasitic agents: Part XV—synthesis of 2–substituted 1(3)H–imidazo[4,5–f]isoquinolines as anthelmintic agents," Indian Journal of Chemistry 31B:177–182 (1992) (Mar., 1992).

Lila et al., "Large scale preparation of protected 4–aminomethylbenzamidine. Application to the synthesis of the thrombin inhibitor, melagatran," Synth. Comm. 28:4419–4429 (1998).

Mooney et al., "Potential antitumor agens, 10. Synthesis and biochemical properties of 5–N–alkylamino–N,N–dialkylamino–, and N–alkylacetamido–1–formylisoquinoline thiosemicarbazones," Journal of Medicinal Chemistry 17(11):1145–1150 (1974) (Orally presented in part on Aug., 1972).

Mukkala et al., "124. New heteromatic complexing agents and luminescence of their europium (III) and terbium(III) chelates," Helvetica Chima Acta 75:1621–1632 (1992).

Naruto et al., "Photo–induced Friedel–Crafts reactions. IV>Indoleacetic acids," Chemical and Pharmaceutical Bulletin, Tokyo, JP 20(10):2163–2171 (1972).

Nolano, et al., "Topical capsaicin in humans: parallel loss of epidermal nerve fibers and pain sensation," Pain 81:135–145 (1999).

Prescott, et al., Methods in Cell Biology, Academic Press, New York, N.Y. vol. 14:33 et seq. (1976), only Chapter 4 (Poste et al.) supplied.

Prijs et al. "9. On a few derivatives of heterocyclic carbonic acids I . . . Metal ions and biological action, $16^{th}$ report," Helv. Chim. Acta 37:90–94 (1954) with translation.

Roe et al., "The preparation of heterocyclic fluorine compounds by the schiemann reaction. III. Some monofluoroisoquinolines," J. Am. Chem. Soc., 73:687–689 (1951) (Feb., 1951).

Sato et al., "Construction of optically pure tryptophans from serine derived aziridine–2–carboxylates," Tetrahedron Letters 30(31):4073–4076 (1989).

Taurins et al., "Thiazoloisoquinolines. IV. The synthesis and spectra of thiazolo[4,5–h]–and thiazolo[5,4–f]isoquinolines. The ultraviolet and proton magnetic resonance spectra of some substituted isoquinolines," Canadian Journal of Chemistry 49(24):4054–4061 (1971).

Warpehoski et al., "Stereoelectronic factors influencing the biological activity and DNA interaction of synthetic antitumor agents modeled on CC–1065," J. Med. Chem. 31:590–603 (1988).

* cited by examiner

FUSED AZABICYCLIC COMPOUNDS THAT INHIBIT VANILLOID RECEPTOR SUBTYPE 1 (VR1) RECEPTOR

This application is a continuation-in-part of U.S. patent application Ser. No. 10/364,210, filed Feb. 11, 2003, incorporated herein by reference.

TECHNICAL BACKGROUND

The present invention relates to compounds of formula (I), which are useful for treating disorders caused by or exacerbated by vanilloid receptor activity, pharmaceutical compositions containing compounds of formula (I) and are useful in treating pain, bladder overactivity, and urinary incontinence.

BACKGROUND OF INVENTION

Nociceptors are primary sensory afferent (C and Aδ fibers) neurons that are activated by a wide variety of noxious stimuli including chemical, mechanical, thermal, and proton (pH <6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6–7), the affinity of capsaicin for the receptor is increased, whereas at pH <6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50–55° C.), and failed to develop thermal hyperalgesia following the intradermal administration of carrageenan.

The compounds of the present invention are novel VR1 antagonists and have utility in treating pain, bladder overactivity, and urinary incontinence.

SUMMARY OF THE PRESENT INVENTION

The present invention discloses fused azabicyclic compounds, a method for inhibiting the VR1 receptor in mammals using these compounds, a method for controlling pain in mammals, and pharmaceutical compositions including those compounds. More particularly, the present invention is directed to compounds of formula (I)

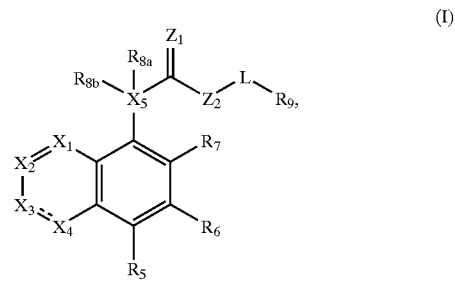

- - - or a pharmaceutically acceptable salt or prodrug thereof, wherein
- - - is absent or a single bond;
$X_1$ is selected from the group consisting of N and $CR_1$;
$X_2$ is selected from the group consisting of N and $CR_2$;
$X_3$ is selected from the group consisting of N, $NR_3$, and $CR_3$;
$X_4$ is a bond or selected from the group consisting of N and $CR_4$;
$X_5$ is selected from the group consisting of N and C;
provided that at least one of $X_1$, $X_2$, $X_3$, and $X_4$ is N; and provided that when $X_4$ is a bond, one of $X_1$, $X_2$, or $X_3$ must be NR;
$Z_1$ is selected from the group consisting of O, NH, and S;
$Z_2$ is a bond or selected from the group consisting of NH and O;
L is selected from the group consisting of ailcenylene, alkylene, alkynylene, cycloalkylene,

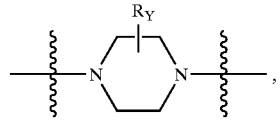

—$(CH_2)_mO(CH_2)_n$—, and $N(R_Y)$, wherein the left end of —$(CH_2)_mO(CH_2)_n$— is attached to $Z_2$ and the right end is attached to $R_9$;
m and n are each independently 0–6;
$R_Y$ is selected from the group consisting of hydrogen and alkyl;
$R_1$, $R_3$, $R_5$, $R_6$, and $R_7$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C$—, —$NR_AS(O)_2R_B$, —$S(O)_2OR_A$, —$S(O)_2R_B$, —$NZ_AZ_B$, $(NZ_AZ_B)$alkyl, $(NZ_AZ_B)$carbonyl, $(NZ_AZ_B)$carbonylalkyl and $(NZ_AZ_B)$ sulfonyl, wherein $Z_A$ and $Z_B$ are each independently selected from the group consisting of hydrogen, alkyl, alkylcarbonyl, formyl, aryl, and arylalkyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C$—, —$NR_AS(O)_2R_B$, —$S(O)_2OR_A$, —$S(O)_2R_B$, —$NZ_AZ_B$, $(NZ_AZ_B)$alkyl, $(NZ_AZ_B)$alkylcarbonyl, $(NZ_AZ_B)$carbonyl, $(NZ_AZ_B)$carbonylalkyl, $(NZ_AZ_B)$ sulfonyl, $(NZ_AZ_B)C(=NH)$—, $(NZ_AZ_B)C(=NCN)NH$—, and $(NZ_AZ_B)C(=NH)NH$—;

$R_A$ is selected from the group consisting of hydrogen and alkyl;

$R_B$ is selected from the group consisting of alkyl, aryl, and arylalkyl;

$R_{8a}$ is selected from the group consisting of hydrogen and alkyl;

$R_{8b}$ is absent when $X_5$ is N or $R_{8b}$ is selected from the group consisting of hydrogen, alkoxy, alkoxycarbonylalkyl, alkyl, alkylcarbonyloxy, alkylsulfonyloxy, halogen, and hydroxy when $X_5$ is C; and $R_9$ is selected from the group consisting of hydrogen, aryl, cycloalkyl, and heterocycle.

DETAILED DESCRIPTION OF THE PRESENT INVENTION

In the principle embodiment, compounds of formula (I) are disclosed

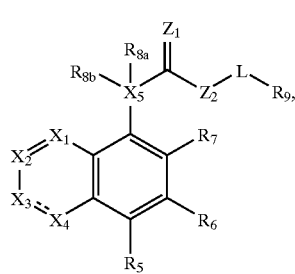

(I)

or a pharmaceutically acceptable salt or prodrug thereof, wherein

- - - is absent or a single bond;

$X_1$ is selected from the group consisting of N and $CR_1$;

$X_2$ is selected from the group consisting of N and $CR_2$;

$X_3$ is selected from the group consisting of N, $NR_3$, and $CR_3$;

$X_4$ is a bond or selected from the group consisting of N and $CR_4$;

$X_5$ is selected from the group consisting of N and C;

provided that at least one of $X_1$, $X_2$, $X_3$, and $X_4$ is N; and provided that when $X_4$ is a bond, one of $X_1$, $X_2$, or $X_3$ must be NR;

$Z_1$ is selected from the group consisting of O, NH, and S;

$Z_2$ is a bond or selected from the group consisting of NH and O;

L is selected from the group consisting of alkenylene, alkylene, alkynylene, (ii) Under "Definition of Terms": cycloalkylene,

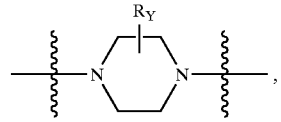

—$(CH_2)_mO(CH_2)_n$—, and $N(R_Y)$), wherein the left end of —$(CH_2)_mO(CH_2)_n$— is attached to $Z_2$ and the right end is attached to $R_9$;

m and n are each independently 0–6;

$R_Y$ is selected from the group consisting of hydrogen and alkyl;

$R_1$, $R_3$, $R_5$, $R_6$, and $R_7$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C$—, —$NR_AS(O)_2R_B$, —$S(O)_2OR_A$, —$S(O)_2R_B$, —$NZ_AZ_B$, $(NZ_AZ_B)$alkyl, $(NZ_AZ_B)$carbonyl, $(NZ_AZ_B)$carbonylalkyl and $(NZ_AZ_B)$ sulfonyl, wherein $Z_A$ and $Z_B$ are each independently selected from the group consisting of hydrogen, alkyl, alkylcarbonyl, formyl, aryl, and arylalkyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C$—, —$NR_AS(O)_2R_B$, —$S(O)_2OR_A$, —$S(O)_2R_B$, —$NZ_AZ_B$, $(NZ_AZ_B)$alkyl, $(NZ_AZ_B)$alkylcarbonyl, $(NZ_AZ_B)$carbonyl, $(NZ_AZ_B)$carbonylalkyl, $(NZ_AZ_B)$ sulfonyl, $(NZ_AZ_B)C(=NH)$—, $(NZ_AZ_B)C(=NCN)NH$—, and $(NZ_AZ_B)C(=NH)NH$—;

$R_A$ is selected from the group consisting of hydrogen and alkyl;

$R_B$ is selected from the group consisting of alkyl, aryl, and arylalkyl;

$R_{8a}$ is selected from the group consisting of hydrogen and alkyl;

$R_{8b}$ is absent when $X_5$ is N or $R_{8b}$ is selected from the group consisting of hydrogen, alkoxy, alkoxycarbonylalkyl, alkyl, alkylcarbonyloxy, alkylsulfonyloxy, halogen, and hydroxy when $X_5$ is C; and $R_9$ is selected from the group consisting of hydrogen, aryl, cycloalkyl, and heterocycle.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; and $R_1$, $R_2$, $R_4$, $R_5$, $R_6$, $R_7$, $R_{8a}$, $R_{8b}$, $R_9$, $X_5$, $Z_1$, $Z_2$, and L are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_{8b}$ is absent; $Z_1$ is O; $Z_2$ is NH; L is alkylene; $R_9$ is aryl; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_6$ and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is hydrogen; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$, and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$ and $R_7$ are each hydrogen; $R_{8b}$ is absent; $Z_1$ is O; $Z_2$ is NH; L is alkylene; $R_9$ is aryl wherein said aryl is substituted with aryloxy; and $R_{8a}$ is as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is NH; L is alkylene; $R_9$ is aryl wherein said aryl is phenyl substituted with aryloxy wherein said aryloxy is phenoxy optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is NH; L is alkylene; and $R_9$ is aryl wherein said aryl is napthyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_{8b}$ is absent; $Z_1$ is O; $Z_2$ is NH; L is alkylene; $R_9$ is cycloalkyl; $R_1$, $R_2$, $R_4$, $R_5$, $R_6$, $R_7$, and $R_{8a}$ is as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_6$ and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is hydrogen; $R_{8b}$ is absent; $Z_1$ is O; $Z_2$ is NH; L is alkylene; $R_9$ is cycloalkyl wherein said cyloalkyl is selected from the group consisting of adamantanyl, bicyclo[3.1.1]heptane, and cyclohexyl, wherein the cycloalkyl is optionally substituted with 1 or 2 alkyl substituents; and $Z_A$ and $Z_B$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_{8b}$ is absent; $Z_1$ is O; $Z_2$ is NH; L is alkylene; $R_9$ is heterocycle; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_6$ and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is hydrogen; $R_{8b}$ is absent; $Z_1$ is O; $Z_2$ is NH; L is alkylene; $R_9$ is heterocycle wherein said heterocycle is pyridinyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$, and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is NH; $R_{8b}$ is absent; $R_9$ is hydrogen; and L, $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is NH; L is alkylene; and $R_9$ is hydrogen.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is NH; L is cycloalkylene; $R_{8b}$ is absent; $R_9$ is aryl; and $R_1$, $R_2$, $R_4$, $R_5$. $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is NH; L is cycloalkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is a bond; L is cycloalkylene; $R_{8b}$ is absent; $R_9$ is aryl; and $R_1$, $R_2$, $R_4$, $R_5$, $R_6$, $R_7$, and $R_{8a}$ are as defined in formula (I).

In another embodiment of the present invention, compounds of formula (1) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is a bond; L is cycloalkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is NH; L is —$(CH_2)_mO(CH_2)_n$— wherein the left end is attached to $Z_2$ and the right end is attached to $R_9$; $R_{8b}$ is absent; $R_9$ is aryl; and m, n, $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is NH; L is —$(CH_2)_mO(CH_2)_n$— wherein the left end is attached to $Z_2$ and the right end is attached to $R_9$; m is 0–2; n is 0–2; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is NH; L is $N(R_Y)$; $R_{8b}$ is absent; $R_9$ is aryl; and $R_Y$, $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_Y$, $R_1$, $R_2$, $R_4$, $R_5$, $R_6$, $R_7$, and $R_{8a}$ are each hydrogen; $R_{8b}$ is absent; $Z_1$ is O; $Z_2$ is NH; L is $N(R_Y)$; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is a bond; L is

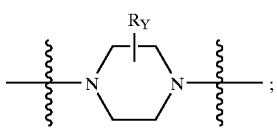

$R_{8b}$ is absent; $R_9$ is aryl; and $R^Y$, $R_1$, $R_2$, $R_4$, $R_5$, $R_6$, $R_7$, and $R_{8a}$ ar defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_5$, $R_6$, $R_7$, and $R_{8a}$ are each hydrogen; $R_{8b}$ is absent; $R_2$ is selected from the group consisting of hydrogen and alkyl; $Z_1$ is O; $Z_2$ is a bond; L is

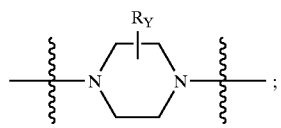

$R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $R^Y$, $Z_C$, and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$ and $R_6$ are each hydrogen; $R_7$ is $(CF_3)_2(HO)C$—; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $R_{8a}$, $Z_C$, and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $Z_1$ is O; $Z_2$ is O; L is alkylene; $R_{8b}$ is absent; $R_9$ is aryl; $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, $R_7$, and $R_{8a}$ are each hydrogen; $R_{8b}$ is absent; $Z_1$ is O; $Z_2$ is O; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$ and $R_7$ are each hydrogen; $Z_1$ is O; $Z_2$ is O; L is alkylene; $R_{8b}$ is absent; $R_9$ is aryl wherein said aryl is naphthyl; and $R_{8a}$ is as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_{8b}$ is absent; $Z_1$ is O; $Z_2$ is a bond; L is alkenylene; $R_9$ is aryl; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is N; $R_1$, $R_6$ and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is hydrogen; $R_{8b}$ is absent; $Z_1$ is O; $Z_2$ is a bond; L is alkenylene; $R_9$ is aryl wherein said aryl is phenyl optionally substituted with 1, 2, or 3 substituents independently selected from the group consisting of alkoxy, alkyl, alkylsulfonyl, 2-azabicyclo [2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $Z_1$ is O; $Z_2$ is NH; L is alkylene; $R_9$ is heterocycle; and $R_1$, $R_2$, $R_4$, $R_5$, $R_6$, $R_7$, $R_{8a}$, and $R_{8b}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$ and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ and $R_{8b}$ are hydrogen; $Z_1$ is O; $Z_2$ is NH; L is alkylene; $R_9$ is heterocycle wherein said heterocycle is selected from the group consisting of imidazolyl, pyridinyl, pyrrolidinyl, and thienyl, wherein the heterocycle is optionally substituted with 1 or 2 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, oxo, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $Z_1$ is O; $Z_2$ is NH; L is —$(CH_2)_mO(CH_2)_n$— wherein the left end is attached to $Z_2$ and the right end is attached to $R_9$; $R_9$ is hydrogen; and m, n, $R_1$, $R_2$, $R_4$, $R_5$, $R_6$, $R_7$, $R_{8a}$ and $R_{8b}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$ and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ and $R_{8b}$ are hydrogen; $Z_1$ is O; $Z_2$ is NH; L is —$(CH_2)_mO(CH_2)_n$— wherein the left end is attached to $Z_2$ and the right end is attached to $R_9$; m is 0–4; n is 0–4; $R_9$ is hydrogen; and $Z_A$ and $Z_B$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $Z_1$ is O; $Z_2$ is NH; L is alkylene; $R_9$ is aryl; and $R_1$, $R_2$, $R_4$, $R_5$, $R_6$, $R_7$, $R_{8a}$, and $R_{8b}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$, $R_7$, $R_{8a}$ and $R_{8b}$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$, $R_7$, $R_{8a}$ and $R_{8b}$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$, and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is selected from the group consisting of hydrogen and alkyl; $R_{8b}$ is alkyl; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$, and $R_7$ and are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is hydrogen; $R_{8b}$ is selected from the group consisting of alkoxy, alkoxycarbonylalkyl, alkylcarbonyloxy, alkylsulfonyl, halogen, and hydroxy; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo [3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is $CR_4$; $X_5$ is C; $R_1$, $R_6$, $R_7$, and $R_7$ are each hydrogen; $R_2$ and $R_4$ are independently selected from the group consisting of hydrogen, alkyl, halogen, hydroxy, and —$NZ_AZ_B$; $R_5$ is selected from the group consisting of hydrogen and halogen; $R_{8a}$ is selected from the group consisting of hydrogen and alkyl; $R_{8b}$ is selected from the group consisting of hydrogen, alkoxycarbonylalkyl, alkyl, and hydroxy; $Z_1$ is O; $Z_2$ is O; L is alkylene; $R_9$ is hydrogen; and $Z_A$ and $Z_B$ are independently selected from the group consisting of hydrogen and alkyl.

In another embodiment of the present invention, compounds of formula (I) are disclosed wherein - - - is a single bond; $X_1$ is $CR_1$; $X_2$ is $CR_2$; $X_3$ is N; $X_4$ is N; and $R_1$, $R_2$, $R_5$, $R_6$, $R_7$, $R_{8a}$, $R_{8b}$, $R_9$, $X_5$, $Z_1$, $Z_2$, and L are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is N; $X_5$ is N; Rb is absent; $Z_1$ is O; $Z_2$ is NH; L is alkylene; $R_9$ is aryl; and $R_1$, $R_2$, $R_5$, $R_6$, $R_7$, $R_{8a}$, and $R_{8b}$ are as defined in formula (I).

In another embodiment of the present invention, compounds of formula (I) are disclosed wherein - - - is a single bond; $X_1$ is $CR_1$; $X_2$ is $CR_2$; $X_3$ is N; $X_4$ is N; $X_5$ is N; $R_1$, $R_5$, $R_6$ and $R_7$ are each hydrogen; $R_{8b}$ is absent; $R_2$ is selected from the group consisting of alkyl and halogen; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $R_{8a}$, $Z_C$, and $Z_D$ are independently selected from the group consisting of hydrogen and alkyl.

In another embodiment of the present invention, compounds of formula (I) are disclosed wherein - - - is a single bond; $X_1$ is $CR_1$; $X_2$ is N; $X_3$ is $CR_3$; $X_4$ is $CR_4$; and $R_1$, $R_3$, $R_5$, $R_6$, $R_7$, $R_{8a}$, $R_{8b}$, $R_9$, $X_5$, $Z_1$, $Z_2$, and L are as defined in formula (I).

In another embodiment of the present invention, compounds of formula (I) are disclosed wherein - - - is a single bond; $X_1$ is $CR_1$; $X_2$ is N; $X_3$ is $CR_3$; $X_4$ is $CR_4$; $X_5$ is N; $R_{8b}$ is absent; $Z_1$ is O; $Z_2$ is NH; L is alkylene; $R_9$ is aryl; and $R_1$, $R_3$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is N; $X_3$ is $CR_3$; $X_4$ is $CR_4$; $X_5$ is N; $R_1$, $R_3$, $R_4$, $R_5$, $R_6$ and $R_7$ are each hydrogen; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $R_{8a}$, $Z_C$, and $Z_D$ are independently selected from the group consisting of hydrogen and alkyl.

In another embodiment of the present invention, compounds of formula (I) are disclosed wherein - - - is absent; $X_1$ is $CR_1$; $X_2$ is $CR_2$; $X_3$ is $NR_3$; $X_4$ is a bond; and $R_1$, $R_2$, $R_3$, $R_5$, $R_6$, $R_7$, $R_{8a}$, $R_{8b}$, $R_9$, $X_5$, $Z_1$, $Z_2$, and L are as defined in formula (I).

In another embodiment of the present invention, compounds of formula (I) are disclosed wherein - - - is absent; $X_1$ is $CR_1$; $X_2$ is $CR_2$; $X_3$ is $NR_3$; $X_4$ is a bond; $X_5$ is N; $R_{8b}$ is absent; $Z_1$ is O; $Z_2$ is NH; L is alkylene; $R_9$ is aryl; and $R_1$, $R_2$, $R_3$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is $CR_2$; $X_3$ is N; $X_4$ is a bond; $X_5$ is N; $R_1$, $R_2$, $R_5$, $R_6$ and $R_7$ are each hydrogen; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $R_{8a}$, $Z_C$, and $Z_D$ are independently selected from the group consisting of hydrogen and alkyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is $CR_2$; $X_3$ is $NR_3$; $X_4$ is a bond; $X_5$ is N; $R_1$ and $R_2$ are each independently alkyl; $R_5$, $R_6$ and $R_7$ are each hydrogen; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $R_{8a}$, $Z_C$, and $Z_D$ are independently selected from the group consisting of hydrogen and alkyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is $CR_2$; $X_3$ is $NR_3$; $X_4$ is a bond; $X_5$ is N; $R_{8b}$ is absent; $Z_1$ is O; $Z_2$ is O; L is alkylene; $R_9$ is aryl; and $R_1$, $R_2$, $R_3$, $R_5$, $R_6$, $R_7$, $R_{8a}$, and $R_9$ are as defined in formula (I).

In another embodiment of the present invention, compounds of formula (I) are disclosed wherein - - - is absent; $X_1$ is $CR_1$; $X_2$ is $CR_2$; $X_3$ is $NR_3$; $X_4$ is a bond; $X_5$ is N; $R_{8a}$, $R_1$, $R_2$, $R_5$, $R_6$ and $R_7$ are each hydrogen; $R_{8b}$ is absent; $Z_1$ is O; $Z_2$ is O; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $R_{8a}$, $Z_C$, and $Z_D$ are independently selected from the group consisting of hydrogen and alkyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; and $R_1$, $R_3$, $R_5$, $R_6$, $R_7$, $R_{8a}$, $R_{8b}$, $R_9$, $X_5$, $Z_1$, $Z_2$, and L are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8b}$ is absent; $Z_1$ is O; $Z_2$ is NH; L is alkylene; $R_9$ is aryl; and $R_1$, $R_3$, $R_5$, $R_6$, $R_7$, and $R_{8a}$ are as defined in formula (I).

In another embodiment of the present invention, compounds of formula (I) are disclosed wherein - - - is absent;

$X_1$ is $CR_1$; $X_2$ is N; $X_3$ is $NR_3$; $X_4$ is a bond; $X_5$ is N; $R_1$, $R_5$, $R_6$ and $R_7$ are each hydrogen; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $R_{8a}$, $Z_C$, and $Z_D$ are independently selected from the group consisting of hydrogen and alkyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8a}$, $R_1$, $R_5$, $R_6$ and $R_7$ are each hydrogen; $R_{8b}$ is absent; $Z_1$ is O; $Z_2$ is NH; L is alkylene wherein the alkylene is —$CH_2$—; $R_9$ is aryl wherein said aryl is phenyl optionally substituted with 2 substituents independently selected from the group consisting of 8-azabicyclo[3.2.1]oct-8-yl, trifluoromethyl, and —Cl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8a}$, $R_1$, $R_5$, $R_6$ and $R_7$ are each hydrogen; $R_{8b}$ is absent; $Z_1$ is O; $Z_2$ is NH; L is alkylene wherein the alkylene is —$CH_2$—; $R_9$ is aryl wherein said aryl is 4-(8-azabicyclo[3.2.1]oct-8-yl)-3-(trifluoromethyl)phenyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8a}$, $R_1$, $R_5$, $R_6$ and $R_7$ are each hydrogen; $R_{8b}$ is absent; $Z_1$ is O; $Z_2$ is NH; L is alkylene wherein the alkylene is —$CH_2$—; $R_9$ is aryl wherein said aryl is 4-(8-azabicyclo[3.2.1]oct-8-yl)-2-chlorophenyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_1$, $R_6$ and $R_7$ are each hydrogen; $R_5$ is alkyl wherein a preferred alkyl is methyl or ethyl; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $Z_C$ and $Z_D$ are independently selected from the group consisting of hydrogen and alkyl; and $R_{8a}$ and $R_3$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8a}$, $R_1$, $R_6$ and $R_7$ are each hydrogen; $R_5$ is alkyl wherein a preferred alkyl is methyl or ethyl; $R_{8b}$ is absent; $Z_1$ is O; $Z_2$ is NH; L is alkylene; $R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $Z_C$ and $Z_D$ are independently selected from the group consisting of hydrogen and alkyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_1$, $R_5$, $R_6$ and $R_7$ are each hydrogen; $R_{8b}$ is absent; $Z_1$ is O; $Z_2$ is NH; L is alkylene; $R_9$ is aryl wherein said aryl is selected from the group consisting of naphthyl and phenyl; and $R_{8a}$ and $R_3$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8a}$, $R_1$, $R_5$, $R_6$ and $R_7$ are each hydrogen; $R_{8b}$ is absent; $Z_1$ is O; $Z_2$ is NH; L is alkylene; $R_9$ is aryl wherein said aryl is selected from the group consisting of naphthyl and phenyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_1$, $R_5$, $R_6$ and $R_7$ are each hydrogen; $R_{8b}$ is absent; $Z_1$ is O; $Z_2$ is NH; L is alkylene; $R_9$ is heterocycle wherein said heterocycle is pyridinyl substituted with alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$, $Z_D$, $R_{8a}$, and $R_3$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $X_5$ is N; $R_{8a}$, $R_1$, $R_5$, $R_6$ and $R_7$ are each hydrogen; $R_{8b}$ is absent; $Z_1$ is O; $Z_2$ is NH; L is alkylene; $R_9$ is heterocycle wherein said heterocycle is pyridinyl substituted with alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $Z_C$ and $Z_D$ are independently selected from the group consisting of hydrogen and alkyl; and $R_3$ is selected from the group consisting of hydrogen and alkoxycarbonyl.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8b}$ is absent; $Z_1$ is O; $Z_2$ is NH; L is

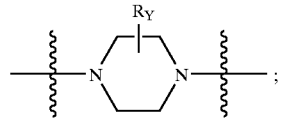

$R_9$ is heterocycle; and $R_{8a}$, $R_1$, $R_3$, $R_5$, $R_6$ and $R_7$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_1$, $R_5$, $R_6$ and $R_7$ are each hydrogen; $R_{8b}$ is absent; $Z_1$ is O; $Z_2$ is NH; L is

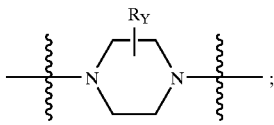

$R_9$ is heterocycle wherein said heterocycle is pyridinyl optionally substituted with 1 or 2 substituents selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $Z_C$ and $Z_D$ are independently selected from the group consisting of hydrogen and alkyl; and $R_{8a}$ and $R_3$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $R_{8a}$, $R_1$, $R_5$, $R_6$ and $R_7$ are each hydrogen; $R_{8b}$ is absent; $Z_1$ is O; $Z_2$ is NH; L is

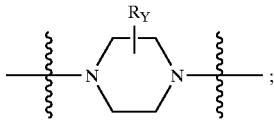

$R_9$ is heterocycle wherein said heterocycle is pyridinyl optionally substituted with 1 or 2 substituents selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; $Z_C$ and $Z_D$ are independently selected from the group consisting of hydrogen and alkyl; and $R_3$ is selected from the group consisting of hydrogen and alkoxycarbonyl.

Another embodiment of the present invention relates to pharmaceutical compositions comprising a therapeutically effective amount of a compound of formula (I) or a pharmaceutically acceptable salt thereof.

Another embodiment of the present invention relates to a method of treating a disorder wherein the disorder is ameliorated by inhibiting vanilloid receptor subtype 1 (VR1) receptor in a host mammal in need of such treatment comprising administering a therapeutically effective amount of a compound of formula (I) or a pharmaceutically acceptable salt thereof.

Another embodiment of the present invention relates to a method for controlling pain in a host mammal in need of such treatment comprising administering a therapeutically effective amount of a compound of formula (I) or a pharmaceutically acceptable salt thereof.

Another embodiment of the present invention relates to a method of treating urinary incontinence in a host mammal in need of such treatment comprising administering a therapeutically effective amount of a compound of formula (I) or a pharmaceutically acceptable salt thereof.

Another embodiment of the present invention relates to a method of treating bladder overactivity in a host mammal in need of such treatment comprising administering a therapeutically effective amount of a compound of formula (I) or a pharmaceutically acceptable salt thereof.

Another embodiment of the present invention relates to a method of treating inflammatory thermal hyperalgesia in a host mammal in need of such treatment comprising administering a therapeutically effective amount of a compound of formula (I) or a pharmaceutically acceptable salt thereof.

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, —$CH_2CH(CH_3)$ $CH_2$—, and —$(CH_2)_pCH(R_Z)(CH_2)_q$—, wherein p and q are independently 0–4 and $R_Z$ is selected from the group consisting of aryl, cycloalkyl, and hydroxy. A preferred aryl group is phenyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —$CH_2$C≡C—, —CH($CH_3$)$CH_2$C≡C—, —C≡CCH_2—, and —C≡CCH($CH_3$)$CH_2$—.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl and tetrahydronaphthyl.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —$NZ_CZ_D$, ($NZ_CZ_D$)alkyl, ($NZ_CZ_D$) carbonyl, ($NZ_CZ_D$)carbonylalkyl, ($NZ_CZ_D$)sulfonyl, —$NR_AS(O)_2R_B$, —$S(O)_2OR_A$ and —$S(O)_2R_A$ wherein $R_A$ and $R_B$ are as defined herein. The aryl groups of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, —$NZ_CZ_D$, ($NZ_CZ_D$)alkyl, ($NZ_CZ_D$)carbonyl, ($NZ_CZ_D$) carbonylalkyl, ($NZ_CZ_D$) sulfonyl, —$NR_AS(O)_2R_B$, —$S(O)_2 OR_A$ and —$S(O)_2R_A$ wherein $R_A$ and $R_B$ are as defined herein. Representative examples include, but are not limited to, 4-(2-azabicyclo[2.2.1]hept-2-yl)-2-(trifluoromethyl) phenyl, 4-(8-azabicyclo[3.2.1]oct-8-yl)-2-chlorophenyl, 4-(8-azabicyclo[3.2.1]oct-8-yl)-3-chlorophenyl, 4-(8-azabicyclo[3.2.1]oct-8-yl)phenyl, 4-(8-azabicyclo[3.2.1] oct-8-yl)-3-(trifluoromethyl)phenyl, 4-(8-azabicyclo[3.2.1] oct-8-yl)-2-(trifluoromethyl)phenyl, 4-(8-azabicyclo[3.2.1] oct-8-yl)-3-fluorophenyl, 3-chloro-4-azepan-1-ylphenyl, 2-chloro-4-azepan-1-ylphenyl, 3,5-difluoro-4-azepan-1-ylphenyl, 4-(8-azabicyclo[3.2.1]oct-8-yl)-3,5-difluorophenyl, 4-bromophenyl, 3-chlorophenyl, 4-chlorophenyl, 3,4-dichlorophenyl, 2,3-dichlorophenyl, 2,4-dichlorophenyl, 3,5-dichlorophenyl, 3,4-difluorophenyl, 4-bromo-2-fluorophenyl, 4-chloro-2-fluorophenyl, 4-(tert-butyl)phenyl), 4-cyanophenyl, 4-ethylphenyl, 3-fluorophenyl, 2,4-difluorophenyl, 4-bromo-3-fluorophenyl, 2,3-difluoro-4-(trifluoromethyl)phenyl, 3-fluoro-4-(trifluoromethyl)phenyl, 3-fluoro-5-(trifluoromethyl)phenyl, 3-(trifluoromethyl)phenyl, 4-(trifluoromethyl)phenyl, 4-(trifluoromethoxy)phenyl, 3-(trifluoromethoxy)phenyl, 4-[(trifluoromethyl)thio] phenyl, 4-azepan-1-yl-3-(trifluoromethyl)phenyl, 4-azepan-1-yl-2-(trifluoromethyl)phenyl, 3-methylphenyl, 3,4-dimethylphenyl, 2,4-dimethylphenyl, 4-isopropylphenyl, 4-methylphenyl, 4-bromo-3-methylphenyl, 4-fluoro-3-(trifluoromethyl)phenyl, 3-chloro-4-fluorophenyl, 4-(1-pyrrolidinyl)phenyl, 4-(1-azepanyl)phenyl, 3-fluoro-4-(1-pyrrolidinyl)phenyl, 3-fluoro-4-(1-azepanyl)phenyl, 4-(1-azocanyl)phenyl, 4-(1-piperidinyl)phenyl, 3-fluoro-4-(1-piperidinyl)phenyl, 4-(2-pyridinyl)phenyl, 1,1'-biphenyl, 3-fluoro-4-(4-methyl-1-piperidinyl)phenyl, 4-(4-methyl-1-piperidinyl)phenyl, 4-(4-morpholinyl)phenyl, 4-(2,6-dimethyl-4-morpholinyl)phenyl, 4-(4-thiomorpholinyl) phenyl, 3,5-difluoro-4-(4-morpholinyl)phenyl, 3,5-bis (trifluoromethyl)phenyl, and 2,5-bis(trifluoromethyl)phenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylthio" as used herein, means an aryl group, as defined herein, appended to the parent molecular moiety through a sulfur atom. Representative examples of arylthio include, but are not limited to, phenylsulfanyl, naphth-2-ylsulfanyl, and 5-phenylhexylsulfanyl.

The term "1-azepanyl" as used herein, means a 7-membered ring wherein one of the atoms is nitrogen.

The term "1-azocanyl" as used herein, means a 8-membered ring wherein one of the atoms is nitrogen.

The term "carbonyl" as used herein, means a —C(O)— group.

The term "carboxy" as used herein, means a —CO₂H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2] nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0³,⁷]nonane and tricyclo[3.3.1.1³,⁷]decane (adamantyl).

The cycloalkyl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylthio, halogen, hydroxy, hydroxyalkyl, mercapto, mercaptoalkyl, nitro, —NZ$_C$Z$_D$, (NZ$_C$Z$_D$)alkyl, (NZ$_C$Z$_D$)carbonyl, (NZ$_C$Z$_D$)carbonylalkyl, (NZ$_C$Z$_D$)sulfonyl, —NR$_A$S(O)$_2$R$_B$, —S(O)$_2$OR$_A$, and —S(O)$_2$R$_A$ wherein R$_A$ and R$_B$ are as defined herein. Representative examples include, but are not limited to, 6,6-dimethylbicyclo[3.1.1]heptyl, 6,6-dimethylbicyclo[3.1.1]hept-2-yl, 4-tert-butylcyclohexyl, and 4-(trifluoromethyl)cyclohexyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylene" as used herein, means a divalent group derived from a cycloalkyl group, as defined herein. Representative examples of cycloalkylene include, but are not limited to

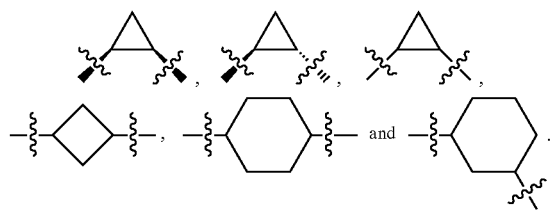

The term "ethylenedioxy" as used herein, means a —O(CH₂)₂O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Additionally, bicyclic ring systems are exemplified by a bridged monocyclic ring system in which two non-adjacent carbon atoms of the monocyclic ring system are linked by an alkylene group. Representative examples of bicyclic ring systems include, but are not limited to, 2-azabicyclo[2.2.1]heptyl, 8-azabicyclo[3.2.1]octyl, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, arylalkyl, aryloxy, arylthio, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, oxo, —$NZ_CZ_D$, ($NZ_CZ_D$)alkyl, ($NZ_CZ_D$)carbonyl, ($NZ_CZ_D$)carbonylalkyl, ($NZ_CZ_D$) sulfonyl, —$NR_AS(O)_2R_B$, —$S(O)_2OR_A$ and —$S(O)_2R_A$ wherein $R_A$ and $R_B$ are as defined herein. The heterocycles of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, mercapto, mercaptoalkyl, nitro, —$NZ_CZ_D$, ($NZ_CZ_D$)alkyl, ($NZ_CZ_D$)carbonyl, ($NZ_CZ_D$)carbonylalkyl, ($NZ_CZ_D$)sulfonyl, —$NR_AS(O)_2R_B$, —$S(O)_2OR_A$ and —$S(O)_2R_A$ wherein $R_A$ and $R_B$ are as defined herein. Representative examples include, but are not limited to, 2,6-dimethylmorpholinyl, 4-(3-chlorophenyl)-1-piperazinyl, 4-(3,4-dimethylphenyl)-1-piperazinyl, 4-(4-chlorophenyl)-1-piperazinyl, 4-(4-methylphenyl)-3-methyl-1-piperazinyl, 4-(2,3-dimethylphenyl)-1-piperazinyl, 4-(2,3-dichlorophenyl)-1-piperazinyl, 4-(3,4-dichlorophenyl)-1-piperazinyl, 4-[3-(trifluoromethyl)phenyl]-1-piperazinyl, 4-(4-bromophenyl)-1-piperazinyl, 4-[4-(trifluoromethyl)-2-pyridinyl]-1-piperazinyl, 2-oxo-1-pyrrolidinyl, 5-(trifluoromethyl)-2-pyridinyl, 6-(trifluoromethyl)-3-pyridinyl.

The term "heterocyclealkyl" as used herein, means a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocyclethio" as used herein, means a heterocycle group, as defined herein, appended to the parent molecular moiety through a sulfur atom. Representative examples of heterocyclethio include, but are not limited to, pyridin-3-ylsulfanyl and quinolin-3-ylsulfanyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —$OCH_2O$— group wherein the oxygen atoms of the methylenedioxy are attached to the parent molecular moiety through two adjacent carbon atoms.

The term "nitro" as used herein, means a —$NO_2$ group.

The term "—$NZ_AZ_B$" as used herein, means two groups, $Z_A$ and $Z_B$, which are appended to the parent molecular moiety through a nitrogen atom. $Z_A$ and $Z_B$ are each independently selected from hydrogen, alkyl, alkylcarbonyl, formyl, aryl and arylalkyl. Representative examples of —$NZ_AZ_B$ include, but are not limited to, amino, methylamino, acetylamino, benzylamino, phenylamino, and acetylmethylamino.

The term "($NZ_AZ_B$)alkyl" as used herein, means a —$NZ_AZ_B$ group, as defined herein, appended to the parent molecular moiety through an alkyl group, as defined herein. Representative examples of ($NZ_AZ_B$)alkyl include, but are not limited to, aminomethyl, 2-(methylamino)ethyl, 2-(dimethylamino)ethyl and (ethylmethylamino)methyl.

The term "($NZ_AZ_B$)alkylcarbonyl" as used herein, means a ($NZ_AZ_B$)alkyl group, as defined herein, appended to the parent molecular moiety through a carbonyl group, as defined herein. Representative examples of ($NZ_AZ_B$) alkylcarbonyl include, but are not limited to, dimethylaminomethylcarbonyl, 2-(dimethylamino) ethylcarbonyl, and (ethylmethylamino)methylcarbonyl.

The term "($NZ_AZ_B$)carbonyl" as used herein, means a —$NZ_AZ_B$ group, as defined herein, appended to the parent molecular moiety through a carbonyl group, as defined herein. Representative examples of ($NZ_AZ_B$)carbonyl include, but are not limited to, aminocarbonyl, (methylamino)carbonyl, (dimethylamino)carbonyl and (ethylmethylamino)carbonyl.

The term "($NZ_AZ_B$)carbonylalkyl" as used herein, means a ($NZ_AZ_B$)carbonyl group, as defined herein, appended to the parent molecular moiety through an alkyl group, as defined herein. Representative examples of $(NZ_AZ_B)$ carbonylalkyl include, but are not limited to, (aminocarbonyl)methyl, 2-((methylamino)carbonyl)ethyl and ((dimethylamino)carbonyl)methyl.

The term "$(NZ_AZ_B)$sulfonyl" as used herein, means a —$NZ_AZ_B$ group, as defined herein, appended to the parent molecular moiety through a sulfonyl group, as defined herein. Representative examples of $(NZ_AZ_B)$sulfonyl include, but are not limited to, aminosulfonyl, (methylamino)sulfonyl, (dimethylamino)sulfonyl and (ethylmethylamino)sulfonyl. The term "—$NZ_AZ_B$" as used herein, means two groups, $Z_A$ and $Z_B$, which are appended to the parent molecular moiety through a nitrogen atom. $Z_A$ and $Z_B$ are each independently selected from hydrogen, alkyl, alkylcarbonyl, formyl, aryl and arylalkyl. Representative examples of —$NZ_AZ_B$ include, but are not limited to, amino, methylamino, acetylamino, benzylamino, phenylamino, and acetylmethylamino.

The term "—$NZ_CZ_D$" as used herein, means two groups, $Z_C$ and $Z_D$, which are appended to the parent molecular moiety through a nitrogen atom. $Z_C$ and $Z_D$ are each independently selected from hydrogen, alkyl, alkylcarbonyl, formyl, aryl and arylalkyl. Representative examples of —$NZ_CZ_D$ include, but are not limited to, amino, methylamino, acetylamino, benzylamino, phenylamino, and acetylmethylamino.

The term "$(NZ_CZ_D)$alkyl" as used herein, means a —$NZ_CZ_D$ group, as defined herein, appended to the parent molecular moiety through an alkyl group, as defined herein. Representative examples of $(NZ_CZ_D)$alkyl include, but are not limited to, aminomethyl, 2-(methylamino)ethyl, 2-(dimethylamino)ethyl and (ethylmethylamino)methyl.

The term "$(NZ_CZ_D)$carbonyl" as used herein, means a —$NZ_CZ_D$ group, as defined herein, appended to the parent molecular moiety through a carbonyl group, as defined herein. Representative examples of $(NZ_CZ_D)$carbonyl include, but are not limited to, aminocarbonyl, (methylamino)carbonyl, (dimethylamino)carbonyl and (ethylmethylamino)carbonyl.

The term "$(NZ_CZ_D)$carbonylalkyl" as used herein, means a $(NZ_CZ_D)$carbonyl group, as defined herein, appended to the parent molecular moiety through an alkyl group, as defined herein. Representative examples of $(NZ_CZ_D)$ carbonylalkyl include, but are not limited to, (aminocarbonyl)methyl, 2-((methylamino)carbonyl)ethyl and ((dimethylamino)carbonyl)methyl.

The term "$(NZ_CZ_D)$sulfonyl" as used herein, means a —$NZ_CZ_D$ group, as defined herein, appended to the parent molecular moiety through a sulfonyl group, as defined herein. Representative examples of $(NZ_CZ_D)$sulfonyl include, but are not limited to, aminosulfonyl, (methylamino)sulfonyl, (dimethylamino)sulfonyl and (ethylmethylamino)sulfonyl.

The term "oxo" as used herein, means =O.

The term "sulfonyl" as used herein, means a —S(O)$_2$— group.

In Vitro Data

Determination of Inhibition Potencies

Dulbecco's modified Eagle medium (D-MEM)(with 4.5 mg/mL glucose) and fetal bovine serum were obtained from Hyclone Laboratories, Inc. (Logan, Utah). Dulbecco's phosphate-buffered saline (D-PBS)(with 1 mg/mL glucose and 3.6 mg/l Na pyruvate)(without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy)methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88: 205–215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ([$Ca^{2+}$]i). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of [$Ca^{2+}$]i in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1–2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration)(final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ from 1000 nM to 0.1 nM. In a preferred range, compounds tested had $IC_{50s}$ from 500 nM to 0.11 nM. In a more preferred range, compounds tested had $IC_{50s}$ from 50 nM to 0.1 nM.

In Vivo Data

Determination of Antinociceptive Effect

Experiments were performed on 400 adult male 129J mice (Jackson laboratories, Bar Harbor, Me.), weighing 20–25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., Br. J. Pharmacol. Chemother. 32 (1968) 295–310. Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The compounds of the present invention tested were found to have antinociceptive effects with $ED_{50s}$ from 1 mg/kg to 500 mg/kg.

The in vitro and in vivo data demonstrates that compounds of the present invention antagonize the VR1 receptor and are useful for treating pain.

Compounds of the present invention, as VR1 antagonists, are also useful for ameliorating or preventing additional disorders that are affected by the VR1 receptors such as, but not limited to, infammatory thermal hyperalgesia, bladder overactivity, and urinary incontinence.

Compounds of the present invention, including but not limited to those specified in the examples, can be used to treat pain as demonstrated by Nolano, M. et al., Pain 81 (1999) 135; Caterina, M. J. and Julius, D., Annu. Rev. Neurosci. 24, (2001) 487–517; Caterina, M. J. et al., Science 288 (2000) 306–313; Caterina, M. J. et al., Nature 389 (1997) 816–824.

Compounds of the present invention, including but not limited to those specified in the examples, can be used to treat bladder overactivity and/or urinary incontinence as demonstrated by Fowler, C. Urology 55 (2000) 60.

Compounds of the present invention, including but not limited to those specified in the examples, can be used to treat inflammatory thermal hyperalgesia as demonstrated by Davis, J. et al., Nature 405 (2000) 183–187.

The present invention also provides pharmaceutical compositions that comprise compounds of the present invention. The pharmaceutical compositions comprise compounds of the present invention that may be formulated together with one or more non-toxic pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofirfturyl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood. Representative examples include, but are not limited to, methyl 4-{[({[4-(8-azabicyclo[3.2.1]oct-8-yl)-3-(trifluoromethyl)phenyl]methyl}amino)carbonyl]amino}-1H-indazole-1-carboxylate, ethyl 4-{[({[4-(8-azabicyclo[3.2.1]oct-8-yl)-3-(trifluoromethyl)phenyl]methyl}amino)carbonyl]amino}-1H-indazole-1-carboxylate, tert-butyl 4-[({[4-(8-azabicyclo[3.2.1]oct-8-yl)-3-(trifluoromethyl)benzyl]amino}carbonyl)amino]-1H-indazole-1-carboxylate, tert-butyl 4-[({[4-(8-azabicyclo[3.2.1]oct-8-yl)-2-chlorobenzyl]amino}carbonyl)amino]-1H-indazole-1-carboxylate, ethyl 4-[({[4-(8-azabicyclo[3.2.1]oct-8-yl)-2-chlorobenzyl]amino}carbonyl)amino]-1H-indazole-1-carboxylate, and methyl 4-[({[4-(8-azabicyclo[3.2.1]oct-8-yl)-2-chlorobenzyl]amino}carbonyl)amino]-1H-indazole-1-carboxylate.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

Compounds of the present invention were named by ACD/ChemSketch version 5.0 (developed by Advanced Chemistry Development, Inc., Toronto, ON, Canada) or were given names which appeared to be consistent with ACD nomenclature.

Abbreviations

Abbreviations which have been used in the descriptions of the Schemes and the Examples that follow are: dba for dibenzylideneacetone; DBU for 1,8-diazabicyclo[5.4.0]undec-7-ene; BINAP for 2,2'-bis(diphenylphosphino)-1,1'-binaphthyl; DCC for 1,3-dicyclohexylcarbodiimide; DIEA for diisopropylethylamine; DMAP for 4-dimethylaminopyridine; DMF for N,N-dimethylformamide; DMSO for dimethylsulfoxide; EDCI or EDC for 1-ethyl-3-[3-(dimethylamino)propyl]-carbodiimide hydrochloride; HMPA for hexamethylphosphoramide; HPLC high pressure liquid chromatography; NBS for N-bromosuccinimide; Pd for palladium; Ph for phenyl; psi for pounds per square inch; and THF for tetrahydrofuran.

Preparation of Compounds of the Present Invention

The compounds and processes of the present invention will be better understood in connection with the following synthetic Schemes and Examples which illustrate a means by which the compounds of the present invention can be prepared.

Scheme 1

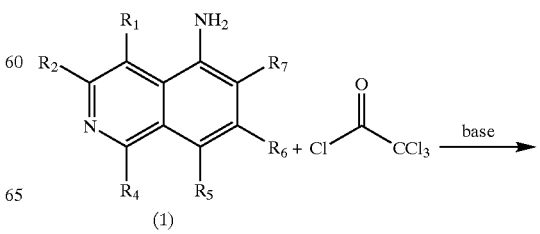

(1)

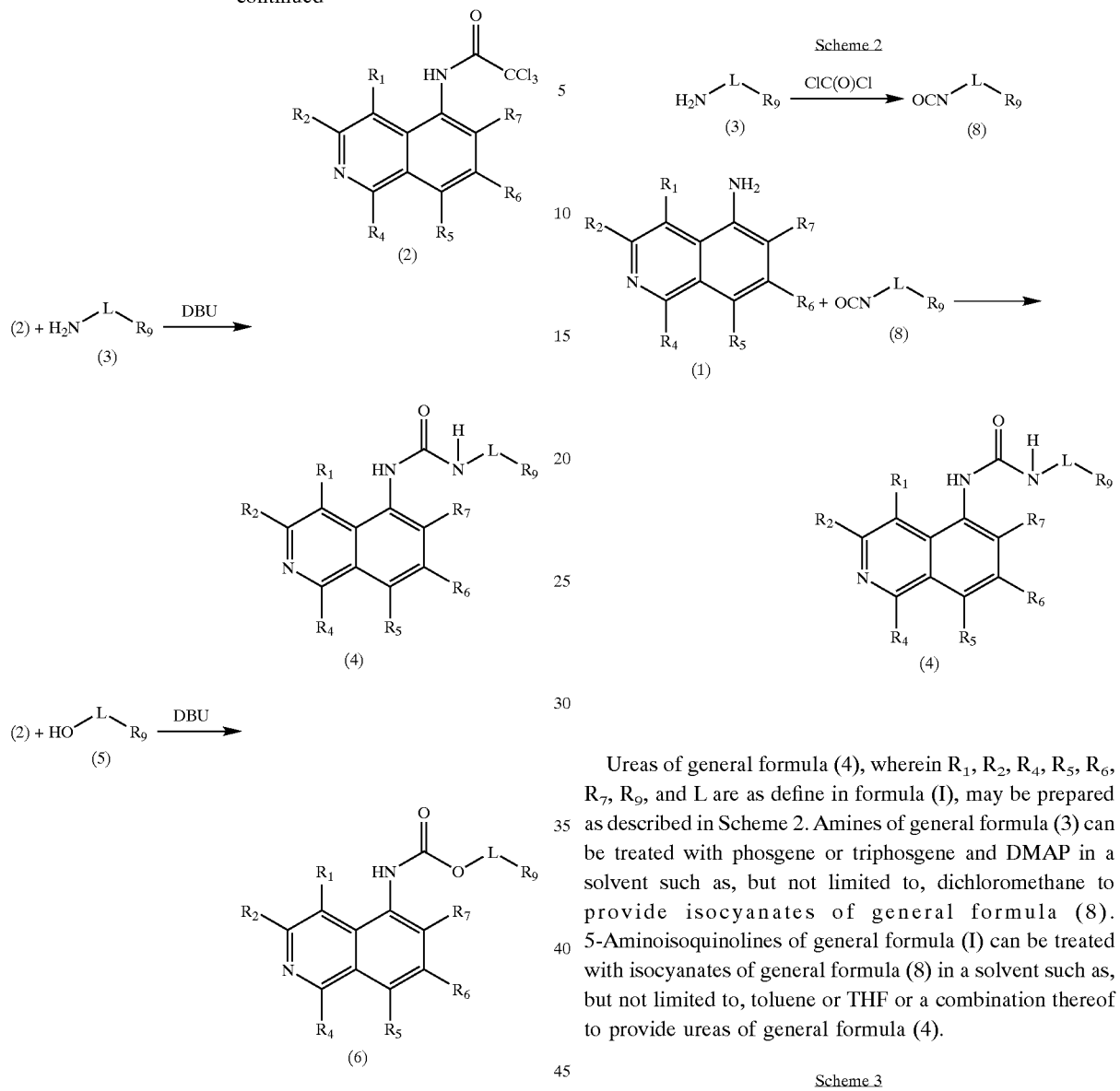

Ureas of general formula (4), wherein $R_1$, $R_2$, $R_4$, $R_5$, $R_6$, $R_7$, $R_9$, and L are as define in formula (I), may be prepared as described in Scheme 1. 5-Aminoisoquinolines of general formula (I), purchased commercially or prepared using standard chemistry known to those in the art, can be treated with trichloroacetyl chloride and a base such as, but not limited to, triethylamine in a solvent such as dichloromethane to provide trichloroacetamides of general formula (2). Trichloroacetamides of general formula (2) can be treated with amines of general formula (3) and a non-nucleophilic base such as, but not limited to, DBU in a solvent such as, but not limited to, acetonitrile to provide ureas of general formula (4).

Carbamates of general formula (6), wherein $R_1$, $R_2$, $R_4$, $R_5$, $R_6$, $R_7$, $R_9$ and L are as defined in formula (I), may also be prepared as described in Scheme 1. Trichloroacetamides of general formula (2) can be treated with alcohols of general formula (5) and a non-nucleophilic base such as, but not limited to, DBU in a solvent such as, but not limited to, acetonitrile to provide carbamates of general formula (6).

Ureas of general formula (4), wherein $R_1$, $R_2$, $R_4$, $R_5$, $R_6$, $R_7$, $R_9$, and L are as define in formula (I), may be prepared as described in Scheme 2. Amines of general formula (3) can be treated with phosgene or triphosgene and DMAP in a solvent such as, but not limited to, dichloromethane to provide isocyanates of general formula (8). 5-Aminoisoquinolines of general formula (I) can be treated with isocyanates of general formula (8) in a solvent such as, but not limited to, toluene or THF or a combination thereof to provide ureas of general formula (4).

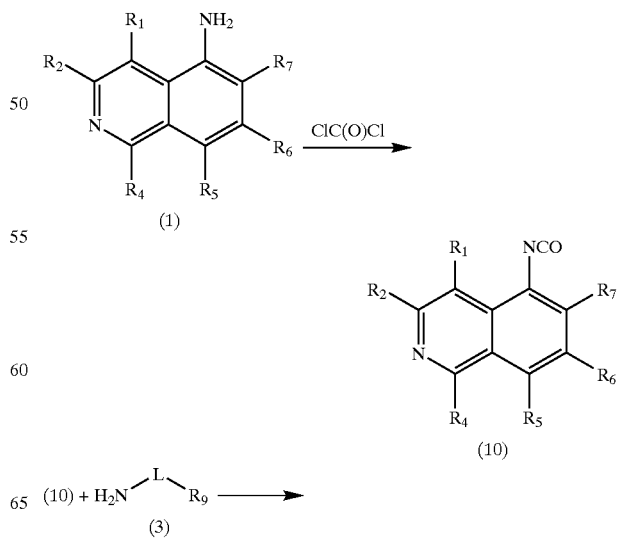

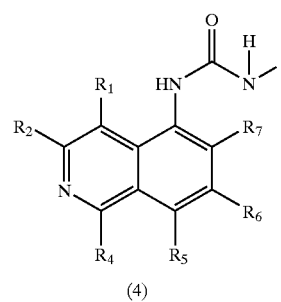

(4)

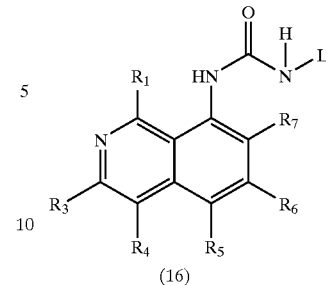

(16)

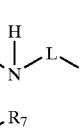

(17)

Ureas of general formula (4), wherein $R_1$, $R_2$, $R_4$, $R_5$, $R_6$, $R_7$, $R_9$, and L are as define in formula (I), may be prepared as described in Scheme 3. 5-Aminoisoquinolines of general formula (I) can be treated with phosgene or triphosgene and DMAP in a solvent such as, but not limited to, dichloromethane to provide isocyanates of general formula (10). Isocyanates of general formula (10) can be treated with amines of general formula (3) in a solvent such as, but not limited to, toluene or THF or a combination thereof to provide ureas of general formula (4).

Ureas of general formula (13), wherein $R_1$, $R_2$, $R_5$, $R_6$, $R_7$, $R_9$, and L are as defined in formula (I), and carbamates of general formula (14), wherein $R_1$, $R_2$, $R_5$, $R_6$, $R_7$, $R_9$ and L are as defined in formula (I), may be prepared as described in Scheme 4. 5-Aminocinnolines of general formula (12), purchased commercially or prepared using standard chemistry known to those in the art, may be processed as described in Schemes 1–3 to provide ureas of general formula (13) and carbamates of general formula (14).

Ureas of general formula (16), wherein $R_1$, $R_3$, $R_4$, $R_5$, $R_6$, $R_7$, $R_9$ and L are as define in formula (I), and carbamates of general formula (17), wherein $R_1$, $R_3$, $R_4$, $R_5$, $R_6$, $R_7$, $R_9$ and L are as defined in formula (I), may be prepared as described in Scheme 4. 8-Aminoisoquinolines of general formula (15), purchased commercially or prepared using standard chemistry known to those in the art, may be processed as described in Schemes 1–3 to provide ureas of general formula (16) and carbamates of general formula (17).

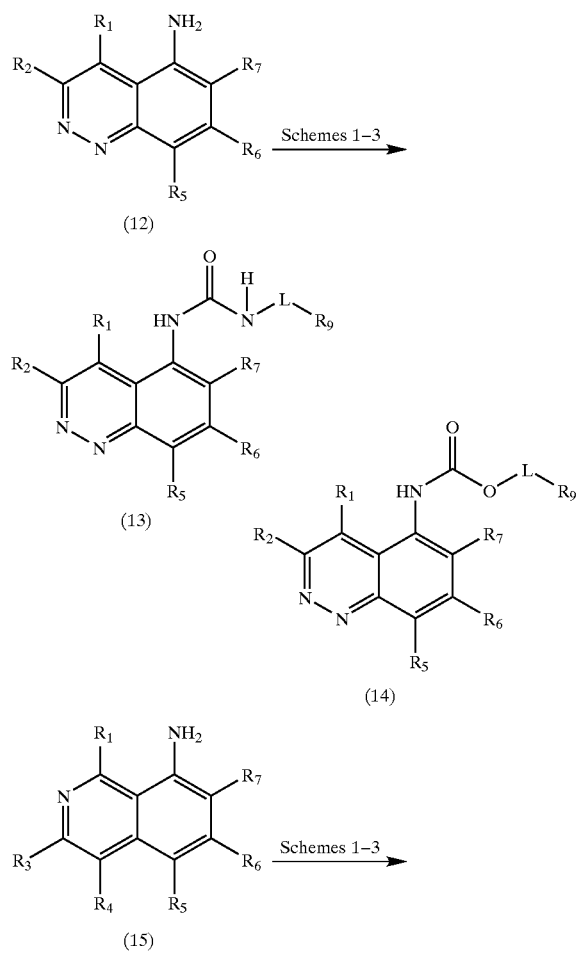

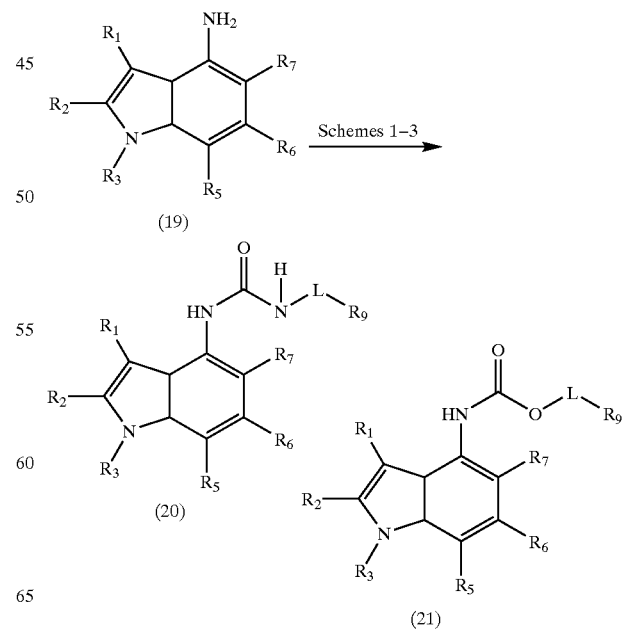

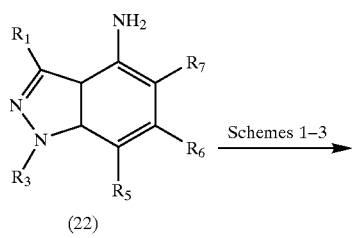

(22)

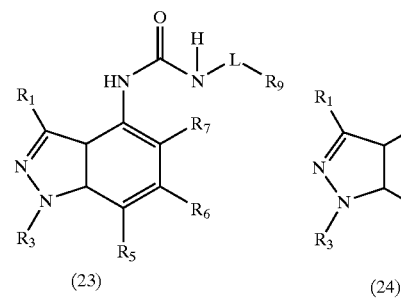

(23)　　　(24)

Ureas of general formula (20), wherein $R_1$, $R_2$, $R_3$, $R_5$, $R_6$, $R_7$, $R_9$, and L are as defined in formula (I), and carbamates of general formula (21), wherein $R_1$, $R_2$, $R_3$, $R_5$, $R_6$, $R_7$, $R_9$, and L are as defined in formula (I), may be prepared as described in Scheme 5. 4-Aminoindoles of general formula (19), purchased commercially or prepared using standard chemistry known to those in the art, may be processed as described in Schemes 1–3 to provide ureas of general formula (20) and carbamates of general formula (21).

Ureas of general formula (23), wherein $R_1$, $R_3$, $R_5$, $R_6$, $R_7$, $R_9$ and L are as defined in formula (I), and carbamates of general formula (24), wherein $R_1$, $R_3$, $R_5$, $R_6$, $R_7$, $R_9$, and L are as defined in formula (I), may be prepared as described in Scheme 5. 4-Aminoindazoles of general formula (22), purchased commercially or prepared using standard chemistry known to those in the art, may be processed as described in Schemes 1–3 to provide ureas of general formula (23) and carbamates of general formula (24).

Scheme 6

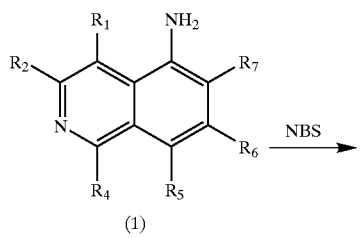

(1)

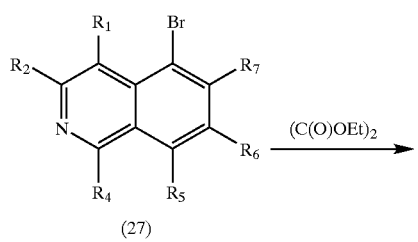

(27)

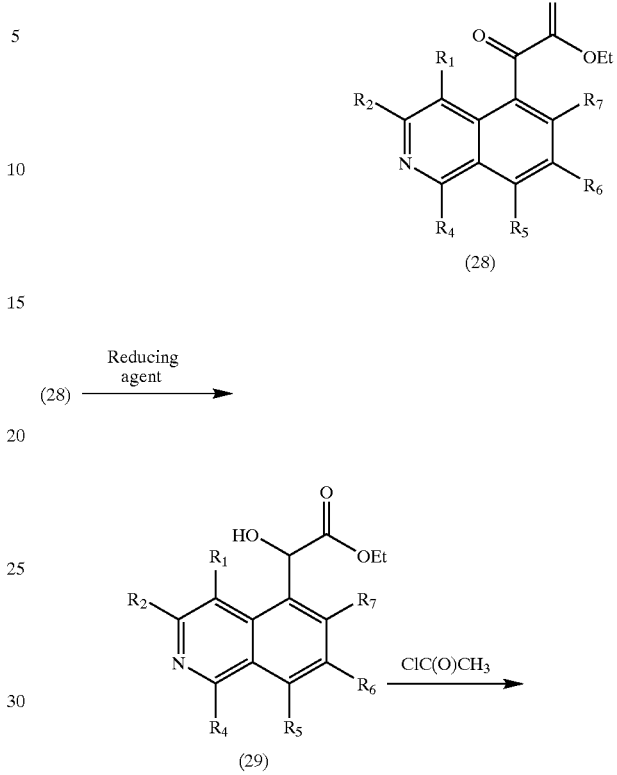

(28)

(29)

(30)

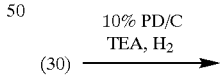

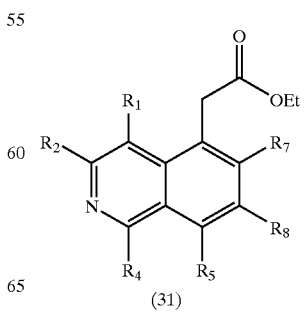

(31)

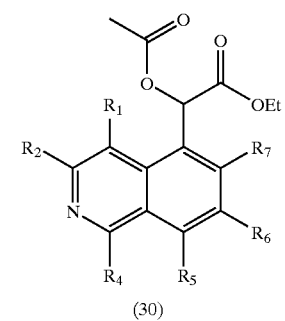

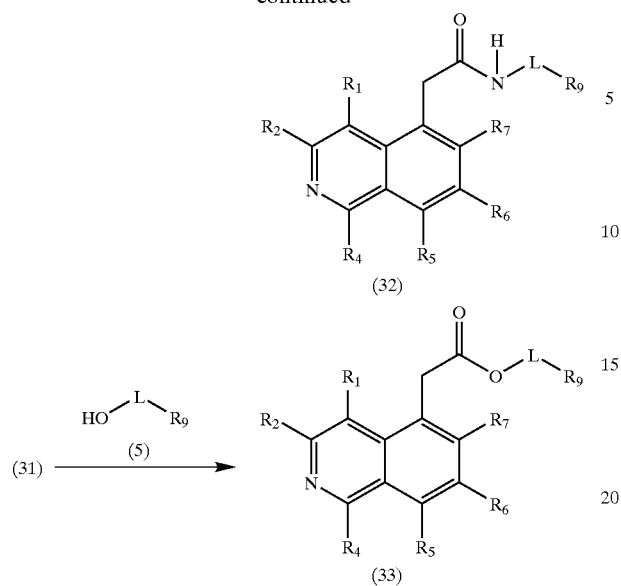

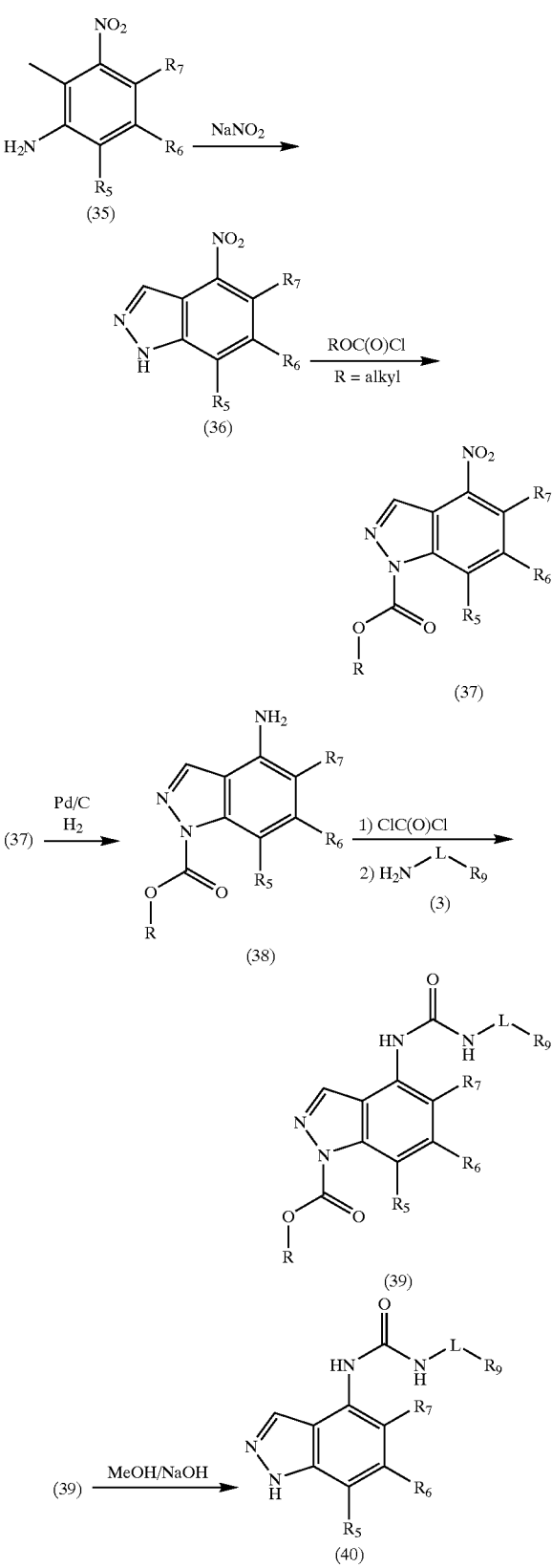

Amides of general formula (32), wherein $R_1$, $R_2$, $R_4$, $R_5$, $R_6$, $R_7$, $R_9$, and L are as defined in formula (I), can be prepared as described in Scheme 6. Amines of general formula (1) can be treated with an acid such as, but not limited to, concentrated sulfuric acid and N-bromosuccinimide to provide bromides of general formula (27). Bromides of general formula (27) can be treated with an organolithium reagent such as, but not limited to, n-butyllithium and diethyl oxalate in a solvent such as, but not limited to, THF to provide keto esters of general formula (28). Keto esters of general formula (28) can be treated with a reducing agent such as, but not limited to, 10% Pd/C under a hydrogen atmosphere (50 psi) in a solvent such as, but not limited to, ethanol to provide hydroxy esters of general formula (29). Hydroxy esters of general formula (29) can be treated with an acid chloride such as, but not limited to, acetyl chloride in a solvent such as, but not limited to, pyridine to provide diesters of general formula (30). Diesters of general formula (30) can be treated with 10% Pd/C and a base such as, but not limited to, triethylamine under a hydrogen atmosphere (60 psi) in a solvent such as, but not limited to, ethanol to provide esters of general formula (31). Esters of general formula (31) can be treated with amines of general formula (3) to provide amides of general formula (32). Alternatively, esters of general formula (31) can be treated with aqueous base such as, but not limited to, aqueous sodium hydroxide or aqueous potassium hydroxide to provide the acids which can then be converted into amides of general formula (32) by treatment with amines of general formula (3) under standard DCC or EDCI coupling procedures that are well known in the art.

Esters of general formula (33), wherein $R_1$, $R_2$, $R_4$, $R_5$, $R_6$, $R_7$, $R_9$ and L are as defin in formula (I), can be prepared as described in Scheme 6. Esters of general formula (31) can be treated with alcohols of general formula (5) under standard transesterification conditions well known to those of skill in the art to provide esters of general formula (33).

Indazoles of general formula (39) and indazoles of general formula (40), wherein L, $R_5$, $R_6$, $R_7$, and $R_9$ are as defined in formula (I) and R is alkyl as defined herein, can be prepared as described in Scheme 7. Nitro anilines of general formula (35) can be treated with sodium nitrite and an acid including, but not limited to, acetic acid in water to provide indazoles of general formula (36). Indazoles of general formula (36) can be treated with chloroformates to provide indazoles of general formula (37). Indazoles of general formula (37) can be treated with a transition metal catalyst including, but not limited to, palladium on carbon under a hydrogen atmosphere (about 1 atm to about 60 atm) to provide indazoles of general formula (38). Indazoles of general formula (38) can be processed as described in Scheme 1–3 to provide indazoles of general formula (39). Indazoles of general formula (39) can be treated with a base including, but not limited to, sodium hydroxide or potassium hydroxide to provide indazoles of general formula (40).

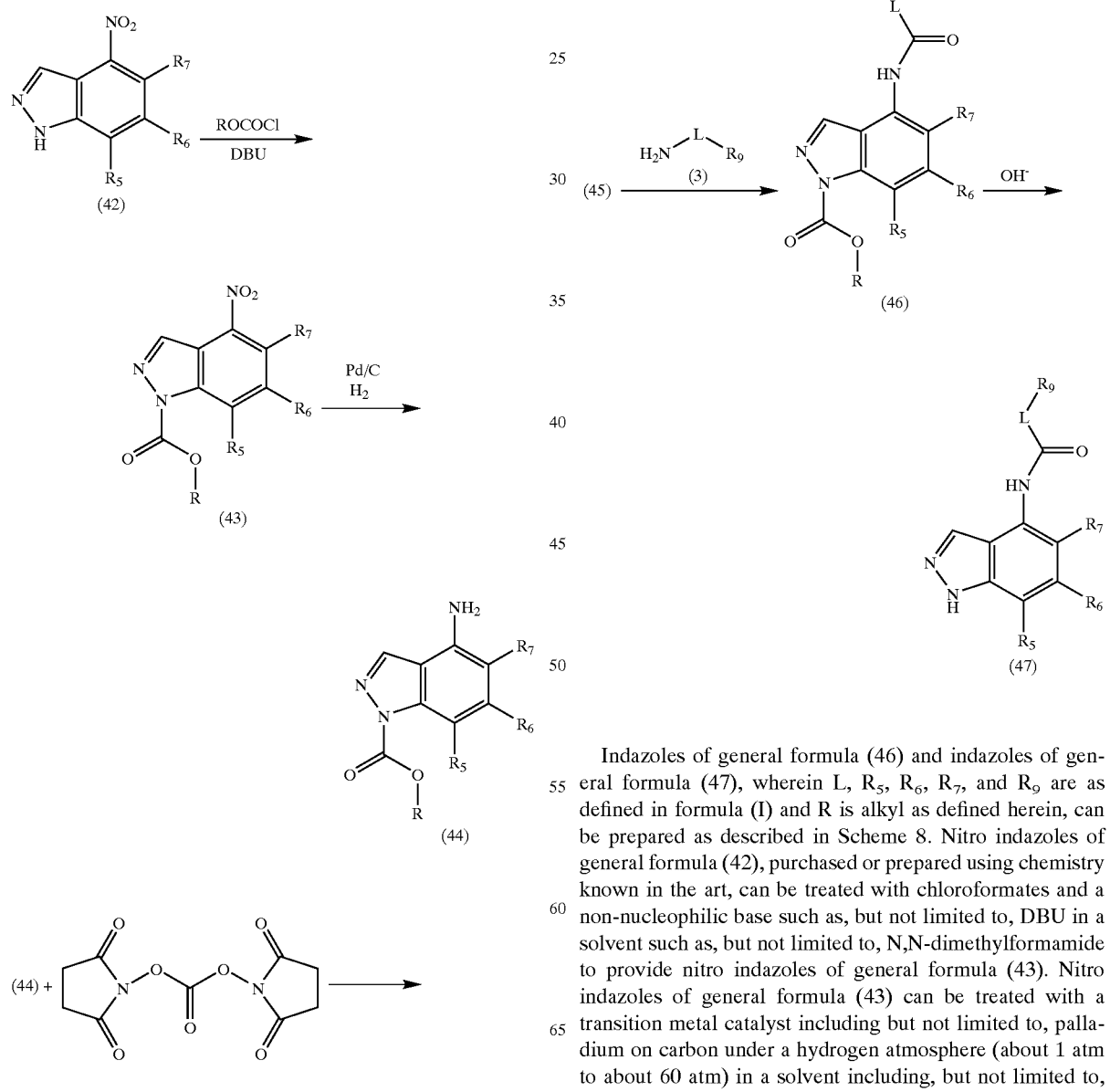

Indazoles of general formula (46) and indazoles of general formula (47), wherein L, $R_5$, $R_6$, $R_7$, and $R_9$ are as defined in formula (I) and R is alkyl as defined herein, can be prepared as described in Scheme 8. Nitro indazoles of general formula (42), purchased or prepared using chemistry known in the art, can be treated with chloroformates and a non-nucleophilic base such as, but not limited to, DBU in a solvent such as, but not limited to, N,N-dimethylformamide to provide nitro indazoles of general formula (43). Nitro indazoles of general formula (43) can be treated with a transition metal catalyst including but not limited to, palladium on carbon under a hydrogen atmosphere (about 1 atm to about 60 atm) in a solvent including, but not limited to, methanol, ethanol, or ethyl acetate to provide amino indazoles of general formula (44). Amino indazoles of general formula (44) can be treated with N,N'-disuccinimidyl carbonate in a solvent including, but not limited to, acetonitrile to provide indazoles of general formula (45). Indazoles of general formula (45) can be treated with an amine of general formula (3) and a base including, but not limited to, diisopropylethylamine or triethylamine in a solvent including, but not limited to, N,N-dimethylformamide to provide indazoles of general formula (46). Indazoles of general formula (46) can be treated with a hydroxide anion source including, but not limited to, sodium hydroxide or potassium hydroxide in a solvent including, but not limited to, acetonitrile, methanol, ethanol, aqueous acetonitrile, aqueous methanol, or aqueous ethanol to provide indazoles of general formula (47).

Amino indazoles of general formula (44) can be processed with phosgene as described in Scheme 2 or Scheme 3 to provide indazoles of general formula (46). Indazoles of general formula (46) can then be treated with hydroxide anion to provide indazoles of general formula (47).

The following Examples are intended as an illustration of and not a limitation upon the scope of the invention as defined in the appended claims.

EXAMPLE 1

N-[2-(3-fluorophenyl)ethyl]-N'-isoquinolin-5-ylurea

EXAMPLE 1A 2,2,2-trichloro-N-isoquinolin-5-ylacetamide

A solution of 5-aminoisoquinoline (1.0 g, 6.9 mmol) in dichloromethane (40 mL) and $Et_3N$ (1 mL) at 5° C. was treated with trichloroacetyl chloride (1.38 g, 7.6 mmol) dropwise. The reaction mixture was stirred at ambient temperature for 14 hours, concentrated, diluted with ethyl acetate and washed with 1N HCl. The aqueous layer was treated with aqueous $NaHCO_3$ and extracted with ethyl acetate. The organic layer the was washed with water and concentrated. The solid residue was suspended in ethyl acetate (5 mL) and filtered to obtain 1.3 g (65%) of the title compound as a tan solid. $^1H$ NMR (300 MHz, $d_6$-DMSO) δ 11.20 (broad s, 1H), 9.41, (s, 1H), 8.60 (d, 1H), 8.18 (m, 1H), 7.77 (m, 2H), 7.66 (d, 1H); MS ($DCI/NH_3$) m/z 289 $(M+H)^+$.

EXAMPLE 1B

N-[2-(3-fluorophenyl)ethyl]-N'-isoquinolin-5-ylurea

The product from Example 1A (0.65 g, 2.25 mmol), DBU (0.85 g, 5.6 mmol) and 2-(3-fluorophenyl)ethylamine (0.35 g, 2.5 mmol) in acetonitrile (50 mL) were refluxed for 10 hours. The mixture was cooled, concentrated, diluted with ethyl acetate, washed twice with aqueous ammonium chloride and concentrated to dryness. The solid obtained was suspended in ethyl acetate and filtered to obtain 0.45 g (65%) of the title compound as a tan solid. $^1H$ NMR (300 MHz, $d_6$-DMSO) δ 9.27 (s, 1H), 8.63 (s, 1H), 8.51 (d, 1H), 8.26 (d, 1H), 7.89 (d, 1H), 7.71 (d, 1H), 7.59 (m, 1H), 7.35 (m, 1H), 7.18–7.0 (m, 3H), 6.60 (t, 1H), 3.42 (m, 2H), 2.72 (m, 2H); MS ($DCI/NH_3$) m/z 310 $(M+H)^+$; Anal. Calcd. For $C_{18}H_{16}N_3FO.0.1H_2O$: C, 69.48; H, 5.25; N, 13.51. Found: C, 69.31; H, 5.25; N, 13.46.

EXAMPLE 2

N-[2-(3-bromophenyl)ethyl]-N'-isoquinolin-5-ylurea

The title compound was prepared using 2-(3-bromophenyl)ethylamine, DBU, the product from Example 1A and the procedure described in Example 1B. $^1H$ NMR (300 MHz, $d_6$-DMSO) δ 9.26 (s, 1H), 8.63 (s, 1H), 8.51 (d, 1H), 8.23 (d, 1H), 7.90 (d, 1H), 7.71 (d, 1H), 7.59 (m, 1H), 7.40 (m, 2H), 7.29 (m, 2H), 6.60 (t, 1H), 3.42 (m, 2H), 2.80 (m, 2H); MS ($DCI/NH_3$) m/z 370 $(M+H)^+$; Anal. Calcd. For $C_{18}H_{16}N_3BrO$: C, 58.39; H, 4.36; N, 11.35. Found: C, 58.17; H, 4.46; N, 11.28.

EXAMPLE 3

N-isoquinolin-5-yl-N'-[4-(trifluoromethyl)benzyl] urea

The title compound was prepared using 4-(trifluoromethyl)benzylamine, DBU, the product from Example 1A and the procedure described in Example 1B. $^1H$ NMR (300 MHz, $d_6$-DMSO) 9.26 (s, 1H), 8.82 (s, 1H), 8.52 (d, 1H), 8.26 (d, 1H), 7.94 (d, 1H), 7.71 (m, 3H), 7.58 (m, 3H), 7.20 (t, 1H), 4.48 (d, 2H); MS ($DCI/NH_3$) m/z 346 $(M+H)^+$; Anal. Calcd. For $C_{18}H_{14}N_3F_3O.0.05H_2O$: C, 62.63; H, 4.19; N, 12.04. Found: C, 62.41; H, 4.58; N, 11.44.

EXAMPLE 4

N-isoquinolin-5-yl-N'-(4-phenoxybenzyl)urea

The title compound was prepared using 4-phenoxybenzylamine, DBU, the product from Example 1A and the procedure described in Example 1B. $^1H$ NMR (300 MHz, $d_6$-DMSO) δ 9.30 (s, 1H), 8.75 (s, 1H), 8.58 (d, 1H), 8.31 (d, 1H), 7.92 (d, 1H), 7.75 (d, 1H), 7.60 (t, 1H), 7.40 (m, 4H), 7.18–6.95 (m, 6H), 4.38 (d, 2H); MS ($DCI/NH_3$) m/z 369 $(M+H)^+$.

EXAMPLE 5

N-[3-fluoro-5-(trifluoromethyl)benzyl]-N'-isoquinolin-5-ylurea

The title compound was prepared using 3-fluoro-5-(trifluoromethyl)benzylamine, DBU, the product from Example 1A and the procedure described in Example 1B. $^1H$ NMR (300 MHz, $d_6$-DMSO) δ 9.28 (s, 1H), 8.88 (s, 1H), 8.53 (d, 1H), 8.22 (d, 1H), 7.90 (d, 1H), 7.77 (d, 1H), 7.55 (m, 4H), 7.20 (t, 1H), 4.45 (d, 2H); MS ($DCI/NH_3$) m/z 364 $(M+H)^+$.

EXAMPLE 6

N-(2,5-dichlorobenzyl)-N'-isoquinolin-5-ylurea

The title compound was prepared using 2,5-dichlorobenzylamine, DBU, the product from Example 1A and the procedure described in Example 1B. $^1H$ NMR (300 MHz, $d_6$-DMSO) δ 9.30 (s, 1H), 8.90 (broad s, 1H), 8.55 (d, 1H), 8.36 (d, 1H), 7.97 (d, 1H), 7.76 (d, 1H), 7.61–7.13 (m, 5H), 4.43 (d, 2H); MS ($DCI/NH_3$) m/z 345 $(M+H)^+$; Anal. Calcd. For $C_{17}H_{13}N_3Cl_2O.0.2H_2O$: C, 58.07; H, 3.90; N, 11.95. Found: C, 57.76; H, 3.84; N, 11.64.

EXAMPLE 7

N-(1,3-benzodioxol-5-ylmethyl)-N'-isoquinolin-5-ylurea

The title compound was prepared using 1,3-benzodioxol-5-ylmethylamine, DBU, the product from Example 1A and the procedure described in Example 1B. $^1H$ NMR (300 MHz, $d_6$-DMSO) δ 9.27 (s, 1H), 8.85 (broad s, 1H), 8.50 (d, 1H), 8.30 (d, 1H), 8.00 (d, 1H), 7.73 (d, 1H), 7.60 (t, 1H), 7.15 (m, 2H), 6.89 (m, 2H), 6.00 (s, 2H), 4.28 (d, 2H); MS (DCI/NH$_3$) m/z 322 (M+H)$^+$; Anal. Calcd. For C$_{17}$H$_{13}$N$_3$O.0.5H$_2$O.0.8NH$_4$Cl: C, 57.94; H, 5.19; N, 14.26. Found: C, 57.63; H, 5.14; N, 14.41.

EXAMPLE 8

N-[2-(4-fluorophenyl)ethyl]-N'-isoquinolin-5-ylurea

The title compound was prepared using 2-(4-fluorophenyl)ethylamine, DBU, the product from Example 1A and the procedure described in Example 1B. $^1$H NMR (300 MHz, d$_6$-DMSO) δ 9.25 (s, 1H), 8.70 (broad s, 1H), 8.50 (d, 1H), 8.27 (d, 1H), 7.93 (d, 1H), 7.71 (d, 1H), 7.60 (t, 1H), 7.30 (m, 2H), 7.13 (m, 2H), 6.70 (t, 1H), 3.40 (m, 2H), 2.80 (m, 2H); MS (DCI/NH$_3$) m/z 310 (M+H)$^+$; Anal. Calcd. For C$_{17}$H$_{13}$N$_3$FO.0.1H$_2$O.0.2NH$_4$Cl: C, 67.18; H, 5.32; N, 13.93. Found: C, 66.86; H, 5.41; N, 13.75.

EXAMPLE 9

N-(3-bromobenzyl)-N'-isoquinolin-5-ylurea

The title compound was prepared using 3-bromobenzylamine, DBU, the product from Example 1A and the procedure described in Example 1B. $^1$H NMR (300 MHz, d$_6$-DMSO) δ 9.29 (s, 1H), 8.80 (broad s, 1H), 8.53 (d, 1H), 8.25 (d, 1H), 7.93 (d, 1H), 7.77 (d, 1H), 7.58 (m, 2H), 7.48 (m, 1H), 7.30 (m, 2H), 7.10 (t, 1H), 4.39 (d, 2H); MS (DCI/NH$_3$) m/z 356 (M+H)$^+$; Anal. Calcd. For C$_{17}$H$_{14}$N$_3$BrO: C, 57.32; H, 3.96; N, 11.80. Found: C, 57.06; H, 3.90; N, 11.45.

EXAMPLE 10

N-[2-(3,4-dimethylphenyl)ethyl]-N'-isoquinolin-5-ylurea

The title compound was prepared using 2-(3,4-dimethylphenyl)ethylamine, DBU, the product from Example 1A and the procedure described in Example 1B. $^1$H NMR (300 MHz, d$_6$-DMSO) δ 9.25 (s, 1H), 8.68 (broad s, 1H), 8.50 (d, 1H), 8.28 (d, 1H), 7.90 (d, 1H), 7.70 (d, 1H), 7.57 (t, 1H), 7.00 (m, 3H), 6.60 (t, 1H), 3.40 (m, 2H), 2.71 (m, 2H), 2.19 (s, 3H), 2.16 (s, 3H); MS (DCI/NH$_3$) m/z 320 (M+H)$^+$; Anal. Calcd. For C$_{20}$H$_{21}$N$_3$O.0.3H$_2$O: C, 73.96; H, 6.70; N, 12.94. Found: C, 73.80; H, 6.32; N, 12.98.

EXAMPLE 11

N-[1-(4-bromophenyl)ethyl]-N'-isoquinolin-5-ylurea

5-Aminoisoquinoline (0.64 g, 4.42 mmol) in dichloromethane (20 mL) was treated with 1-bromo-4-(1-isocyanatoethyl)benzene (1.0 g, 4.42 mmol) in toluene (10 mL). The mixture was stirred 14 hours at ambient temperature and filtered to obtain 1.2 g (74%) of the product as light grey solid. $^1$H NMR (300 MHz, d$_6$-DMSO) δ 9.28 (s, 1H), 8.68 (broad s, 1H), 8.56 (d, 1H), 8.28 (d, 1H), 7.90 (d, 1H), 7.72 (d, 1H), 7.59 (m, 2H), 7.35 (m, 2H), 7.10 (d, 1H), 4.85 (m, 1H), 1.40 (d, 3H); MS (DCI/NH$_3$) m/z 370 (M+H)$^+$; Anal. Calcd. For C$_{18}$H$_{16}$N$_3$BrO.0.1H$_2$O: C, 58.11; H, 4.39; N, 11.29. Found: C, 57.79; H, 4.21; N, 11.16.

EXAMPLE 12

4-(trifluoromethyl)benzyl isoquinolin-5-ylcarbamate

The title compound was prepared using [4-(trifluoromethyl)phenyl]methanol, DBU, the product from Example 1A and the procedure described in Example 1B. $^1$H NMR (300 MHz, d$_6$-DMSO) δ 9.90 (broad s, 1H), 9.30 (s, 1H), 8.52 (d, 1H), 7.94 (m, 3H), 7.80 (d, 2H), 7.70 (m, 3H), 5.30 (s, 2H); MS (DCI/NH$_3$) m/z 347 (M+H)$^+$; Anal. Calcd. For C$_{18}$H$_{13}$N$_2$O$_2$F$_3$: C, 62.43; H, 3.78; N, 8.09. Found: C, 62.23; H, 3.83; N, 7.99.

EXAMPLE 13

2-(3-bromophenyl)ethyl isoquinolin-5-ylcarbamate

The title compound was prepared using 2-(3-bromophenyl)ethanol, DBU, the product from Example 1A and the procedure described in Example 1B. $^1$H NMR (300 MHz, d$_6$-DMSO) δ 9.70 (broad s, 1H), 9.30 (s, 1H), 8.50 (d, 1H), 7.88 (m, 3H), 7.64 (t, 1H), 7.56 (s, 1H), 7.45 (m, 1H), 7.30 (m, 2H), 4.34 (t, 2H), 3.00 (t, 2H); MS (DCI/NH$_3$) m/z 371 (M+H)$^+$; Anal. Calcd. For C$_{18}$H$_{15}$N$_2$O$_2$Br: C, 58.24; H, 4.07; N, 7.55. Found: C, 58.35; H, 4.07; N, 7.51.

EXAMPLE 14

1-naphthylmethyl isoquinolin-5-ylcarbamate

The title compound was prepared using 1-naphthylmethanol, DBU, the product from Example 1A and the procedure described in Example 1B. $^1$H NMR (DMSO-d$_6$) δ 9.85 (s, 1H), 9.31 (s, 1H), 8.48 (d, 1H), 8.15 (d, 1H), 8.04–7.91 (m, 5H), 7.72–7.52 (m, 5H), 5.69 (s, 2H); MS (ESI+) m/z 328 (M+H)$^+$; Anal. Calcd. For C$_{21}$H$_{16}$N$_2$O$_2$: C, 76.81; H, 4.91; N, 8.53; Found: C, 76.64; H, 4.73; N, 8.29.

EXAMPLE 15

N-isoquinolin-5-yl-N'-[4-(trifluoromethoxy)benzyl]urea

The title compound was prepared using 4-(trifluoromethoxy)benzylamine, DBU, the product from Example 1A and the procedure described in Example 1B. MS (ESI+) m/z 362 (M+H)$^+$; $^1$H NMR (DMSO-d$_6$) δ 4.41 (d, 2H), 7.14 (t, 1H), 7.35 (d, 2H), 7.48 (d, 2H), 7.60 (t, 1H), 7.75 (d, 1H), 7.95 (d, 1H), 8.28 (d, 1H), 8.53 (d, 1H), 8.79 (s, 1H), 9.27 (s, 1H).

EXAMPLE 16

N-(3,4-dichlorobenzyl)-N'-(3-methylcinnolin-5-yl)urea

EXAMPLE 16A 2,2,2-trichloro-N-(3-methylcinnolin-5-yl)acetamide

The title compound was prepared using 3-methylcinnolin-5-amine (commercially available, Maybridge), triethylamine, trichloroacetyl chloride and the procedure described in Example 1A.

EXAMPLE 16B

N-(3,4-dichlorobenzyl)-N'-(3-methylcinnolin-5-yl)urea

The title compound was prepared using 3,4-dichlorobenzylamine, the product from Example 16A, DBU and the procedure described in Example 1B. MS (ESI+) m/z 362 (M+H)$^+$; $^1$H NMR (DMSO-d$_6$) δ 2.88 (s, 3H), 4.36 (d, 2H), 7.10 (t, 1H), 7.34 (dd, 1H), 7.59 (m, 2H), 7.76 (t, 1H), 8.04 (d, 2H), 8.19 (d, 1H), 8.93 (s, 1H).

EXAMPLE 17

N-isoquinolin-5-yl-N'-(4-methylbenzyl)urea

The title compound was prepared using 4-methylbenzylamine, the product from Example 1A, DBU and the procedure described in Example 1B. MS (ESI+) m/z 292 (M+H)$^+$; $^1$H NMR (DMSO-d$_6$) δ 2.29 (s, 3H), 4.33 (d, 2H), 7.00 (t, 1H), 7.17 (d, 2H), 7.24 (d, 2H), 7.60 (t, 1H), 7.73 (d, 1H), 7.93 (d, 1H), 8.30 (d, 1H), 8.53 (d, 1H), 8.70 (s, 1H), 9.26 (s, 1H).

426934 Example 18

N-(4-fluorobenzyl)-N'-isoquinolin-5-ylurea

The title compound was prepared using 4-fluorobenzylamine, the product from Example 1A, DBU and the procedure described in Example 1B. MS (APCI+) m/z 296 (M+H)$^+$; $^1$H NMR (DMSO-d$_6$) δ 4.37 (d, 2H), 7.07 (t, 1H), 7.18 (t, 2H), 7.40 (dd, 2H), 7.60 (t, 1H), 7.74 (d, 1H), 7.94 (d, 1H), 8.28 (d, 1H), 8.54 (d, 1H), 8.74 (s, 1H), 9.27 (s, 1H).

EXAMPLE 19

N-isoquinolin-5-yl-N'-[(trans)-2-phenylcyclopropyl]urea

The title compound was prepared using trans 2-phenylcyclopropylamine hydrochloride, the product from Example 1A, DBU and the procedure described in Example 1B. MS (ESI+) m/z 304 (M+H)$^+$; $^1$H NMR (DMSO-d$_6$) δ 1.21 (m, 2H), 2.05 (m, 1H), 2.82 (m, 1H), 7.00 (d, 1H), 7.17 (t, 3H), 7.27 (t, 2H), 7.60 (t, 1H), 7.74 (d, 1H), 7.88 (d, 1H), 8.26 (d, 1H), 8.53 (d, 1H), 8.57 (s, 1H), 9.27 (s, 1H).

EXAMPLE 20

N-[2-(3,4-dichlorophenyl)ethyl]-N'-isoquinolin-5-ylurea

The title compound was prepared using 2-(3,4-dichlorophenyl)ethylamine, the product from Example 1A, DBU and the procedure described in Example 1B. MS (ESI+) m/z 361 (M+H)$^+$; $^1$H NMR (DMSO-d$_6$) δ 2.82 (t, 2H), 3.43 (q, 2H), 6.63 (t, 1H), 7.29 (dd, 1H), 7.59 (m, 3H), 7.73 (d, 1H), 7.88 (d, 1H), 8.23 (d, 1H), 8.52 (d, 1H), 8.65 (s, 1H), 9.26 (s, 1H).

EXAMPLE 21

N-[2-(3,5-dimethoxyphenyl)ethyl]-N'-isoquinolin-5-ylurea

The title compound was prepared using 2-(3,5-dimethoxyphenyl)ethylamine, the product from Example 1A, DBU and the procedure described in Example 1B. MS (ESI+) m/z 352 (M+H)$^+$; $^1$H NMR (DMSO-d$_6$) δ 2.74 (t, 2H), 3.42 (q, 2H), 3.73 (s, 6H), 6.36 (t, 1H), 6.44 (d, 2H), 6.59 (t, 1H), 7.59 (t, 1H), 7.72 (d, 1H), 7.91 (d, 1H), 8.27 (d, 1H), 8.52 (d, 1H), 8.67 (s, 1H), 9.26 (s, 1H).

EXAMPLE 22

N-(4-chlorobenzyl)-N'-isoquinolin-5-ylurea

The title compound was prepared using 4-chlorobenzylamine, the product from Example 1A, DBU and the procedure described in Example 1B. MS (ESI+) m/z 313 (M+H)$^+$; $^1$H NMR (DMSO-d$_6$) δ 4.37 (d, 2H), 7.14 (t, 1H), 7.40 (q, 4H), 7.60 (t, 1H), 7.74 (d, 1H), 7.95 (d, 1H), 8.28 (dd, 1H), 8.53 (d, 1H), 8.80 (s, 1H), 9.27 (s, 1H).

EXAMPLE 23

N-isoquinolin-5-yl-N'-{2-[3-(trifluoromethyl)phenyl]ethyl}urea

The title compound was prepared using 2-[3-(trifluoromethyl)phenyl]ethylamine, the product from Example 1A, DBU and the procedure described in Example 1B. MS (ESI+) m/z 360 (M+H)$^+$; $^1$H NMR (DMSO-d$_6$) δ 2.91 (t, 2H), 3.46 (q, 2H), 6.62 (t, 1H), 7.59 (m, 4H), 7.64 (s, 1H), 7.73 (d, 1H), 7.87 (d, 1H), 8.23 (d, 1H), 8.51 (d, 1H), 8.64 (s, 1H), 9.26 (s, 1H).

EXAMPLE 24

N-[2-(2,6-dichlorophenyl)ethyl]-N'-isoquinolin-5-ylurea

The title compound was prepared using 2-(2,6-dichlorophenyl)ethylamine, the product from Example 1A, DBU and the procedure described in Example 1B. MS (ESI+) m/z 361 (M+H)$^+$; $^1$H NMR (DMSO-d$_6$) δ 3.12 (t, 2H), 3.40 (q, 2H), 6.72 (t, 1H), 7.28 (t, 1H), 7.46 (d, 2H), 7.58 (t, 1H), 7.72 (d, 1H), 7.87 (d, 1H), 8.19 (d, 1H), 8.51 (d, 1H), 8.60 (s, 1H), 9.25 (s, 1H).

EXAMPLE 25

N-[2-(2,3-dichlorophenyl)ethyl]-N'-isoquinolin-5-ylurea

The title compound was prepared using 2-(2,3-dichlorophenyl)ethylamine, the product from Example 1A, DBU and the procedure described in Example 1B. MS (ESI+) m/z 361 (M+H)$^+$; $^1$H NMR (DMSO-d$_6$) δ 3.01 (t, 2H), 3.46 (q, 2H), 6.67 (t, 1H), 7.34 (t, 1H), 7.38 (dd, 1H), 7.53 (dd, 1H), 7.59 (t, 1H), 7.74 (d, 1H), 7.87 (d, 1H), 8.21 (d, 1H), 8.52 (d, 1H), 8.64 (s, 1H), 9.26 (s, 1H).

EXAMPLE 26

N-isoquinolin-5-yl-N'-[3-(trifluoromethoxy)benzyl]urea

The title compound was prepared using 3-(trifluoromethoxy)benzylamine, the product from Example 1A, DBU and the procedure described in Example 1B. MS (ESI+) m/z 362 (M+H)$^+$; $^1$H NMR (DMSO-d$_6$) δ 4.44 (d, 2H), 7.15 (t, 1H), 7.26 (d, 1H), 7.34 (s, 1H), 7.40 (d, 1H), 7.50 (t, 1H), 7.61 (t, 1H), 7.76 (d, 1H), 7.95 (d, 1H), 8.25 (d, 1H), 8.53 (d, 1H), 8.80 (s, 1H), 9.28 (s, 1H).

EXAMPLE 27

N-[2-(4-ethoxy-3-methoxyphenyl)ethyl]-N'-isoquinolin-5-ylurea

The title compound was prepared using 2-(4-ethoxy-3-methoxyphenyl)ethylamine, the product from Example 1A, DBU and the procedure described in Example 1B. MS (ESI+) m/z 366 (M+H)$^+$; $^1$H NMR (DMSO-d$_6$) δ 1.31 (t, 3H), 2.73 (t, 2H), 3.40 (q, 2H), 3.76 (s, 3H), 3.97 (q, 2H), 6.62 (t, 1H), 6.76 (dd, 1H), 6.87 (d, 2H), 7.59 (t, 1H), 7.72 (d, 1H), 7.93 (d, 1H), 8.28 (d, 1H), 8.52 (d, 1H), 8.69 (s, 1H), 9.26 (s, 1H).

EXAMPLE 28

N-[2-(2,4-dichlorophenyl)ethyl]-N'-isoquinolin-5-ylurea

The title compound was prepared using 2-(2,4-dichlorophenyl)ethylamine, the product from Example 1A, DBU and the procedure described in Example 1B. $^1$H NMR (DMSO-d$_6$) δ 9.26 (s, 1H); 8.62 (s, 1H); 8.53 (d, 1H); 8.22 (dd, 1H); 7.88 (d, 1H); 7.74 (d, 1H); 7.61 (m, 1H); 7.57 (d, 1H); 7.42 (m, 2H); 6.64 (t, 1H); 3.43 (q, 2H); 2.93 (t, 2H).

EXAMPLE 29

N-(3-bromo-4-fluorobenzyl)-N'-isoquinolin-5-ylurea

The title compound was prepared using 3-bromo-4-fluorobenzylamine, the product from Example 1A, DBU and the procedure described in Example 1B. MS (ESI+) m/z 376 (M+H)$^+$; $^1$H NMR (DMSO-d$_6$) δ 9.55 (s, 1H); 9.06 (s, 1H); 8.64 (d, 1H); 8.42 (d, 1H); 8.25 (d, 1H); 7.95 (d, 1H); 7.76 (t, 1H); 7.70 (dd, 1H); 7.38 (m, 2H); 7.15 (m, 2H); 4.35 (d, 2H).

EXAMPLE 30

N-(3,4-dimethylbenzyl)-N'-isoquinolin-5-ylurea

The title compound was prepared using 3,4-dimethylbenzylamine, the product from Example 1A, DBU and the procedure described in Example 1B. MS (ESI+) m/z 307 M+H)$^+$; $^1$H NMR (DMSO-d$_6$) δ 9.55 (s, 1H); 8.98 (s, 1H); 8.62 (d, 1H); 8.46 (d, 1H); 8.25 (d, 1H); 7.94 (d, 1H); 7.78 (t, 1H); 7.08 (m, 3H); 6.95 (m, 2H); 4.30 (d, 2H); 2.20 (s, 3H); 2.18 (s, 3H).

EXAMPLE 31

N-isoquinolin-5-yl-N'-(3-phenylpropyl)urea

The title compound was prepared using 3-phenylpropylamine, the product from Example 1A, DBU and the procedure described in Example 1B. MS (ESI+) m/z 306 (M+H)$^+$; $^1$H NMR (DMSO-d$_6$) δ 9.61 (s, 1H); 9.05 (s, 1H); 8.65 (d, 1H); 8.50 (d, 1H); 8.40 (d, 1H); 7.96 (d, 1H); 7.80 (t, 1H); 7.21 (m, 6H); 6.92 (t, 1H); 3.18 (q, 2H); 2.65 (t, 2H); 1.78 (m, 2H).

EXAMPLE 32

N-(3,5-dichlorobenzyl)-N'-isoquinolin-5-ylurea

The title compound was prepared using 3,5-dichlorobenzylamine, the product from Example 1A, DBU and the procedure described in Example 1B. MS (ESI+) m/z 347 (M+H)$^+$; $^1$H NMR (DMSO-d$_6$) δ 9.60 (s, 1H); 9.18 (s, 1H); 8.65 (d, 1H); 8.44 (d, 1H); 8.35 (d, 1H); 7.96 (d, 1H); 7.80 (t, 1H); 7.43 (dt, 1H); 7.40 (m, 2H); 7.35 (m, 1H); 7.25 (d, 1H); 4.40 (d, 2H).

432465 Example 33

N-(3-chloro-4-methylbenzyl)-N'-isoquinolin-5-ylurea

The title compound was prepared using 3-chloro-4-methylbenzylamine, the product from Example 1A, DBU and the procedure described in Example 1B. MS (ESI+) m/z 326 (M+H)$^+$; $^1$H NMR (DMSO-d$_6$) δ 9.65 (s, 1H); 9.20 (s, 1H); 8.65 (d, 1H); 8.50 (d, 1H); 8.40 (d, 1H); 8.00 (d, 1H); 7.80 (t, 1H); 7.30 (m, 5H); 4.35 (d, 2H); 2.30 (s, 3H).

EXAMPLE 34

N-isoquinolin-5-yl-N'-(2-phenoxyethyl)urea

The title compound was prepared using 2-phenoxyethylamine, the product from Example 1A, DBU and the procedure described in Example 1B. MS (ESI+) m/z 308 (M+H)$^+$; $^1$H NMR (DMSO-d$_6$) δ 9.50 (s, 1H); 8.98 (s, 1H); 8.61 (d, 1H); 8.45 (d, 1H); 8.20 (d, 1H); 7.90 (d, 1H); 7.75 (t, 1H); 7.26 (m, 3H); 6.95 (m, 4H); 4.00 (t, 2H); 3.50 (m, 2H).

EXAMPLE 35

N-(3,4-dichlorobenzyl)-N'-isoquinolin-5-ylurea

The title compound was prepared using 3,4-dichlorobenzylamine, the product from Example 1A, DBU and the procedure described in Example 1B. MS (ESI−) m/z 344 (M−H)$^-$; $^1$H NMR (300 MHz, DMSO-d$_6$) δ 9.27 (s, 1H), 8.82 (bs, 1H), 8.54 (d, 1H), 8.25 (m, 1H), 7.94 (d, 1H), 7.76 (d, 1H), 7.56–7.65 (m, 3H), 7.35 (m, 1H), 7.15 (t, 1H), 4.38 (d, 2H); Anal. Calcd for C$_{17}$H$_{13}$Cl$_2$N$_3$O: C, 58.98; H, 3.78; N, 12.14. Found: C, 59.02; H, 3.70; N, 12.10.

EXAMPLE 36

N-(3-fluorobenzyl)-N'-isoquinolin-5-ylurea

The title compound was prepared using 3-fluorobenzylamine, the product from Example 1A, DBU and the procedure described in Example 1B. MS (ESI−) m/z 294 (M−H)$^-$; $^1$H NMR (300 MHz, DMSO-d$_6$) δ 9.28 (s, 1H), 8.80 (bs, 1H), 8.54 (d, 1H), 8.28 (m, 1H), 7.95 (d, 1H), 7.76 (d, 1H), 7.60 (t, 1H), 7.35–7.45 (m, 1H), 7.05–7.15 (m, 4H), 4.40 (d, 2H); Anal. Calcd for C$_{17}$H$_{14}$FN$_3$O: C, 69.14; H, 4.78; N, 14.23. Found: C, 68.98; H, 4.83; N, 14.27.

EXAMPLE 37

N-(4-tert-butylbenzyl)-N'-isoquinolin-5-ylurea

The title compound was prepared using 4-tert-butylbenzylamine, the product from Example 1A, DBU and the procedure described in Example 1B. MS (ESI+) m/z 334 (M+H)$^+$; $^1$H NMR (300 MHz, DMSO-d$_6$) δ 9.26 (s, 1H), 8.70 (bs, 1H), 8.53 (d, 1H), 8.31 (dd, 1H), 7.92 (d, 1H), 7.73 (d, 1H), 7.60 (t, 1H), 7.38 (m, 2H), 7.28 (m, 2H), 7.01 (t, 1H), 4.32 (d, 2H), 1.27 (s, 9H). Anal. Calcd for C$_{21}$H$_{23}$N$_3$O.0.3H$_2$O: C, 74.44; H, 7.02; N, 12.40. Found: C, 74.19; H, 6.88; N, 12.33.

EXAMPLE 38

N-isoquinolin-5-yl-N'-[2-(3-methylphenyl)ethyl]urea

The title compound was prepared using 2-(3-methylphenyl)ethylamine, the product from Example 1A, DBU and the procedure described in Example 1B. MS (ESI+) m/z 306 (M+H)$^+$; $^1$H NMR (300 MHz, DMSO-d$_6$) δ 9.26 (m, 1H), 8.66 (bs, 1H), 8.52 (d, 1H), 8.28 (dd, 1H), 7.90 (d, 1H), 7.72 (d, 1H), 7.59 (t, 1H), 7.21 (t, 1H), 7.00–7.11 (m, 3H), 6.60 (t, 1H), 3.41 (m, 2H), 2.76 (t, 2H), 2.30 (s, 3H); Anal. Calcd for C$_{19}$H$_{19}$N$_3$O$_{00.1}$H$_2$O: C, 74.29; H, 6.30; N, 13.68. Found: C, 74.06; H, 6.43; N, 13.76.

EXAMPLE 39

N-isoquinolin-5-yl-N'-[2-(4-methylphenyl)ethyl]urea

The title compound was prepared using 2-(3-methylphenyl)ethylamine, the product from Example 1A, DBU and the procedure described in Example 1B. MS (ESI+) m/z 306 (M+H)$^+$; $^1$H NMR (300 MHz, DMSO-d$_6$) δ 9.26 (s, 1H), 8.66 (bs, 1H), 8.52 (d, 1H), 8.28 (m, 1H), 7.90 (d, 1H), 7.72 (d, 1H), 7.59 (t, 1H), 7.10–7.20 (m, 4H), 6.58

(t, 1H), 3.40 (m, 2H), 2.75 (t, 2H), 2.28 (s, 3H); Anal. Calcd for $C_{19}H_{19}N_3O \cdot 0.2H_2O$: C, 73.86; H, 6.33; N, 13.60. Found: C, 73.69; H, 6.53; N, 13.51.

EXAMPLE 40

N-[2-(2,4-dimethylphenyl)ethyl]-N'-isoquinolin-5-ylurea

The title compound was prepared using 2-(2,4-dimethylphenyl)ethylamine, the product from Example 1A, DBU and the procedure described in Example 1B. MS (ESI+) m/z 320 (M+H)$^+$; $^1$H NMR (300 MHz, DMSO-d$_6$) δ 9.26 (s, 1H), 8.66 (bs, 1H), 8.53 (d, 1H), 8.28 (m, 1H), 7.90 (d, 1H), 7.73 (d, 1H), 7.59 (t, 1H), 7.08 (d, 1H), 6.92–7.02 (m, 2H), 6.63 (t, 1H), 3.34 (m, 2H), 2.75 (t, 2H), 2.29 (s, 3H), 2.24 (s, 3H); Anal. Calcd for $C_{20}H_{21}N_3O \cdot 0.45H_2O$: C, 73.35; H, 6.74; N, 12.83. Found: C, 73.70; H, 6.53; N, 12.45.

EXAMPLE 41

N-isoquinolin-5-yl-N'-[2-(2-methylphenyl)ethyl]urea

The title compound was prepared using 2-(2-methylphenyl)ethylamine, the product from Example 1A, DBU and the procedure described in Example 1B. MS (ESI–) m/z 324 (M–H)$^-$; $^1$H NMR (300 MHz, DMSO-d$_6$) δ 9.26 (s, 1H), 8.64 (bs, 1H), 8.53 (d, 1H), 8.25 (m, 1H), 7.89 (d, 1H), 7.73 (d, 1H), 7.59 (t, 1H), 7.46 (dd, 1H), 7.40 (dd, 1H), 7.23–7.36 (m, 2H), 6.67 (t, 1H), 3.44 (m, 2H), 2.94 (t, 2H); Anal. Calcd for $C_{18}H_{16}ClN_3O$: C, 66.36; H, 4.95; N, 12.90. Found: C, 66.19; H, 4.87; N, 12.91.

EXAMPLE 42

N-isoquinolin-5-yl-N'-{4-[(trifluoromethyl)thio]benzyl}urea

The title compound was prepared using 4-[(trifluoromethyl)thio]benzylamine, the product from Example 1A, DBU and the procedure described in Example 1B. MS (ESI–) m/z 376 (M–H)$^-$; $^1$H NMR (300 MHz, DMSO-d$_6$) δ 9.27 (s, 1H), 8.82 (bs, 1H), 8.54 (d, 1H), 8.27 (dd, 1H), 7.95 (d, 1H), 7.68–7.78 (m, 3H), 7.60 (t, 1H), 7.51 (d, 2H), 7.17 (t, 1H), 4.45 (d, 2H); Anal. Calcd for $C_{18}H_{14}F_3N_3OS$: C, 57.29; H, 3.74; N, 11.13. Found: C, 57.00; H, 3.73; N, 11.04.

EXAMPLE 42

N-isoquinolin-5-yl-N'-[3-(trifluoromethyl)benzyl]urea

The title compound was prepared using 3-(trifluoromethyl)benzylamine, the product from Example 1A, DBU and the procedure described in Example 1B. MS (ESI–) m/z 344 (M–H)$^-$; $^1$H NMR (300 MHz, DMSO-d$_6$) δ 9.27 (s, 1H), 8.82 (bs, 1H), 8.53 (d, 1H), 8.25 (dd, 1H), 7.94 (d, 1H), 7.55–7.79 (m, 6H), 7.18 (t, 1H), 4.47 (d, 2H); Anal. Calcd for $C_{18}H_{14}F_3N_3O$: C, 62.61; H, 4.09; N, 12.17. Found: C, 62.39; H, 3.87; N, 12.28.

EXAMPLE 43

N-isoquinolin-5-yl-N'-(4-methoxybenzyl)urea

The title compound was prepared using 4-methoxybenzylamine, the product from Example 1A, DBU and the procedure described in Example 1B. MS (ESI–) m/z 306 (M–H)$^-$; $^1$H NMR (300 MHz, DMSO-d$_6$) δ 9.26 (s, 1H), 8.70 (bs, 1H), 8.53 (d, 1H), 8.31 (dd, 1H), 7.92 (d, 1H), 7.73 (d, 1H), 7.60 (t, 1H), 7.29 (m, 2H), 6.88–7.03 (m, 3H), 4.30 (d, 2H), 3.74 (s, 3H); Anal. Calcd for $C_{18}H_{17}N_3O_2$: C, 70.34; H, 5.58; N, 13.67. Found: C, 70.21; H, 5.47; N, 13.46.

EXAMPLE 44

N-[4-chloro-3-(trifluoromethyl)benzyl]-N'-isoquinolin-5-ylurea

The title compound was prepared using 4-chloro-3-(trifluoromethyl)benzylamine, the product from Example 1A, DBU and the procedure described in Example 1B. MS (ESI–) m/z 378 (M–H)$^-$; $^1$H NMR (300 MHz, DMSO-d$_6$) δ 9.73 (s, 1H), 9.53 (s, 1H), 8.69 (d, 1H), 8.61 (d, 1H), 8.54 (d, 1H), 8.07 (d, 1H), 7.82–7.92 (m, 2H), 7.63–7.75 (m, 3H), 4.47 (d, 2H); Anal. Calcd for $C_{18}H_{13}ClF_3N_3O \cdot 1.2$ HCl: C, 51.05; H, 3.38; N, 9.92. Found: C, 51.26; H, 3.68; N, 9.50.

EXAMPLE 45

N-(3,5-dimethylbenzyl)-N'-isoquinolin-5-ylurea

The title compound was prepared using 3,4-dimethylbenzylamine, the product from Example 1A, DBU and the procedure described in Example 1B. MS (ESI–) m/z 304 (M–H)$^-$; $^1$H NMR (300 MHz, DMSO-d$_6$) δ 9.74 (s, 1H), 9.41 (bs, 1H), 8.69 (d, 1H), 8.62 (d, 2H), 8.05 (d, 1H), 7.88 (t, 1H), 7.44 (t, 1H), 6.96 (bs, 2H), 6.89 (bs, 1H), 4.31 (d, 2H), 2.26 (s, 6H); Anal. Calcd for $C_{19}H_{19}N_3O_{01.1}$ HCl: C, 66.05; H, 5.86; N, 12.16. Found: C, 66.09; H, 5.83; N, 12.14.

EXAMPLE 46

N-(3,5-difluorobenzyl)-N'-isoquinolin-5-ylurea

The title compound was prepared using 3,5-difluorobenzylamine, the product from Example 1A, DBU and the procedure described in Example 1B. MS (ESI+) m/z 312 (M–H)$^-$; $^1$H NMR (300 MHz, DMSO-d$_6$) δ 9.76 (s, 1H), 9.66 (bs, 1H), 8.65–8.79 (m, 2H), 8.60 (d, 1H), 8.08 (d, 1H), 7.89 (t, 1H), 7.77 (t, 1H), 7.02–7.18 (m, 3H), 4.43 (d, 2H); Anal. Calcd for $C_{17}H_{13}F_2N_3O \cdot HCl \cdot 0.3H_2O$: C, 57.49; H, 4.14; N, 11.83. Found: C, 57.76; H, 4.59; N, 11.76.

EXAMPLE 47

N-hexyl-N'-isoquinolin-5-ylurea

The title compound was prepared using hexylamine, the product from Example 1A, DBU and the procedure described in Example 1B. MS (ESI–) m/z 270 (M–H)$^-$; $^1$H NMR (DMSO-d$_6$) δ 9.25 (s, 1H), 8.60 (s, 1H), 8.55 (d, 1H), 8.39 (d, 1H), 7.93 (d, 1H), 7.71 (d, 1H), 7.59 (t, 1H), 6.60 (t, 1H), 3.15 (q, 2H), 1.49 (m, 2H), 1.32 (m, 6H), 0.90 (m, 3H).

EXAMPLE 48

N-(4-bromobenzyl)-N'-isoquinolin-5-ylurea

The title compound was prepared using 4-bromobenzylamine, the product from Example 1A, DBU and the procedure described in Example 1B. MS (ESI–) m/z 355 (M–H)$^-$; $^1$H NMR (DMSO-d$_6$) δ 9.27 (s, 1H), 8.78 (s, 1H), 8.53 (d, 1H), 8.27 (d, 1H), 7.93 (d, 1H), 7.74 (d, 1H), 7.61 (d, 1H), 7.55 (d, 2H), 7.42 (d, 2H) 7.10 (t, 1H); Anal. Calcd for $C_{17}H_{14}BrN_3O$: C, 57.32; H, 3.96; N, 11.80. Found C, 57.05; H, 3.79; N, 11.64.

EXAMPLE 49

N-(3,5-dimethoxybenzyl)-N'-isoquinolin-5-ylurea

The title compound was prepared using 3,5-dimethoxybenzylamine, the product from Example 1A, DBU and the procedure described in Example 1B. MS (ESI−) m/z 336 (M−H)$^−$; $^1$H NMR (DMSO-d$_6$) δ 9.70 (s, 1H), 9.32 (s, 1H), 8.69 (d, 1H), 8.55 (dd, 2H), 8.10 (d, 1H), 7.85 (t, 1H), 7.39 (t, 1H), 6.54 (s, 2H), 6.41 (s, 1H), 4.35 (d, 2H), 3.75 (s, 6H); Anal. Calcd for C$_{19}$H$_{19}$N$_3$O$_3$ 1.25 HCl C, 59.59; H, 5.33; N, 10.97. Found C, 59.22; H, 5.41; N, 10.84.

EXAMPLE 50

N-isoquinolin-5-yl-N'-(3,4,5-trimethoxybenzyl)urea

The title compound was prepared using 3,4,5-trimethoxybenzylamine, the product from Example 1A, DBU and the procedure described in Example 1B. MS (ESI−) m/z 366 (M−H)$^−$; $^1$H NMR (DMSO-d$_6$) δ 9.79 (s, 1H), 9.50 (s, 1H), 8.69 (d, 1H), 8.80 (d, 1H), 8.65 (dd, 2H), 8.08 (d, 1H), 7.90 (d, 1H), 7.68 (m, 1H), 6.71 (s, 2H), 4.53 (d, 2H), 3.79 (s, 6H), 3.53 (s, 3H). Anal. Calcd for C$_{20}$H$_{21}$N$_3$O$_4$ 1.3 HCl: C, 57.91; H, 5.42; N, 10.13. Found C, 57.65; H, 5.60; N, 10.09.

EXAMPLE 51

N-isoquinolin-5-yl-N'-[4-(methylsulfonyl)benzyl]urea

The title compound was prepared using 4-(methylsulfonyl)benzylamine, the product from Example 1A, DBU and the procedure described in Example 1B. MS (ESI−) m/z 354 (M−H)$^−$; $^1$H NMR (DMSO-d$_6$) δ 9.65 (s, 1H), 9.30 (s, 1H), 8.65 (d, 1H), 8.49 (d, 1H), 8.42 (d, 1H), 8.00 (d, 1H), 7.91 (d, 2H), 7.82 (t, 1H), 7.61 (d, 2H), 7.47 (t, 1H), 4.50 (d, 2H), 3.20 (s, 3H); Anal. Calcd for C$_{20}$H$_{21}$N$_3$O$_4$ 1.0 HCl: C, 55.17; H, 4.63; N, 10.72. Found C, 54.92; H, 4.54; N, 10.42.

EXAMPLE 52

N-(3,4-dimethoxybenzyl)-N'-isoquinolin-5-ylurea

The title compound was prepared using 3,4-dimethoxybenzylamine, the product from Example 1A, DBU and the procedure described in Example 1B. MS (ESI−) m/z (M−H)-336; $^1$H NMR (DMSO-d$_6$) δ 9.78 (s, 1H), 9.50 (s, 1H), 8.70 (s, 2H), 8.62 (d, 1H), 8.05 (d, 1H), 7.87 (t, 1H), 7.51 (t, 1H), 6.99 (s, 1H), 6.79 (ds, 2H), 4.32 (d, 2H), 3.75 (s, 3H), 3.71 (s. 3H); Anal. Calcd for C$_{19}$H$_{19}$N$_3$O$_3$ 1.0 HCl: C, 61.04; H, 5.39; N, 11.24. Found C, 60.82; H, 5.38; N, 11.19.

EXAMPLE 53

N-isoquinolin-5-yl-N'-(3-phenoxybenzyl)urea

The title compound was prepared using 3,4-dimethoxybenzylamine, the product from Example 1A, DBU and the procedure described in Example 1B. MS (ESI−) m/z 368 (M−H)$^−$; $^1$H NMR (DMSO-d$_6$) δ 9.65 (s, 1H), 9.25 (s, 1H), 8.65 (d, 1H), 8.52 (d, 1H), 8.48 (d, 1H), 8.03 (d, 1H), 7.82 (t, 1H), 7.35 (m, 4H), 7.15 (d, 2H), 7.05 (s, 2H), 7.00 (s, 1H), 6.84 (d, 1H), 2.37 (d, 2H); Anal. Calcd for C$_{23}$H$_{19}$N$_3$O$_2$ 1.25 HCl: C, 66.57; H, 4.92; N, 10.13. Found C, 66.49; H, 5.02; N, 10.14.

EXAMPLE 54

N-isoquinolin-5-yl-N'-(1-naphthylmethyl)urea

The title compound was prepared using 1-naphthylmethylamine, the product from Example 1A, DBU and the procedure described in Example 1B. MS (ESI+) m/z 328 (M+H)$^+$; HRMS (FAB): Calculated for C$_{21}$H$_{18}$N$_3$O 328.1450; observed 328.1438 (M+H)$^+$; $^1$H NMR (DMSO-d$_6$) δ 9.25 (s, 1H), 8.48, (d, 1H), 8.39 (d, 1H), 8.22 (d, 1H), 8.19 (d, 1H), 7.97 (d, 1H), 7.87 (d, 1H), 7.78–7.71 (m, 2H), 7.63–7.49 (m, 6H), 4.85 (d, 2H).

EXAMPLE 55

N-(2,4-dimethylbenzyl)-N'-isoquinolin-5-ylurea

The title compound was prepared using 2,4-dimethylbenzylamine, the product from Example 1A, DBU and the procedure described in Example 1B. MS (ESI+) m/z 306 (M+H)$^+$; $^1$H NMR (DMSO-d$_6$) δ 9.26 (s, 1H), 8.67 (s, 1H), 8.53 (d, 1H), 8.32 (d, 1H), 7.92 (d, 1H), 7.72 (d, 1H), 7.60 (t, 1H), 7.19 (d, 1H), 7.03–6.95 (m, 2H), 9.90 (t, 1H), 4.31 (d, 2H), 2.30 (s, 3H), 2.26 (s, 3H); Anal. Calcd for C$_{19}$H$_{19}$N$_3$O.0.2H$_2$O: C, 73.86, H, 6.33, N, 13.60. Found: C, 73.75; H, 6.49; N, 13.49.

EXAMPLE 56

N-[4-(dimethylamino)benzyl]-N'-isoquinolin-5-ylurea

The title compound was prepared using 4-(aminomethyl)-N,N-dimethylaniline, the product from Example 1A, DBU and the procedure described in Example 1B. MS (ESI+) m/z 321 (M+H)$^+$; $^1$H NMR (DMSO-d$_6$) δ 9.26 (s, 1H), 8.71 (s, 1H), 8.52 (d, 1H), 8.32 (d, 1H), 7.93 (d, 1H), 7.72 (d, 1H), 7.59 (t, 1H), 7.18 (d, 2H), 6.96 (t, 1H), 6.71 (d, 2H), 4.23 (d, 2H), 2.86 (s, 6H); Anal. Calcd for C$_{19}$H$_{20}$N$_4$O.0.7H$_2$O: C, 68.53, H, 6.48, N, 16.82. Found: C, 68.59, H, 6.48, N, 16.60.

EXAMPLE 57

N-isoquinolin-8-yl-N'-[4-(trifluoromethyl)benzyl]urea

EXAMPLE 57A 5-bromoisoquinoline

Concentrated H$_2$SO$_4$ (260 mL) was cooled to −25° C. while stirring with a mechanical stirrer. Isoquinoline (30 mL, 0.25 mol) was added slowly so the temperature did not exceed 0° C. After the addition was complete the red solution was recooled to −25° C. and treated with N-bromosuccinimide (55.49 g, 0.31 mol) in small portions so that the temperature did not exceed −20° C. The reaction mixture was stirred for 5 hours keeping the temperature between −30° C. and −18° C. The reaction mixture was then allowed to warm to −10° C. and was poured carefully over 600 g of ice. The resulting slurry was adjusted to pH 10 using 25% NH$_4$OH. The mixture was then extracted with diethyl ether (3×600 mL). The ether fractions were combined, filtered through a celite plug and the filtrate concentrated under reduced pressure. The residue was suspended in hot heptane (600 mL). The heptane was decanted. This procedure was repeated with hexane (2×200 mL). The combined heptane and hexane fractions were concentrated under reduced pressure to give a mustard yellow solid. The title compound was obtained by recrystallization from heptane (26.37 g, 50%). mp 78°–80° C.; MS (ESI+) m/z 209 (M+H)$^+$; $^1$H NMR (DMSO, 300 MHz) δ 7.65 (t, J 7.9, 1H), 7.94 (d, J 8.1, 1H), 8.17 (dd, J 1.0, 7.4, 1H), 8.22 (d, J 8.1, 1H), 8.68 (d, J 6.1, 1H), 9.37 (s, 1H); Anal. Calcd for C$_9$H$_6$BrN: C, 51.96; H, 2.91; N, 6.73; Br, 38.41. Found: C, 51.24; H, 2.79; N, 6.52; Br, 38.81.

EXAMPLE 57B 5-bromo-8-nitroisoquinoline

The diethyl ether solution from Example 57A was treated with potassium nitrate (10.1 g, 100 mmol). After stirring for one hour, The mixture was poured onto ice and neutralized with concentrated ammonium hydroxide (~300 ml). The crude product was collected by filtration, dried, and recrystalization from methanol to provide the title compound (8.83 g).

EXAMPLE 57C isoquinolin-8-amine

The product from Example 57B was treated with Pd/C under a hydrogen atmosphere to provide the title compound.

EXAMPLE 57D 2,2,2-trichloro-N-isoquinolin-8-ylacetamide

The product from Example 57C and trichloroacetylchloride were processed as described in Example 1A to provide the title compound.

EXAMPLE 57E

N-isoquinolin-8-yl-N'-[4-(trifluoromethyl)benzyl] urea

The title compound was prepared using 4-(trifluoromethyl)benzylamine, the product from Example 57D, DBU and the procedure described in Example 1B. MS (ESI+) m/z 346 (M+H)$^+$; $^1$H NMR (DMSO-d$_6$) δ 9.58 (s, 1H), 9.10 (s, 1H), 8.49 (d, 1H), 8.12 (d, 1H), 7.81–7.54 (m, 7H), 7.20 (t, 1H), 4.47 (d, 2H); Anal. Calcd for C$_{18}$H$_{14}$F$_3$N$_3$O.0.2H$_2$O: C, 61.96, H, 4.16, N, 12.04. Found: C, 62.06; H, 4.23; N, 11.91.

EXAMPLE 58

N-(4-bromobenzyl)-N'-isoquinolin-8-ylurea

The title compound was prepared using 4-bromobenzylamine, the product from Example 57D, DBU and the procedure described in Example 1B. MS (ESI+) m/z 356 (M+H)$^+$; $^1$H NMR (DMSO-d$_6$) δ 9.52 (s, 1H), 9.15 (s, 1H), 8.49 (d, 1H), 8.11 (d, 1H), 7.77 (d, 1H), 7.67 (t, 1H), 7.55 (m, 3H), 7.32 (d, 2H), 7.25 (t, 1H), 4.34 (d, 2H); Anal. Calcd for C$_{17}$H$_{14}$BrN$_3$O.0.25H$_2$O.0.16 MeOH: C, 56.34; H, 4.17; N, 11.49. Found C, 56.32, H, 4.45, N, 11.70.

EXAMPLE 60

N-(4-bromobenzyl)-N'-(3-chloroisoquinolin-5-yl) urea

EXAMPLE 60A isoquinoline-1,3(2H,4H)-dione 2-(Carboxymethyl)benzoic acid (10 g, 55.6 mmol) was dissolved in concentrated NH$_4$OH (15 mL) and then was evaporated to dryness under reduced pressure. The process was repeated with additional NH$_4$OH (5 mL). The resulting residue was treated with 1,2-dichlorobenzene (20 mL) and heated with stirring at 200° C. without a condenser allowing the solvent to evaporate. The concentrated mixture was allowed to cool to room temperature, diluted with methanol (20 mL), and allowed to stand overnight. The precipitate was collected by filtration, washed with methanol, and dried under reduced pressure to provide the title compound as tan needles (6.6 g, 74%).

EXAMPLE 60B 1,3-dichloroisoquinoline

The product from Example 60A (6.5 g, 40.4 mmol) was treated with phenylphosphonic dichloride (11.5 mL, 81.1 mmol) and heated at 160° C. for 3 hours. The reaction was allowed to cool to room temperature and stand overnight. The resulting waxy orange material was dissolved in tetrahydrofuran (200 mL), treated with water (60 mL), and then concentrated under reduced to remove the tetrahydrofuran. The remaining aqueous material was neutralized with concentrated NH$_4$OH and extracted with ethyl acetate. The ethyl acetate phases were combined, washed with water, brine, dried over Na$_2$SO$_4$ and concentrated under reduced pressure to provide the title compound as yellow flakes (6.92 g, 74%).

EXAMPLE 60C 3-chloroisoquinoline

The product from Example 60B (6.73 g, 33.8 mmol) was suspended in glacial acetic acid (37 mL) and concentrated HCl (13 mL), treated with tin powder (12.1 g, 101.9 mmol), and heated at 55–60° C. for 3 hours with stirring. The mixture was allowed to cool to room temperature and the precipitated tin salts were removed by filtration through Celite. The filtrate was basified to pH 9 with concentrated NH$_4$OH and then extracted with ethyl acetate. The organic extracts were combined, washed with saturated NaHCO$_3$ solution, dried over Na$_2$SO$_4$, and concentrated under reduced pressure to provide the title compound as a gummy yellow residue (1.28 g, 23%).

EXAMPLE 60D 3-chloro-5-nitroisoquinoline

The product from Example 60C (1.28 g, 7.85 mmol) in concentrated H$_2$SO$_4$ (30 mL) at 0° C. was treated with a solution of KNO$_3$ (0.84 g, 8.32 mmol) in concentrated H$_2$SO$_4$ (5 mL) dropwise over 5 minutes. The mixture was stirred at 0° C. for 10 minutes, allowed to warm to room temperature, and stirred overnight. The mixture was poured onto 65 g of ice and the precipitated yellow solid was collected by filtration. The solid was slurried in water, collected by filtration, washed with water, and allowed to air-dry to provide the title compound as a pale yellow solid (0.45 g, 28%).

EXAMPLE 60E 3-chloroisoquinolin-5-amine

The product from Example 60D (0.45 g, 2.16 mmol) was suspended in glacial acetic acid (4 mL) and warmed to 60° C. while adding water (4 mL). The heated mixture was treated with powdered iron (0.33 g, 5.91 mmol) in three portions over about 2 minutes. The reaction mixture stirred at 60° C. for 2 hours, allowed to cool to room temperature and stir overnight. The mixture was basified with 25% aqueous NaOH, diluted with a little water, and the brown precipitate was collected by filtration and dried overnight at 50° C. in a vacuum oven. The filter cake was then broken up and extracted with boiling ethyl acetate. The extracts were combined, dried over Na$_2$SO$_4$, filtered, and the filtrate was concentrated under reduced pressure to provide the title compound as a gold-orange solid (200 mg, 52%).

EXAMPLE 60F

N-(4-bromobenzyl)-N'-(3-chloroisoquinolin-5-yl)urea

The product from Example 60E (250 mg, 1.4 mmol) and 1-bromo-4-(isocyanatomethyl)benzene (0.22 mL, 1.57 mmol) were heated in toluene (5 mL) at 80° C. for 3 hours. The mixture was allowed to cool to room temperature, filtered, the filter cake was washed with toluene, and air-dried to provide the title compound (335 mg, 61%). $^1$H NMR (300 MHz, DMSO-d$_6$) δ 9.18 (s, 1H), 8.81 (s, 1H), 8.32 (dd, J=7.8 Hz, 0.7 Hz, 1H), 8.09 (s, 1H), 7.80 (d, J=8.2 Hz, 1H), 7.53–7.65 (m, 3H), 7.32 (m, 2H), 7.05 (t, J=5.7 Hz, 1H), 4.35 (d, J=5.7 Hz, 2H); MS (ESI$^+$) m/z 391/393 (M+H$^+$, $^{35}$Cl/$^{37}$Cl).

EXAMPLE 61

4-cyanobenzyl isoquinolin-5-ylcarbamate

EXAMPLE 61A 5-isocyanatoisoquinoline

Phosgene (20 ml, 20% in toluene from Fluka) in CH$_2$Cl$_2$ (300 mL) at 0° C. was treated with DMAP (10 g) in CH$_2$Cl$_2$ (100 mL) slowly. After complete addition, the mixture was treated with 5-aminoisoquinoline (5 g) in CH$_2$Cl$_2$ (100 mL) dropwise. The mixture was allowed to warm to room temperature and then stirred overnight. The solvent was removed under reduced pressure. The solid residue was extracted with diethyl ether (400 mL). The diethyl ether was filtered to provide the title compound in diethyl ether as a pale yellow solution. The diethyl ether solution was used in subsequent reactions without further purification.

EXAMPLE 61B 4-cyanobenzyl isoquinolin-5-ylcarbamate

4-Cyanobenzyl alcohol (150 mg, 1.13 mmol) in diethyl ether (10 mL) was treated with the product from Example 61A as an ethereal solution. The mixture was stirred for 2 hours, filtered, and the filter cake was washed with diethyl ether to provide the title compound as an off-white solid (150 mg, 44%). $^1$H NMR (300 MHz, DMSO-d$_6$) δ 9.95 (s, 1H), 9.32 (d, J=1.0 Hz, 1H), 8.52 (d, J=6.1 Hz, 1H), 7.88–7.99 (m, 5H), 7.65–7.70 (m, 3H), 5.31 (s, 2H); MS (ESI$^+$) m/z 304 (M+H)$^+$.

EXAMPLE 62

N-[(4-cyanophenyl)methyl]-N'-isoquinolin-5-ylurea

N,N-bis(tert-butoxycarbonyl)-4-cyanobenzyl amine (0.75 g, 2.25 mmol, prepared according to Synth. Comm. (1998) 28, 4419) in CH$_2$Cl$_2$ (15 mL) was treated with trifluoroacetic acid (8 mL), and the resulting mixture was stirred at room temperature for 3 hours. The mixture was concentrated under reduced pressure and then azeotroped with diethyl ether. The residue was taken up in diethyl ether (10 mL) and treated with N,N-diisopropylethylamine (5 mL) and the product from Example 61A. After stirring for 1 hour, the mixture was filtered and the filter was purified by chromatography (95:5 CH$_2$Cl$_2$—MeOH) to provide the title compound as a white solid (65 mg). The corresponding hydrochloride salt was prepared using methanolic HCl. $^1$H NMR (300 MHz, DMSO-d$_6$) δ 9.75 (s, 1H), 9.62 (s, 1H), 8.69 (s, 2H), 8.58 (dd, J=7.8 Hz, 1.0 Hz, 1H), 8.07 (d, J=7.4 Hz, 1H), 7.90 (d, J=8.1 Hz, 1H), 7.81–7.85 (m, 2H), 7.74 (t, J=6.1 Hz, 1H), 7.54–7.57 (m, 2H), 4.48 (d, J=6.1 Hz, 2H); MS (ESI$^+$) m/z 303 (M+H)$^+$.

EXAMPLE 63

N-[(4-bromophenyl)methyl]-N'-(3-methylisoquinolin-5-yl)urea

EXAMPLE 63A 3-methylisoquinolin-5-amine

3-Methylisoquinoline was processed as described in Examples 60D and 60E to provide the title compound.

EXAMPLE 63B

N-[(4-bromophenyl)methyl]-N'-(3-methylisoquinolin-5-yl)urea

The product from Example 63A (500 mg, 3.1 mmol) in toluene (10 mL) was treated with 1-bromo-4-(isocyanatomethyl)benzene (0.5 mL, 3.57 mmol) with stirring and then the mixture was heated at 80° C. overnight. The mixture was allowed to cool to room temperature, filtered, the filter cake was washed with toluene, and allowed to air-dry to provide the title compound. The corresponding hydrochloride salt was prepared using methanolic HCl to afford a tan solid (919 mg, 73%). $^1$H NMR (300 MHz, DMSO-d$_6$) δ 9.70 (s, 1H), 9.54 (s, 1H), 8.63 (s, 1H), 8.57 (dd, J=7.8 Hz, 1.0 Hz, 1H), 8.02 (d, J=8.2 Hz, 1H), 7.78–7.83 (m, 1H), 7.67–7.71 (m, 1H), 7.52–7.57 (m, 2H), 7.30–7.35 (m, 2H), 4.36 (d, J=5.7 Hz, 2H), 2.78 (s, 3H); MS (ESI$^+$) m/z 370/372 (M+H, $^{79}$Br/$^{81}$Br).

EXAMPLE 64

N-[(4-bromophenyl)methyl]-N'-(1-chloroisoquinolin-5-yl)urea

EXAMPLE 64A 1-chloroisoquinolin-5-amine

1-Chloroisoquinoline was processed as described in Examples 60D and 60E to provide the title compound.

EXAMPLE 64B

N-[(4-bromophenyl)methyl]-N'-(1-chloroisoquinolin-5-yl)urea

The product from Example 64A (520 mg, 2.91 mmol) in toluene (8 mL) was treated with 1-bromo-4-(isocyanatomethyl)benzene (0.41 mL, 2.93 mmol) with stirring and then the mixture was heated at 90° C. for 2 hours. The mixture was allowed to cool to room temperature, filtered, the filter cake washed with toluene, and air-dried to provide the title compound as an off-white solid (717 mg, 63%). $^1$H NMR (300 MHz, DMSO-d$_6$) δ 8.89 (s, 1H), 8.34–8.37 (m, 2H), 8.00 (dd, J=6.1 Hz, 0.7 Hz, 1H), 7.92–7.95 (m, 1H), 7.73 (t, J=8.1, 1H), 7.53–7.56 (m, 2H), 7.30–7.33 (m, 2H), 7.12 (t, J=5.8 Hz, 1H), 4.35 (d, J=5.8 Hz, 2H); MS (ESI$^+$) m/z 390/392 (M+H$^+$, $^{35}$Cl/$^{37}$Cl).

EXAMPLE 65

N-[(4-bromophenyl)methyl]-N'-(1-methylisoquinolin-5-yl)urea

EXAMPLE 65A 1-methylisoquinolin-5-amine

1-Methylisoquinoline was processed as described in Examples 60D and 60E to provide the title compound.

EXAMPLE 65B

N-[(4-bromophenyl)methyl]-N'-(1-methylisoquinolin-5-yl)urea

The product from Example 65A (480 mg, 3.04 mmol) in toluene (9 mL) was treated with 1-bromo-4-(isocyanatomethyl)benzene (0.43, 3.07 mmol) with stirring. After heating the mixture at 90° C. for 1 hour, the mixture was allowed to cool to room temperature, filtered, and the filter cake washed with toluene to provide the title compound. The corresponding di-hydrochloride salt was prepared using methanolic HCl (680 mg, 50%). $^1$H NMR (300 MHz, DMSO-$d_6$) δ 8.74 (s, 1H), 8.38 (d, J=6.1 Hz, 1H), 8.25 (d, J=7.8 Hz, 1H), 7.78–7.85 (m, 2H), 7.53–7.61 (m, 3H), 7.32 (d, J=8.5 Hz, 2H), 7.11 (t, J=6.1 Hz, 1H), 4.34 (d, J=6.1 Hz, 2H), 2.88 (s, 3H); MS (ESI$^+$) m/z 370/372 (M+H$^+$, $^{79}$Br/$^{81}$Br).

EXAMPLE 66

N-isoquinolin-5-yl-N'-[(4-morpholin-4-ylphenyl)methyl]urea

EXAMPLE 66A 4-morpholin-4-ylbenzonitrile

4-Fluorobenzonitrile (1 g, 8.26 mmol) and morpholine (2.2 mL, 25.2 mmol) were combined in DMSO (25 mL) and heated at 100° C. for 2.5 hours. The mixture was allowed to cool to room temperature, poured into water, and extracted with diethyl ether. The organic extracts were combined, washed with water and brine, dried over Na$_2$SO$_4$, and concentrated under reduced pressure to provide the title compound as a white solid (1.24 g, 80%).

EXAMPLE 66B (4-morpholin-4-ylphenyl)methylamine

The product from Example 66A (1.24 g, 6.6 mmol) in THF (25 mL) was treated with LiAlH$_4$ (2.5 g, 65.9 mmol) at 0° C. The mixture was allowed to warm to room temperature and then refluxed for 1 hour. The mixture was allowed to cool to room temperature and then treated with 1N NaOH carefully followed by water. The mixture was concentrated under reduced pressure and the resulting aqueous mixture was extracted with diethyl ether. The organic extracts were combined, washed with saturated NaHCO$_3$ solution, dried over Na$_2$SO$_4$, filtered, and the filtrate concentrated under reduced pressure to provide the title compound as a yellow oil (286 mg, 23%).

EXAMPLE 66C

N-isoquinolin-5-yl-N'-[(4-morpholin-4-ylphenyl)methyl]urea

The product from Example 66B (285 mg, 1.48 mmol) in diethyl ether (10 mL) was treated with the product from Example 61A. The mixture was filtered and the filter cake purified by chromatography (95:5 CH$_2$Cl$_2$—MeOH, eluant) to provide that title compound as a white solid. The corresponding di-hydrochloride salt was prepared using methanolic HCl to afford a yellow solid (505 mg, 78%). $^1$H NMR (300 MHz, DMSO-$d_6$) δ 9.26 (s, 1H), 8.67 (s, 1H), 8.52–8.55 (m, 1H), 8.32 (dd, J=7.8 Hz, 1.1 Hz, 1H), 7.92 (d, J=6.1 Hz, 1H), 7.73 (d, J=8.2 Hz, 1H), 7.60 (m, 1H), 7.23 (d, J=8.8 Hz, 2H), 6.92–6.96 (m, 3H), 4.26 (d, 5.4 Hz, 2H), 3.72–3.75 (m, 4H), 3.06–3.12 (m, 4H); MS (ESI$^+$) m/z 363 (M+H)$^+$.

EXAMPLE 67

N-{[4-(2,6-dimethylmorpholin-4-yl)phenyl]methyl}-N'-isoquinolin-5-ylurea

EXAMPLE 67A

[4-(2,6-dimethylmorpholin-4-yl)phenyl]methylamine

4-Fluorobenzonitrile and 2,6-dimethylmorpholine were processed as described in Examples 66A and 66B to provide the title compound.

EXAMPLE 67B

N-{[4-(2,6-dimethylmorpholin-4-yl)phenyl]methyl}-N'-isoquinolin-5-ylurea

The product from Example 67A and the product from Example 61A were processed as described in Example 66C to provide a waxy material which was purified by chromatography (95:5 CH$_2$Cl$_2$—MeOH, eluant) to provide the title compound as a white solid. The corresponding di-hydrochloride salt was prepared using methanolic HCl. $^1$H NMR (300 MHz, DMSO-$d_6$) δ 9.26 (s, 1H), 8.67 (s, 1H), 8.53 (d, J=6.1 Hz, 1H), 8.31 (dd, J=7.6 Hz, 1.1 Hz, 1H), 7.92 (d, J=6.1 Hz, 1H), 7.73 (d, J=8.1 Hz, 1H), 7.57–7.62 (m, 1H), 7.22 (d, J=8.8 Hz, 2H), 6.92–6.95 (m, 3H), 4.26 (d, J=5.7 Hz, 2H), 3.68 (m, 2H), 3.54–3.57 (m, 2H), 2.21 (m, 2H), 1.16 (s, 3H), 1.14 (s, 3H); MS (ESI$^+$) m/z 391 (M+H).

EXAMPLE 68

N-isoquinolin-5-yl-N'-[(4-thiomorpholin-4-ylphenyl)methyl]urea

EXAMPLE 68A (4-thiomorpholin-4-ylphenyl)methylamine

4-Fluorobenzonitrile and thiomorpholine were processed as described in Examples 66A and 66B to provide the title compound.

EXAMPLE 68B

N-isoquinolin-5-yl-N'-[(4-thiomorpholin-4-ylphenyl)methyl]urea

The product from Example 68A and the product from Example 61A were processed as described in Example 66C to provide the title compound. The free base was treated with methanolic HCl to form the corresponding di-hydrochloride salt. $^1$H NMR (300 MHz, DMSO-$d_6$) δ 9.26 (s, 1H), 8.67 (s, 1H), 8.53 (d, J=6.1 Hz, 1H), 8.32 (dd, J=7.8 Hz, 1.1 Hz, 1H), 7.92 (d, J=6.1 Hz, 1H), 7.73 (d, J=8.2 Hz, 1H), 7.60 (m, 1H), 7.20–7.23 (m, 2H), 6.90–6.96 (m, 3H), 4.25 (d, J=5.8 Hz, 2H), 3.45–3.51 (m, 4H), 2.64–2.67 (m, 4H); MS (ESI$^+$) m/z 379 (M+H)$^+$.

EXAMPLE 69

4-(3,4-dichlorophenyl)-N-isoquinolin-5-ylpiperazine-1-carboxamide 1-(3,4-Dichlorophenyl)piperazine (1280 mg, 5.55 mmol) in diethyl ether (30 mL) was treated with the product from Example 61A (~40 mL). The mixture was filtered, the filter cake washed with diethyl ether, and dried under reduced pressure to provide the title compound as a white solid (1.78 g, 80%). $^1$H NMR (300 MHz, DMSO-d$_6$) δ 9.29 (d, J=1.0 Hz, 1H), 8.84 (s, 1H), 8.49 (d, J=5.8 Hz, 1H), 7.92 (d, J=7.8 Hz, 1H), 7.78 (m, 1H), 7.61–7.71 (m, 2H), 7.44 (d, J=8.8 Hz, 1H), 7.22 (d, J=3.1 Hz, 1H), 7.01 (dd, J=9.1, 2.7 Hz, 1H), 3.68 (m, 4H), 3.30 (m, 4H); MS (ESI$^+$) m/z 401/403 (M+H$^+$, $^{35}$Cl/$^{37}$Cl).

EXAMPLE 70

2-isoquinolin-5-yl-N-[4-(trifluoromethyl)benzyl]acetamide

EXAMPLE 70A ethyl isoquinolin-5-yl(oxo)acetate

The product from Example 57A (11.80 g, 56.6 mmol) in THF (200 mL) at −78° C. was treated with n-butyllithium (30 mL, 75.0 mmol, 2.5M in hexanes) dropwise. After 30 minutes, the mixture was treated with diethyl oxalate (25.0 mL, 184 mmol). After 20 minutes, the solution was allowed to warm to room temperature and was treated with saturated NH$_4$Cl (150 mL). The mixture was conentrated under reduced pressure. The residue was treated with dichloromethane (100 mL) filtered, and the filtrate concentrated under reduced pressure. The residue was purified by column chromatography (20% ethyl acetate/hexanes) to provide the title compound as light brown oil (4.57 g, 35%). MS (ESI+) m/z 248 (100), 230 (M+H)$^+$, (ESI−) m/z 200 (M−Et)$^−$; $^1$H NMR (DMSO-d$_6$, 300 MHz) rotomers δ 1.26 (t, J 7.1, 0.6H), 1.37 (t, J 7.1, 2.4H), 4.21 (q, J 7.1, 0.4H), 4.47 (q, J 7.1, 1.6H), 7.89 (t, J 7.5, 1H), 8.41 (dd, J 1.0, 7.5, 1H), 8.57 (d, J 8.1, 1H), 8.64 (d, J 5.7, 1H), 8.73 (d, J 6.3, 1H), 9.50 (s, 1H).

EXAMPLE 70B ethyl hydroxy(isoquinolin-5-yl)acetate

The product of Example 70A (1.11 g, 4.83 mmol) in absolute ethanol (20 mL) was added to 10% Pd/C (115.5 mg) under an argon atmosphere. The reaction mixture was stirred under H$_2$ (50 psi) for 5 hours at which time an additional 105.9 mg of catalyst was added as a suspension in ethanol. After 3 additional hours, the reaction mixture was filtered though a nylon membrane and the filtrate concentrated under reduced pressure to provide the title compound as dark brown oil (1.02 g, 91%). MS (ESI+) m/z 232 (M+H)$^+$, (ESI−) m/z 202 (M−Et)$^−$; $^1$H NMR (DMSO-d$_6$, 300 MHz) δ 1.05 (t, J 7.1, 3H), 4.07 (m, 2H), 5.77 (d, J 4.7, 1H), 6.36 (d, J 4.7, 1H), 7.68 (dd, J 7.3, 8.1, 1H), 7.85 (d, J 7.0, 1H), 8.09 (t, J 7.5, 2H), 8.53 (d, J 6.2, 1H), 9.33 (s, 1H).

EXAMPLE 70C ethyl (acetyloxy)(isoquinolin-5-yl)acetate

The product of Example 70B (1.0202 g, 4.41 mmol) in pyridine (15 mL) was treated with acetyl chloride (0.35 mL, 4.92 mmol) dropwise. The solution was stirred at room temperature for 4 hours and concentrated under reduced pressure. The residue was purified by column chromatography (2% methanol/CH$_2$Cl$_2$) to provide the title compound as yellow oil (0.8100 g, 67%). MS (ESI+) m/z 274 (M+H)$^+$; $^1$H NMR (DMSO-d$_6$, 300 MHz) δ 1.07 (t, J 7.1, 3H), 2.17 (s, 3H), 4.13 (m, 2H), 6.62 (s, 1H), 7.74 (m, 1H), 7.94 (d, J 7.1, 1H), 8.03 (d, J 6.1, 1H), 8.22 (d, J 7.6, 1H), 8.60 (d, J 5.7, 11H), 9.39 (s, 1H).

EXAMPLE 70D ethyl isoquinolin-5-ylacetate

The product of Example 70C (1.43 g, 5.23 mmol) in absolute ethanol (200 mL) was treated with dry 10% Pd/C (0.122 g) and triethylamine (10.4 mL). The reaction mixture was stirred at 60° C. for 6 hours under H$_2$ (60 psi), filtered and the filtrate concentrated under reduced pressure. The residue was purified by column chromatography (5% methanol/CH$_2$Cl$_2$) to provide the title compound as light brown oil (0.93 g, 67%). MS (ESI+) m/z 216 (M+H)$^+$, (ESI−) m/z 214 (M−H)$^−$; $^1$H NMR (DMSO-d$_6$, 300 MHz) δ 1.17 (t, J 7.1, 3H), 4.09 (q, J 7.1, 2H), 4.17 (s, 2H), 7.64 (m, 1H), 7.72 (d, J 6.2, 1H), 7.81 (d, J 5.7, 1H), 8.07 (d, J 7.9, 1H), 8.54 (d, J 6.1, 1H), 9.33 (s, 1H).

EXAMPLE 70E

2-isoquinolin-5-yl-N-[4-(trifluoromethyl)benzyl]acetamide

The product from Example 70D (0.207 g, 0.96 mmol) in dichloromethane (10 mL) was treated with trimethylaluminum (1 mL, 2.0 mmol, 2M in toluene) dropwise. After 30 minutes, the mixture was teated with 4-(trifluoromethyl)benzylamine (0.350 g, 2.0 mmol) in dichloromethane (2 mL) and then refluxed for 16 hours. The reaction mixture was allowed to cool to room temperature, treated with 1M HCl (3 mL), basified to between pH 9 and 10 with concentrated NH$_4$OH, treated with water and CH$_2$Cl$_2$ and the phases separated. The organic layer was washed with water (1×10 mL), brine (1×10 mL), dried (MgSO$_4$), and the filtrate was concentrated under reduced pressure. The residue was purified by column chromatography (5% methanol/CH$_2$Cl$_2$) to provide a yellow residue which was triturated with diethyl ether to provide the title compound as a white solid (0.122 g, 37%). MS (ESI+) m/z 345 (M+H)$^+$; MS (ESI−) m/z 343 (M−H)$^−$; $^1$H NMR (DMSO, 300 MHz) δ 4.00 (s, 2H), 4.37 (d, J 5.7, 2H), 7.46 (d, J 7.8, 2H), 7.67 (m, 4H), 7.93 (d, J 5.4, 1H), 8.03 (d, J 7.8, 1H), 8.52 (d, J 5.8, 1H), 8.80 (t, J 5.7, 1H), 9.31 (s, 1H); Anal. Calcd for C$_{19}$H$_{15}$F$_3$N$_2$O: C, 66.28; H, 4.39; N, 8.14. Found: C, 66.16; H, 4.27; N, 7.96.

EXAMPLE 71 methyl 5-({[(4-bromobenzyl)amino]carbonyl}amino)isoquinoline-3-carboxylate

EXAMPLE 71A methyl 5-nitroisoquinoline-3-carboxylate

Methyl isoquinoline-3-carboxylate (9.58 g, 51.2 mmol) in concentrated H$_2$SO$_4$ (100 mL) at 0° C. was treated with sodium nitrate (4.79 g, 56.4 mmol) in small portions such that the temperature was maintained below 5° C. Ten minutes after addition was complete, the reaction mixture was allowed to warm to room temperature and stirred for 2 hours. The mixture was poured over ice and adjusted to pH between 7 and 8 and filtered to afford the title compound as a bright yellow solid (11.44 g, 96%). MS (ESI+) m/z 233 (M+H)$^+$; $^1$H NMR (DMSO, 300 MHz) δ 3.97 (s, 3H), 8.06 (t, J 8.2, 1H), 8.72 (dt, J 1.0, 8.2, 1H), 8.78 (dd, J 1.0, 7.8, 1H), 9.11 (s, 1H), 9.65 (s, 1H).

EXAMPLE 71B methyl 5-aminoisoquinoline-3-carboxylate

The product of Example 71A (10.33 g, 44.5 mmol) in acetic acid/water (3/1) (320 mL) was treated with iron powder (5.06 g, 90.7 mmol). After stirring for 16 hours at room temperature, the reaction mixture was filtered the filtrate concentrated under reduced pressure to approximately half the original volume. The mixture was then extracted with dichloromethane (3×200 mL). The organic fractions were combined, dried (MgSO$_4$), and the filtrate concentrated under reduced pressure to afford crude material. A precipitate formed in the aqueous phase after sitting for several hours. This was filtered to afford additional crude material. The crude material was purfidied by column chromatography (2% methanol/CH$_2$Cl$_2$) to provide the title compound. MS (ESI+) m/z 203 (M+H)$^+$; MS (ESI−) m/z 201 (M−H)$^−$; $^1$H NMR (DMSO-d$_6$, 300 MHz) δ 3.92 (s, 3H), 6.34 (s, 2H), 6.96 (dd, J 1.0, 7.8, 1H), 7.31 (d, J 8.1, 1H), 7.51 (t, J 7.9, 1H), 8.82 (s, 1H), 9.15 (s, 1H); Anal. Calcd for C$_{11}$H$_{10}$N$_2$O$_2$: C, 65.34; H, 4.99; N, 13.85. Found: C, 65.03; H, 4.95; N, 13.65.

EXAMPLE 71C methyl 5-({[(4-bromobenzyl)amino]carbonyl}amino)isoquinoline-3-carboxylate The product of Example 71B (0.156 g, 0.77 mmol) in THF:toluene (10 mL, 1:1) was treated with a solution of 1-bromo-4-(isocyanatomethyl)benzene (0.201 g, 0.95 mmol) in THF (1.0 mL). After stirring for 16 hours at room temperature, the reaction mixture was concentrated under reduced pressure and the residue was triturated with diethyl ether to provide the title compound as a tan solid (0.272 g, 85%). MS (ESI+) m/z 415 (M+H)$^+$; MS (ESI−) m/z 413 (M−H)$^−$; $^1$H NMR (DMSO-d$_6$, 300 MHz) δ 3.95 (s, 3H), 4.36 (d, J 5.6, 2H), 7.23 (t, J 5.6, 1H), 7.33 (m, 2H), 7.56 (m, 2H), 7.76 (t, J 7.8, 1H), 7.85 (d, J 8.3, 1H), 8.41 (dd, J 1.5, 7.8, 11H), 8.82 (s, 1H), 9.06 (s, 1H), 9.35 (s, 1H); Anal. Calcd for C$_{19}$H$_{16}$BrN$_3$O$_3$: C, 55.09; H, 3.89; N, 10.14. Found: C, 55.06; H, 3.56; N, 9.84.

EXAMPLE 72 methyl 5-({[(2,4-dichlorobenzyl)amino]carbonyl}amino)isoquinoline-3-carboxylate

The product of Example 71 B (0.156 g, 0.77 mmol) in THF:toluene (10 mL, 1:1) was treated with a solution of 2,4-dichloro-1-(isocyanatomethyl)benzene (0.195 g, 0.97 mmol) in THF (1.0 mL). After stirring for 16 hours at room temperature, the reaction mixture was concentrated under reduced pressure and the residue was triturated with diethyl ether to provide the title compound as a tan solid (0.226 g, 73%). MS (ESI+) m/z 404 (M+H)$^+$; MS (ESI−) m/z 402 (M−H)$^−$; $^1$H NMR (DMSO-d$_6$, 300 MHz) δ 3.96 (s, 3H), 4.44 (d, J 6.0, 2H), 7.29 (m, 1H), 7.48 (m, 1H), 7.65 (d, J 1.7, 1H), 7.76 (t, J 7.8, 1H), 7.86 (d, J 7.8, 1H), 8.41 (dd, J 1.0, 7.8, 1H), 8.84 (s, 1H), 9.15 (s, 1H), 9.35 (s, 1H); Anal. Calcd for C$_{19}$H$_{15}$Cl$_2$N$_3$O$_3$: C, 56.45; H, 3.74; N, 10.39. Found: C, 56.08; H, 3.67; N, 10.03.

EXAMPLE 73

N-(8-bromoisoquinolin-5-yl)-N'-(2,4-dichlorobenzyl)urea

EXAMPLE 73A 8-bromoisoquinolin-5-amine

5-Aminoisoquinoline (5.50 g, 38.1 mmol) and aluminium trichloride (15.1 g, 113 mmol) were combined and heated at 80° C. in a 3-necked flask equipped with a dropping funnel, stirrer bar, needle and sintered glass tube. Bromine (3.04 g, 19.05 mmol) was dripped onto the sintered glass funnel and the vapour diffused onto the complex over a period of 2 hours. Heating was continued for 2 hours. The suspension was added portionwise to crushed ice and the solution basified with concentrated NaOH solution. The aqueous layer was extracted with ethyl acetate (4×100 mL) and the layers were separated. The organic layers were combined, dried (Na$_2$SO$_4$), filtered and the filtrate was concentrated to give a grey solid. The grey solid was subjected to column chromatography (hexanes:ethyl acetate, 3:1) to provide the title compound (2.96 g, 35%). MS (ESI+) m/z 225 (M+H)$^+$; MS (ESI−) m/z 223 (M−H)$^−$; $^1$H NMR (CDCl$_3$, 300 MHz) δ 4.22 (br s, 2H), 6.83 (d, J 8.1, 1H), 7.25 (s, 1H), 7.54 (d, J 5.8, 11H), 7.61 (d, J 8.1, 11H), 8.59 (d, J 5.8, 11H), 9.56 (s, 1H).

EXAMPLE 73B

N-(8-bromoisoquinolin-5-yl)-N'-(2,4-dichlorobenzyl)urea

The product from Example 73A (120 mg, 0.52 mmol) in THF:toluene (1:4, 5 mL) was treated with a solution of 2,4-dichloro-1-(isocyanatomethyl)benzene (108 mg, 0.52 mmol) in THF (0.5 mL). After stirring for 16 hours at room temperature, the mixture was filtered and the filter cake dried under reduced pressure to provide the title compound as a white solid (178 mg, 78%). The hydrochloride salt was obtained by dissolving the product in hot THF and adding HCl in diethyl ether (2M). The yellow precipitate was collected by filtration and dried under reduced pressure. MS (ESI+) m/z 426 (M+H)$^+$; MS (ESI−) m/z 424 (M−H)$^−$; $^1$H NMR (DMSO-d$_6$, 300 MHz) δ 4.42 (d, 5.8, 2H), 7.22 (t, J 5.8, 1H), 7.65 (m, 1H), 7.91 (d, J 8.5, 1H), 8.02 (d, J 6.1, 1H), 8.22 (d, J 8.5, 1H), 8.69 (d, J 5.8, 1H), 9.01 (s, 1H), 9.44 (s, 1H); Anal. Calcd for C$_{17}$H$_{12}$BrCl$_2$N$_3$OHCl0.25EtOH: C, 44.41; H, 3.14; N, 8.88. Found: C, 44.80; H, 2.76; N, 8.84.

EXAMPLE 74

N-(8-bromoisoquinolin-5-yl)-N'-(4-fluorobenzyl)urea

The title compound was prepared using 1-fluoro-4-(isocyanatomethyl)benzene, the product of Example 73A and the procedure described in Example 73B (white solid, 108 mg, 65%). MS (ESI+) m/z 376 (M+H)$^+$; MS (ESI−) m/z 374 (M−H)$^−$; $^1$H NMR (DMSO-d$_6$, 300 MHz) δ 4.35 (d, 5.8, 2H), 7.12 (m, 1H), 7.18 (m, 2H), 7.40 (m, 1H), 7.91 (d, J 8.5, 1H), 7.99 (d, J 6.1, 1H), 8.24 (d, J 8.5, 1H), 8.69 (d, J 5.8, 1H), 8.88 (s, 1H), 9.44 (s, 1H); Anal. Calcd for C$_{17}$H$_{13}$BrFN$_3$O: C, 54.56; H, 3.50; N, 11.23. Found: C, 54.61; H, 3.35; N, 11.14.

EXAMPLE 75

N-(8-bromoisoquinolin-5-yl)-N'-(3-fluorobenzyl)urea

The title compound was prepared using 1-fluoro-3-(isocyanatomethyl)benzene, the product of Example 73A and the procedure described in Example 73 (white solid, 108 mg, 65%). MS (ESI+) m/z 376 (M+H)$^+$; MS (ESI−) m/z 374 (M−H)$^-$; $^1$H NMR (DMSO-d$_6$, 300 MHz) δ 4.39 (d, 5.8, 2H), 7.09 (m, 1H), 7.17 (m, 2H), 7.40 (m, 1H), 7.91 (d, J 8.5, 1H), 8.01 (d, J 6.1, 1H), 8.23 (d, J 8.5, 1H), 8.69 (d, J 5.8, 1H), 8.93 (s, 1H), 9.44 (s, 1H); Anal. Calcd for C$_{17}$H$_{13}$BrFN$_3$O: C, 54.56; H, 3.50; N, 11.23. Found: C, 54.64; H, 3.33; N, 11.19.

EXAMPLE 76

N-[1-(4-chlorophenyl)-1-methylethyl]-N'-isoquinolin-5-ylurea

EXAMPLE 76A 2-(4-chlorophenyl)-2-methylpropanoyl chloride 2-(4-Chlorophenyl)-2-methylpropanoic acid (3.85 g, 19.4 mmol) in toluene (5 mL) was treated with thionyl chloride (5.00 g, 3.1 mL) and heated at 80° C. for 2 hours. The cooled solution was concentrated under reduced pressure to provide a yellow oil containing a crystalline residue. The mixture was dissolved in hexane, filtered and the filtrate concentrated to provide the compound as a pale yellow oil (4.10 g, 98%).

EXAMPLE 76B 1-chloro-4-(1-isocyanato-1-methylethyl)benzene

The product of Example 76A (4.00 g, 19.4 mmol) in acetone (9 mL) at 0° C. was treated with a solution of sodium azide (1.27 g) in water (9 mL) dropwise over 15 minutes. After stirring for 30 minutes at 0° C., the mixture was extracted with toluene (20 mL). The organic extract was dried with MgSO$_4$, filtered, and the filtrate heated at reflux for 1 hour. The mixture was allowed to cool to room temperature and was concentrated under reduced pressure to provide the title compound as a pale yellow oil (3.45 g, 96%).

EXAMPLE 76C

N-[1-(4-chlorophenyl)-1-methylethyl]-N'-isoquinolin-5-ylurea

The title compound was prepared using 5-aminoisoquinoline, the product of Example 76B and the procedure described in Example 73B except that THF was used as solvent. The product was recrystallized from ethyl acetate to provide the title compound as a white solid (840 mg, 34%). MS (ESI+) m/z 355 (M+H)$^+$; MS (ESI−) m/z 353 (M−H)$^-$; $^1$H NMR (DMSO-d$_6$, 300 MHz) δ 1.63 (s, 6H), 7.23 (s, 1H), 7.37 (d, J 8.8, 2H), 7.47 (d, J 8.8, 2H), 7.73 (t, J 9.2, 1H), 7.93 (d, J 8.1, 1H), 8.25 (d, J 6.4, 1H), 8.39 (d, J 8.1, 1H), 8.67 (d, J 6.4, 1H), 8.87 (s, 1H), 9.58 (s, 1H); Anal. Calcd for C$_{19}$H$_{18}$ClN$_3$O HCl 0.25EtOH: C, 60.40; H, 5.33; N, 10.54. Found: C, 60.82; H, 5.23; N, 10.45.

EXAMPLE 77

N-(4-bromobenzyl)-N'-{6-[2,2,2-trifluoro-1-hydroxy-1-(trifluoromethyl)ethyl]isoquinolin-5-yl}urea

EXAMPLE 77A 2-(5-aminoisoquinolin-6-yl)-1,1,1,3,3,3-hexafluoropropan-2-ol

5-Aminoisoquinoline (288 mg, 2.00 mmol) and p-toluenesulfonic acid (5 mg) were combined and treated with hexafluoroacetone hexahydrate (0.29 mL, 462 mg, 2.10 mmol). The mixture was stirred in a sealed pressure tube and heated to 150° C. for 18 hours. The reaction was allowed to cool to room temperature and partitioned between CH$_2$Cl$_2$ (20 mL) and water (10 mL). The organic layer was passed thru Na$_2$SO$_4$ and then filtered through activated charcoal. The charcoal was washed with methanol (3×10 mL) and the filtrate and washings were collected and concentrated under reduced pressure to provide the title compound (130 mg, 30%) as a yellow solid. MS (ESI+) m/z 311 (M+H)$^+$; MS (ESI−) m/z 309 (M−H)$^-$; $^1$H NMR (DMSO, 300 MHz) δ 6.64 (br s, 2H), 7.30 (d, J 8.7, 1H), 7.40 (d, J 8.7, 1H), 8.09 (d, J 6.1, 1H), 8.49 (d, J 6.1, 1H), 9.14 (s, 1H); $^{13}$C NMR (DMSO, 100 MHz) δ 107.02, 110.60, 113.95 (1), 115.46 (1), 122.03, 124.92, 124.92, 125.94, 126.98 (1), 128.17, 142.43 (1), 144.82, 151.85 (1).

EXAMPLE 77B

N-(4-bromobenzyl)-N'-{6-[2,2,2-trifluoro-1-hydroxy-1-(trifluoromethyl)ethyl]isoquinolin-5-yl}urea The title compound was prepared using 1-bromo-4-(isocyanatomethyl)benzene, the product of Example 77A and the procedure described in Example 73B except that THF was used as solvent (white solid, 840 mg, 34%). MS (ESI+) m/z 376 (M+H)$^+$; MS (ESI−) m/z 374 (M−H)$^-$; $^1$H NMR (DMSO-d$_6$, 300 MHz) δ 4.35 (d, 5.8, 2H), 7.12 (m, 1H), 7.18 (m, 2H), 7.40 (m, 1H), 7.91 (d, J 8.5, 1H), 7.99 (d, J 6.1, 1H), 8.24 (d, J 8.5, 1H), 8.69 (d, J 5.8, 1H), 8.88 (s, 1H), 9.44 (s, 1H); Anal. Calcd for C$_{20}$H$_{14}$BrF$_6$N$_3$O$_2$: C, 46.00; H, 3.50; N, 11.23. Found: C, 54.61; H, 3.35; N, 11.14.

EXAMPLE 78

N-(4-bromobenzyl)-N'-1H-indol-4-ylurea 4-aminoindole (0.13 g, 1 mmol) in THF (3 mL) was treated with 1-bromo-4-(isocyanatomethyl)benzene (0.23 g, 1.1 mmol) for 3 hours at ambient temperature. Hexane was added to the reaction mixture to precipitate 0.26 g of the title compound as a tan solid. mp 198° C.; $^1$H NMR (300 MHz, DMSO-d$_6$) δ 4.30 (d, 2H), 6.51 (t, 1H), 6.89 (t, 1H), 6.95 (d, 2H), 7.29 (t, 1H), 7.31 (d, 2H), 7.55 (d, 2H), 7.62 (dd, 1H), 8.3 (s, 1H), 11.04 (s, 1H); MS (DCI+) m/z 346 (M+H); Anal. Calcd. For C$_{16}$H$_{14}$N$_3$BrO: C, 55.83; H, 4.10; N, 12.21. Found: C, 55.71, H, 4.12; N, 12.01.

EXAMPLE 79

N-(3,4-dichlorobenzyl)-N'-1H-indol-4-ylurea

4-Aminoindole (0.13 g, 1 mmol) in THF (3 mL) was treated with 1,2-dichloro-4-(isocyanatomethyl)benzene (0.22 g, 1.1 mmol) for 3 h at ambient temperature. Hexane was added to the reaction mixture to precipitate 0.25 g of the title compound as a tan solid. mp 201° C.; $^1$H NMR (300 MHz, DMSO-d$_6$) δ 4.23 (d, 2H), 6.36 (s, 1H), 6.54 (t, 1H), 7.0 (dd, 1H), 7.25 (m, 2H), 7.30 (d, 2H), 7.45 (d, 1H), 7.6 (m, 2H), 8.31 (s, 1H), 10.87 (s, 1H) MS (DCI+) m/z 336 (M+H); Anal. Calcd. For C$_{16}$H$_{13}$N$_3$Cl$_2$O: C, 57.50; H, 3.92; N, 12.57. Found: C, 56.94, H, 3.68; N, 11.97.

EXAMPLE 80

N-1H-indol-4-yl-N'-[4-(trifluoromethyl)benzyl]urea

EXAMPLE 80A 4-isocyanato-1H-indole

4-Aminoindole (0.5 g, 3.78 mmol) in toluene (50 mL) was treated with triphosgene (0.4 g, 1.35 mmol) and heated at reflux for 5 hours. The reaction mixture was allowed to cool to room temperature and concentrated under reduced pressure. The residue was taken up in diethyl ether, filtered, and the filtrate was concentrated under reduced pressure to provide title compound as yellow oil (0.4 g). $^1$H NMR (300 MHz, CDCl$_3$-d$_6$) δ 6.62 (m, 1H), 6.84 (d, 1H), 7.1 (t, 1H), 7.23 (m, 2H), 8.3 (s, 1H).

EXAMPLE 80B

N-1H-indol-4-yl-N'-[4-(trifluoromethyl)benzyl]urea

The product of Example 80A (0.16 g, 1 mmol) in THF (3 mL) was treated with 4-(trifluoromethyl)benzylamine (0.19 g, 1.1 mmol) at ambient temperature. After stirring for 3 hours, hexane was added to the reaction mixture to precipitate the title compound as a solid. mp 178° C. $^1$H NMR (300 MHz, DMSO-d$_6$) δ 4.43 (d, 2H), 6.53 (t, 1H), (6.98 (m, 3H), 7.26 (t, 1H), 7.57 (d, 2H), 7.62 (d, 1H), 7.71 (d, 2H), 8.37 (s, 1H), 11.04 (s, 1H); MS (DCI+) m/z 334 (M+H); Anal. Calcd. For C$_{17}$H$_{14}$N$_3$F$_3$O: C, 61.26; H, 4.23; N, 12.61. Found: C, 61.28, H, 3.83; N, 12.31.

EXAMPLE 81

N-1H-indol-4-yl-N'-[4-(trifluoromethoxy)benzyl]urea 4-(Trifluoromethoxy)benzylamine (0.21 g, 1.1 mmol) and the product of Example 80A (0.16 g, 1 mmol) were treated as described in Example 80B to provide the title compound (0.23 g). mp 177° C.; $^1$H NMR (300 MHz, DMSO-d$_6$) δ 4.36 (d, 2H), 6.52 (m, 1H), 6.95 (m, 3H), 7.24 (t, 1H), 7.36 (d, 2H), 7.48 (d, 2H), 7.63 (dd, 1H), 8.32 (1H), 11.06 (s, 1H); MS (DCI+) m/z 349.9 (M+H)$^+$; Anal. Calcd. For C$_{17}$H$_{14}$N$_3$F$_3$O$_2$: C, 58.63, H, 4.34, N, 12.07. Found: C, 58.51, H, 3.98, N, 12.03.

EXAMPLE 82

N-[3-fluoro-4-(trifluoromethyl)benzyl]-N'-1H-indol-4-ylurea

3-Fluoro-4-(trifluoromethyl)benzylamine (0.22 g, 1.1 mmol) and the product of Example 80A (0.16 g, 1 mmol) were treated as described in Example 80B to provide the title compound (0.24 g). mp 198° C.; $^1$H NMR (300 MHz, DMSO-d$_6$) δ 4.43 (d, 2H), 6.52 (m, 1H), 6.98 (m, 3H), 7.26 (m, 1H), 7.39 (m, 2H), 7.57 (dd, 1H), 7.77 (t, 1H), 8.40 (s, 1H), 11.05 (s, 1H); MS (DCI+) m/z 349.9 (M+H)$^+$. Anal. Calcd. for C$_{17}$H$_{13}$N$_3$F$_4$O: C, 58.12; H, 3.73; N, 11.96. Found C, 58.52; H, 3.99; N, 11.55.

EXAMPLE 83

1-(4-Chloro-3-trifluoromethyl-benzyl)-3-(1H-indol-4-yl)-urea

4-Chloro-3-(trifluoromethyl)benzylamine (0.27 g, 1.1 mmol) and the product of Example 80A (0.16 g, 1 mmol) were treated as described in Example 80B to provide the title compound. mp 197° C.; $^1$H NMR (300 MHz, DMSO-d$_6$) δ 4.42 (d, 2H), 6.52 (m, 1H), 6.96 (m, 3H), 7.25 (m, 1H), 7.56 (dd, 1H), 7.67 (dd, 1H), 7.70 (t, 1H), 7.81 (s, 1H), 8.37 (s, 1H), 11.06 (s, 1H); MS (DCI+) m/z 368 (M+H). Anal. Calcd. for C$_{17}$H$_{13}$N$_3$ClF$_3$O: C, 55.52, H, 3.56; N, 11.43. Found C, 55.46; H, 3.65; N, 11.58.

EXAMPLE 84

1-(4-Chloro-3-trifluoromethyl)-3-(1H-indol-4-yl)-urea

4-Chlorobenzylamine (0.2 g, 1.4 mmol) and the product of Example 80A (0.2 g, 1.27 mmol) were treated as described in Example 80B to provide the title compound. mp 205° C. $^1$H NMR (300 MHz, DMSO-d$_6$) δ 4.32 (d, 2H), 6.52 (m, 1H), 6.87 (m, 1H), 6.97 (m, 2H), 7.25 (m, 1H), 7.37 (m, 4H), 7.6 (m, 1H), 8.30 (s, 1H), 11.06 (s, 1H). MS (DCI+) m/z 300 (M+H). Anal. Calcd. for C$_{16}$H$_{14}$N$_3$Cl$_3$O: C, 64.11; H, 4.71; N, 14.02. Found: C, 63.99; H, 4.70; N, 13.77.

EXAMPLE 85

N-[2-(2,4-dichlorophenyl)ethyl]-N'-1H-indol-4-ylurea 2-(2,4-Dichlorophenyl)ethylamine (0.21 g, 1.1 mmol) and the product of Example 80A (0.16 g, 1. mmol) were treated as described in Example 80B to provide the title compound. mp 170° C.; $^1$H NMR (300 MHz, DMSO-d$_6$) δ 2.90 (m, 2H), 3.31 (m, 2H), 6.47 (m, 2H), 6.93 (m, 2H), 7.23 (m, 1H), 7.40 (m, 2H), 7.60 (m, 2H), 8.15 (s, 1H), 11.02 (s, 1H). MS (DCI+) m/z 347 (M+H). Anal. Calcd. for C$_{17}$H$_{15}$N$_3$Cl$_2$O: C, 58.63; H, 4.34; N, 12.07. Found: C, 58.49; H, 4.49; N, 12.38.

EXAMPLE 86

4-(trifluoromethyl)benzyl 1H-indol-4-ylcarbamate

[4-(Trifluoromethyl)phenyl]methanol (0.09 g, 0.55 mmol) and the product of Example 80A (0.08 g, 0.5 mmol) in THF (5 mL) were heated at reflux for 16 hours with a catalytic amount of triethylamine. The reaction mixture was concentrated under reduced pressure and the residue was purified by chromatography on silica gel eluting with 50% hexane:ethylacetate to provide the title compound as an oil (0.09 g). $^1$H NMR (300 MHz, DMSO-d$_6$) δ 5.32 (s, 2H), 6.73 (s, 1H), 7.0 (t, 1H), 7.11 (d, 1H), 7.23 (t, 1H), 7.38 (d, 1H), 7.66 (d, 2H), 7.78 (d, 2H), 9.52 (s, 1H), 11.08 (s, 1H). Anal. Calcd. for C$_{17}$H$_{13}$N$_2$F$_3$O$_2$: C, 61.08; H, 3.92; N, 8.38. Found: C, 60.97; H, 4.21; N, 8.17.

EXAMPLE 87

4-(trifluoromethoxy)benzyl 1H-indol-4-ylcarbamate

[4-(Trifluoromethoxy)phenyl]methanol (0.13 g, 0.7 mmol) and the product of Example 80A (0.1 g, 0.63 mmol) in THF (5 mL) were heated at reflux for 16 hours with a catalytic amount of triethylamine. The reaction mixture was concentrated under reduced pressure and the residue was triturated with diethyl ether/hexane to provide the title compound as tan crystals (0.12 g). $^1$H NMR (300 MHz, DMSO-d$_6$) δ 5.21 (s, 2H), 6.73 (s, 1H), 7.0 (t, 1H), 7.1 (d, 1H), 7.23 (t, 1H), 7.38 (dd, 1H), 7.4 (d, 2H), 7.6 (d, 2H), 9.5 (s, 1H), 11.06 (s, 1H).). Anal. Calcd. for C$_{17}$H$_{13}$N$_2$F$_3$O$_3$.0.25H$_2$O: C, 57.55; H, 3.84; N, 7.90. Found: C, 57.42; H, 3.81; N, 7.32.

EXAMPLE 88

N-(4-bromobenzyl)-N'-(2,3-dimethyl-1H-indol-4-yl)urea 2,3-Dimethyl-4-aminoindole (0.11 g, 0.7 mmol) in THF (3 mL) was treated with 1-bromo-4-(isocyanatomethyl)benzene (0.17 g, 0.8 mmol) at ambient temperature. After stirring for 3 hours at ambient temperature, hexane was added to the reaction mixture to precipitate the title compound as a tan solid (0.12 g). mp 190° C. $^1$H NMR (300 MHz, DMSO-d$_6$) δ 2.24 (s, 3H), 2.25 (s, 3H), 4.25 (d, 2H), 6.51 (t, 1H), 6.82 (t, 1H), 6.85 (d, 2H), 6.95 (m, 2H), 7.25 (d, 2H), 7.53 (d, 2H), 7.78 (s, 1H), 11.04 (s, 1H); MS (DCI+) m/Z 346 (M+H)$^+$; Anal. Calcd. for C$_{18}$H$_{18}$N$_3$BrO: C, 58.08; H, 4.87; N, 11.29. Found: C, 57.97, H, 4.92; N, 11.30.

EXAMPLE 89

N-(4-bromobenzyl)-N'-1H-indazol-4-ylurea

EXAMPLE 89A 1H-indazol-4-amine

4-Nitro-1H-indazole (1.63 g, 10 mmol) in ethanol (100 mL) was treated with $BiCl_3$ (3.46 g, 11 mmol) followed by a portionwise addition of $NaBH_4$. The reaction mixture was stirred at ambient temperature for 20 minutes and filtered through Celite. The filtrate was evaporated under reduced pressure and the residue was partitioned between ethyl acetate/dilute $NaHCO_3$ solution. The organic layer was dried over $MgSO_4$, filtered, and the filtrate concentrated under reduced pressure to provide the title compound as a tan solid (1.0 g). $^1H$ NMR (300 MHz, DMSO-$d_6$) δ 5.64 (s, 2H), 6.1 (d, 1H), 6.6 (d, 1H), 6.98 (t, 1H), 8.03 (s, 1H), 12.6 (s, 1H).

EXAMPLE 89B

N-(4-bromobenzyl)-N'-1H-indazol-4-ylurea hydrochloride salt

The product of Example 89A (0.16 g, 1.2 mmol) in THF (10 mL) was treated with 1-bromo-4-(isocyanatomethyl) benzene (0.52 g, 2.4 mmol) at room temperature. After stirring for 16 hours, the reaction mixture was concentrated and the residue was treated with methanol (20 mL) and 3N HCl (10 mL) and heated at reflux for 3 hours. The reaction mixture was allowed to cool to room temperature, evaporated under reduced pressure, and the residue was treated with water and the pH adjusted to 5. The obtained compound was purified by chromatography eluting with 5% of ethanol:methylene chloride and converted to HCl salt mp 126° C. $^1H$ NMR (300 MHz, DMSO-$d_6$) δ 4.32 (d, 2H), 7.0 (t, 1H), 7.05 (d, 1H), 7.18 (t, 1H), 7.3 (d, 2H), 7.55 (d, 2H), 7.61 (d, 1H), 8.16 (s, 1H), 8.92 (s, 1H); Analysis Calcd for $C_{15}H_{13}N_4BrO$ HCl: C, 47.21; H, 3.70; N, 14.68. Found C, 46.99; H, 4.08; N, 14.13.

EXAMPLE 90

N-(3,4-dichlorobenzyl)-N'-1H-indazol-4-ylurea

EXAMPLE 90A methyl 4-nitro-1H-indazole-1-carboxylate

Sodium hydride (0.3 g, 12.5 mmol) suspended in DMF (5 mL) at 0° C. was treated with 4-nitro-1H-indazole (1.33 g, 10 mmol). After stirring at room temperature for 1 hour, the mixture was treated with methylchloroformate (0.9 mL). After stirring at room temperature for 3 hours, the mixture was carefully treated with water and filtered to provide the title compound (1.2 g). $^1H$ NMR (300 MHz, DMSO-$d_6$) δ 4.19 (s, 3H), 7.9 (t, 1H), 8.38 (d, 1H), 8.62 (d, 1H), 8.85 (s, 1H).

EXAMPLE 90B methyl 4-amino-1H-indazole-1-carboxylate

The product of Example 90A (1.66 g, 7.5 mmol) in ethanol (20 mL) was treated with $BiCl_3$ (8.2 g, 2.6 mmol) followed by the addition of $NaBH_4$ (1.13 g, 30.5 mmol). The reaction mixture was stirred at room temperature for 20 minutes, filtered through Celite, and the filtrate was evaporated under reduced pressure. The residue was partitioned between ethyl acetate/dilute $NaHCO_3$ solution. The organic phase was separated, dried over $MgSO_4$, filtered and the filtrate concentrated under reduced pressure to provide the title compound (1.2 g). $^1H$ NMR (300 MHz, DMSO-$d_6$) δ 6.1 (s, 2H), 6.41 (dd, 1H), 7.21 (m, 2H), 8.42 (s, 1H).

EXAMPLE 90C methyl 4-({[(3,4-dichlorobenzyl)amino] carbonyl}amino)-1H-indazole-1-carboxylate The product of Example 90B (0.19 g, 1 mmol) in THF (3 mL) was treated with 1,2-dichloro-4-(isocyanatomethyl) benzene (0.22 g, 1.1 mmol) at ambient temperature. After stirring for 3 hours, hexane was added to the reaction mixture to precipitate the title compound as a tan solid (0.25 g). $^1H$ NMR (300 MHz, DMSO-$d_6$) δ 4.38 (d, 2H), 6.97 (t, 1H), 7.36 (dd, 1H), 7.48 (t, 1H), 7.6 (m, 2H), 7.7 (d, 1H), 7.8 (d, 1H), 8.45 (s, 1H), 9.16 (s, 1H).

EXAMPLE 90D

N-(3,4-dichlorobenzyl)-N'-1H-indazol-4-ylurea

The product of Example 90C (0.25 g, 0.6 mmol) was heated at reflux in methanol (5 mL) and 0.5N KOH (1 mL) for 0.5 hours. The reaction mixture was allowed to cool to ambient temperature, pH was adjusted to 5, and volume was reduced under reduced pressure. Methylene chloride and water was added, the phases were separated, and the organic phase concentrated under reduced pressure to provide the title compound. $^1H$ NMR (300 MHz, DMSO-$d_6$) δ 4.38 (d, 2H), 6.9 (t, 1H), 7.05 (d, 1H), 7.19 (t, 1H), 7.35 (dd, 1H), 7.6 (m, 2H), 8.06 (s, 1H), 8.82 (s, 1H). MS (DCI+) m/z 336 (M+H)$^+$; Anal. Calcd. For $C_{15}H_{13}N_4Cl_2O$: C, 53.75; H, 3.62; N, 16.72. Found: C, 53.84, H, 3.44; N, 16.88.

EXAMPLE 97

N-(1,1'-biphenyl-4-ylmethyl)-N'-5-isoquinolinylurea

The title compound was prepared using the procedure described in Example 1B using 1,1'-biphenyl-4-ylmethylamine instead of 2-(3-fluorophenyl)ethylamine. NMR (DMSO-$d_6$) δ 9.78 (s, 1H), 9.57 (s, 1H), 8.69 (s, 2H), 8.53 (d, 1H), 8.11 (d, 1H), 7.87 (t, 1H), 7.64 (m, 5H), 7.45 (m, 4H), 7.35 (m, 1H), 4.43 (d, 2H); MS (ESI) (M+H)$^+$ 354.

EXAMPLE 98

N-[3-fluoro-4-(trifluoromethyl)benzyl]-N'-5-isoquinolinylurea

The title compound was prepared using the procedure described in Example 1B using 3-fluoro-4-(trifluoromethyl) benzylamine instead of 2-(3-fluorophenyl)ethylamine. NMR (DMSO-$d_6$) δ 9.78 (s, 1H), 9.74 (s, 1H), 8.77 (d, 1H), 8.71 (d, 1H), 8.61 (d, 1H), 8.08 (d, 1H), 7.87 (m, 2H), 7.78 (d, 1H), 7.43 (m, 2H), 4.49 (d, 2H); MS (ESI) (M+H)$^+$ 364.

EXAMPLE 99

N-5-isoquinolinyl-N'-(3-methylbenzyl)urea

The title compound was prepared using the procedure described in Example 1B using 3-methylbenzylamine instead of 2-(3-fluorophenyl)ethylamine. NMR (DMSO-$d_6$) δ 9.68 (s, 1H), 9.18 (s, 1H), 9.23 (s, 1H), 8.66 (d, 1H), 8.37 (d, 1H), 8.48 (d, 1H), 8.04 (d, 1H), 7.85 (t, 1H), 7.35 (t, 1H), 7.23 (t, 1H), 7.7.26 (m, 1H), 7.06 (m, 1H), 4.28 (d, 2H), 2.31 (s, 3H); MS (ESI) (M+H)$^+$ 291.

EXAMPLE 100

N-[4-fluoro-3-(trifluoromethyl)benzyl]-N'-5-isoquinolinylurea

The title compound was prepared using the procedure described in Example 61B using 4-fluoro-3-(trifluoromethyl)benzylamine instead of 4-cyanobenzyl alcohol. NMR (DMSO-$d_6$) δ 9.31 (s, 1H), 8.84 (s, 1H), 8.65 (d, 2H), 7.95 (d, 2H), 7.86 (m, 2H), 7.60 (t, 1H), 7.50 (d, 1H), 7.17 (t, 1H), 4.43 (d, 2H); MS (ESI) (M+H)$^+$ 364.

EXAMPLE 101

N-(3-chloro-4-fluorobenzyl)-N'-5-isoquinolinylurea

The title compound was prepared using the procedure described in Example 61B using 3-chloro-4-fluorobenzylamine instead of 4-cyanobenzyl alcohol. NMR (DMSO-$d_6$) δ 9.72 (s, 1H), 9.42 (s, 1H), 8.68 (d, 1H), 8.58 (d, 2H), 8.05 (d, 1H), 7.88 (t, 1H), 7.67 (m, 2H), 7.20 (m, 2H), 4.38 (d, 2H); MS (ESI) (M+H)$^+$ 330.

EXAMPLE 102

N-5-isoquinolinyl-N'-pentylurea

The title compound was prepared using the procedure described in Example 60F using 1-isocyanatopentane and 5-isoquinolinamine instead of the product from Example 60E and 1-bromo-4-(isocyanatomethyl)benzene. NMR (DMSO-$d_6$) δ 9.70 (s, 1H), 9.19 (s, 1H), 8.64 (d, 1H), 8.57 (m, 2H), 8.01 (d, 1H), 7.84 (d, 1H), 7.85 (t, 1H), 6.95 (m, 1H), 3.17 (m, 2H), 2.48 (m, 2H), 1.23 (m, 4H), 0.86 (m, 3H); MS (ESI) (M+H)$^+$ 339.

EXAMPLE 103

N-5-isoquinolinyl-N'-octylurea

The title compound was prepared using the procedure described in Example 60F using 1-isocyanatooctane and 5-isoquinolinamine instead of the product from Example 60E and 1-bromo-4-(isocyanatomethyl)benzene. NMR (DMSO-$d_6$) δ 9.53 (s, 1H), 9.23 (s, 1H), 8.65 (d, 1H), 8.99 (d, 1H), 8.05 (d, 1H), 7.86 (t, 1H), 7.01 (m, 1H), 3.15 (m, 2H), 1.51 (m, 2H), 1.28 (m, 5H), 0.83 (m, 3H); MS (ESI) (M+H)$^+$ 300.

EXAMPLE 104

N-(1-adamantylmethyl)-N'-5-isoquinolinylurea

The title compound was prepared using the procedure described in Example 61B using 1-(1-adamantyl)methanamine instead of 4-cyanobenzyl alcohol. NMR (DMSO-$d_6$) δ 9.68 (s, 1H), 9.20 (s, 1H), 8.64 (d, 2H), 8.60 (d, 1H), 8.65 (m, 1H), 8.00 (d, 1H), 7.83 (t, 1H), 6.95 (m, 1H), 2.90 (d, 2H), 1.99 (m, 2H), 1.64 (m, 5H), 1.53 (m, 5H); MS (ESI) (M+H)$^+$ 336.

EXAMPLE 105

N-(cyclohexylmethyl)-N'-5-isoquinolinylurea

The title compound was prepared using the procedure described in Example 61B using 1-cyclohexylmethanamine instead of 4-cyanobenzyl alcohol. NMR (DMSO-$d_6$) δ 9.70 (s, 1H), 9.18 (s, 1H), 8.67 (d, 2H), 8.57 (m, 3H), 8.00 (d, 1H), 7.84 (t, 1H), 7.00 (m, 1H), 3.06 (m, 2H), 1.70 (m, 5H), 1.43 (m, 1H), 1.21 (m, 3H). 0.97 (m, 2H); MS (ESI) (M+H)$^+$ 284.

619946 Example 107

N-[(6,6-dimethylbicyclo[3.1.1]hept-2-yl)methyl]-N'-5-isoquinolinylurea

The title compound was prepared using the procedure described in Example 61B using [6,6-dimethylbicyclo[3.1.1]hept-2-yl]methylamine instead of 4-cyanobenzyl alcohol. NMR (DMSO-$d_6$) δ 9.74 (s, 1H), 9.28 (s, 1H), 8.64 (d, 1H), 8.60 (m, 2H), 8.03 (s, 1H), 7.85 (t, 1H), 7.08 (m, 1H), 3.17 (m, 2H), 2.38 (m, 1H), 2.18 (m, 3H), 2.00 (m, 1H), 1.88 (m, 5H), 1.20 (s, 3H), 1.03 (s, 3H); MS (ESI) (M+H)$^+$ 324.

EXAMPLE 108

N-5-isoquinolinyl-N'-[4-(1-pyrrolidinyl)benzyl]urea

The title compound was prepared using the procedure described in Example 61B using 4-(1-pyrrolidinyl)benzylamine instead of 4-cyanobenzyl alcohol. NMR (DMSO-$d_6$) δ 9.81 (s, 1H), 9.58 (s, 1H), 8.80 (d, 1H), 8.71 (m, 2H), 8.11 (d, 1H), 7.93 (t, 1H), 7.48 (bs, 1H), 7.20 (m, 2H), 6.65 (m, 2H), 4.43 (d, 2H), 3.13 (m, 4H), 1.97 (m, 4H); MS (ESI) (M+H)+347.

EXAMPLE 109

N-[4-(1-azepanyl)benzyl]-N'-5-isoquinolinylurea

The title compound was prepared using the procedure described in Example 61B using 4-(1-azepanyl)benzylamine instead of 4-cyanobenzyl alcohol. NMR (DMSO-$d_6$) δ 9.80 (s, 1H), 9.58 (s, 1H), 8.79 (m, 1H), 8.71 (m, 2H), 8.11 (d, 1H), 7.95 (t, 1H), 7.48 (bs, 1H), 7.20 (m, 2H), 6.85 (bs, 2H), 4.23 (d, 2H), 3.45 (m, 4H), 1.69 (bs, 4H), 1.50 (bs, 4H); MS (ESI) (M+H)$^+$ 375.

EXAMPLE 110

N-[3-fluoro-4-(1-pyrrolidinyl)benzyl]-N'-5-isoquinolinylurea

The title compound was prepared using the procedure described in Example 61B using 3-fluoro-4-(1-pyrrolidinyl)benzylamine instead of 4-cyanobenzyl alcohol. NMR (DMSO-$d_6$) δ 9.82 (s, 1H), 9.72 (s, 1H), 8.85 (d, 1H), 8.70 (m, 2H), 8.14 (d, 1H), 7.95 (t, 1H), 7.64 (bs, 1H), 7.03 (m, 2H), 6.75 (t, 1H), 4.25 (d, 2H), 3.30 (m, 4H), 1.74 (m, 4H); MS (ESI) (M+H)$^+$ 365.

EXAMPLE 111

N-[4-(1-azepanyl)-3-fluorobenzyl]-N'-5-isoquinolinylurea

The title compound was prepared using the procedure described in Example 61B using 4-(1-azepanyl)-3-fluorobenzylamine instead of 4-cyanobenzyl alcohol. NMR (DMSO-$d_6$) δ 9.85 (s, 1H), 9.77 (s, 1H), 8.71 (m, 2H), 8.13 (d, 1H), 7.94 (t, 1H), 7.77 (bs, 1H), 7.64 (bs, 1H), 7.10–6.90 (m, 2H), 4.28 (d, 2H), 3.35 (m, 4H), 1.77 (m, 4H), 1.58 (m, 4H); MS (ESI) (M+H)$^+$ 393.

EXAMPLE 112

N-[4-(1-azocanyl)benzyl]-N'-5-isoquinolinylurea

The title compound was prepared using the procedure described in Example 61B using 4-(1-azocanyl)benzylamine instead of 4-cyanobenzyl alcohol. NMR (DMSO-$d_6$) δ 9.85

(s, 1H), 9.67 (s, 1H), 8.70 (s, 1H), 8.77 (m, 2H), 8.13 (s, 1H), 7.95 (t, 1H), 7.45 (bs, 1H), 7.17 (d, 2H), 6.63 (d, 2H), 4.23 (d, 2H), 3.43 (m, 6H), 1.68 (m, 3H), 1.44 (m, 5H); MS (ESI) (M+H)+ 389.

EXAMPLE 114

N-1H-indazol-4-yl-N'-[4-(1-piperidinyl)benzyl]urea

The title compound was prepared using the procedure described in Example 89B using 1-[4-(isocyanatomethyl) phenyl]piperidine instead of 1-bromo-4-(isocyanatomethyl) benzene. NMR (DMSO-$d_6$) δ 9.23 (s, 1H), 9.30 (s, 1H), 7.78 (d, 2H), 7.64 (d, 1H), 7.63 (d, 2H), 7.53 (s, 1H), 7.38 (bs, 1H), 7.19 (t, 1H), 7.06 (d, 1H), 4.39 (d, 2H), 3.53 (m, 4H), 1.97 (bs, 4H), 1.64 (bs, 2H); MS (ESI) (M+H)+ 350.

EXAMPLE 115

N-[3-fluoro-4-(1-piperidinyl)benzyl]-N'-1H-indazol-4-ylurea

The title compound was prepared using the procedure described in Example 89B using 1-[2-fluoro-4-(isocyanatomethyl)phenyl]piperidine instead of 1-bromo-4-(isocyanatomethyl)benzene. NMR (DMSO-$d_6$) δ 9.17 (s, 1H), 8.28 (s, 1H), 7.63 (d, 1H), 7.40–7.15 (m, 6H), 7.05 (d, 1H), 4.37 (s, 2H), 3.17 (m, 4H), 1.77 (m, 4H), 1.58 (m, 2H). 4H), 1.64 (bs, 2H); MS (ESI) (M+H)+ 368.

EXAMPLE 116

N-1H-indazol-4-yl-N'-[4-(1-pyrrolidinyl)benzyl]urea

The title compound was prepared using the procedure described in Example 89B using 1-[4-(isocyanatomethyl) phenyl]pyrrolidine instead of 1-bromo-4-(isocyanatomethyl)benzene. NMR (DMSO-$d_6$) δ 8.83 (s, 1H), 8.15 (s, 1H), 8.01 (bs, 1H), 7.63 (d, 1H), 7.21 (m, 3H), 7.04 (d, 1H), 6.70 (bs, 1H), 6.63 (m, 1H), 6.56 (d, 1H), 4.12 (d, 2H), 3.13 (m, 4H), 1.97 (m, 4H); MS (ESI) (M+H)+ 336.

EXAMPLE 117

N-[3-fluoro-4-(1-pyrrolidinyl)benzyl]-N'-1H-indazol-4-ylurea

The title compound was prepared using the procedure described in Example 89B using 1-[2-fluoro-4-(isocyanatomethyl)phenyl]pyrrolidine instead of 1-bromo-4-(isocyanatomethyl)benzene. NMR (DMSO-$d_6$) δ 9.89 (s, 1H), 8.17 (s, 1H), 7.63 (d, 1H), 7.19 (t, 1H), 7.07 (m, 1H), 7.02 (d, 1H), 6.99 (s, 1H), 6.93 (bs, 2H), 6.74 (t, 1H), 4.23 (s, 2H), 3.29 (m, 4H), 1.87 (m, 4H); MS (ESI) (M+H)+ 354.

EXAMPLE 118

N-[4-(1-azepanyl)benzyl]-N'-1H-indazol-4-ylurea

The title compound was prepared using the procedure described in Example 89B using 1-[4-(isocyanatomethyl) phenyl]azepane instead of 1-bromo-4-(isocyanatomethyl) benzene. NMR (DMSO-$d_6$) δ 8.86 (s, 1H), 8.17 (s, 1H), 8.00 (bs, 1H), 7.64 (d, 1H), 7.20 (m, 3H), 7.02 (d, 1H), 6.25 (bs, 2H), 6.70 (d, 1H), 4.21 (s, 2H), 1.88 (m, 6H), 1.47 (m, 6H); MS (ESI) (M+H)+ 364.

764293 Example 119

N-[4-(1-azepanyl)-3-fluorobenzyl]-N'-1H-indazol-4-ylurea

The title compound was prepared using the procedure described in Example 89B using 1-[2-fluoro-4-(isocyanatomethyl)phenyl]azepane instead of 1-bromo-4-(isocyanatomethyl)benzene. NMR (DMSO-$d_6$) δ 9.04 (s, 1H), 8.13 (s, 1H), 7.63 (d, 1H), 7.19 (t, 1H), 7.10 (s, 1H), 7.02 (d, 4H), 4.23 (s, 2H), 3.37 (m, 4H), 1.79 (m, 4H), 1.57 (m, 4H); MS (ESI) (M+H)+ 382.

EXAMPLE 120

N-(1-methyl-1H-indazol-4-yl)-N'-[4-(1-piperidinyl) benzyl]urea

The title compound was prepared using the procedure described in Example 89B using 1-[4-(isocyanatomethyl) phenyl]piperidine and 1-methyl-1H-indazol-4-amine instead of 1-bromo-4-(isocyanatomethyl)benzene and the product from Example 89A. NMR (DMSO-$d_6$) δ 9.43 (s, 1H), 8.37 (s, 1H), 7.82 (d, 2H), 7.69 (d, 1H), 7.63 (m, 3H), 7.22 (t, 1H), 7.11 (t, 1H), 4.40 (d, 2H), 3.99 (s, 3H), 3.50 (m, 4H), 1.98 (m, 4H), 1.67 (m, 2H); MS (ESI) (M+H)+364.

EXAMPLE 121

N-[3-fluoro-4-(1-piperidinyl)benzyl]-N'-(1-methyl-1H-indazol-4-yl)urea

The title compound was prepared using the procedure described in Example 89B using 1-[2-fluoro-4-(isocyanatomethyl)phenyl]piperidine and 1-methyl-1H-indazol-4-amine instead of 1-bromo-4-(isocyanatomethyl) benzene and the product from Example 89A. NMR (DMSO-$d_6$) δ 9.19 (s, 1H), 8.22 (s, 1H), 7.25 (m, 4H), 7.18 (d, 2H), 4.31 (s, 2H), 4.00 (s, 3H), 3.15 (m, 4H), 1.77 (m, 4H), 1.66 (m, 2H); MS (ESI) (M+H)+ 382.

EXAMPLE 122

N-(1-methyl-1H-indazol-4-yl)-N'-[4-(1-pyrrolidinyl) benzyl]urea

The title compound was prepared using the procedure described in Example 89B using 1-[4-(isocyanatomethyl) phenyl]pyrrolidine and 1-methyl-1H-indazol-4-amine instead of 1-bromo-4-(isocyanatomethyl)benzene and the product from Example 89A. NMR (DMSO-$d_6$) δ 8.98 (s, 1H), 8.16 (s, 1H), 7.63 (d, 1H), 7.13 (m, 3H), 7.12 (d, 1H), 6.94 (m, 1H), 6.73 (bs, 2H), 4.23 (s, 2H), 3.99 (s, 3H), 3.24 (m, 4H), 1.98 (m, 4H); MS (ESI) (M+H)+350.

764300 Example 123

N-[3-fluoro-4-(1-pyrrolidinyl)benzyl —N'-(1-methyl-1H-indazol-4-yl)urea

The title compound was prepared using the procedure described in Example 89B using 1-[2-fluoro-4-(isocyanatomethyl)phenyl]pyrrolidine and 1-methyl-1H-indazol-4-amine instead of 1-bromo-4-(isocyanatomethyl) benzene and the product from Example 89A. NMR (DMSO-$d_6$) δ 8.98 (s, 1H), 8.18 (s, 1H), 7.63 (d, 1H), 7.12 (t, 1H), 7.10 (m, 2H), 7.01 (m, 2H), 6.75 (t, 1H), 4.22 (s, 2H), 3.99 (s, 3H), 3.30 (m, 4H), 1.89 (m, 4H); MS (ESI) (M+H)+368.

EXAMPLE 124

N-[4-(1-azepanyl)benzyl]-N'-(1-methyl-1H-indazol-4-yl)urea

The title compound was prepared using the procedure described in Example 89B using 1-[4-(isocyanatomethyl) phenyl]azepane and 1-methyl-1H-indazol-4-amine instead of 1-bromo-4-(isocyanatomethyl)benzene and the product from Example 89A. NMR (DMSO-$d_6$) δ 8.97 (s, 1H), 8.18 (s, 1H), 7.65 (d, 1H), 7.14 (m, 4H), 7.11 (d, 1H), 6.95 (bs, 2H), 4.23 (s, 2H), 3.99 (s, 3H), 3.27 (m, 4H), 1.90 (m, 4H), 1.53 (m, 4H); MS (ESI) (M+H)$^+$ 378.

EXAMPLE 125

N-[4-(1-azepanyl)-3-fluorobenzyl]-N'-(1-methyl-1H-indazol-4-yl)urea

The title compound was prepared using the procedure described in Example 89B using 1-[2-fluoro-4-(isocyanatomethyl)phenyl]azepane and 1-methyl-1H-indazol-4-amine instead of 1-bromo-4-(isocyanatomethyl)benzene and the product from Example 89A. NMR (DMSO-$d_6$) δ 9.03 (s, 1H), 8.19 (s, 1H), 7.67 (d, 1H), 7.24 (t, 1H), 7.12–6.95 (m, 5H), 4.22 (s, 2H), 3.99 (s, 3H), 3.35 (m, 4H), 1.78 (m, 4H), 1.55 (m, 4H); MS (ESI) (M+H)$^+$ 396.

EXAMPLE 126

4-methylbenzyl 5-isoquinolinylcarbamate

The title compound was prepared using the procedure described in Example 1B using 4-methylbenzyl alcohol instead of 2-(3-fluorophenyl)ethylamine. $^1$H NMR (300 MHz, $d_6$-DMSO) 9.82 (s, 1H), 9.31 (s, 1H), 8.50 (d, 1H), 7.93 (m, 3H), 7.68 (t, 1H), 7.37 (d, 2H), 7.25 (d, 2H), 5.19 (s, 2H), 2.32 (s, 3H); MS (DCI/NH$_3$) m/e 293 (M+H)$^+$.

EXAMPLE 127

N-5-isoquinolinyl-2-[4-(trifluoromethyl)phenyl]hydrazinecarboxamide

The title compound was prepared using the procedure described in Example 61B using 4-trifluoromethylphenyl hydrazine instead of 4-cyanobenzyl alcohol. $^1$H NMR (300 MHz, $d_6$-DMSO) 9.80 (m, 2H), 9.10 (broad s, 1H), 8.90–8.43 (m, 3H), 8.40 (broad s, 1H), 8.20 (d, 1H), 7.93 (t, 1H), 7.58 (d, 2H), 6.96 (d, 2H); MS (DCI/NH$_3$) m/e 347 (M+H)$^+$; Anal. Calcd. For C$_{17}$H$_{13}$N$_4$OF$_3$. 1.0 HCl 0.1H$_2$O: C, 53.09; H, 3.72; N, 14.57. Found: C, 52.80; H, 3.81; N, 14.51.

EXAMPLE 128

4-bromobenzyl 5-isoquinolinylcarbamate

The title compound was prepared using the procedure described in Example 1B using 4-bromobenzyl alcohol instead of 2-(3-fluorophenyl)ethylamine. $^1$H NMR (300 MHz, $d_6$-DMSO) 10.23 (s, 1H), 9.86 (s, 1H), 8.69 (d, 1H), 8.50 (d, 1H), 8.30 (d, 2H), 7.98 (t, 1H), 7.60 (m, 2H), 7.44 (d, 2H), 5.20 (s, 2H); MS (DCI/NH$_3$) m/e 357 (M+H)$^+$; Anal. Calcd. For C$_{17}$H$_{13}$N$_2$O$_2$Br. 1.0 HCl: C, 51.87; H, 3.58; N, 7.12. Found: C, 51.95; H, 3.45; N, 7.03.

EXAMPLE 129

N-benzhydryl-N'-5-isoquinolinylurea

The title compound was prepared using the procedure described in Example 61B using benzhydrylamine instead of 4-cyanobenzyl alcohol. $^1$H NMR (300 MHz, $d_6$-DMSO) 9.26 (s, 1H), 8.78 (s, 1H), 8.57 (d, 1H), 8.31 (m, 1H), 7.94 (d, 1H), 7.70 (d, 1H), 7.60 (m, 2H), 7.38 (m, 8H), 7.27 (m, 2H), 6.02 (d, 1H); MS (DCI/NH$_3$) m/e 354 (M+H)$^+$; Anal. Calcd. For C$_{23}$H$_{19}$N$_3$O.0.1H$_2$O: C, 77.77; H, 5.45; N, 11.83. Found: C, 77.52; H, 5.30; N, 11.98.

EXAMPLE 130

N-[(1S)-1-(4-bromophenyl)ethyl]-N'-5-isoquinolinylurea

The title compound was prepared using the procedure described in Example 61B using (1S)-1-(4-bromophenyl)ethanamine instead of 4-cyanobenzyl alcohol. $^1$H NMR (300 MHz, $d_6$-DMSO) 9.78 (s, 1H), 9.46 (s, 1H), 8.70 (s, 2H), 8.59 (d, 1H), 8.04 (d, 1H), 7.84 (t, 1H), 7.75 (d, 1H), 7.58 (d, 2H), 7.40 (d, 2H), 4.85 (m, 1H), 1.40 (d, 3H); MS (DCI/NH$_3$) m/e 370 (M+H)$^+$. Anal. Calcd. For C$_{18}$H$_{16}$N$_3$OBr. 1.2 HCl: C, 52.22; H, 4.19; N, 10.15. Found: C, 51.86; H, 4.28; N, 9.78.

EXAMPLE 131

N-[(1R)-1-(4-bromophenyl)ethyl]-N'-5-isoquinolinylurea

The title compound was prepared using the procedure described in Example 61B using (1R)-1-(4-bromophenyl)ethanamine instead of 4-cyanobenzyl alcohol. $^1$H NMR (300 MHz, $d_6$-DMSO) 9.65 (s, 1H), 9.46 (s, 1H), 8.71 (s, 2H), 8.60 (d, 1H), 8.04 (d, 1H), 7.84 (t, 1H), 7.78 (d, 1H), 7.58 (d, 2H), 7.38 (d, 2H), 4.87 (m, 1H), 1.40 (d, 3H); MS (DCI/NH$_3$) m/e 370 (M+H)$^+$; Anal. Calcd. For C$_{18}$H$_{16}$N$_3$OBr. 1.1 HCl: C, 52.69; H, 4.20; N, 10.24. Found: C, 52.52; H, 4.28; N, 10.00.

EXAMPLE 132

N-(4-bromobenzyl)-2-(3-methyl-5-isoquinolinyl)acetamide

EXAMPLE 132A 5-allyl-3-methylisoquinoline

3-Methyl-5-bromoisoquinoline (1.0 g, 4.5 mmol), tributylallyltin (1.6 mL, 5.0 mmol), and dichlrobis(tri-o-tolylphosphine)palladium (II) were combined in toluene (100 mL) and refluxed for 14 hours. The mixture was cooled, diluted with ethyl acetate, and washed twice with aqueous NH$_4$Cl. The organic phase was separated, concentrated, and the residue was purified by chromatography (ethyl acetate:hexanes, 30:70) to provide the title compound. $^1$H NMR (300 MHz, $d_6$-DMSO) 9.21 (s, 1H), 8.00 (d, 1H), 7.63 (m, 2H), 7.58 (m, 1H), 4.18 (s, 2H), 3.62 (s, 3H), 2.62 (s, 3H). MS (DCI/NH$_3$) m/e 216 (M+H)$^+$.

EXAMPLE 132B methyl (3-methyl-5-isoquinolinyl)acetate

The product from Example 132A (0.8 g, 4.37 mmol) in CH$_2$CL$_2$ (40 mL) and 2.5 MNaOH in MeOH (9 mL, 22 mmol, 5 eq.) was ozonized at −78° C. for 3 hours. The mixture was diluted with diethyl ether and washed with aqueous NH$_4$Cl. The organic phase was separated, concentrated, and the residue was purified by chromatography (ethyl acetate:hexanes, 40:60) to provide the title compound. $^1$H NMR (300 MHz, $d_6$-DMSO) 9.20 (s, 1H), 7.92 (d, 1H), 7.73 (s, 1H), 7.55 (m, 2H), 6.08 (m, 1H), 5.15–5.04 (m, 2H), 3.80 (d, 2H), 2.63 (s, 3H); MS (DCI/NH$_3$) m/e 184 (M+H)$^+$.

EXAMPLE 132C

N-(4-bromobenzyl)-2-(3-methyl-5-isoquinolinyl)acetamide

4-Bromobenzylamine (3.06 mmol) in CH$_2$Cl$_2$ (30 mL) was treated with 2M Me$_3$Al (1.53 mL, 3.06 mmol) in toluene. After 30 minutes, the mixture was treated with the product from Example 132B (0.33 g, 1.53 mmol) and refluxed for 16 hours. The mixture was cooled, quenched with 1N HCl, diluted with ethyl acetate, and washed with water, aqueous NaHCO$_3$ and aqueous NH$_4$Cl. The organic phase was evaporated and the residue dissolved in CH$_2$Cl$_2$:MeOH and 1M HCl (3 mL) in diethyl ether. After stirring for 2 hours, the mixture was concentrated under reduced pressure to provide the title compound. $^1$H NMR (300 MHz, d$_6$-DMSO) 9.75 (s, 1H), 8.92 (m, 1H), 8.30 (m, 2H), 8.00 (d, 1H), 7.82 (m, 1H), 7.60 (d, 2H), 7.20 (d, 2H), 4.22 (d, 2H), 4.08 (s, 2H), 2.78 (s, 3H); MS (DCI/NH$_3$) m/e 369 (M+H)$^+$; Anal. Calcd. For C$_{19}$H$_{17}$N$_2$OBr.2.0 HCl.1.7H$_2$O: C, 48.27; H, 4.78; N, 5.92. Found: C, 47.89; H, 4.21; N, 6.32.

EXAMPLE 133

N-(4-bromobenzyl)-2-(5-isoquinolinyl)acetamide

EXAMPLE 133A 5-allylisoquinoline

The title compound was prepared using the procedure described in Example 132A using 5-bromoisoquinoline instead of 3-methyl-5-bromoisoquinoline.

EXAMPLE 133B methyl 5-isoquinolinylacetate

The title compound was prepared using the procedure described in Example 132B using the product from Example 133A instead of the product from Example 132A.

EXAMPLE 133C

N-(4-bromobenzyl)-2-(5-isoquinolinyl)acetamide

The title compound was prepared using the procedure described in Example 132C using the product from Example 133B instead of the product from Example 132B. $^1$H NMR (300 MHz, d$_6$-DMSO) 9.78 (s, 1H), 8.85 (m, 1H), 8.68 (d, 1H), 8.42 (d, 1H), 7.90 (d, 1H), 8.01 (d, 1H), 7.94 (m, 1H), 7.52 (d, 2H), 7.20 (d, 2H), 4.22 (d, 2H), 4.10 (s, 2H); MS (DCI/NH$_3$) m/e 355 (M+H)$^+$; Anal. Calcd. For C$_{18}$H$_{15}$N$_2$OBr. 1.0 HCl. 0.3H$_2$O: C, 54.44; H, 4.21; N, 7.05. Found: C, 54.11; H, 4.18; N, 6.86.

EXAMPLE 134

N-[1-(4-bromophenyl)ethyl]-2-(5-isoquinolinyl) acetamide

The title compound was prepared using the procedure described in Example 132C using the product from Example 133B and 1-(4-bromophenyl)ethanamine instead of the product from Example 132B and 4-bromobenzylamine. $^1$H NMR (300 MHz, d$_6$-DMSO) 9.81 (s, 1H), 9.00 (d, 1H), 8.70 (d, 1H), 8.48 (d, 1H), 8.40 (d, 1H), 8.04 (d, 1H), 7.92 (m, 1H), 7.51 (d, 2H), 7.23 (d, 2H), 4.84 (m, 1H), 4.10 (s, 2H), 1.35 (d, 3H). MS (DCI/NH$_3$) m/e 369 (M+H)$^+$; Anal. Calcd. For C$_{19}$H$_{17}$N$_2$OBr.1.0 HCl.1.0H$_2$O: C, 53.86; H, 4.76; N, 6.61. Found: C, 53.47; H, 4.53; N, 6.76.

EXAMPLE 135

N-[1-(4-bromophenyl)ethyl]-2-(3-methyl-5-isoquinolinyl)acetamide

The title compound was prepared using the procedure described in Example 132C using 1-(4-bromophenyl) ethanamine instead of 4-bromobenzylamine. $^1$H NMR (300 MHz, d$_6$-DMSO) 9.68 (s, 1H), 8.84 (d, 1H), 8.24 (m, 2H), 7.92 (d, 1H), 7.80 (m, 1H), 7.50 (d, 2H), 7.28 (d, 2H), 4.02 (s, 2H), 2.75 (s, 3H), 1.38 (s, 3H); MS (DCI/NH$_3$) m/e 383 (M+H)$^+$; Anal. Calcd. For C$_{20}$H$_{19}$N$_2$OBr. 0.9 HCl: C, 57.73; H, 4.82; N, 6.73. Found: C, 57.69; H, 4.80; N, 6.07.

EXAMPLE 136

N-5-isoquinolinyl-N'-{1-[4-(trifluoromethyl)phenyl] ethyl}urea

EXAMPLE 136A

1-[4-(trifluoromethyl)phenyl]ethanone oxime

4-Trifluoromethylacetophenone (13.6 g, 72.3 mmol) and O-methylhydroxylamine hydrochloride were combined in pyridine (100 mL) and stirred at ambient temperature for 16 hours. The mixture was concentrated under reduced pressure and the residue was suspended in diethyl ether. The suspension was filtered and the filter cake was washed with diethyl ether. The filtrate was washed with water, 1N HCl, and water. The organic phase was concentrated to provide the title compound. $^1$H NMR (300 MHz, d$_6$-DMSO) 7.90–7.68 (m, 4H), 3.97 and 3.78 (2s, 1H), 2.20 and 2.17 (2s, 3H); MS (DCI/NH$_3$) m/e 218 (M+H)$^+$.

EXAMPLE 136B

1-[4-(trifluoromethyl)phenyl]ethanamine

The product from Example 136A (21.0 g, 100 mmol) in MeOH (220 mL) and ammonia (30 mL) was treated with 10% Pd/C under 60 psi of hydrogen gas for 2 hours. The mixture was filtered and the filtrate was concentrated to provide the title compound. $^1$H NMR (300 MHz, d$_6$-DMSO) 7.60 (q, 4H), 4.07 (q, 1H), 3.28 (broad s, 2H), 1.24 (d, 3H); MS (DCI/NH$_3$) m/e 190 (M+H)$^+$.

EXAMPLE 136C

N-5-isoquinolinyl-N'-{1-[4-(trifluoromethyl)phenyl] ethyl}urea

The title compound was prepared using the procedure described in Example 61B using the product from Example 136B instead of 4-cyanobenzyl alcohol. $^1$H NMR (300 MHz, d$_6$-DMSO) 9.80 (s, 1H), 9.75 (s, 1H), 8.90 (d, 1H), 8.73 (d, 1H), 8.63 (d, 1H), 8.08 (m, 2H), 7.90 (t, 1H), 7.77 (d, 2H), 7.64 (d, 2H), 4.95 (m, 1H), 1.41 (d, 3H); MS (DCI/NH$_3$) m/e 360 (M+H)$^+$; Anal. Calcd. For C$_{19}$H$_{16}$N$_3$OF$_3$.1.0 HCl.0.3H$_2$O: C, 56.88; H, 4.42; N, 10.47. Found: C, 56.61; H, 4.49; N, 10.28.

EXAMPLE 138

(−) N-5-isouinolinyl-N'-{(1S)-1-[4-(trifluoromethyl) phenyl]ethyl}urea

EXAMPLE 138A (1R)-2-oxo-1-phenyl-2-({1-[4-(trifluoromethyl) phenyl]ethyl}amino)ethyl acetate 1-[4-(Trifluoromethyl)phenyl]ethanamine (37.5 g, 198.4 mmol) and (R)-acetylmandelic acid (40.4 g, 208.3 mmol, 1.05 eq.) were combined in DMAP (0.7 g, 5.7 mmol) and treated with DCC (45.0 g, 218 mmol). After stirring overnight at ambient temperature, the mixture was filtered through a plug of silica. The filtrate was concentrated and the residue was purified by chromatography on Biotage Flash 75 column (ethyl acetate:hexanes, 25:75) to provide a faster running diastereomer and a slower running diastereomer. (fast diastereomer) $^1$H NMR (300 MHz, CDCl$_3$) 7.58 (d, 2H), 7.39 (m, 7H), 6.30 broad (d, 1H), 6.08 (s, 1H), 5.18 (m, 1H), 2.20 (s, 3H), 1.29 (d, 3H); MS (DCI/NH$_3$) m/e 366 (M+H)$^+$. (slow diastereomer) $^1$H NMR (300 MHz, CDCl$_3$) 7.58 (d, 2H), 7.40 (m, 5H), 7.31 (d, 2H), 6.21 (broad d, 1H), 6.06 (s, 1H), 5.18 (m, 1H), 2.20 (s, 3H), 1.50 (d, 3H); MS (DCI/NH$_3$) m/e 366 (M+H)$^+$.

EXAMPLE 138B (−) 1-[4-(trifluoromethyl)phenyl]ethanamine

The faster running diastereomer from Example 138A (29.2 g, 80 mmol) was treated with 48% aqueous HBr (350 mL) and water (50 mL) and was refluxed for 16 hours. The mixture was cooled and extracted with diethyl ether. The aqueous phase was basified with 2N NaOH (pH 12–13) and extracted with diethyl ether. The organic phase was concentrated to provide the title compound. 94% ee (by Mosher amide NMR). [α]$_D$ −19.1° (c 1.15; MeOH); $^1$H NMR (300 MHz, CDCl$_3$) 7.60 (d, 2H), 7.47 (d, 2H), 4.20 (m, 1H), 1.65 (br s, 2H), 1.40 (s, 3H); MS (DCI/NH$_3$) m/e 190 (M+H)$^+$.

EXAMPLE 138C (+) 1-[4-(trifluoromethyl)phenyl]ethanamine

The slower running diastereomer from Example 138A (29.2 g, 80 mmol) was treated with 48% aqueous HBr (350 mL) and water (50 mL) and was refluxed for 16 hours. The mixture was cooled and extracted with diethyl ether. The aqueous phase was basified with 2N NaOH (pH 12–13) and extracted with diethyl ether. The organic phase was concentrated to provide the title compound. [α]$_D$ +20.5° (c 1.47; MeOH). 94% ee (Mosher amide NMR); $^1$H NMR (300 MHz, CDCl$_3$) 7.60 (d, 2H), 7.47 (d, 2H), 4.20 (m, 1H), 1.60 (br s, 2H), 1.40 (s, 3H); MS (DCI/NH$_3$) m/e 190 (M+H)$^+$.

EXAMPLE 138D (−) N-5-isouinolinyl-N'-{(1S)-1-[4-(trifluoromethyl)phenyl]ethyl}urea The title compound was prepared using the procedure described in Example 61B using the product from Example 138B instead of 4-cyanobenzyl alcohol. $^1$H NMR (300 MHz, d$_6$-DMSO) 9.90 (s, 1H), 9.83 (s, 1H), 9.00 (d, 1H), 8.72 (d, 1H), 8.66 (d, 1H), 8.23 (d, 1H), 8.10 (d, 1H), 7.90 (t, 1H), 7.72 (d, 2H), 7.64 (d, 2H), 4.98 (m, 1H), 1.43 (d, 3H); MS (DCI/NH$_3$) m/e 360 (M+H)$^+$; [α]$_D$ −18.4° (c 1.24; MeOH); Anal. Calcd. For C$_{19}$H$_{16}$N$_3$OF$_3$. 1.0 HCl. 0.7H$_2$O: C, 55.88; H, 4.54; N, 10.29. Found: C, 55.70; H, 4.40; N, 10.12.

EXAMPLE 139

(+) N-5-isoquinolinyl-N'-{(1S)-1-[4-(trifluoromethyl)phenyl]ethyl}urea

The title compound was prepared using the procedure described in Example 61B using the product from Example 138C instead of 4-cyanobenzyl alcohol. $^1$H NMR (300 MHz, d$_6$-DMSO) 9.90 (s, 2H), 8.98 (d, 1H), 8.72 (d, 1H), 8.66 (d, 1H), 8.19 (d, 1H), 8.10 (d, 1H), 7.90 (t, 1H), 7.72 (d, 2H), 7.64 (d, 2H), 4.98 (m, 1H), 1.43 (d, 3H); MS (DCI/NH$_3$) m/e 360 (M+H)$^+$. [α]$_D$ +17.0° (c 1.55; MeOH); Anal. Calcd. For C$_{19}$H$_{16}$N$_3$OF$_3$. 1.0 HCl. 0.4H$_2$O: C, 56.63; H, 4.45; N, 10.43. Found: C, 56.43; H, 4.52; N, 10.24.

EXAMPLE 140

N-[1-(4-tert-butylphenyl)ethyl]-N'-5-isoquinolinylurea

EXAMPLE 140A 1-(4-tert-butylphenyl)ethanamine

The title compound was prepared using 1-(4-tert-butylphenyl)ethanone and the procedures described in Examples 136A and 136B Example 140B N-[1-(4-tert-butylphenyl)ethyl]-N'-5-isoquinolinylurea The title compound was prepared using the procedure described in Example 61B using the product from Example 140A instead of 4-cyanobenzyl alcohol. $^1$H NMR (300 MHz, d$_6$-DMSO) 9.88 (s, 1H), 9.72 (broad s, 1H), 8.90 (d, 1H), 8.70 (d, 1H), 8.64 (d, 1H), 8.07 (d, 1H), 7.87 (t, 1H), 7.78 (d, 1H), 7.38 (m, 4H), 4.94 (m, 1H), 1.42 (d, 3H), 1.27 (s, 9H); MS (DCI/NH$_3$) m/e 348 (M+H)$^+$; Anal. Calcd. For C$_{22}$H$_{25}$N$_3$O.1.0 HCl.0.6H$_2$O: C, 66.94; H, 6.96; N, 10.65. Found: C, 66.69; H, 6.92; N, 10.52.

EXAMPLE 141

N-1 cyclopropyl[4-(trifluoromethyl)phenyl]methyl]-N'-5-isoquinolinylurea

EXAMPLE 141A

N-methoxy-N-methyl-4-(trifluoromethyl)benzamide 4-(Trifluoromethyl)benzoyl chloride (5.0 g, 23.9 mmol) and N,O-dimethylhydroxylamine hydrochloride (2.55 g, 26.3 mmol, 1.1 eq.) were combined in CH$_2$Cl$_2$ (200 mL) at 0° C. and treated with pyridine (4.3 mL, 52.6 mmol). After stirring for 2 hours, the mixture was allowed to attain ambient temperature, diluted with diethyl ether and washed with water, aqueous HCl, and water. the organic phase was separated and concentrated to provide the title compound which was used directly in the next step. $^1$H NMR (300 MHz, d$_6$-DMSO) 7.90 (m, 4H), 3.52 (s, 3H), 3.28 (s, 3H); MS (DCI/NH$_3$) m/e 234 (M+H)$^+$.

EXAMPLE 141B cyclopropyl[4-(trifluoromethyl)phenyl]methanone

The product from Example 141A (1.02 g, 4.38 mmol) in THF (50 mL) at 0° C. was treated with 0.8M solution of cyclopropylmagnesium bromide (7.1 mL, 5.7 mmol, 1.3 eq.) in THF. After stirring for 1 hour, the mixture was treated with water (5 mL), 3N HCl (0.5 mL), diluted with diethyl ether, and washed with water. The organic phase was separated, evaporated, and and the residue was purified by chromatography (ethyl acetate:hexanes, 5:95) to provide the title compound. $^1$H NMR (300 MHz, d$_6$-DMSO) 8.24 (d, 2H), 7.92 (d, 2H), 2.92 (m, 1H), 1.10 (m, 4H).

EXAMPLE 141C 1-cyclopropyl-1-[4-(trifluoromethyl)phenyl]methanamine

The title compound was prepared using the product from Example 141 B and the procedures described in Examples 136A and 136B. $^1$H NMR (300 MHz, d$_6$-DMSO) 7.92 (m, 4H), 3.24 (d, 1H), 1.92 (broad s, 2H), 0.93 (m, 1H), 0.50–0.27 (m, 4H); MS (DCI/NH$_3$) m/e 216 (M+H)$^+$.

EXAMPLE 141D

N-{cyclopropyl [4-(trifluoromethyl)phenyl]methyl}-N'-5-isoquinolinylurea

The title compound was prepared using the procedure described in Example 61B using the product from Example 141C instead of 4-cyanobenzyl alcohol. $^1$H NMR (300 MHz, d$_6$-DMSO) 9.78 (s, 1H), 9.63 (s, 1H), 8.80 (d, 1H), 8.70 (d, 1H), 8.60 (d, 1H), 8.07 (m, 2H), 7.86 (t, 1H), 7.73 (d, 2H), 7.63 (d, 2H), 4.37 (t, 1H), 1.10 (m, 1H), 0.60–0.40 (m, 4H); MS (DCI/NH$_3$) m/e 386 (M+H)$^+$; Anal. Calcd. For C$_{21}$H$_{18}$N$_3$OF$_3$.1.0 HCl.0.25H$_2$O: C, 59.16; H, 4.81; N, 9.86. Found: C, 58.81; H, 4.76; N, 9.62.

EXAMPLE 142

(2E)-N-5-isoquinolinyl-3-[4-(trifluoromethyl)phenyl]-2-butenamide

EXAMPLE 142A ethyl (2E)-3-[4-(trifluoromethyl)phenyl]-2-butenoate

A suspension of 98% NaH (0.81 g, 33.7 mmol) in THF (100 mL) at ambient temperature was treated with triethyl phosphonate (6.9 g, 31 mmol) dropwise and the resulting mixture was stirred for 15 minutes. The mixture was treated with 1-[4-(trifluoromethyl)phenyl]ethanone (5.0 g, 26.6 mmol) portion wise and refluxed for 6 hours. After cooling to ambient temperature, the mixture was quenched with aqueous NH$_4$Cl, diluted with diethyl ether, and washed with water and aqueous NH$_4$Cl. The organic phase was separated, concentrated, and the residue purified by chromatography (ethyl acetate:hexanes, 2:98) to provide the (E) isomer (3.4 g, 50%) and the (Z) isomer (1.3 g, 19%). Geometry of the double bond was established by NOE studies. (E) isomer: $^1$H NMR for (300 MHz, d$_6$-DMSO) 7.78 (m, 4H), 6.25 (m, 1H), 4.19, (q, 2H), 2.51, (s, 3H), 1.22 (t, 3H); MS (DCI/NH$_3$) m/e 259 (M+H)$^+$.

EXAMPLE 142B ethyl (2Z)-3-[4-(trifluoromethyl)phenyl]-2-butenoate

The title compound was isolated from the chromatography described in Example 142A. (Z) isomer: $^1$H NMR (300 MHz, d$_6$-DMSO) 7.71 (d, 2H), 7.42 (d, 2H), 6.03 (m, 1H), 3.90 (q, 2H), 2.18 (d, 3H), 1.00 (t, 3H); MS (DCI/NH$_3$) m/e 259 (M+H)$^+$.

EXAMPLE 142C (2E)-3-[4-(trifluoromethyl)phenyl]-2-butenoic acid

The product from Example 142A (3.5 g, 13.5 mmol) in EtOH (80 mL) was treated with aqueous 1M NaOH (40 mL) and stirred for 16 hours at ambient temperature. The reaction mixture was neutralized with 1N HCl (40 mL), diluted with brine, and extracted with diethyl ether to provide the title compound. NMR (CDCl$_3$) 2.60 (s, 3H), 6.82 (s, 1H), 7.58 (d, 2H), 7.65 (d, 2H).

EXAMPLE 142D (2E)-N-5-isoquinolinyl-3-[4-(trifluoromethyl)phenyl]-2-butenamide The product from Example 142C (0.23 g, 1.00 mmol) in CH$_2$Cl$_2$ (5 mL) was treated with oxalyl chloride (0.15 g, 1.2 mmol), 1 drop of DMF, and stirred at ambient temperature for 45 minutes. The mixture was treated with a solution of 5-aminoisoquinoline (0.14 g, 1.0 mmol) and 98% NaH (0.048 g, 1.2 mmol) in DMF (5 mL) prepared separately by stirring for 45 minutes. The resulting mixture was stirred for 15 minutes, poured into water, and extracted with CH$_2$Cl$_2$. The organic phase was dried (MgSO$_4$), evaporated, and the residue triturated with diethyl ether. The solid was dried under reduced pressure to provide the title compound. $^1$H NMR (300 MHz, d$_6$-DMSO) 2.61 (s, 3H), 2.73 (s, 0.45H, DMF)), 2.89 (s, 0.45H (DMF)), 6.82 (br s, 1H), 7.70 (t, 1H), 7.83 (s, 4H), 7.95 (d, 1H), 8.04 (d, 1H), 8.21 (d, 1H), 8.56 (d, 1H), 9.33 (s, 1H), 10.20 (s, 1H); MS (ESI+) 357 (M+H)$^+$; Elemental: Calculated for C$_{20}$H$_{15}$N$_2$OF$_3$.HCl.0.15C$_3$H$_7$NO: C, 66.87, H, 4.40, N, 8.20; Found: C, 66.83, H, 4.20, N, 8.27.

EXAMPLE 143

N-5-isoquinolinyl-3-[4-(trifluoromethyl)phenyl]-3-butenamide

The title compound was isolated from the procedure described Example 142D as a side-product. $^1$H NMR (300 MHz, d$_6$-DMSO) 3.83 (s, 2H), 5.49 (s, 1H), 5.74 (s, 1H), 7.64 (t, 1H), 7.77 (m, 4H), 7.93 (m, 2H), 8.49 (d, 1H), 9.30 (s, 1H), 10.18 (s, 1H); MS (ESI+) 357 (M+H)$^+$; Elemental: Calculated for C$_{20}$H$_{15}$N$_2$OF$_3$.0.6H$_2$O: C, 65.43, H, 4.45, N, 7.63; Found: C, 65.49, H, 4.08, N, 7.93.

EXAMPLE 144

(2Z)-N-5-isoquinolinyl-3-[4-(trifluoromethyl)phenyl]-2-butenamide

EXAMPLE 144A (2Z)-3-[4-(trifluoromethyl)phenyl]-2-butenoic acid

The title compound was prepared using the procedure described in Example 142C using the product from Example 142B instead of the product from Example 142A.

EXAMPLE 144B (2Z)-N-5-isoquinolinyl-3-[4-(trifluoromethyl)phenyl]-2-butenamide The title compound was prepared using the procedure described in Example 142D using the product from Example 144A instead of the product from Example 142C. $^1$H NMR (300 MHz, d$_6$-DMSO) 2.21 (s, 3H), 6.48 (s, 1H), 7.50 (d, 2H), 7.60 (t, 1H), 7.67 (d, 2H), 7.90 (d, 1H), 7.95 (d, 1H), 8.44 (d, 1H), 9.27 (s, 1H), 10.03 (s, 1H); MS (ESI+) 357 (M+H)$^+$; Elemental: Calculated for C$_{20}$H$_{15}$N$_2$OF$_3$: C, 67.41, H, 4.24, N, 7.86; Found: C, 67.16, H, 4.15, N, 7.59.

EXAMPLE 145

(2E)-3-[3-fluoro-4-(trifluoromethyl)phenyl]-N-5-isoquinolinyl-2-butenamide

EXAMPLE 145A (2E)-3-[3-fluoro-4-(trifluoromethyl)phenyl]-2-butenoic acid

The title compound was prepared using 1-[3-fluoro-4-(trifluoromethyl)phenyl]ethanone and the procedures described in Examples 142A and 142C.

EXAMPLE 145B (2E)-3-[3-fluoro-4-(trifluoromethyl)phenyl]-2-butenoic acid

The title compound was prepared using the procedure described in 142D using the product from Example 145A instead of the product from Example 142C. $^1$H NMR (300 MHz, d$_6$-DMSO) 2.59 (s, 3H), 6.92 (s, 1H), 7.68 (d, 1H), 7.78 (d, 1H), 7.93 (m, 2H), 8.25 (d, 1H), 8.44 (d, 1H), 8.49 (d, 1H), 8.70 (d, 1H), 9.76 (s, 1H), 10.59 (s, 1H); MS (ESI+) 375 (M+H)$^+$; Elemental: Calculated for C$_{20}$H$_{14}$N$_2$OF$_4$.1.6HCl: C, 55.52, H, 3.63, N, 6.47; Found: C, 55.60, H, 3.80, N, 6.09.

EXAMPLE 146

3-[3-fluoro-4-(trifluoromethyl)phenyl]-N-5-isoquinolinyl-3-butenamide

The title compound was isolated from the procedure described in Example 145B as a side-product. $^1$H NMR (300 MHz, d$_6$-DMSO) 3.88 (s, 2H), 5.57 (s, 1H), 5.86 (s, 1H), 7.60–7.88 (m, 4H), 8.18 (m, 3H), 8.64 (d, 1H), 9.65 (s, 1H), 10.50 (s, 1H); MS (ESI+) 375 (M+H)$^+$; Elemental: Calculated for C$_{20}$H$_{14}$N$_2$OF$_4$.HCl.0.2NH$_4$Cl: C, 56.99, H, 3.78, N, 7.31; Found: C, 56.73, H, 3.69, N, 7.43.

768062 Example 147

(2E)-N-5-isoquinolinyl-3-[4-(1-piperidinyl)phenyl]-2-butenamide

EXAMPLE 147A (2E)-3-[4-(1-piperidinyl)phenyl]-2-butenoic acid

The title compound was prepared using 1-[4-(1-piperidinyl)phenyl]ethanone and the procedures described in Examples 142A and 142C.

EXAMPLE 147B (2E)-N-5-isoquinolinyl-3-[4-(1-piperidinyl)phenyl]-2-butenamide The title compound was prepared using the procedure described in 142D using the product from Example 147A instead of the product from Example 142C. $^1$H NMR (300 MHz, d$_6$-DMSO) 10.50 (s, 1H), 9.82 (s, 1H), 8.71 (d, 1H), 8.58 (d, 1H), 8.47 (d, 1H), 8.26 (d, 1H), 7.95 (m, 2H), 7.62 (m, 2H), 6.80 (s, 1H), 3.20 (m, 4H), 2.58 (s, 3H), 1.90–1.56 (m, 6H); MS (DCI/NH$_3$) m/e 372 (M+H)$^+$; Anal. Calcd. For C$_{24}$H$_{25}$N$_3$O.2.0 HCl.2.0H$_2$O.0.3 DMF: C, 59.24; H, 6.69; N, 9.27. Found: C, 59.44; H, 6.83; N, 9.24.

EXAMPLE 148

N-(3-fluorobenzyl)-N'-(3-methyl-5-isoquinolinyl)urea

The title compound was prepared using the procedure described in Example 60F using 1-fluoro-3-(isocyanatomethyl)benzene and 3-methyl-5-isoquinolinamine instead of the product from Example 60E and 1-bromo-4-(isocyanatomethyl)benzene. $^1$H NMR (300 MHz, DMSO-d$_6$) δ 9.18 (s, 1H), 8.69 (bs, 1H), 8.87 (bs, 1H), 8.20 (d, 1H, J=6.9 Hz), 7.76 (s, 1H), 7.70 (d, 1H, J=7.8 Hz), 7.50 (t, 1H, J=7.8 Hz), 7.41 (m, 1H), 7.23–7.05 (m, 3H), 4.39 (d, 2H, J=6 Hz), 2.65 (s, 3H). MS (ESI) 310 (M+H)$^+$. Anal. Calcd for C$_{18}$H$_{16}$FN$_3$O: C, 69.89; H, 5.21; N, 13.58. Found: C, 69.86; H, 5.24; N, 13.56.

EXAMPLE 149

N-(4-bromo-3-fluorobenzyl)-N'-5-isoquinolinylurea

The title compound was prepared using the procedure described in Example 1B using 4-bromo-3-fluorobenzylamine instead of 2-(3-fluorophenyl)ethylamine. $^1$H NMR (300 MHz, DMSO-d$_6$) δ 9.74 (s, 1H), 9.55 (s, 1H), 8.67 (m, 2H), 8.57 (dd, 1H, J=7.8, 1.5 Hz), 8.06 (d, 1H, J=7.8 Hz), 7.88 (t, 1H, J=7.8 Hz), 7.67 (m, 2H), 7.35 (dd, 1H, J=9.6, 2.4 Hz), 7.17 (dd, 1H, J=8.7, 1.8 Hz), 4.39 (d, 2H, J=6.3 Hz). MS (ESI) 374/376 (M+H)$^+$. Anal. Calcd for C$_{17}$H$_{13}$BrFN$_3$OHCl: C, 49.72; H, 3.44; N, 10.23. Found: C, 50.04; H, 3.50; N, 10.25

EXAMPLE 150

N-(3-amino-5-isoquinolinyl)-N'-[4-(1-piperidinyl)benzyl]urea

EXAMPLE 150A

N-(3-amino-5-isoquinolinyl)-2,2,2-trichloroacetamide

The title compound was prepared using the procedure described in Example 1A using 3,5-isoquinolinediamine instead of 5-aminoisoquinoline.

EXAMPLE 150B

N-(3-amino-5-isoquinolinyl)-N'-[4-(1-piperidinyl)benzyl]urea

The title compound was prepared using the procedure described in Example 1B using 4-(1-piperidinyl)benzylamine and the product from Example 150A instead of 2-(3-fluorophenyl)ethylamine and the product from Example 1A. $^1$H NMR (300 MHz, DMSO-d$_6$) δ 8.77 (s, 1H), 8.22 (s, 1H), 7.87 (d, 1H, J=8 Hz), 7.46 (d, 1H, J=8 Hz), 7.16 (d, 2H, J=8.4 Hz), 7.07 (t, 1H, J=8 Hz), 6.91 (d, 2H, J=8.4 Hz), 6.82 (t, 1H, J=6 Hz), 6.70 (s, 1H), 5.91 (s, 2H), 4.22 (d, 2H, J=6 Hz), 3.10 (m, 4H), 1.70–1.45 (m, 6H). MS (ESI) 376 (M+H)$^+$. Anal. Calcd for C$_{22}$H$_{25}$N$_5$O.0.1H$_2$O: C, 70.04; H, 6.73; N, 18.56. Found: C, 69.66; H, 6.50; N, 18.55.

EXAMPLE 151

N-(3-amino-5-isoquinolinyl)-N'-[4-(1-azepanyl)benzyl]urea

The title compound was prepared using the procedure described in Example 1B using 4-(1-azepanyl)benzylamine and the product from Example 150A instead of 2-(3-fluorophenyl)ethylamine and the product from Example 1A. $^1$H NMR (300 MHz, DMSO-d$_6$) δ 8.77 (s, 1H), 8.19 (s, 1H), 7.88 (d, 1H, J=8.7 Hz), 7.45 (d, 1H, J=8.7 Hz), 7.09 (m, 3H), 6.76 (t, 1H, J=5.4 Hz), 6.66 (m, 3H), 5.90 (s, 2H), 4.17 (d, 2H, J=5.4 Hz), 3.24 (m, 4H), 1.71 (m, 4H), 1.44 (m, 4H); MS (ESI) 390 (M+H)$^+$; Anal. Calcd for C$_{23}$H$_{27}$N$_5$O.0.4H$_2$O: C, 69.64; H, 7.06; N, 17.65. Found: C, 69.53; H, 6.81; N, 17.38.

EXAMPLE 152

N-(1,1'-biphenyl-3-ylmethyl)-N'-5-isoquinolinylurea

The title compound was prepared using the procedure described in Example 61B using 1,1'-biphenyl-3-ylmethylamine instead of 4-cyanobenzyl alcohol. $^1$H NMR (300 MHz, DMSO-d$_6$) δ 9.73 (s, 1H), 9.47 (s, 1H), 8.64 (m, 3H), 8.05 (d, 1H, J=9 Hz), 7.87 (t, 1H, J=9 Hz), 7.68 (m, 3H), 7.58 (m, 2H), 7.47 (m, 3H), 7.37 (m, 2H), 4.48 (d, 2H, J=6 Hz); MS (ESI) 354 (M+H)$^+$. Anal. Calcd for C$_{23}$H$_{19}$N$_3$O$_0$HCl: C, 70.86; H, 5.17; N, 10.78. Found: C, 70.77; H, 5.16; N, 10.74.

EXAMPLE 153

N-5-isoquinolinyl-N'-[4-(2-pyridinyl)benzyl]urea

The title compound was prepared using the procedure described in Example 61B using 4-(2-pyridinyl)benzylamine instead of 4-cyanobenzyl alcohol. $^1$H NMR (300 MHz, DMSO-d$_6$) δ 9.83 (s, 1H), 9.81 (s, 1H), 8.88 (d, 1H, J=6.3 Hz), 8.72 (m, 3H), 8.10 (m, 5H), 7.92 (m, 2H), 7.56 (m, 3H), 4.49 (d, 2H, J=5.4 Hz); MS (ESI) 355 (M+H)$^+$; Anal. Calcd for C$_{22}$H$_{18}$N$_4$O.1.8HCl: C, 62.91; H, 4.75; N, 13.34. Found: C, 62.95; H, 4.99; N, 13.27.

EXAMPLE 154

N-(4-bromo-3-fluorobenzyl)-N'-(3-methyl-5-isoquinolinyl)urea

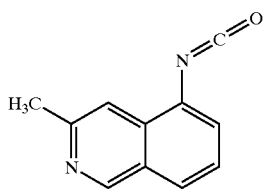

EXAMPLE 154A

5-isocyanato-3-methylisoquinoline

The title compound was prepared using the procedure described in Example 61A using 3-methyl-5-isoquinolinamine instead of 5-aminoisoquinoline.

EXAMPLE 154B

N-(4-bromo-3-fluorobenzyl)-N'-(3-methyl-5-isoquinolinyl)urea

The title compound was prepared using the procedure described in Example 61B using 4-bromo-3-fluorobenzylamine and the product from Example 154A instead of 4-cyanobenzyl alcohol and the product from Example 61A. $^1$H NMR (300 MHz, DMSO-d$_6$) δ 9.68 (s, 1H), 9.46 (s, 1H), 8.51 (m, 2H), 8.01 (d, 1H, J=7.8 Hz), 7.80 (t, 1H, J=7.8 Hz), 7.67 (m, 2H), 7.36 (dd, 1H, J=9, 1.5 Hz), 7.18 (dd, 1H, J=9, 1 Hz), 4.39 (d, 2H, J=6 Hz), 2.77 (s, 3H); MS (ESI) 388/390 (M+H)$^+$; Anal. Calcd for C$_{18}$H$_{15}$BrFN$_3$O.HCl: C, 50.91; H, 3.80; N, 9.89. Found: C, 50.81; H, 3.74; N, 9.87

EXAMPLE 155

N-[3-fluoro-4-(4-methyl-1-piperidinyl)benzyl]-N'-(3-methyl-5-isoquinolinyl)urea The title compound was prepared using the procedure described in Example 61B using 3-fluoro-4-(4-methyl-1-piperidinyl)benzylamine and the product from Example 154A instead of 4-cyanobenzyl alcohol and the product from Example 61A. $^1$H NMR (300 MHz, DMSO-d$_6$) δ 9.74 (s, 1H), 9.52 (s, 1H), 8.66 (s, 1H), 8.59 (d, 1H, J=8.4 Hz), 8.04 (d, 1H, J=8.4 Hz), 7.83 (t, 1H, J=8.4 Hz), 7.62 (t, 1H, J=6 Hz), 7.10 (m, 3H), 4.32 (d, 2H, J=6 Hz), 3.31 (m, 2H), 2.79 (s, 3H), 2.69 (m, 2H), 1.71 (m, 2H), 1.49 (m, 1H), 1.32 (m, 2H), 0.95 (d, 3H, J=6 Hz). MS (ESI) 407 (M+H)$^+$; Anal. Calcd for C$_{24}$H$_{27}$FN$_4$O.2.3HCl: C, 58.79; H, 6.02; N, 11.43. Found: C, 58.73; H, 6.18; N, 11.19.

EXAMPLE 156

N-(3-methyl-5-isoquinolinyl)-N'-[4-(4-methyl-1-piperidinyl)benzyl]urea

The title compound was prepared using the procedure described in Example 61B using 4-(4-methyl-1-piperidinyl)benzylamine and the product from Example 154A instead of 4-cyanobenzyl alcohol and the product from Example 61A. $^1$H NMR (300 MHz, DMSO-d$_6$) δ 9.70 (s, 1H), 9.66 (s, 1H), 8.74 (s, 1H), 8.59 (d, 1H, J=8.7 Hz), 8.01 (d, 1H, J=8.7 Hz), 7.82 (m, 2H), 7.65 (m, 2H), 7.48 (m, 2H), 4.40 (d, 2H, J=6 Hz), 3.54 (m, 4H), 2.78 (s, 3H), 1.90–1.50 (m, 5H), 0.98 (d, 3H, J=6 Hz); MS (ESI) 389 (M+H)$^+$; Anal. Calcd for C$_{24}$H$_{28}$N$_4$O.2.6HCl: C, 59.64; H, 6.38; N, 11.59. Found: C, 59.31; H, 6.39; N, 11.19.

EXAMPLE 157

N-[3-fluoro-4-(1-piperidinyl)benzyl]-N'-(3-methyl-5-isoquinolinyl)urea

The title compound was prepared using the procedure described in Example 61B using 3-fluoro-4-(1-piperidinyl)benzylamine and the product from Example 154A instead of 4-cyanobenzyl alcohol and the product from Example 61A. $^1$H NMR (300 MHz, DMSO-d$_6$) δ 9.73 (s, 1H), 9.47 (s, 1H), 8.62 (s, 1H), 8.58 (d, 1H, J=8.4 Hz), 8.04 (d, 1H, J=8.4 Hz), 7.83 (t, 1H, J=8.4 Hz), 7.57 (t, 1H), 7.10 (m, 3H), 4.32 (d, 2H, J=6 Hz), 2.98 (m, 4H), 2.79 (s, 3H), 1.67 (m, 4H), 1.53 (m, 2H); MS (ESI) 393 (M+H)$^+$; Anal. Calcd for C$_{23}$H$_{25}$FN$_4$O.1.5HCl: C, 61.78; H, 5.97; N, 12.53. Found: C, 61.40; H, 6.04; N, 12.18.

EXAMPLE 158

N-(3-methyl-5-isoquinolinyl)-N'-[4-(1-piperidinyl)benzyl]urea

The title compound was prepared using the procedure described in Example 61B using 4-(1-piperidinyl)benzylamine and the product from Example 154A instead of 4-cyanobenzyl alcohol and the product from Example 61A. $^1$H NMR (300 MHz, DMSO-d$_6$) δ 9.69 (s, 1H), 9.60 (s, 1H), 8.68 (s, 1H), 8.57 (d, 1H, J=7.5 Hz), 8.00 (d, 1H, J=7.5 Hz), 7.85–7.55 (m, 4H), 7.43 (m, 2H), 4.40 (d, 2H, J=6 Hz), 3.44 (m, 4H), 2.77 (s, 3H), 1.90 (m, 4H), 1.65 (m, 2H); MS (ESI) 375 (M+H)$^+$; Anal. Calcd for C$_{23}$H$_{26}$N$_4$O.2.4HCl: C, 59.80; H, 6.20; N, 12.13. Found: C, 59.91; H, 6.45; N, 11.78

EXAMPLE 159

N-[4-(1-azepanyl)benzyl]-N'-(3-methyl-5-isoquinolinyl)urea

The title compound was prepared using the procedure described in Example 61B using 4-(1-azepanyl)benzylamine and the product from Example 154A instead of 4-cyanobenzyl alcohol and the product from Example 61A. $^1$H NMR (300 MHz, DMSO-d$_6$) δ 9.16 (s, 1H), 8.53 (s, 1H), 8.28 (d, 1H, J=8 Hz), 7.74 (s, 1H), 7.67 (d, 1H, J=8 Hz), 7.50 (t, 1H, J=8 Hz), 7.14 (d, 2H, J=9 Hz), 6.84 (t, 1H, J=6 Hz), 6.66 (d, 2H, J=9 Hz), 4.20 (d, 2H, J=6 Hz), 3.44 (m, 4H), 2.63 (s, 3H), 1.71 (m, 4H), 1.45 (m, 4H). MS (ESI) 389 (M+H)$^+$; Anal. Calcd for C$_{24}$H$_{28}$N$_4$O.0.3H$_2$O: C, 73.18; H, 7.32; N, 14.22. Found: C, 73.08; H, 7.38; N, 14.22.

EXAMPLE 160

N-(3-methyl-5-isoquinolinyl)-N'-[4-(1-pyrrolidinyl)benzyl]urea

The title compound was prepared using the procedure described in Example 61B using 4-(1-pyrrolidinyl)

benzylamine and the product from Example 154A instead of 4-cyanobenzyl alcohol and the product from Example 61A. $^1$H NMR (300 MHz, DMSO-d$_6$) δ 9.15 (s, 1H), 8.54 (s, 1H), 8.27 (d, 1H, J=7.5 Hz), 7.73 (s, 1H), 7.67 (d, 1H, J=7.5 Hz), 7.49 (t, 1H, J=7.5 Hz), 7.16 (d, 2H, J=9 Hz), 6.84 (t, 1H, J=6 Hz), 6.53 (d, 2H, J=9 Hz), 4.22 (d, 2H, J=6 Hz), 3.20 (m, 4H), 2.63 (s, 3H), 1.94 (m, 4H); MS (ESI) 361 (M+H)$^+$. Anal. Calcd for C$_{22}$H$_{24}$N$_4$O.0.2H$_2$O: C, 72.58; H, 6.76; N, 15.39. Found: C, 72.33; H, 6.64; N, 15.22.

EXAMPLE 161

N-[3-fluoro-4-(1-pyrrolidinyl)benzyl]-N'-(3-methyl-5-isoquinolinyl)urea

The title compound was prepared using the procedure described in Example 61B using 3-fluoro-4-(1-pyrrolidinyl)benzylamine and the product from Example 154A instead of 4-cyanobenzyl alcohol and the product from Example 61A. $^1$H NMR (300 MHz, DMSO-d$_6$) δ 9.17 (s, 1H), 8.59 (s, 1H), 8.22 (d, 1H, J=7.5 Hz), 7.73 (s, 1H), 7.69 (d, 1H, J=7.5 Hz), 7.50 (t, 1H, J=7.5 Hz), 7.03 (m, 2H), 6.93 (t, 1H, J=6 Hz), 6.72 (m, 1H), 4.24 (d, 2H, J=6 Hz), 3.28 (m, 4H), 2.64 (s, 3H), 1.88 (m, 4H); MS (ESI) 379 (M+H)$^+$; Anal. Calcd for C$_{22}$H$_{23}$FN$_4$O: C, 69.82; H, 6.13; N, 14.80. Found: C, 69.76; H, 6.06; N, 14.69.

EXAMPLE 162

N-[4-(1-azepanyl)-3-fluorobenzyl]-N'-(3-methyl-5-isoquinolinyl)urea

The title compound was prepared using the procedure described in Example 61B using 4-(1-azepanyl)-3-fluorobenzylamine and the product from Example 154A instead of 4-cyanobenzyl alcohol and the product from Example 61A. $^1$H NMR (300 MHz, DMSO-d$_6$) δ 9.74 (s, 1H), 8.50 (s, 1H), 8.67 (s, 1H), 8.60 (d, 1H, J=8.1 Hz), 8.14 (d, 1H, J=8.1 Hz), 7.83 (t, 1H, J=8.1 Hz), 7.56 (t, 1H), 7.04 (m, 2H), 6.90 (m, 1H), 4.26 (d, 2H, J=6 Hz), 3.32 (m, 4H), 2.79 (s, 3H), 1.75 (m, 4H), 1.55 (m, 4H); MS (ESI) 407 (M+H)$^+$; Anal. Calcd for C$_{24}$H$_{27}$FN$_4$O.2HCl: C, 60.13; H, 6.10; N, 11.69. Found: C, 60.09; H, 6.35; N, 11.47.

EXAMPLE 163

N-[4-(1-azocanyl)benzyl]-N'-(3-methyl-5-isoquinolinyl)urea

The title compound was prepared using the procedure described in Example 61B using 4-(1-azocanyl)benzylamine and the product from Example 154A instead of 4-cyanobenzyl alcohol and the product from Example 61A. $^1$H NMR (300 MHz, DMSO-d$_6$) δ 9.15 (s, 1H), 8.53 (s, 1H), 8.27 (d, 1H, J=7.5 Hz), 7.73 (s, 1H), 7.67 (d, 1H, J=7.5 Hz), 7.50 (t, 1H, J=7.5 Hz), 7.15 (m, 2H), 6.83 (t, 1H, J=5.4 Hz), 6.63 (m, 2H), 4.20 (d, 2H, J=5.4 Hz), 3.43 (m, 4H), 2.63 (s, 3H), 1.67 (m, 4H), 1.48 (m, 6H); MS (ESI) 403 (M+H)$^+$; Anal. Calcd for C$_{25}$H$_{30}$N$_4$O: C, 74.60; H, 7.51; N, 13.92. Found: C, 74.26; H, 7.48; N, 13.64.

EXAMPLE 164

N-[4-(1-azocanyl)-3-fluorobenzyl]-N'-(3-methyl-5-isoquinolinyl)urea

The title compound was prepared using the procedure described in Example 61B using 4-(1-azocanyl)-3-fluorobenzylamine and the product from Example 154A instead of 4-cyanobenzyl alcohol and the product from Example 61A. $^1$H NMR (300 MHz, DMSO-d$_6$) δ 9.70 (s, 1H), 9.37 (s, 1H), 8.56 (m, 2H), 8.01 (d, 1H, J=8.4 Hz), 7.81 (t, 1H, J=8.4 Hz), 7.45 (t, 1H), 7.02 (m, 2H), 6.90 (m, 1H), 4.25 (d, 2H, J=6 Hz), 3.35 (m, 4H), 2.77 (s, 3H), 1.67 (m, 4H), 1.54 (m, 6H); MS (ESI) 421 (M+H)$^+$; Anal. Calcd for C$_{25}$H$_{29}$FN$_4$O.HCl: C, 65.71; H, 6.62; N, 12.26. Found: C, 65.44; H, 6.49; N, 12.15.

EXAMPLE 165

N-[(1S)-1-(4-bromophenyl)ethyl]-N'-(3-methyl-5-isoquinolinyl)urea

The title compound was prepared using the procedure described in Example 61B using (1S)-1-(4-bromophenyl)ethanamine and the product from Example 154A instead of 4-cyanobenzyl alcohol and the product from Example 61A.

EXAMPLE 166

N-{(1S)-1-[4-(1-azepanyl)phenyl]ethyl}-N'-(3-methyl-5-isoquinolinyl)urea

The product from Example 165 (568 mg, 1.48 mmol, hexamethyleneimine (834 μL, 7.39 mmol), Pd$_2$ dba$_3$ (271 mg, 0.30 mmol), BINAP (460 mg, 0.74 mmol), and sodium tert-butoxide (1.42 g, 14.8 mmol) were combined in 1,4-dioxane (20 mL) and heated to reflux. After 16 hours, the reaction was cooled to ambient temperature and concentrated in vacuo. The residue was purified by flash chromatography (1% to 5% CH$_3$OH/CH$_2$Cl$_2$) to provide the title compound. $^1$H NMR (300 MHz, DMSO-d$_6$) δ 9.15 (s, 1H), 8.48 (s, 1H), 8.28 (d, 1H, J=8.4 Hz), 7.72 (s, 1H), 7.64 (d, 1H, J=8.4 Hz), 7.47 (t, 1H, J=8.4 Hz), 7.16 (m, 2H), 6.90 (d, 1H, J=7.5 Hz), 6.66 (m, 2H), 4.74 (m, 1H), 3.43 (m, 4H), 2.64 (s, 3H), 1.71 (m, 4H), 1.44 (m, 7H). MS (ESI) 403 (M+H)$^+$. Anal. Calcd for C$_{25}$H$_{30}$N$_4$O.0.2CH$_3$OH: C, 74.01; H, 7.59; N, 13.70. Found: C, 74.39; H, 7.60; N, 13.32.

EXAMPLE 167

N-benzyl-N'-(3-chloro-5-isoquinolinyl)urea

The product from Example 60E (250 mg, 1.4 mmol) and 1-bromo-4-(isocyanatomethyl)benzene (0.22 mL, 1.57 mmol) were heated in toluene (5 mL) at 80° C. for 3 hours. The mixture was cooled to room temperature and the precipitated solid was collected by filtration, washed with toluene, and air-dried to provide the title compound. $^1$H NMR (300 MHz, DMSO-d$_6$) δ 9.18 (s, 1H), 8.81 (s, 1H), 8.32 (dd, J=7.8 Hz, 0.7 Hz, 1H), 8.09 (s, 1H), 7.80 (d, J=8.2 Hz, 1H), 7.53–7.65 (m, 3H), 7.32 (m, 2H), 7.05 (t, J=5.7 Hz, 1H), 4.35 (d, J=5.7 Hz, 2H); MS (ESI$^+$) m/z 391/393 (M+H, $^{35}$Cl/$^{37}$Cl).

EXAMPLE 168

N-(4-bromobenzyl)-N'-(1-chloro-5-isoquinolinyl)urea

EXAMPLE 168A 1-chloro-5-isoquinolinamine

The title compound was prepared using the procedures described in Examples 60D and 60E using 1-chloroisoquinoline instead of the product from Example 60C.

EXAMPLE 168B

N-(4-bromobenzyl)-N'-(1-chloro-5-isoquinolinyl)urea

The title compound was prepared using the procedure described in Example 60F using the product from Example 168A instead of the product from Example 60E. $^1$H NMR (300 MHz, DMSO-d$_6$) δ 8.89 (s, 1H), 8.34–8.37 (m, 2H), 8.00 (dd, J=6.1 Hz, 0.7 Hz, 1H), 7.92–7.95 (m, 1H), 7.73 (t, J=8.1, 1H), 7.53–7.56 (m, 2H), 7.30–7.33 (m, 2H), 7.12 (t, J=5.8 Hz, 1H), 4.35 (d, J=5.8 Hz, 2H); MS (ESI+) m/z 390/392 (M+H, $^{35}$C/$^{37}$CI).

EXAMPLE 169

N-(4-cyanobenzyl)-N'-5-isoquinolinylurea

EXAMPLE 169A 4-(aminomethyl)benzonitrile

A solution of N,N-bis(tert-butoxycarbonyl)-4-cyanobenzylamine (0.75 g, 2.25 mmol, prepared according to the literature described in Synthetic Communications 4419:28 (1998), in CH$_2$Cl$_2$ (15 mL) was treated with trifluoroacetic acid (8 mL). After stirring at room temperature for 3 hours, the mixture was concentrated under reduced pressure and the residue was azeotroped with diethyl ether.

EXAMPLE 169B

N-(4-cyanobenzyl)-N'-5-isoquinolinylurea

The title compound was prepared using the procedure described in Example 61B using the product from Example 169A instead of 4-cyanobenzyl alcohol. Purification was by chromatography (95:5 CH$_2$Cl$_2$:MeOH) to provide the title compound. $^1$H NMR (300 MHz, DMSO-d$_6$) δ 9.75 (s, 1H), 9.62 (s, 1H), 8.69 (s, 2H), 8.58 (dd, J=7.8 Hz, 1.0 Hz, 1H), 8.07 (d, J=7.4 Hz, 1H), 7.90 (d, J=8.1 Hz, 1H), 7.81–7.85 (m, 2H), 7.74 (t, J=6.1 Hz, 1H), 7.54–7.57 (m, 2H), 4.48 (d, J=6.1 Hz, 2H); MS (ESI+) m/z 303 (M+H)$^+$.

EXAMPLE 170

N-(4-bromobenzyl)-N'-(3-methyl-5-isoquinolinyl) urea

The product from Example 63A (500 mg, 3.1 mmol) and 1-bromo-4-(isocyanatomethyl)benzene (0.5 mL, 3.57 mmol) were stirred in toluene (10 mL) at 80° overnight. The mixture was cooled to room temperature, and the resulting precipitate was collected by filtration, washed with toluene, and allowed to air-dry. The corresponding hydrochloride salt was prepared using methanolic HCl to afford a tan solid. $^1$H NMR (300 MHz, DMSO-d$_6$) δ 9.70 (s, 1H), 9.54 (s, 1H), 8.63 (s, 1H), 8.57 (dd, J=7.8 Hz, 1.0 Hz, 1H), 8.02 (d, J=8.2 Hz, 1H), 7.78–7.83 (m, 1H), 7.67–7.71 (m, 1H), 7.52–7.57 (m, 2H), 7.30–7.35 (m, 2H), 4.36 (d, J=5.7 Hz, 2H), 2.78 (s, 3H); MS (ESI$^+$) m/z 370/372 (M+H, $^{79}$Br/$^{81}$Br)$^+$.

EXAMPLE 171

N-(4-bromobenzyl)-N'-(1-methyl-5-isoquinolinyl) urea

EXAMPLE 171A 1-methyl-5-isoquinolinamine

The title compound was prepared using the procedures described in Examples 60D and 60E using 1-methylisoquinoline instead of the product from Example 60C.

EXAMPLE 171B

N-(4-bromobenzyl)-N'-(1-methyl-5-isoquinolinyl) urea

The product from Example 171A (480 mg, 3.04 mmol) and 1-bromo-4-(isocyanatomethyl)benzene (0.43, 3.07 mmol) were stirred in toluene (9 mL) at 90° for 1 hour, then the mixture was cooled to room temperature. The precipitate was collected by filtration and washed with toluene. The corresponding di-hydrochloride salt was prepared using methanolic HCl. $^1$H NMR (300 MHz, DMSO-d$_6$) δ 8.74 (s, 1H), 8.38 (d, J=6.1 Hz, 1H), 8.25 (d, J=7.8 Hz, 1H), 7.78–7.85 (m, 2H), 7.53–7.61 (m, 3H), 7.32 (d, J=8.5 Hz, 2H), 7.11 (t, J=6.1 Hz, 1H), 4.34 (d, J=6.1 Hz, 2H), 2.88 (s, 3H); MS (ESI$^+$) m/z 370/372 (M+H, $^{79}$Br/$^{81}$Br)$^+$.

EXAMPLE 172

N-5-isoquinolinyl-N'-[4-(4-morpholinyl)benzyl]urea

EXAMPLE 172A 4-(4-morpholinyl)benzonitrile

4-Fluorobenzonitrile (1 g, 8.26 mmol) and morpholine (2.2 mL, 25.2 mmol) were stirred in DMSO (25 mL) at 100° C. for 2.5 hours, cooled to room temperature, poured into H$_2$O, and extracted with diethyl ether. The combined organic extracts were washed with H$_2$O and brine, dried over Na$_2$SO$_4$, and evaporated in vacuo to provide the title compound.

EXAMPLE 172B 4-(4-morpholinyl)benzylamine 4-(4-Morpholinyl)benzonitrile (1.24 g, 6.6 mmol) in THF (25 mL) at 0° C. was treated with LiAlH$_4$ (2.5 g, 65.9 mmol) and refluxed for 1 hour. The mixture was cooled to room temperature and quenched by careful addition of 1N NaOH and then H$_2$O. The mixture was concentrated, extracted with diethyl ether. The combined ethereal extracts were washed with saturated NaHCO$_3$ solution, dried over Na$_2$SO$_4$, and evaporated in vacuo to provide the title compound which was dried over MgSO$_4$ as a THF:diethylether solution before the next step.

EXAMPLE 172C

N-5-isoquinolinyl-N'-[4-(4-morpholinyl)benzyl]urea

The product from Example 172B (285 mg, 1.48 mmol) in diethyl ether (10 mL) was treated with an ethereal solution of 5-isocyanatoisoquinoline, causing a white precipitate to form. This precipitate was collected by filtration and purified by chromatography (95:5 CH$_2$Cl$_2$—MeOH, eluant) to provide the title compound. The corresponding di-hydrochloride salt was prepared using methanolic HCl to afford a yellow solid. $^1$H NMR (300 MHz, DMSO-d$_6$) δ 9.26 (s, 1H), 8.67 (s, 1H), 8.52–8.55 (m, 1H), 8.32 (dd, J=7.8 Hz, 1.1 Hz, 1H), 7.92 (d, J=6.1 Hz, 1H), 7.73 (d, J=8.2 Hz, 1H), 7.60 (m, 1H), 7.23 (d, J=8.8 Hz, 2H), 6.92–6.96 (m, 3H), 4.26 (d, 5.4 Hz, 2H), 3.72–3.75 (m, 4H), 3.06–3.12 (m, 4H); MS (ESI$^+$) m/z 363 (M+H)$^+$.

EXAMPLE 173

N-[4-(2,6-dimethyl-4-morpholinyl)benzyl]-N'-5-isoquinolinylurea

EXAMPLE 173A 4-(2,6-dimethyl-4-morpholinyl)benzylamine

The title compound was prepared using the procedures described in Examples 172A and 172B using 2,6-dimethylmorpholine instead of morpholine.

EXAMPLE 173B

N-[4-(2,6-dimethyl-4-morpholinyl)benzyl]-N'-5-isoquinolinylurea

The title compound was prepared using the procedure described in Example 172C using the product from Example 173A instead of the product from Example 172B. $^1$H NMR (300 MHz, DMSO-$d_6$) δ 9.26 (s, 1H), 8.67 (s, 1H), 8.53 (d, J=6.1 Hz, 1H), 8.31 (dd, J=7.6 Hz, 1.1 Hz, 1H), 7.92 (d, J=6.1 Hz, 1H), 7.73 (d, J=8.1 Hz, 1H), 7.57–7.62 (m, 1H), 7.22 (d, J=8.8 Hz, 2H), 6.92–6.95 (m, 3H), 4.26 (d, J=5.7 Hz, 2H), 3.68 (m, 2H), 3.54–3.57 (m, 2H), 2.21 (m, 2H), 1.16 (s, 3H), 1.14 (s, 3H); MS (ESI$^+$) m/z 391 (M+H).

EXAMPLE 174

N-5-isoquinolinyl-N'-[4-(4-thiomorpholinyl)benzyl]urea

EXAMPLE 174A 4-(4-thiomorpholinyl)benzylamine

The title compound was prepared using the procedures described in Examples 172A and 172B using thiomorpholine instead of morpholine.

EXAMPLE 174B

N-5-isoquinolinyl-N'-[4-(4-thiomorpholinyl)benzyl]urea

The title compound was prepared using the procedure described in Example 172C using the product from Example 174A instead of the product from Example 172B. $^1$H NMR (300 MHz, DMSO-$d_6$) δ 9.26 (s, 1H), 8.67 (s, 1H), 8.53 (d, J=6.1 Hz, 1H), 8.32 (dd, J=7.8 Hz, 1.1 Hz, 1H), 7.92 (d, J=6.1 Hz, 1H), 7.73 (d, J=8.2 Hz, 1H), 7.60 (m, 1H), 7.20–7.23 (m, 2H), 6.90–6.96 (m, 3H), 4.25 (d, J=5.8 Hz, 2H), 3.45–3.51 (m, 4H), 2.64–2.67 (m, 4H); MS (ESI+) m/z 379 (M+H).

EXAMPLE 175

N-(4-bromobenzyl)-N'-(3-fluoro-5-isoquinolinyl)urea

EXAMPLE 175A 3-fluoro-5-isoquinolinamine

The title compound was prepared using the procedures described in Examples 60D and 60E using 3-fluoroisoquinoline, prepared according to the procedure described in J. Am. Chem. Soc., 687:73 (1951), instead of the product from Example 60C.

EXAMPLE 175B

N-(4-bromobenzyl)-N'-(3-fluoro-5-isoquinolinyl)urea

The title compound was prepared using the procedure described in Example 60F using the product from Example 175A instead of the product from Example 60E. $^1$H NMR (300 MHz, DMSO-$d_6$) δ 9.09 (s, 1H), 8.74 (s, 1H), 8.28 (d, 1H, J=7.8 Hz), 7.83 (d, 1H, J=8.4 Hz), 7.66 (s, 1H), 7.55 (m, 3H), 7.32 (d, 2H, J=8.5 Hz), 7.03 (t, 1H, J=5.9 Hz), 4.35 (d, 2H, J=6.1 Hz); MS (ESI$^+$) m/z 373/375 (M+H, $^{79}$Br/$^{81}$Br).

EXAMPLE 176

N-(3-chloro-5-isoquinolinyl)-N'-[4-(4-morpholinyl)benzyl]urea

EXAMPLE 176A 3-chloro-5-isocyanatoisoquinoline

5-Amino-3-chloroisoquinoline (740 mg, 4.15 mmol) was suspended in toluene (20 mL) and treated with 20% w/v phosgene solution in toluene (9 mL) and triethylamine (5 mL). The mixture was refluxed overnight and was then concentrated in vacuo and used in the next step without further purification.

EXAMPLE 176B

N-(3-chloro-5-isoquinolinyl)-N'-[4-(4-morpholinyl)benzyl]urea

The product from Example 176A in diethyl ether (40 mL) was treated with the product from Example 172B (300 mg, 1.56 mmol) and triethylamine (3 mL) in 1:1 diethyl ether:CH$_3$CN (10 mL). After stirring for 3 hours, the mixture was filtered, and the collected solid was washed with diethyl ether. The solid was purified by silica gel chromatography (95:5 CH$_2$Cl$_2$:MeOH) to provide the title compound. $^1$H NMR (300 MHz, DMSO-$d_6$) δ 9.18 (s, 1H), 8.71 (s, 1H), 8.37 (d, 1H, J=6.7 Hz), 8.08 (s, 1H), 7.79 (d, 2H, J=8.2 Hz), 7.63 (t, 1H, J=8.0 Hz), 7.23 (d, 2H, J=8.7 Hz), 6.94 (d, 2H, J=8.4 Hz), 6.91 (t, 1H, 5.5 Hz), 4.26 (d, 2H, 5.7 Hz), 3.73 (m, 4H), 3.07 (m, 4H); MS (ESI$^+$) m/z 397/399 (M+H, $^{35}$Cl/$^{37}$Cl).

EXAMPLE 177

N-[3,5-difluoro-4-(4-morpholinyl)benzyl]-N'-5-isoquinolinylurea

EXAMPLE 177A 3,5-difluoro-4-(4-morpholinyl)benzylamine

The title compound was prepared using the procedures described in Examples 172A and 172B using 3,4,5-trifluorobenzonitrile instead of 4-fluorobenzonitrile.

EXAMPLE 177B

N-[3,5-difluoro-4-(4-morpholinyl)benzyl]-N'-5-isoquinolinylurea

The product from Example 177A (500 mg, 2.19 mmol) in diethyl ether (5 mL) was treated with an ethereal solution of 5-isocyanatoisoquinoline. The resulting waxy precipitate was collected by filtration and air-dried to provide the title compound. $^1$H NMR (300 MHz, DMSO-$d_6$) δ 9.27 (s, 1H), 8.79 (s, 1H), 8.54 (d, 1H, J=6.1 Hz), 8.26 (dd, 1H, J=7.8 Hz, 1.0 Hz), 7.94 (d, 1H, 6.1 Hz), 7.76 (d, 1H, 8.2 Hz), 7.60 (t, 3H, J=7.6 Hz), 7.10 (t, 1H, J=6.0 Hz), 7.03 (m, 2H), 4.31 (d, 2H), 3.68 (m, 4H), 3.07 (m, 4H); MS (ESI$^+$) m/z 399 (M+H).

EXAMPLE 178

N-(4-bromobenzyl)-N'-(1,3-dimethyl-5-isoquinolinyl)urea

EXAMPLE 178A 1,3-dimethyl-5-isoquinolinamine

The title compound was prepared using the procedures described in Examples 60D and 60E using 1,3-dimethylisoquinoline, prepared according to the procedure described in Helv. Chim. Acta 1627:75 (1992), instead of the product from Example 60C.

EXAMPLE 178B

N-(4-bromobenzyl)-N'-(1,3-dimethyl-5-isoquinolinyl)urea

The product from Example 178A (375 mg, 2.2 mmol) in toluene (7 mL) was treated with 1-bromo-4-

(isocyanatomethyl)benzene (0.31 mL, 2.2 mmol). After stirring at 85–90° C. for 3 hours, the mixture was cooled to room temperature and filtered. The filter cake was treated with methanolic HCl to provide the title compound as the hydrochloride salt. $^1$H NMR (300 MHz, DMSO-d$_6$) δ 8.62 (s, 1H), 8.17 (d, 1H, J=7.8 Hz), 7.80 (d, 1H, J=8.5 Hz), 7.45–7.60 (m, 4H), 7.32 (d, 2H, J=8.1 Hz), 7.06 (t, 1H, 5.7 Hz), 4.34 (d, 2H, 5.8 Hz), 2.84 (s, 3H), 2.75 (s, 3H); MS (ESI$^+$) m/z 383/385 (M+H, $^{79}$Br/$^{81}$Br).

EXAMPLE 179

N-(3,4-dimethylbenzyl)-N'-(3-methyl-5-isoquinolinyl)urea 3,4-Dimethylbenzylamine (0.3 mL, 2.1 mmol) in toluene (11 mL) was added carefully to a 20% w/v solution of phosgene in toluene (4.5 mL). The mixture was refluxed overnight and was then concentrated in vacuo. The residue was then taken up in toluene (10 mL) and treated with DIEA (1.5 mL, 8.63 mmol) and 5-amino-3-methylisoquinoline (155 mg, 1.08 mmol). The reaction mixture was stirred at 80° for 2 h and was then cooled to room temperature. The precipitated solid was collected by filtration and was chromatographed on silica gel (97:3 CH$_2$Cl$_2$—CH$_3$OH to 9:1 CH$_2$Cl$_2$—CH$_3$OH, eluant gradient) to afford the desired product, A-473191. Treatment of this solid with methanolic HCl yielded the corresponding hydrochloride salt. $^1$H NMR (300 MHz, DMSO-d$_6$) δ 9.16 (s, 1H), 8.59 (s, 1H), 8.24 (d, 1H, J=7.8 Hz), 7.74 (s, 1H), 7.68 (d, 1H, J=8.2 Hz), 7.50 (t, 1H, J=7.9 Hz), 7.08–7.12 (m, 3H), 6.95 (m, 1H), 4.28 (d, 2H, 5.8 Hz), 2.64 (s, 3H), 2.22 (s, 3H), 2.20 (s, 3H); MS (ESI$^+$) m/z 320 (M+H).

EXAMPLE 180

N-[3,5-bis(trifluoromethyl)benzyl]-N'-(3-methyl-5-isoquinolinyl)urea

The title compound was prepared using the procedure described in Example 179 using 3,5-bis(trifluoromethyl)benzylamine instead of 3,4-dimethylbenzylamine. $^1$H NMR (300 MHz, DMSO-d$_6$) δ 9.18 (s, 1H), 8.79 (s, 1H), 8.01–8.13 (m, 4H), 7.73 (m, 2H), 7.51 (t, 1H, J=8.0 Hz), 7.23 (t, 1H, J=6.0 Hz), 4.55 (d, 2H, J=6.1 Hz), 2.64 (s, 3H); MS (ESI+) m/z 428 (M+H).

EXAMPLE 181

N-(3-amino-5-isoquinolinyl)-N'-(4-bromobenzyl)urea

EXAMPLE 181A

N-3-isoquinolinylacetamide

3-Aminoisoquinoline (495 mg, 3.44 mmol) was stirred in Ac$_2$O (9 mL) at 60° for 16 hours. The mixture was cooled to room temperature and concentrated in vacuo to provide the title compound which was used in the next step without further purification.

EXAMPLE 181B 3,5-isoquinolinediamine

The title compound was prepared using the procedures described in Examples 60D and 60E using the product from Example 181A instead of the product from Example 60C.

EXAMPLE 181C

N-(3-amino-5-isoquinolinyl)-N'-(4-bromobenzyl)urea

The title compound was prepared using the procedure described in Example 179 using 4-bromobenzylamine and the product from Example 181 B instead of 3,4-dimethylbenzylamine and 5-amino-3-methylisoquinoline. The corresponding hydrochloride salt was formed by treatment of the free base with methanolic HCl. $^1$H NMR (300 MHz, DMSO-d$_6$) δ 8.78 (s, 1H), 8.33 (s, 1H), 7.82 (d, 1H, J=7.5 Hz), 7.47–7.56 (m, 3H), 7.29 (d, 2H, J=8.1 Hz), 7.08 (t, 1H, J=7.8 Hz), 6.99 (m, 1H), 6.71 (s, 1H), 5.94 (br s, 2H), 4.31 (d, 2H, J=6.1 Hz); MS (ESI$^+$) m/z 370/372 (M+H, $^{79}$Br/$^{81}$Br).

EXAMPLE 182

N-(3-methyl-5-isoquinolinyl)-N'-[4-(trifluoromethyl)benzyl]urea 4-(Trifluoromethyl)benzylamine (1 mL, 7.02 mmol) in toluene (4 mL) was treated with 20% w/v phosgene solution in toluene (5 mL), and the whole mixture was refluxed overnight. After this time, the mixture was concentrated in vacuo, then was taken up again in toluene (8 mL). To this was added 5-amino-3-methylisoquinoline (340 mg, 2.15 mmol) and DIEA (4 mL) in toluene (8 mL). The reaction was allowed to stir at 80° for 3 h and then was cooled to room temperature. The precipitate was collected by filtration and purified by chromatography on silica gel (97:3 CH$_2$Cl$_2$—CH$_3$OH to 95:5 CH$_2$C$_{12}$—CH$_3$OH, eluant gradient) to afford A-638488 as a white solid. Treatment with methanolic HCl yielded the corresponding hydrochloride salt. $^1$H NMR (300 MHz, DMSO-d$_6$) δ 9.18 (s, 1H), 8.73 (s, 1H), 8.20 (d, 1H, J=7.3 Hz), 7.69–7.75 (m, 4H), 7.58 (d, 2H, J=8.2 Hz), 7.50 (t, 1H, 7.8 Hz), 7.16 (t, 1H, J=5.9 Hz), 4.47 (d, 2H, J=6.1 Hz), 2.65 (s, 3H); MS (ESI$^+$) m/z 360 (M+H).

EXAMPLE 183

N-(4-tert-butylbenzyl)-N'-(3-methyl-5-isoquinolinyl)urea

The title compound was prepard using the procedure described in Example 182 using 4-tert-butylbenzylamine instead of 4-(trifluoromethyl)benzylamine. The corresponding hydrochloride salt was obtained after treatment of the free base with methanolic HCl. $^1$H NMR (300 MHz, DMSO-d$_6$) δ 9.16 (s, 1H), 8.60 (s, 1H), 8.24 (dd, 1H, J=7.8 Hz, 1.1 Hz), 7.74 (s, 1H), 7.68 (d, 2H, J=8.2 Hz), 7.50 (t, 1H, J=7.9 Hz), 7.38 (m, 2H), 7.29 (m, 2H), 6.99 (t, 1H, J=5.8 Hz), 4.32 (d, 2H, J=5.8 Hz), 2.64 (s, 3H), 1.28 (s, 9H); MS (ESI$^+$) m/z 348 (M+H).

EXAMPLE 184

N-(4-tert-butylbenzyl)-N'-(1,3-dimethyl-5-isoquinolinyl)urea

EXAMPLE 184A 1-(isocyanatomethyl)-4-(trifluoromethyl)benzene

The title compound was prepared using the procedure described in Example 61A using 4-(trifluoromethyl)benzylamine instead of 5-aminoisoquinoline.

EXAMPLE 184B

N-(4-tert-butylbenzyl)-N'-(1,3-dimethyl-5-isoquinolinyl)urea

The product from Example 184A (3.16 mmol) in toluene (12 mL) was treated with the product from Example 178A (273 mg, 1.59 mmol) and DIEA (5 mL). The mixture was heated at 80° for 3 hours before being cooled to room temperature and filtered. The precipitate thus obtained was purified by silica gel chromatography (97:3 CH$_2$Cl$_2$—CH$_3$OH to 95:5 CH$_2$Cl$_2$—CH$_3$OH, eluant gradient) to provide the title compound. The corresponding hydrochloride salt was prepared by treatment with methanolic HCl. $^1$H NMR (300 MHz, DMSO-d$_6$) δ 8.68 (s, 1H), 8.16 (d, 1H, J=7.5 Hz), 7.80 (d, 1H, J=8.1 Hz), 7.73 (d, 2H, J=8.2 Hz), 7.56–7.61 (m, 3H), 7.48 (t, 1H, J=8.1 Hz), 7.15 (t, 1H, J=5.7 Hz), 4.46 (d, 2H, J=5.7 Hz), 2.84 (s, 3H), 2.58 (s, 3H); MS (ESI+) m/z 374 (M+H).

EXAMPLE 185

4-(3-chlorophenyl)-N-5-isoquinolinyl-1-piperazinecarboxamide 1-(3-Chlorophenyl)piperazine (206 mg, 1.05 mmol) in diethyl ether (20 mL) was treated with an ethereal solution of 5-isocyanatoisoquinoline. The precipitate that formed was collected by filtration, washed with diethyl ether and air-dried to provide the title compound. $^1$H NMR (300 MHz, DMSO-d$_6$) δ 9.30 (s, 1H), 8.84 (s, 1H), 8.49 (d, 1H, J=7.1 Hz), 7.92 (d, 1H, J=7.8 Hz), 7.78 (d, 1H, 6.8 Hz), 7.61–7.72 (m, 2H), 7.25 (t, 1H, J=8.1 Hz), 6.96–7.04 (m, 2H), 6.81–6.84 (m, 1H), 3.68 (m, 4H), 3.29 (m, 4H); MS (ESI+) m/z 367 (M+H).

EXAMPLE 186

N-(4-tert-butylbenzyl)-N'-(1,3-dimethyl-5-isoquinolinyl)urea

EXAMPLE 186A 1-tert-butyl-4-(isocyanatomethyl)benzene

The title compound was prepared using the procedure described in Example 61A using 4-tert-butylbenzylamine instead of 5-aminoisoquinoline.

EXAMPLE 186B

N-(4-tert-butylbenzyl)-N'-(1,3-dimethyl-5-isoquinolinyl)urea

The product from Example 186A (3.42 mmol) in toluene (12 mL) was treated with 5-amino-1,3-dimethylisoquinoline (245 mg, 1.42 mmol) and DIEA (5 mL). The mixture was heated at 800 for 3 hours, cooled to room tempoerature, and filtered. The precipitate thus obtained was purified by silica gel chromatography (97:3 CH$_2$Cl$_2$:CH$_3$OH to 95:5 CH$_2$Cl$_2$:CH$_3$OH) to provide the title compound. The corresponding hydrochloride salt was prepared by treatment with methanolic HCl. $^1$H NMR (300 MHz, DMSO-d$_6$) δ 8.55 (s, 1H), 8.21 (d, 1H, J=7.1 Hz), 7.78 (d, 1H, 8.5 Hz), 7.59 (s, 1H), 7.48 (t, 1H, J=8.0 Hz), 7.36–7.40 (m, 2H), 7.27–7.29 (m, 2H), 6.98 (m, 1H), 4.31 (d, 2H, J=5.8 Hz), 2.84 (s, 3H), 2.58 (s, 3H), 1.28 (s, 9H); MS (ESI+) m/z 362 (M+H).

EXAMPLE 187

4-(3,4-dimethylphenyl)-N-5-isoquinolinyl-1-piperazinecarboxamide 1-(3,4-Dimethylphenyl)piperazine (194 mg, 1.02 mmol) in diethyl ether (20 mL) was treated with an ethereal solution of 5-isocyanatoisoquinoline. The precipitate that formed was collected by filtration, washed with diethyl ether, and air-dried to provide the title compound. $^1$H NMR (300 MHz, DMSO-d$_6$) δ 9.29 (d, 1H, J=0.7 Hz), 8.82 (s, 1H), 8.49 (d, J=6.2 Hz, 1H), 7.90–7.93 (m, 1H), 7.76–7.79 (m, 1H), 7.61–7.71 (m, 2H), 7.00 (d, 1H, 8.5 Hz), 6.83 (d, 1H, J=2.4 Hz), 6.73 (dd, 1H, J=8.3 Hz, 2.5 Hz), 3.67 (m, 4H), 3.15 (m, 4H), 2.19 (s, 3H), 2.13 (s, 3H); MS (ESI$^+$) m/z 361 (M+H).

EXAMPLE 188

4-(4-chlorophenyl)-N-5-isoquinolinyl-1-piperazinecarboxamide 1-(4-Chlorophenyl)piperazine (197 mg, 1.01 mmol) in diethyl ether (20 mL) was treated with an ethereal solution of 5-isocyanatoisoquinoline. The precipitate that formed was collected by filtration, washed with diethyl ether, and air-dried to provide the title compound. $^1$H NMR (300 MHz, DMSO-d$_6$) δ 9.29 (d, 1H, J=1.0 Hz), 8.83 (s, 1H), 8.49 (d, 1H, 6.1 Hz), 7.93 (d, 1H, J=7.8 Hz), 7.77 (m, 1H), 7.61–7.72 (m, 2H), 7.26–7.29 (m, 2H), 7.01–7.04 (m, 2H), 3.68 (m, 4H), 3.23 (m, 4H); MS (ESI$^+$) m/z 367 (M+H).

EXAMPLE 189

N-5-isoquinolinyl-3-methyl-4-(4-methylphenyl)-1-piperazinecarboxamide

The title compound was prepared using the procedure described in Example 188 using 2-methyl-1-(4-methylphenyl)piperazine instead of 1-(4-chlorophenyl)piperazine. $^1$H NMR (300 MHz, DMSO-d$_6$) δ 9.29 (d, 1H, J=0.6 Hz), 8.77 (d, 1H, J=5.1 Hz), 8.49 (d, 1H, J=5.7 Hz), 7.92 (d, 1H, 7.5 Hz), 7.61–7.77 (m, 3H), 7.06 (d, 2H, 8.2 Hz), 6.86–6.91 (m, 2H), 3.61 and 4.53 (2m, 1H), 4.09 (m, 1H), 3.93 (m, 1H), 3.49 (m, 1H), 3.39 (m, 1H), 2.62–3.24 (m, 2H), 2.22 (s, 3H), 1.35 and 0.98 (2d, 3H, J=6.4 and 6.1 Hz); MS (ESI$^+$) m/z 361 (M+H).

EXAMPLE 190

4-(2,3-dimethylphenyl)-N-5-isoquinolinyl-1-piperazinecarboxamide

The title compound was prepared using the procedure described in Example 188 using 1-(2,3-dimethylphenyl)piperazine instead of 1-(4-chlorophenyl)piperazine. $^1$H NMR (300 MHz, DMSO-d$_6$) δ 9.29 (d, 1H, J=1.0 Hz), 8.80 (s, 1H), 8.50 (d, 1H, J=5.7 Hz), 7.92 (d, 1H, J=8.2 Hz), 7.79 (dd, 1H, J=6.1 Hz, 1.0 Hz), 7.61–7.73 (m, 2H), 7.07 (m, 1H0, 6.90–6.96 (m, 2H), 3.70 (m, 4H), 2.87 (m, 4H), 2.23 (s, 3H), 2.23 (s, 3H); MS (ESI+) m/z 361 (M+H).

EXAMPLE 191

4-(2,3-dichlorophenyl)-N-5-isoquinolinyl-1-piperazinecarboxamide

The title compound was prepared using the procedure described in Example 188 using 1-(2,3-dichlorophenyl)piperazine instead of 1-(4-chlorophenyl)piperazine. $^1$H NMR (300 MHz, DMSO-d$_6$) δ 9.30 (d, 1H, J=0.7 Hz), 8.83 (s, 1H), 8.50 (d, 1H, J=5.8 Hz), 7.92 (d, 1H, J=7.8 Hz), 7.79 (dd, 1H, J=5.1 Hz, 1.0 Hz), 7.62–7.73 (m, 2H), 7.33–7.36 (m, 2H), 7.21–7.24 (m, 1H), 3.71 (m, 4H), 3.07 (m, 4H); MS (ESI$^+$) m/z 401/403 (M+H, $^{35}$Cl/$^{37}$Cl).

EXAMPLE 192

N-[3-fluoro-4-(trifluoromethyl)benzyl]-N'-(3-methyl-5-isoquinolinyl)urea

EXAMPLE 192A 2-fluoro-4-(isocyanatomethyl)-1-(trifluoromethyl)benzene

The title compound was prepared using the procedure described in Example 61A using 3-fluoro-4-

(trifluoromethyl)benzylamine instead of 5-aminoisoquinoline.

EXAMPLE 192B

N-[3-fluoro-4-(trifluoromethyl)benzyl]-N'-(3-methyl-5-isoquinolinyl)urea

The product from Example 192A (4.4 mmol) in toluene (10 mL) was treated with 5-amino-3-methylisoquinoline (460 mg, 2.9 mmol) and DIEA (3 mL). The mixture was heated at 80° for 1.5 hours, cooled to room temperature, and filtered. The precipitate thus obtained was purified by silica gel chromatography (97:3 $CH_2Cl_2$:$CH_3OH$ to 95:5 $CH_2Cl_2$:$CH_3OH$) to provide the title compound. The corresponding hydrochloride salt was prepared by treatment with methanolic HCl. $^1H$ NMR (300 MHz, DMSO-$d_6$) δ 9.18 (s, 1H), 8.77 (s, 1H), 8.17 (dd, 1H, J=7.8 Hz, 1.0 Hz), 7.70–7.81 (m, 3H), 7.38–7.53 (m, 3H), 7.19 (t, 1H, 6.1 Hz), 4.47 (d, 2H, J=5.8 Hz), 2.65 (s, 3H); MS (ESI$^+$) m/z 378 (M+H).

EXAMPLE 193

N-[1-(4-bromophenyl)ethyl]-N'-(3-methyl-5-isoquinolinyl)urea

EXAMPLE 193A 1-bromo-4-(1-isocyanatoethyl)benzene

The title compound was prepared using the procedure described in Example 61A using 1-(4-bromophenyl) ethylamine instead of 5-aminoisoquinoline.

EXAMPLE 193B

N-[1-(4-bromophenyl)ethyl]-N'-(3-methyl-5-isoquinolinyl)urea

The title compound was prepared using the procedure described in Example 192B using the product from Example 193A instead of the product from Example 192A. The corresponding hydrochloride salt was prepared by treatment with methanolic HCl. $^1H$ NMR (300 MHz, DMSO-$d_6$) δ 9.16 (s, 1H), 8.56 (s, 1H), 8.20 (dd, 1H, J=7.8 Hz, 1.0 Hz), 7.72 (s, 1H), 7.67 (d, 1H, J=8.2 Hz), 7.56 (m, 2H), 7.47 (t, 1H, J=7.8 Hz), 7.35 (m, 2H), 7.12 (d, 1H, J=7.4 Hz), 4.85 (m, 1H), 2.65 (s, 3H), 1.43 (d, 3H, J=7.1 Hz); MS (ESI$^+$) m/z 384/386 (M+H, $^{79}Br$/$^{81}Br$).

EXAMPLE 194

N-(3,4-dichlorobenzyl)-N'-(3-methyl-5-isoquinolinyl)urea

EXAMPLE 194A 1,2-dichloro-4-(isocyanatomethyl)benzene

The title compound was prepared using the procedure described in Example 61A using 3,4-dichlorobenzylamine instead of 5-aminoisoquinoline.

EXAMPLE 194B

N-(3,4-dichlorobenzyl)-N'-(3-methyl-5-isoquinolinyl)urea

5-Amino-3-methylisoquinoline (390 mg, 2.47 mmol) and the product from Example 194A (0.36 mL, 2.45 mmol) were heated in toluene (10 mL) at 80° for 2.5 hours. Upon cooling to room temperature, a precipitate formed, which was collected by filtration, washed with toluene, and air-dried. Remaining impurities were removed by slurrying the solid in 9:1 $CH_2Cl_2$:$CH_3OH$ and then filtering the mixture to provide the title compound. The corresponding hydrochloride salt was formed by treatment of the free base with methanolic HCl. $^1HNMR$ (300 MHz, DMSO-$d_6$) 69.17 (s, 1H), 8.27 (s, 1H), 8.17 (dd, 1H, J=7.8 Hz, 1.0 Hz), 7.74 (s, 1H), 7.71 (d, 1H, J=8.1 Hz), 7.61 (m, 2H), 7.50 (t, 1H, J=8.0 Hz), 7.35 (dd, 1H, J=8.3 Hz, 2.2 Hz), 7.12 (t, 1H, 5.9 Hz), 4.37 (d, 2H, J=6.1 Hz), 2.65 (s, 3H); MS (ESI$^+$) m/z 360/362 (M+H, $^{35}Cl$/$^{37}Cl$).

EXAMPLE 195

N-(2,4-dichlorobenzyl)-N'-(3-methyl-5-isoquinolinyl)urea

EXAMPLE 195A 2,4-dichloro-1-(isocyanatomethyl)benzene

The title compound was prepared using the procedure described in Example 61A using 2,4-dichlorobenzylamine instead of 5-aminoisoquinoline.

EXAMPLE 195B

N-(2,4-dichlorobenzyl)-N'-(3-methyl-5-isoquinolinyl)urea

5-Amino-3-methylisoquinoline (390 mg, 2.47 mmol) and the product from Example 195A (0.36 mL, 2.47 mmol) were heated in toluene (10 mL) at 80° for 2.5 hours. Upon cooling to room temperature, a precipitate formed, which was collected by filtration, washed with toluene, and air-dried. Remaining impurities were removed by slurrying the solid in 9:1 $CH_2Cl_2$:$CH_3OH$ and then filtering the mixture to provide the title compound. The corresponding hydrochloride salt was formed by treatment of the free base with methanolic HCl. $^1H$ NMR (300 MHz, DMSO-$d_6$) δ 9.17 (s, 1H), 8.78 (s, 1H), 8.21 (dd, 1H, J=7.4 Hz, 1.0 Hz), 7.77 (s, 1H), 7.70 (d, 1H, J=8.1 Hz), 7.64 (m, 1H), 7.44–7.52 (m, 3H), 7.14 (t, 1H, J=6.1 Hz), 4.38 (d, 2H, J=6.0 Hz), 2.65 (s, 3H); MS (ESI$^+$) m/z 360/362 (M+H, $^{35}Cl$/$^{37}Cl$).

EXAMPLE 196

N-(3-chlorobenzyl)-N'-(3-methyl-5-isoquinolinyl) urea 3-chlorobenzylamine (141 mg, 1.0 mmol) in ether (20 mL) was treated with an ethereal solution of 5-isocyanato-3-methylisoquinoline. The precipitate that formed was collected by filtration, washed with diethyl ether, and air-dried to provide the title compound. $^1H$ NMR (300 MHz, DMSO-$d_6$) δ 9.18 (s, 1H), 8.69 (s, 1H), 8.20 (d, 1H, J=7.8 Hz), 7.75 (s, 1H), 7.70 (d, 1H, J=8.2 Hz), 7.51 (t, 1H, J=7.8 Hz), 7.31–7.43 (m, 4H), 7.10 (m, 1H), 4.38 (d, 2H, J=5.7 Hz), 2.65 (s, 3H); MS (ESI$^+$) m/z 326/328 (M+H, $^{35}Cl$/$^{37}Cl$).

EXAMPLE 197

N-(3-methyl-5-isoquinolinyl)-N'-[4-(trifluoromethoxy)benzyl]urea

The title compound was prepared using the procedure described in Example 196 using 4-(trifluoromethoxy) benzylamine instead of 3-chlorobenzylamine. $^1H$ NMR (300 MHz, DMSO-$d_6$) δ 9.17 (s, 1H), 8.68 (s, 1H), 8.21 (d, 1H, J=7.8 Hz), 7.75 (s, 1H), 7.70 (d, 1H, J=8.1 Hz), 7.46–7.53 (m, 3H), 7.35–7.37 (m, 2H), 7.10 (t, 1H, 5.9 Hz), 4.40 (d, 2H, J=5.7 Hz), 2.64 (s, 3H); MS (ESI+) m/z 376 (M+H).

EXAMPLE 198

N-[2-(3,4-dichlorophenyl)ethyl]-N'-(3-methyl-5-isoquinolinyl)urea

The title compound was prepared using the procedure described in Example 196 using 2-(3,4-dichlorophenyl) ethylamine instead of 3-chlorobenzylamine. $^1$H NMR (300 MHz, DMSO-d$_6$) δ 9.16 (s, 1H), 8.54 (s, 1H), 8.17 (d, 1H, J=7.5 Hz), 7.67–7.70 (m, 2H), 7.57–7.60 (m, 2H), 7.49 (t, 1H, 7.8 Hz), 7.29 (dd, 1H, J=8.1 Hz, 2.0 Hz), 6.57 (t, 1H, J=5.7 Hz), 3.43 (m, 2H), 2.82 (m, 2H), 2.64 (s, 3H); MS (ESI$^+$) m/z 374/376 (M+H, $^{35}$Cl/$^{37}$Cl).

EXAMPLE 199

N-(4-ethylbenzyl)-N'-(3-methyl-5-isoquinolinyl)urea

The title compound was prepared using the procedure described in Example 196 using 4-ethylbenzylamine instead of 3-chlorobenzylamine. $^1$H NMR (300 MHz, DMSO-d$_6$) δ 9.17 (s, 1H), 8.61 (s, 1H), 8.24 (d, 1H, J=7.8 Hz), 7.74 (s, 1H), 7.68 (d, 1H, J=7.8 Hz), 7.50 (t, 1H, J=7.8 Hz), 7.19–7.29 (m, 4H), 6.99 (m, 1H), 4.32 (d, 2H, J=5.7 Hz), 2.64 (s, 3H), 2.59 (q, 2H, J=7.6 Hz), 1.17 (t, 3H, J=7.6 Hz); MS (ESI$^+$) m/z 320 (M+H).

EXAMPLE 200

N-(3-methyl-5-isoquinolinyl)-N'-{2-[4-(trifluoromethyl)phenyl]ethyl}urea

The title compound was prepared using the procedure described in Example 196 using 2-[4-(trifluoromethyl) phenyl]ethylamine instead of 3-chlorobenzylamine. $^1$H NMR (300 MHz, DMSO-d$_6$) δ 9.16 (s, 1H), 8.55 (s, 1H), 8.20 (d, 1H, J=7.8 Hz), 7.67–7.70 (m, 4H), 7.46–7.53 (m, 3H), 6.60 (t, 1H, J=5.6 Hz), 3.46 (m, 2H), 2.91 (m, 2H), 2.64 (s, 3H); MS (ESI$^+$) m/z 374 (M+H).

EXAMPLE 201

N-(3-methyl-5-isoquinolinyl)-N'-{4-[(trifluoromethyl)thio]benzyl}urea

The title compound was prepared using the procedure described in Example 196 using 4-[(trifluoromethyl)thio] benzylamine instead of 3-chlorobenzylamine. $^1$H NMR (300 MHz, DMSO-d$_6$) δ 9.18 (s, 1H), 8.72 (s, 1H), 8.21 (d, 1H, J=7.8 Hz), 7.69–7.76 (m, 4H), 7.50–7.53 (m, 3H), 7.15 (m, 1H), 4.44 (d, 2H, J=6.1 Hz), 2.65 (s, 3H); MS (ESI$^+$) m/z 392 (M+H).

EXAMPLE 202

N-(4-chlorobenzyl)-N'-(3-methyl-5-isoquinolinyl) urea

The title compound was prepared using the procedure described in Example 196 using 4-chlorobenzylamine instead of 3-chlorobenzylamine. $^1$H NMR (300 MHz, DMSO-d$_6$) δ 9.17 (s, 1H), 8.67 (s, 1H), 8.21 (m, 1H), 7.66–7.74 (m, 2H), 7.37–7.53 (m, 5H), 7.08 (m, 1H), 4.36 (d, 2H, J=5.8 Hz), 2.64 (s, 3H); MS (ESI$^+$) m/z 326/328 (M+H, $^{35}$Cl/$^{37}$Cl).

EXAMPLE 203

4-(3,4-dichlorophenyl)-N-(3-methyl-5-isoquinolinyl)-1-piperazinecarboxamide

The title compound was prepared using the procedure described in Example 196 using 1-(3,4-dichlorophenyl) piperazine instead of 3-chlorobenzylamine. $^1$H NMR (300 MHz, DMSO-d$_6$) δ 9.20 (s, 1H), 8.74 (s, 1H), 7.86 (d, 1H, J=8.1 Hz), 7.51–7.66 (m, 3H), 7.43 (d, 1H, J=8.8 Hz), 7.22 (d, 1H, J=3.1 Hz), 7.01 (dd, 1H, J=9.1 Hz, 3.1 Hz), 3.67 (m, 4H), 3.28 (m, 4H), 2.62 (s, 3H); MS (ESI$^+$) m/z 415/417 (M+H, $^{35}$Cl/$^{37}$C).

EXAMPLE 204

N-(2,4-difluorobenzyl)-N'-(3-methyl-5-isoquinolinyl)urea

The title compound was prepared using the procedure described in Example 196 using 2,4-difluorobenzylamine instead of 3-chlorobenzylamine. $^1$H NMR (300 MHz, DMSO-d$_6$) δ 9.17 (s, 1H), 8.67 (s, 1H), 8.21 (dd, 1H, J=7.5 Hz, 1.0 Hz), 7.74 (s, 1H), 7.70 (d, 1H, J=8.1 Hz), 7.47–7.52 (m, 2H), 7.05–7.29 (m, 3H), 4.38 (d, 2H, J=5.7 Hz), 2.64 (s, 3H); MS (ESI$^+$) m/z 328 (M+H).

EXAMPLE 205

N-(1,3-dimethyl-5-isoquinolinyl)-N'-[3-fluoro-4-(trifluoromethyl)benzyl]urea

EXAMPLE 205A 2-fluoro-4-(isocyanatomethyl)-1-(trifluoromethyl) benzene

The title compound was prepared using the procedure described in Example 61A using 3-fluoro-4-(trifluoromethyl)benzylamine instead of 5-aminoisoquinoline.

EXAMPLE 205B

N-(1,3-dimethyl-5-isoquinolinyl)-N'-[3-fluoro-4-(trifluoromethyl)benzyl]urea

The product from Example 205A (4.4 mmol) in toluene (10 mL) was treated with 1,3-dimethyl-5-isoquinolinamine (375 mg, 2.18 mmol) and DIEA (3.5 mL). The mixture was heated at 80° overnight. After cooling to room temperature, the precipitated solids were collected by filtration and chromatographed on silica gel (98:2 CH$_2$Cl$_2$:CH$_3$OH to 95:5 CH$_2$Cl$_2$:CH$_3$OH) to provide the title compound. The corresponding hydrochloride salt was prepared by treatment with methanolic HCl. $^1$H NMR (300 MHz, DMSO-d$_6$) δ 8.72 (s, 1H), 8.13 (d, 1H, J=7.8 Hz), 7.75–7.83 (m, 2H), 7.61 (s, 1H), 7.38–7.51 (m, 3H), 7.18 (t, 1H, J=6.1 Hz), 4.46 (d, 2H, J=5.8 Hz), 2.84 (s, 3H), 2.59 (s, 3H); MS (ESI$^+$) m/z 392 (M+H).

EXAMPLE 206

N-5-isoquinolinyl-4-[3-(trifluoromethyl)phenyl]-1-piperazinecarboxamide

The title compound was prepared using the procedure described in Example 188 using 1-[3-(trifluoromethyl) phenyl]piperazine instead of 1-(4-chlorophenyl)piperazine. $^1$H NMR (300 MHz, DMSO-d$_6$) δ 9.30 (d, 1H, J=1.0 Hz), 8.85 (s, 1H), 8.49 (d, 1H, J=5.7 Hz), 7.93 (d, 1H, J=7.7 Hz), 7.78 (m, 1H), 7.61–7.72 (m, 2H), 7.46 (m, 1H), 7.26–7.31 (m, 2H), 7.12 (d, 1H, J=7.5 Hz), 3.70 (m, 4H), 3.35 (m, 4H); MS (ESI$^+$) m/z 401 (M+H).

EXAMPLE 207

4-(4-bromophenyl)-N-5-isoquinolinyl-1-piperazinecarboxamide

The title compound was prepared using the procedure described in Example 188 using 1-(4-bromophenyl)

piperazine instead of 1-(4-chlorophenyl)piperazine. The precipitate that formed was collected by filtration, washed with diethyl ether, and air-dried. Purification by silica gel chromatography provided the title compound. $^1$H NMR (300 MHz, DMSO-d$_6$) δ 9.29 (d, 1H, J=1.0 Hz), 8.83 (s, 1H), 8.49 (d, 1H, J=6.1 Hz), 7.92 (d, 1H, J=7.8 Hz), 7.77 (m, 1H), 7.61–7.71 (m, 2H), 7.37–7.40 (m, 2H), 6.96–6.99 (m, 2H), 3.68 (m, 4H), 3.23 (m, 4H); MS (ESI$^+$) m/z 411/413 (M+H, $^{79}$Br/$^{81}$Br).

EXAMPLE 208

N-(4-isopropylbenzyl)-N'-(3-methyl-5-isoquinolinyl) urea

4-Isopropylbenzylamine (748 mg, 5.02 mmol) in toluene (20 mL) was refluxed with 20% w/v phosgene solution in toluene (3 mL) overnight. The mixture was cooled to room temperature and concentrated in vacuo. The residue was taken up in toluene (20 mL) and was treated with DIEA (4 mL) and 5-amino-3-methylisoquinoline (500 mg, 3.16 mmol). The reaction mixture was stirred was at 80° C. for 6 hours. After cooling to room temperature, a precipitate formed which was collected by filtration and purified by silica gel chromatography (98:2 CH$_2$Cl$_2$:CH$_3$OH) to provide the title compound. The corresponding hydrochloride salt was formed by treatment with methanolic HCl. $^1$H NMR (300 MHz, DMSO-d$_6$) δ 9.16 (s, 1H), 8.60 (s, 1H), 8.24 (dd, 1H, J=7.5 Hz, 1.0 Hz), 7.74 (s, 1H), 7.68 (d, 1H, J=8.2 Hz), 7.50 (t, 1H, J=8.0 Hz), 7.22–7.30 (m, 4H), 6.99 (t, 1H, 5.6 Hz), 4.32 (d, 2H, J=7.8 Hz), 2.88 (m, 1H), 2.64 (s, 3H), 1.20 (d, 6H, J=6.8 Hz); MS (ESI$^+$) m/z 334 (M+H).

EXAMPLE 209

N-[4-fluoro-3-(trifluoromethyl)benzyl]-N'-(3-methyl-5-isoquinolinyl)urea

4-Fluoro-3-(trifluoromethyl)benzylamine (0.8 g, 4.15 mmol) in toluene (20 mL) was refluxed with 20% w/v phosgene solution in toluene (2.1 mL) overnight. The mixture was cooled to room temperature and concentrated in vacuo. The residue was again taken up in toluene (25 mL) and was stirred overnight at 80° C. with DIEA (2 mL, 11.5 mmol) and 5-amino-3-methylisoquinoline (500 mg, 3.16 mmol). The mixture was cooled to room temperature, concentrated in vacuo, and the residue was purified by silica gel chromatography (97:3 CH$_2$Cl$_2$:CH$_3$OH, eluant) to provide the title compound. The corresponding hydrochloride salt was prepared by treatment with methanolic HCl. $^1$H NMR (300 MHz, DMSO-d$_6$) δ 9.18 (s, 1H), 8.72 (s, 1H), 8.16 (d, 1H, J=7.8 Hz), 7.70–7.77 (m, 4H), 7.48–7.54 (m, 3H), 7.14 (t, 1H, J=5.9 Hz), 4.42 (d, 2H, J=6.1 Hz), 2.64 (s, 3H); MS (ESI$^+$) m/z 378 (M+H).

EXAMPLE 210

N-(3-amino-5-isoquinolinyl)-N'-{1-[4-(trifluoromethyl)phenyl]ethyl}urea 1-(1-Isocyanatoethyl)-4-(trifluoromethyl)benzene (1.64 mmol) in toluene (8 mL) was treated with N-(5-amino-3-isoquinolinyl)acetamide (220 mg, 1.09 mmol) and DIEA (1.4 mL). The mixture was heated at 80° C. for 6 hours, cooled to room temperature, and the precipitate was collected by filtration. The solid was triturated with 97:3 CH$_2$Cl$_2$:CH$_3$OH and stirred as a suspension in 48% aqueous HBr (8 mL) at 60° C. for 4 hours. After cooling to room temperature, the mixture was poured into concentrated NH$_4$OH (20 mL) and filtered. The solid was washed with water and air-dried to provide the title compound. The corresponding hydrochloride salt was prepared by treatment with methanolic HCl. $^1$H NMR (300 MHz, DMSO-d$_6$) δ 9.05 (s, 1H), 8.64 (s, 1H), 7.91 (d, 1H), 7.58–7.74 (m, 4H), 7.22–7.36 (m, 3H), 7.14–7.18 (m, 2H), 6.97 (s, 1H), 4.94 (m, 1H), 1.44 (d, 3H, J=6.8 Hz); MS (ESI$^+$) m/z 375 (M+H).

EXAMPLE 211

N-(3-amino-5-isoquinolinyl)-N'-[3-fluoro-4-(trifluoromethyl)benzyl]urea

2-Fluoro-4-(isocyanatomethyl)-1-(trifluoromethyl) benzene (2.59 mmol) in toluene (10 mL) was treated with N-(5-amino-3-isoquinolinyl)acetamide (400 mg, 1.99 mmol) and DIEA (1.8 mL). The mixture was heated at 80° C. for 5 hours, cooled to room temperature, and filtered. The solid was triturated with 97:3 CH$_2$Cl$_2$:CH$_3$OH and stirred as a suspension in 48% aqueous HBr (8 mL) at 60° C. for 2 hours. After cooling to room temperature, the mixture was poured into concentrated NH$_4$OH (20 mL). The solid was washed with water and air-dried to provide the title compound. The corresponding hydrochloride salt was prepared by treatment with methanolic HCl. $^1$H NMR (300 MHz, DMSO-d$_6$) δ 8.81 (s, 1H), 8.68 (s, 1H), 7.94 (s, 1H), 7.76 (t, 1H, J=7.9 Hz), 7.35–7.49 (m, 3H), 7.26 (s, 1H), 7.09 (s, 1H), 6.92 (s, 1H), 6.84 (t, 1H, J=6.0 Hz), 6.62 (s, 1H), 4.41 (d, 2H, J=6.1 Hz).

EXAMPLE 212

N-[(2,4-dichlorobenzyl)oxy]-N'-5-isoquinolinylurea

The title compound was prepared using the procedure described in Example 61B using O-(2,5-dichlorobenzyl) hydroxylamine instead of 4-cyanobenzyl alcohol. MS (ESI) m/z: 361.96 (M+H)$^+$; $^1$H NMR (DMSO-d$_6$) δ 5.03 (s, 2H), 7.52 (dd, 1H), 7.69 (m, 4H), 7.88 (d, 1H), 7.93 (d, 1H), 8.52 (d, 1H), 9.00 (s, 1H), 9.31 (s, 1H), 9.77 (s, 1H).

EXAMPLE 213

N-(5-bromo-2-fluorobenzyl)-N'-5-isoquinolinylurea

The title compound was prepared using the procedure described in Example 61B using 5-bromo-2-fluorobenzylamine instead of 4-cyanobenzyl alcohol. MS (ESI) m/z: 373.93 (M+H)$^+$; $^1$H NMR (DMSO-d$_6$) δ 4.42 (d, 2H), 7.22 (t, 1H), 7.54 (m, 2H), 7.60 (dd, 1H), 7.86 (t, 1H), 8.05 (d, 1H), 8.56 (t, 2H), 8.69 (d, 1H), 9.45 (s, 1H), 9.72 (s, 1H).

EXAMPLE 214

N-(4-chloro-2-fluorobenzyl)-N'-5-isoquinolinylurea

The title compound was prepared using the procedure described in Example 61B using 4-chloro-2-fluorobenzylamine instead of 4-cyanobenzyl alcohol. MS (ESI) m/z: 329.99 (M+H)$^+$; $^1$H NMR (DMSO-d$_6$) δ 4.41 (d, 2H), 7.31 (dd, 1H), 7.47 (m, 3H), 7.85 (t, 1H), 8.04 (d, 1H), 8.56 (d, 2H), 8.68 (d, 1H), 9.42 (s, 1H), 9.71 (s, 1H).

EXAMPLE 215

2-(4-chlorophenyl)ethyl 5-isoquinolinylcarbamate

The title compound was prepared using the procedure described in Example 61B using 2-(4-chlorophenyl)ethanol instead of 4-cyanobenzyl alcohol. MS (ESI) m/z: 327.04 (M+H)+; $^1$H NMR (DMSO-d$_6$) δ 2.99 (t, 2H), 4.37 (t, 2H), 7.36 (q, 4H), 7.89 (t, 1H), 8.12 (d, 1H), 8.20 (d, 1H), 8.30 (d, 1H), 8.63 (d, 1H), 9.72 (s, 1H), 9.97 (s, 1H).

EXAMPLE 216

2-[2-(trifluoromethyl)phenyl]ethyl 5-isoquinolinylcarbamate

The title compound was prepared using the procedure described in Example 61B using 2-[2-(trifluoromethyl)phenyl]ethanol instead of 4-cyanobenzyl alcohol. MS (ESI) m/z: 361.06 (M+H)+; $^1$H NMR (DMSO-d$_6$) δ 3.18 (t, 2H), 4.42 (t, 2H), 7.48 (t, 1H), 7.63 (m, 2H), 7.72 (d, 1H), 7.90 (t, 1H), 8.13 (d, 1H), 8.20 (d, 1H), 8.30 (d, 1H), 8.63 (d, 1H), 9.72 (s, 1H), 10.01 (s, 1H).

EXAMPLE 217

N-(4-tert-butylbenzyl)-N'-5-isoquinolinylurea

The title compound was prepared using the procedure described in Example 61B using 4(-tert-butyl)benzylamine instead of 4-cyanobenzyl alcohol. MS (ESI) m/z: 333 (M+H)+; $^1$H NMR (DMSO-d$_6$) δ 1.27 (s, 9H), 2.80 (t, 2H), 2.95 (t, 2H), 7.22 (d, 2H), 7.33 (d, 2H), 7.67 (t, 1H), 7.80 (d, 1H), 7.96 (t, 2H), 8.48 (d, 1H), 9.33 (s, 1H), 9.99 (s, 1H).

EXAMPLE 218

N-[(4-tert-butylcyclohexyl)methyl]-N'-5-isoquinolinylurea

The title compound was prepared using the procedure described in Example 61B using (4-tert-butylcyclohexyl)methylamine instead of 4-cyanobenzyl alcohol. MS (ESI) m/z: 340.18 (M+H)+; $^1$H NMR (DMSO-d$_6$) δ 0.82 (d, 9H), 0.93 (d, 4H), 1.09–1.50 (m, 2H), 1.74 (d, 2H), 1.82 (d, 2H), 3.01 & 3.19 (t & dd, 2H), 7.19 & 7.24 (t & t, 1H), 7.87 (t, 1H), 8.03 (d, 1H), 8.63 (dd, 1H), 8.67 (d, 1H), 8.76 (dd, 1H), 9.47 (d, 1H), 9.74 (s, 1H).

EXAMPLE 219

N-(3,4-difluorobenzyl)-N'-5-isoquinolinylurea

The title compound was prepared using the procedure described in Example 61B using 3,4-difluorobenzylamine instead of 4-cyanobenzyl alcohol. MS (ESI) m/z: 314.07 (M+H)+; $^1$H NMR (DMSO-d$_6$) δ 4.36 (d, 2H), 7.12 (t, 1H), 7.20 (m, 1H), 7.40 (t, 2H), 7.60 (t, 1H), 7.75 (d, 1H), 7.94 (d, 1H), 8.26 (dd, 1H), 8.54 (d, 1H), 8.79 (s, 1H), 9.27 (s, 1H).

EXAMPLE 220

N-5-isoquinolinyl-N'-{[4-(trifluoromethyl)cyclohexyl]methyl}urea

The title compound was prepared using the procedure described in Example 61B using [4-(trifluoromethyl)cyclohexyl]methylamine instead of 4-cyanobenzyl alcohol. MS (ESI) m/z: 352.07 (M+H)+; $^1$H NMR (CDCl$_3$) δ 1.05 & 1.27 (q & q, 1H), 1.58 (m, 2H), 1.66 (m, 2H), 1.70 (m, 2H), 1.94 (m, 2H), 2.08 (m, 1H), 3.21 & 3.34 (d & d, 2H), 7.16 (br, 1H), 7.84 (s, 2H), 8.35 (s, 1H), 8.82 (d, 1H), 9.12 (d, 1H), 9.36 (s, 1H), 9.49 (s, 1H).

EXAMPLE 221 ethyl 5-isoquinolinylacetate

5-Bromoisquinoline (7.19 g, 34.5 mmol) in toluene (80 mL) was treated with dichlorobis(tri-o-tolylphosphine)palladium(II) (5 mol %, 1.3639 g, 1.7 mmol) and tributylstannanylacetic acid ethyl ester in toluene (20 mL). This mixture was heated at 125° C. overnight, cooled, diluted with ethyl acetate (100 mL), washed with water (2×50 mL), dried (MgSO$_4$), and the filtrate was concentrated under reduced pressure. The residue was puified by column chromatography (20% ethyl acetate in hexanes to 50% ethyl acetate in hexanes) to provide the title compound. MS (ESI+) m/z 216 (M+H)+, (ESI−) m/z 214 (M−H)−; $^1$HNMR (DMSO, 300 MHz) δ 1.17 (t, J 7.1, 3H), 4.09 (q, J 7.1, 2H), 4.17 (s, 2H), 7.64 (m, 1H), 7.72 (d, J 6.2, 1H), 7.81 (d, J 5.7, 1H), 8.07 (d, J 7.9, 1H), 8.54 (d, J 6.1, 1H), 9.33 (s, 1H); Anal. Calcd for C$_{13}$H$_{13}$NO$_2$.0.6H$_2$O: C, 69.07; H, 6.33; N, 6.2. Found: C, 59.4; H, 6.09; N, 5.89.

EXAMPLE 222

2-(5-isoquinolinyl)-N-[4-(trifluoromethoxy)benzyl]acetamide

EXAMPLE 222A 5-isoquinolinylacetic acid

Ethyl 5-isoquinolinylacetate (1.15 g, 5.34 mmol) was dissolved in concentrated H$_2$SO$_4$ (12 mL) and heated at 100° C. for 2 hours. The reaction mixture was poured into ice (20 g) and the pH was adjusted to 6 with 50% NaOH/H$_2$O. The mixture was allowed to set of several hours, filtered, and the filter cake was rinsed with water to provide the title compound. MS (ESI+) m/z 188 (M+H)+; $^1$H NMR (DMSO, 300 MHz) δ 4.07 (s, 2H), 7.67 (m, 2H), 7.83 (d, J 5.7, 1H), 8.05 (d, J 8.1, 1H), 8.53 (d, J 6.1, 1H), 9.32 (s, 1H), 12.50 (s, 1H); $^{13}$C NMR (DMSO, 75 MHz) δ 37.6 (CH$_2$CO), 117.1 (CH, C4), 126.8, 127.0 (CH, C7 & C8), 128.4 (C), 131.1 (C), 132.0 (CH, C6), 134.4 (C), 143.0 (CH, C3), 152.7 (CH, C1), 172.3 (CO); Anal. Calcd for C$_{11}$H$_9$NO$_2$: C, 70.58; H, 4.85; N, 7.48. Found: C, 70.42; H, 4.93; N, 7.34.

EXAMPLE 222B 2-(5-isoquinolinyl)-N-[4-(trifluoromethoxy)benzyl]acetamide

Polymer supported 1,3-dicyclohexylcarbodiimide (0.845 g) in dichloromethane (5 mL) was treated with 5-isoquinolinylacetic acid (0.075 g, 0.40 mmol) in dichloromethane (1 mL), 1-hydroxy-7-azabenzotriazole (0.049 g), and triethylamine (0.080 g) in dichloromethane (1 mL). After stirring for 5 minutes, the mixture was treated with 4-(trifluoromethoxy)benzylamine (0.40 mmol). After stirring for 16 hours, the mixture was treated with MP-Carbonate resin (0.310 g), stirred for 5 minutes, and filtered. The filtrate was diluted with dichloromethane (40 mL), washed with water (4×20 mL), brine (1×20 mL), dried (Na$_5$SO$_4$), filtered, and the filtrate was concentrated under reduced pressure to provide the title compound which was purified by forming the hydrochloride salt and triturating the solid with hot ethyl acetate. MS (ESI+) m/z 361 (M+H)+; MS (ESI−) m/z 359 (M−H)−; $^1$H NMR (DMSO, 300 MHz) δ 3.99 (s, 2H), 4.31 (d, J 5.7, 2H), 7.31 (d, J 8.8, 2H), 7.36 (d, J 6.4, 2H), 7.66 (m, 2H), 7.93 (d, J 6.1, 1H), 8.03 (d, J 8.2, 1H), 8.51 (d, J 6.1, 1H), 8.74 (t, J 6.1, 1H), 9.31 (s, 1H); Anal. Calcd for C$_{19}$H$_{15}$F$_3$N$_2$O$_2$+1 HCl: C, 57.51; H, 4.06; N, 7.06. Found: C, 57.42; H, 3.98; N, 6.72.

EXAMPLE 223

N-(4-tert-butylbenzyl)-2-(5-isoquinolinyl)acetamide

The title compound was prepared using the procedure described in Example 222B using 4-(tert-butyl)benzylamine instead of 4-(trifluoromethoxy)benzylamine. MS (ESI+) m/z 333 (M+H)+; MS (ESI−) m/z 331 (M−H); $^1$H NMR (DMSO, 300 MHz) δ 1.26 (s, 9H), 3.96 (s, 2H), 4.24 (d, J 6.1, 2H), 7.17 (d, J 8.5, 2H), 7.32 (d, J 6.4, 2H), 7.66 (m, 2H), 7.83 (d, J 6.1, 1H), 8.03 (d, J 8.1, 1H), 8.51 (d, J 6.1, 1H), 8.65 (t, J 5.8, 1H), 9.30 (s, 1H); Anal. Calcd for $C_{22}H_{24}N_2O$+1.15 HCl: C, 70.58; H, 6.77; N, 7.48. Found: C, 70.56; H, 6.80; N, 7.39.

EXAMPLE 224

N-[3-fluoro-4-(trifluoromethyl)benzyl]-2-(5-isoquinolinyl)acetamide

The title compound was prepared using the procedure described in Example 222B using 3-fluoro-4-(trifluoromethyl)benzylamine instead of 4-(trifluoromethoxy)benzylamine. MS (ESI+) m/z 363 (M+H)+; MS (ESI−) m/z 361 (M−H)−; $^1$H NMR (DMSO, 300 MHz) δ 4.21 (s, 2H), 4.38 (d, J 6.1, 2H), 7.32 (m, 2H), 7.73 (t, J 7.8, 1H), 7.98 (t, J 8.1, 1H), 8.13 (d, J 7.1, 1H), 8.44 (d, J 8.4, 1H), 8.72 (d, J 6.8, 1H), 9.07 (t, J 6.1, 1H), 9.88 (s, 1H); Anal. Calcd for $C_{19}H_{14}F_4N_2O$+1.15 HCl: C, 56.45; H, 3.78; N, 6.93. Found: C, 56.57; H, 3.69; N, 6.88.

EXAMPLE 225

N-{1-[3-fluoro-4-(trifluoromethyl)phenyl]ethyl}-2-(5-isoquinolinyl)acetamide

The title compound was prepared using the procedure described in Example 222B using 1-[3-fluoro-4-(trifluoromethyl)phenyl]ethylamine instead of 4-(trifluoromethoxy)benzylamine. MS (ESI+) m/z 377 (M+H)+; MS (ESI−) m/z 375, 411 (M−H)−; $^1$H NMR (DMSO, 300 MHz) δ 1.41 (d, J 7.1, 3H), 4.17 (s, 2H), 4.93 (q, J 7.4, 1H), 7.39 (m, 2H), 7.72 (t, J 7.8, 1H), 7.96 (t, J 8.1, 1H), 8.10 (d, J 6.4, 1H), 8.42 (d, J 8.2, 1H), 8.55 (d, J 6.8, 1H), 8.71 (d, J 6.8, 1H), 9.07 (d, J 7.5, 1H), 9.86 (s, 1H); Anal. Calcd for $C_{20}H_{16}F_4N_2O$+1.55 HCl: C, 55.50; H, 4.18; N, 6.52. Found: C, 55.49; H, 4.09; N, 6.47.

EXAMPLE 226

N-{1-[3-fluoro-4-(trifluoromethyl)phenyl]propyl}-2-(5-isoquinolinyl)acetamide

The title compound was prepared using the procedure described in Example 222B using 1-[3-fluoro-4-(trifluoromethyl)phenyl]propylamine instead of 4-(trifluoromethoxy)benzylamine. MS (ESI+) m/z 391 (M+H)+; MS (ESI−) m/z 389, 425 (M−H)−; $^1$H NMR (DMSO, 300 MHz) δ 1.06 (t, J 6.8, 3H), 3.44 (q, J 7.1, 2H), 4.20 (s, 2H), 4.73 (q, J 7.5, 1H), 7.41 (m, 2H), 7.72 (t, J 7.8, 1H), 7.97 (t, J 8.2, 1H), 8.12 (d, J 7.1, 1H), 8.44 (d, J 8.1, 1H), 8.59 (d, J 6.7, 1H), 8.72 (d, J 6.8, 1H), 9.10 (d, J 8.2, 1H), 9.88 (s, 1H); Anal. Calcd for $C_{21}H_{18}F_4N_2O$+1.3 HCl: C, 57.46; H, 4.70; N, 6.51. Found: C, 57.62; H, 4.44; N, 6.40.

EXAMPLE 227

2-(3-methyl-5-isoquinolinyl)-N-[4-(trifluoromethyl)benzyl]acetamide

EXAMPLE 227A ethyl (3-methyl-5-isoquinolinyl)acetate

The title compound was prepared using the procedure described in Example 221 using 5-bromo-3-methylisoquinoline instead of 5-bromoisoquinoline. MS (ESI+) m/z 230 (M+H)+; MS (ESI−) m/z 228 (M−H)−; $^1$H NMR (DMSO, 300 MHz) δ 1.18 (t, J=7.1, 3H), 2.63 (s, 3H), 4.10 (m, 5H), 7.54 (t, J=7.1, 1H), 7.65 (m, 2H), 8.01 (d, J 8.1, 1H), 9.22 (s, 1H).

EXAMPLE 227B (3-methyl-5-isoquinolinyl)acetic acid

The title compound was prepared using the procedure described in Example 222A using ethyl (3-methyl-5-isoquinolinyl)acetate instead of ethyl 5-isoquinolinylacetate. MS (ESI+) m/z 202 (M+H)+; MS (ESI−) m/z 200, 156 (M−H)−; $^1$H NMR (DMSO, 300 MHz) δ 2.62 (s, 3H), 4.03 (s, 2H), 7.58 (t, J 8.2, 1H), 7.64 (m, 2H), 7.99 (d, J 8.1, 1H), 9.21 (s, 1H), 12.46 (s, 1H); Anal. Calcd for $C_{12}H_{11}NO_2$: C, 71.63; H, 5.51; N, 6.96. Found: C, 71.00; H, 5.42; N, 6.79.

EXAMPLE 227C 2-(3-methyl-5-isoquinolinyl)-N-[4-(trifluoromethyl)benzyl]acetamide The title compound was prepared using the procedure described in Example 222B using (3-methyl-5-isoquinolinyl)acetic acid and 4-(trifluoromethyl)benzylamine instead of 5-isoquinolinylacetic acid and 4-(trifluoromethoxy)benzylamine. MS (ESI+) m/z 359 (M+H)+; MS (ESI−) m/z 357 (M−H)−; $^1$H NMR (DMSO, 300 MHz) δ 2.77 (s, 3H), 4.12 (s, 2H), 4.37 (d, J 6.1, 2H), 7.47 (d, J 7.8, 2H), 7.68 (d, J 8.1, 2H), 7.86 (t, J 7.4, 1H), 8.03 (d, J 6.4, 1H), 8.36 (m, 2H), 9.03 (t, J 5.8, 1H), 9.77 (s, 1H); Anal. Calcd for $C_{20}H_{17}F_3N_2O$+1.85 HCl: C, 56.44; H, 4.57. Found: C, 56.41; H, 4.46.

EXAMPLE 228

N-[3-fluoro-4-(trifluoromethyl)benzyl]-2-(3-methyl-5-isoquinolinyl)acetamide

The title compound was prepared using the procedure described in Example 222B using (3-methyl-5-isoquinolinyl)acetic acid and 3-fluoro-4-(trifluoromethyl)benzylamine instead of 5-isoquinolinylacetic acid and 4-(trifluoromethoxy)benzylamine. MS (ESI+) m/z 377 (M+H)+; MS (ESI−) m/z 375 (M−H)−; $^1$H NMR (DMSO, 300 MHz) δ 2.77 (s, 3H), 4.14 (s, 2H), 4.38 (d, J 6.1, 2H), 7.33 (m, 2H), 7.72 (t, J 7.8, 1H), 7.86 (t, J 7.5, 1H), 8.04 (d, J 6.8, 1H), 8.36 (m, 2H), 9.07 (t, J 6.1, 1H), 9.77 (s, 1H); Anal. Calcd for $C_{20}H_{16}F_4N_2O$+1.2 HCl+0.3 DMF: C, 56.62; H, 4.20; N, 7.48. Found: C, 56.79; H, 4.40; N, 7.29.

EXAMPLE 229

2-(5-isoquinolinyl)-N-{2-[3-(trifluoromethyl)phenyl]ethyl}acetamide

The title compound was prepared using the procedure described in Example 222B using 2-[3-(trifluoromethyl)phenyl]ethylamine instead of 4-(trifluoromethoxy)benzylamine. MS (ESI+) m/z 359 (M+H)+; MS (ESI−) m/z 357, 393 (M−H)−; $^1$H NMR (DMSO, 300 MHz) δ 2.83 (t, J 7.1, 2H), 3.35 (q, J 6.8, 2H), 4.03 (s, 2H), 7.50 (m, 4H), 7.98 (m, 2H), 8.47 (m, 3H), 8.68 (d, J 6.8, 1H), 9.89 (s, 1H); Anal. Calcd for $C_{20}H_{17}F_3N_2O$+1.55 HCl: C, 57.94; H, 4.64; N, 6.73. Found: C, 57.90; H, 4.51; N, 6.75.

EXAMPLE 230

N-(3,3-diphenylpropyl)-2-(5-isoquinolinyl)acetamide

The title compound was prepared using the procedure described in Example 222B using 3,3-diphenylpropylamine instead of 4-(trifluoromethoxy)benzylamine. MS (ESI+) m/z 381 (M+H)⁺; MS (ESI−) m/z 379 (M−H)⁻; ¹H NMR (DMSO, 300 MHz) δ 2.17 (q, J 7.8, 2H), 2.96 (q, J 5.8, 2H), 3.99 (s, 2H), 7.16 (m, 2H), 7.25 (m, 9H), 7.84 (t, J 7.5, 1H), 7.93 (d, J 6.5, 1H), 8.29 (m, 3H), 8.63 (d, J 6.5, 1H), 9.64 (s, 1H); Anal. Calcd for $C_{26}H_{24}N_2O$+1 HCl+0.45$H_2O$: C, 73.47; H, 6.14; N, 6.59. Found: C, 73.84; H, 6.17; N, 6.07.

EXAMPLE 231

N-(3-butoxypropyl)-2-(5-isoquinolinyl)acetamide

The title compound was prepared using the procedure described in Example 222B using 3-butoxypropylamine instead of 4-(trifluoromethoxy)benzylamine. MS (ESI+) m/z 301 (M+H)⁺; MS (ESI−) m/z 299 (M−H)⁻; ¹H NMR (DMSO, 300 MHz) δ 0.85 (t, J 7.5, 3H), 1.28 (m, 2H), 1.43 (m, 2H), 1.63 (m, 2H), 3.11 (m, 2H), 3.32 (m, 4H), 3.97 (s, 2H), 7.81 (t, J 7.2, 1H), 7.89 (d, J 6.8, 1H), 8.22 (m, 3H), 8.63 (d, J 5.9, 1H), 9.59 (s, 1H).

EXAMPLE 232

2-(5-isoquinolinyl)-N-(3-phenylpropyl)acetamide

The title compound was prepared using the procedure described in Example 222B using 3-phenylpropylamine instead of 4-(trifluoromethoxy)benzylamine. MS (ESI+) m/z 305 (M+H)⁺; MS (ESI−) m/z 303 (M−H)⁻; ¹H NMR (DMSO, 300 MHz) δ 1.70 (p, J 7.1, 2H), 2.55 (t, J 7.1, 2H), 3.07 (q, J 6.8, 2H), 4.05 (s, 2H), 7.21 (m, 5H), 7.92 (t, J 7.5, 1H), 8.04 (d, J 6.4, 1H), 8.38 (m, 2H), 8.48 (d, J 6.5, 1H), 8.69 (d, J 6.5, 1H), 9.79 (s, 1H); Anal. Calcd for $C_{20}H_{20}N_2O$+1.5 HCl: C, 66.97; H, 6.18; N, 8.06. Found: C, 66.90; H, 6.04; N, 7.80.

EXAMPLE 233

2-(5-isoquinolinyl)-N-[2-(2-thienyl)ethyl]acetamide

The title compound was prepared using the procedure described in Example 222B using 2-(2-thienyl)ethylamine instead of 4-(trifluoromethoxy)benzylamine. MS (ESI+) m/z 297 (M+H)⁺; MS (ESI−) m/z 295 (M−H)⁻; ¹H NMR (DMSO, 300 MHz) δ 2.93 (t, J 6.8, 2H), 3.32 (q, J 6.9, 2H), 3.96 (s, 2H), 6.83 (d, J 2.5, 1H), 6.93 (q, J 3.4, 1H), 7.31 (t, J 3.7, 1H), 7.77 (t, J 8.1, 1H), 7.82 (d, J 7.2, 1H), 8.14 (d, J 6.2, 1H), 8.18 (d, J 8.1, 1H), 8.35 (t, J 6.1, 1H), 8.59 (d, J 6.2, 1H), 9.53 (s, 1H).

EXAMPLE 234

N-[3-(1H-imidazol-1-yl)propyl]-2-(5-isoquinolinyl) acetamide

The title compound was prepared using the procedure described in Example 222B using 3-(1H-imidazol-1-yl)propylamine instead of 4-(trifluoromethoxy)benzylamine. MS (ESI+) m/z 295 (M+H)⁺; MS (ESI−) m/z 293 (M−H)⁻; ¹H NMR (DMSO, 300 MHz) δ 1.96 (m, 2H), 3.07 (q, J 6.9, 2H), 3.97 (s, 2H), 4.19 (t, J 6.8, 2H), 7.73 (m, 4H), 8.09 (d, J 5.9, 1H), 8.14 (d, J 8.1, 1H), 8.32 (t, J 5.3, 1H), 8.58 (d, J 5.9, 1H), 9.07 (s, 1H), 9.46 (s, 1H).

EXAMPLE 235

2-(5-isoquinolinyl)-N-[3-(2-oxo-1-pyrrolidinyl) propyl]acetamide

The title compound was prepared using the procedure described in Example 222B using 1-(3-aminopropyl)-2-pyrrolidinone instead of 4-(trifluoromethoxy)benzylamine. MS (ESI+) m/z 312 (M+H)⁺; MS (ESI−) m/z 310 (M−H)⁻; ¹H NMR (DMSO, 300 MHz) δ 1.59 (p, J 7.5, 15.3, 2H), 1.89 (p, J 7.2, 14.0, 2H), 2.19 (t, J 8.2, 2H), 3.04 (q, J 5.9, 2H), 3.15 (t, J 7.1, 2H), 3.28 (t, J 7.2, 2H), 3.99 (s, 2H), 7.81 (t, J 7.2, 1H), 7.99 (d, J 6.9, 1H), 8.23 (m, 3H), 8.63 (d, J 6.3, 1H), 9.60 (s, 1H).

EXAMPLE 236

N-(2,2-diphenylethyl)-2-(5-isoquinolinyl)acetamide

The title compound was prepared using the procedure described in Example 222B using 2,2-diphenylethylamine instead of 4-(trifluoromethoxy)benzylamine. MS (ESI+) m/z 367 (M+H)⁺; MS (ESI−) m/z 365 (M−H)⁻; ¹H NMR (DMSO, 300 MHz) δ 3.73 (q, J 6.0, 2H), 3.83 (s, 2H), 4.18 (t, J 8.1, 1H), 7.18 (m, 2H), 7.25 (m, 9H), 7.60 (m, 2H), 7.81 (d, J 6.5, 1H), 8.06 (d, J 8.1, 1H), 8.25 (t, J 4.7, 1H), 8.43 (d, J 5.6, 1H), 9.37 (s, 1H).

EXAMPLE 237

N-benzyl-2-(5-isoquinolinyl)acetamide

The title compound was prepared using the procedure described in Example 222B using 2,2-diphenylethylamine instead of 4-(trifluoromethoxy)benzylamine. MS (ESI+) m/z 277 (M+H)⁺; MS (ESI−) m/z 275 (M−H)⁻; ¹H NMR (DMSO, 300 MHz) δ 4.05 (s, 2H), 4.29 (d, J 5.9, 2H), 7.23 (t, J 5.3, 3H), 7.30 (t, J 3.4, 2H), 7.78 (t, J 7.8, 1H), 7.88 (d, J 6.9, 1H), 8.20 (t, J 7.8, 2H), 8.60 (d, J 6.3, 1H), 8.72 (t, J 5.3, 1H), 9.54 (s, 1H).

EXAMPLE 238

2-(5-isoquinolinyl)-N-{4-[(trifluoromethyl)thio] benzyl}acetamide

The title compound was prepared using the procedure described in Example 222B using 4-[(trifluoromethyl)thio]benzylamine instead of 4-(trifluoromethoxy)benzylamine. MS (ESI+) m/z 377 (M+H)⁺; MS (ESI−) m/z 375 (M−H)⁻; ¹H NMR (DMSO, 300 MHz) δ 4.06 (s, 2H), 4.35 (d, J 5.9, 2H), 7.40 (d, J 8.1, 2H), 7.66 (d, J 8.2, 2H), 7.75 (t, J 7.5, 1H), 7.85 (d, J 6.6, 1H), 8.16 (m, 2H), 8.59 (d, J 5.9, 1H), 8.79 (t, J 5.9, 1H), 9.50 (s, 1H).

EXAMPLE 239

2-(5-isoquinolinyl)-N-(2-phenylethyl)acetamide

The title compound was prepared using the procedure described in Example 222B using 2-phenylethylamine instead of 4-(trifluoromethoxy)benzylamine. MS (ESI+) m/z 291 (M+H)⁺; MS (ESI−) m/z 289 (M−H)⁻; ¹H NMR (DMSO, 300 MHz) δ 2.71 (t, J 7.1, 2H), 3.31 (q, J 7.1, 2H), 3.94 (s, 2H), 7.17 (m, 3H), 7.25 (t, J 7.5, 2H), 7.77 (t, J 7.5, 1H), 7.82 (d, J 6.6, 1H), 8.15 (d, J 6.2, 1H), 8.19 (d, J 7.8, 1H), 8.27 (t, J 5.3, 1H), 8.59 (d, J 5.0, 1H), 9.55 (s, 1H).

EXAMPLE 240

2-(5-isoquinolinyl)-N-[2-(3-pyridinyl)ethyl] acetamide

The title compound was prepared using the procedure described in Example 222B using 2-(2-pyridinyl)ethylamine instead of 4-(trifluoromethoxy)benzylamine. MS (ESI+) m/z 292 (M+H)⁺; MS (ESI−) m/z 290 (M−H)⁻; ¹H NMR (DMSO, 300 MHz) δ 2.84 (t, J 6.9, 2H), 3.39 (q, J 6.5, 2H), 3.92 (s, 2H), 7.58 (t, J 5.3, 1H), 7.75 (m, 2H), 7.97 (d, J 7.8, 1H), 8.05 (d, J 5.9, 1H), 8.16 (d, J 7.8, 1H), 8.29 (t, J 5.6, 1H), 8.57 (m, 3H), 9.51 (s, 1H).

EXAMPLE 241

N-{1-[3-fluoro-4-(trifluoromethyl)phenyl]ethyl}-N'-5-isoquinolinylurea

The title compound was prepared using the procedure described in Example 61B using 1-[3-fluoro-4-(trifluoromethyl)phenyl]ethylamine instead of 4-cyanobenzyl alcohol. MS (ESI+) m/z 378 (M+H)$^+$; MS (ESI−) m/z 376 (M−H)$^−$; $^1$H NMR (DMSO, 300 MHz) δ 1.46 (d, J 7.1, 3H), 4.97 (p, J 7.1, 1H), 7.51 (m, 2H), 7.77 (t, J 7.8, 1H), 7.86 (t, J 8.2, 1H), 7.99 (d, J 7.1, 1H), 8.06 (d, J 8.1, 1H), 8.58 (d, J 6.8, 1H), 8.71 (d, J 6.8, 1H), 8.78 (d, J 6.8, 1H), 9.62 (s, 1H), 9.76 (s, 1H); Anal. Calcd for $C_{19}H_{15}F_4N_3O+1$ HCl: C, 54.93; H, 3.99; N, 10.09. Found: C, 55.15; H, 3.90; N, 10.15.

EXAMPLE 242

N-{1-[3-fluoro-4-(trifluoromethyl)phenyl]propyl}-N'-5-isoquinolinylurea

The title compound was prepared using the procedure described in Example 61B using 1-[3-fluoro-4-(trifluoromethyl)phenyl]propylamine instead of 4-cyanobenzyl alcohol. MS (ESI+) m/z 392 (M+H)$^+$; MS (ESI−) m/z 390 (M−H)$^−$; $^1$H NMR (DMSO, 300 MHz) δ 0.94 (t, J 7.4, 3H), 1.78 (m, 2H), 4.80 (q, J 7.5, 1H), 7.59 (m, 2H), 7.77 (t, J 8.1, 1H), 7.84 (t, J 8.2, 1H), 7.96 (d, J 8.2, 1H), 8.04 (d, J 8.1, 1H), 8.56 (d, J 7.1, 1H), 8.73 (m, 2H), 9.59 (s, 1H), 9.73 (s, 1H); Anal. Calcd for $C_{20}H_{17}F_4N_3O+1$ HCl: C, 56.10; H, 4.26; N, 9.81. Found: C, 56.15; H, 4.24; N, 9.82.

EXAMPLE 243

N-[3-bromo-4-(trifluoromethyl)benzyl]-2-(5-isoquinolinyl)acetamide

EXAMPLE 243A 3-bromo-4-trifluoromethylbenzoic acid

3-Amino-4-trifluoromethylbenzoic acid (8.20 g, 40.0 mmol), prepared according to Astrid Giencke and Helmut Lackner, Liebigs Ann. Chem., 569–579:6 (1990), in 48% HBr (20 mL) and H$_2$O (67 mL) at 0° C. was treated with NaNO$_2$ (2.99 g) in small portions over 15 minutes. After stirring for 30 minutes, the mixture was treated with urea (0.250 g) and then the mixture was added dropwise to a solution of CuBr (10.0 g) in 48% HBr (40 mL) and H$_2$O (100 mL). The reaction mixture was heated at 75° C., stirred for 2 hours, cooled to room temperature, and stirred overnight. The mixture was treated with with 20% NaOH until the pH>10. The resulting blue copper salts were removed by filtration through Celite. The mixture was acidified to pH 1 with HCl, extracted with CH$_2$Cl$_2$ (3×200 mL), dried over Na$_2$SO$_4$, filtered, and the filtrate was concentrated under reduced pressure to provide the title compound.

EXAMPLE 243B 3-bromo-4-(trifluoromethyl)benzamide

The product from Example 243A (4.00 g, 14.9 mmol) in thionyl chloride (20 mL) was heated at 80° C. for 2 hours. The mixture was concentrated under reduced pressure and the residue was dissolved in MeOH (30 mL) and cooled to −60° C. The mixture was treated with ammonium hydroxide (10 mL) and allowed to reach room temperature over 3 hours. The solvent was removed to give crude 3-bromo-4-trifluoromethylbenzamide. mp 148–150° C.

EXAMPLE 243C 3-bromo-4-(trifluoromethyl)benzylamine

LiAlH$_4$ (0.906 g, 23.9 mmol) was suspended in 60 mL of dry THF and cooled to 0° C. The mixture was treated with the product from Example 243B (3.2 g, 11.9 mmol) in THF (10 mL) dropwise with stirring. After 20 minutes, the mixture was warmed to room temperature 12 hours and treated in succession with ethyl acetate (2 mL), NaOH (50%, 5 mL), and diethyl ether (100 mL). The organic phase decanted, dried (Na$_2$SO$_4$), filtered and the filtrate was concentrated under reduced pressure to provide the title compound.

EXAMPLE 243D

N-[3-bromo-4-(trifluoromethyl)benzyl]-2-(5-isoquinolinyl)acetamide

The title compound was prepared using the procedure described in Example 222B using 3-bromo-4-(trifluoromethyl)benzylamine instead of 4-(trifluoromethoxy)benzylamine. MS (ESI+) m/z 425, 423 (M+H)$^+$; MS (ESI−) m/z 423, 421 (M−H)$^−$; $^1$H NMR (DMSO, 300 MHz) δ 4.09 (s, 2H), 4.36 (d, J 6.1, 2H), 7.43 (d, J 7.2, 2H), 7.67 (s, 1H), 7.79 (m, 2H), 7.90 (d, J 7.9, 1H), 8.22 (m, 2H), 8.61 (d, J 6.4, 1H), 8.86 (t, J 6.8, 1H), 9.56 (s, 1H); Anal. Calcd for $C_{19}H_{14}BrF_3N_2O+0.9$ TFA: C, 47.51; H, 2.86; N, 5.33. Found: C, 47.53; H, 2.92; N, 5.22.

EXAMPLE 244

N-(4-bromo-3-methylbenzyl)-2-(5-isoquinolinyl)acetamide

EXAMPLE 244A 4-bromo-3-methylbenzylamine

LiAlH$_4$ (0.68 g) in diethyl ether (30 mL) was treated with 4-bromo-3-methylbenzonitrile (15 mmol) and refluxed for 2 hours. The mixture was cooled to 0° C. and treated in succession with water (0.7 mL), 20% NaOH (0.5 mL), and water (2.5 mL). The mixture was filtered through a celite pad and the filter cake was washed several times with diethyl ether. The filtrate was dried over Na$_2$SO$_4$, filtered, and the filtrate was concentrated under reduced pressure to provide the title compound. MS (ESI+) m/z 194 (M+H)$^+$; MS (ESI−) m/z 192 (M−H)$^−$; $^1$H NMR (DMSO, 300 MHz) δ 3.97 (s, 2H), 7.30 (m, 1H), 7.46 (m, 2H).

EXAMPLE 244B

N-(4-bromo-3-methylbenzyl)-2-(5-isoquinolinyl)acetamide

The title compound was prepared using the procedure described in Example 222B using 4-bromo-3-methylbenzylamine instead of 4-(trifluoromethoxy)benzylamine. MS (ESI+) m/z 371, 369 (M+H)$^+$; MS (ESI−) m/z 369, 367 (M−H)$^−$; $^1$H NMR (DMSO, 300 MHz) δ 2.28 (s, 3H), 4.13 (s, 2H), 4.22 (d, J 6.1, 2H), 7.00 (d, J 8.1, 1H), 7.10 (s, 1H), 7.50 (d, J 8.1, 1H), 7.92 (m, 1H), 8.05 (d, J 7.1, 1H), 8.38 (d, J 8.1, 1H), 8.48 (d, J 6.8, 1H), 8.70 (d, J 6.8, 1H), 8.86 (t, J 6.8, 1H), 9.80 (s, 1H); Anal. Calcd for $C_{19}H_{17}BrN_2O+1.1$ HCl: C, 55.75; H, 4.46; N, 6.84. Found: C, 55.76; H, 4.23; N, 6.93.

EXAMPLE 245

N-[2,4-bis(trifluoromethyl)benzyl]-2-(5-isoquinolinyl)acetamide

The title compound was prepared using the procedure described in Example 222B using 2,4-bis(trifluoromethyl) benzylamine instead of 4-(trifluoromethoxy)benzylamine. MS (ESI+) m/z 413 (M+H)$^+$; MS (ESI−) m/z 411 (M−H)$^−$; $^1$H NMR (DMSO, 300 MHz) rotamers δ 4.22 (s, 2H), 4.53 (d, J 6.1, 2H), 5.97 (d, J 6.4, 1H), 7.57–8.48 (m, 6H), 8.72 (d, J 6.4, 1H), 8.84 (m, 1H), 9.12 (t, J 6.8, 1H), 9.73 (s, 1H), 9.82 (s, 1H); Anal. Calcd for $C_{20}H_{14}F_6N_2O$ 1.2 HCl: C, 52.67; H, 3.36; N, 6.14. Found: C, 52.67; H, 3.21; N, 6.09.

EXAMPLE 246

N-[2-chloro-4-(trifluoromethyl)benzyl]-2-(5-isoquinolinyl)acetamide

EXAMPLE 246A 2-chloro-4-(trifluoromethyl)benzylamine

The title compound was prepared using the procedure described in Example 244A using 2-chloro-4-(trifluoromethyl)benzonitrile instead of 4-bromo-3-methylbenzonitrile. MS (ESI+) m/z 209 (M+H)$^+$; $^1$H NMR (DMSO, 300 MHz) δ 3.97 (s, 2H), 7.50–7.70 (m, 3H).

EXAMPLE 246B

N-[2-chloro-4-(trifluoromethyl)benzyl]-2-(5-isoquinolinyl)acetamide

The title compound was prepared using the procedure described in Example 222B using 2-chloro-4-(trifluoromethyl)benzylamine instead of 4-(trifluoromethoxy)benzylamine. MS (ESI+) m/z 379 (M+H)$^+$; MS (ESI−) m/z 377 (M−H)$^−$; $^1$H NMR (DMSO, 300 MHz) δ 4.19 (s, 2H), 4.41 (d, J 6.1, 2H), 7.56 (d, J 8.1, 1H), 7.70 (d, J 8.1, 1H), 7.83 (s, 1H), 7.92 (m, 1H), 8.06 (d, J 7.1, 1H), 8.37 (d, J 8.1, 1H), 8.45 (d, J 6.8, 1H), 8.70 (d, J 6.8, 1H), 8.97 (t, J 6.8, 1H), 9.77 (s, 1H); Anal. Calcd for $C_{19}H_{14}ClF_3N_2O+1$ HCl: C, 54.96; H, 3.64; N, 6.75. Found: C, 54.75; H, 3.47; N, 6.90.

EXAMPLE 247

N-[2,3-difluoro-4-(trifluoromethyl)benzyl]-2-(5-isoquinolinyl)acetamide

EXAMPLE 247A 2,3-difluoro-4-(trifluoromethyl)benzylamine

The title compound was prepared using the procedure described in Example 244A using 2,3-difluoro-4-(trifluoromethyl)benzonitrile instead of 4-bromo-3-methylbenzonitrile.

EXAMPLE 247B

N-[2,3-difluoro-4-(trifluoromethyl)benzyl]-2-(5-isoquinolinyl)acetamide

The title compound was prepared using the procedure described in Example 222B using 2,3-difluoro-4-(trifluoromethyl)benzylamine instead of 4-(trifluoromethoxy)benzylamine. MS (ESI+) m/z 381 (M+H)$^+$; MS (ESI−) m/z 379 (M−H)$^−$; $^1$H NMR (DMSO, 300 MHz) rotamers δ 4.16 (s, 2H), 4.42 (d, J 6.1, 2H), 7.35 (m, 1H), 7.59 (m, 1H), 7.93 (m, 1H), 8.07 (m, 1H), 8.39 (d, J 7.1, 1H), 8.46 (m, 1H), 8.70 (d, J 6.8, 1H), 9.05 (t, J 6.8, 1H), 9.81 (s, 1H); Anal. Calcd for $C_{19}H_{14}ClF_3N_2O+1$ HCl: C, 54.96; H, 3.64; N, 6.75. Found: C, 54.75; H, 3.47; N, 6.90.

EXAMPLE 248 ethyl 2-(5-isoquinolinyl)propanoate

Lithium diisopropylamide (12.75 mL, 2M, 25.5 mmol) in THF (160 mL) at −78° C. under nitrogen was treated with ethyl 5-isoquinolinylacetate (5.00 g, 23.2 mmol) in THF (5 mL). After stirring for 30 minutes at −78° C., the mixture was treated with HMPA (5.2 mL) and methyl iodide (1.62 mL, 25.5 mmol). After stirring for 30 minutes at −78° C., the mixture was warmed to 0° C. over 1 hour and quenched by addition of saturated NH$_4$Cl solution. The mixture was concentrated under reduced pressure to a volume of ~10 mL, diluted with ethyl acetate (200 mL), washed with water (100 mL×5), washed with brine, dried with anhydrous MgSO$_4$, filtered, and the filtrate was concentrated under reduced pressure to provide the title compound. MS (ESI+) m/z 230 (M+H)$^+$; MS (ESI−) m/z 228 (M−H)$^−$; $^1$H NMR (DMSO, 300 MHz) δ 1.53 (d, J 7.1, 3H), 4.35 (d, J 6.1, 2H), 4.47 (q, J 7.1, 1H), 7.18 (m, 2H), 7.70 (m, 3H), 8.05 (m, 2H), 8.53 (d, J 6.1, 1H), 8.68 (t, J 6.8, 1H), 9.32 (s, 1H); Anal. Calcd for $C_{20}H_{16}F_4N_2O+1.25$ HCl: C, 56.93; H, 4.12; N, 6.64. Found: C, 56.72; H, 4.45; N, 7.03.

EXAMPLE 249

N-[3-fluoro-4-(trifluoromethyl)benzyl]-2-(5-isoquinolinyl)propanamide

EXAMPLE 249A 2-(5-isoquinolinyl)propanoic acid

Ethyl 2-(5-isoquinolinyl)propanoate (1.00 g, 4.36 mmol) was heated at 85° C. in NaOH (25%, 20 mL) for 1 hour. The mixture was allowed to cool to room temperature, acidified to around pH 1 with HCl, and concentrated to a dry residue. The solid was extracted with CHCl$_3$:isopropyl alcohol (3:1, 50 mL×4). The extracts were combined, filtered, and the filtrate concentrated under reduced pressure to provide the title compound. MS (ESI+) m/z 202 (M+H)$^+$; MS (ESI−) m/z 200 (M−H)$^−$; $^1$H NMR (DMSO, 300 MHz) δ 1.42 (d, J 7.1, 3H), 4.01 (q, J 7.1, 1H), 7.58 (t, J 8.1, 1H), 7.63 (d, J 7.5, 1H), 7.86 (d, J 8.1, 1H), 8.19 (d, J 6.8, 1H), 8.43 (d, J 6.8, 1H), 9.22 (s, 1H); Anal. Calcd for $C_{12}H_{10}NO_2Na+$ 0.9H$_2$O: C, 60.20; H, 4.97; N, 5.85. Found: C, 60.45; H, 5.26; N, 5.46.

EXAMPLE 249B

N-[3-fluoro-4-(trifluoromethyl)benzyl]-2-(5-isoquinolinyl)propanamide

The title compound was prepared using the procedure described in Example 222B using 3-fluoro-4-(trifluoromethyl)benzylamine and 2-(5-isoquinolinyl) propanoic acid instead of 4-(trifluoromethoxy)benzylamine and 5-isoquinolinylacetic acid. MS (ESI+) m/z 377 (M+H)$^+$; MS (ESI−) m/z 375 (M−H)$^−$; $^1$H NMR (DMSO, 300 MHz)

δ 1.53 (d, J 7.1, 3H), 4.35 (d, J 6.1, 2H), 4.47 (q, J 7.1, 1H), 7.18 (m, 2H), 7.70 (m, 3H), 8.05 (m, 2H), 8.53 (d, J 6.1, 1H), 8.68 (t, J 6.8, 1H), 9.32 (s, 1H); Anal. Calcd for $C_{20}H_{16}F_4N_2O$+1.25 HCl: C, 56.93; H, 4.12; N, 6.64. Found: C, 56.72; H, 4.45; N, 7.03.

EXAMPLE 250

2-(5-isoquinolinyl)-N-[4-(trifluoromethyl)benzyl] propanamide

The title compound was prepared using the procedure described in Example 222B using 4-(trifluoromethyl) benzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^-$; $^1$H NMR (DMSO, 300 MHz) δ 1.59 (d, J 7.1, 3H), 4.35 (d, J 6.1, 2H), 4.69 (q, J 7.1, 1H), 7.40 (d, J 8.1, 1H), 7.65 (d, J 8.1, 1H), 7.78 (m, 2H), 8.03 (t, 1H), 8.20 (d, J 7.1, 1H), 8.47 (d, J 7.8, 1H), 8.65 (br s, 1H), 8.75 (s, 1H), 9.05 (t, J 5.8, 1H), 9.93 (s, 1H); Anal. Calcd for $C_{20}H_{17}F_3N_2O$+1.6 HCl+1.3$H_2O$: C, 54.58; H, 4.86. Found: C, 54.70; H, 5.10.

EXAMPLE 251

2-(5-isoquinolinyl)-N-[3-(trifluoromethyl)benzyl] propanamide

The title compound was prepared using the procedure described in Example 222B using 3-(trifluoromethyl) benzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^-$; $^1$H NMR (DMSO, 300 MHz) δ 1.54 (d, J 7.1, 3H), 4.28 (d, J 6.1, 2H), 4.50 (q, J 7.1, 1H), 7.41 (s, 1H), 7.49 (m, 2H), 7.56 (m, 1H), 7.80 (t, J 7.8, 1H), 7.95 (d, J 7.2, 1H), 8.21 (d, J 8.1, 1H), 8.32 (d, J 6.2, 1H), 8.60 (d, J 6.8, 1H), 8.72 (t, J 5.8, 1H), 9.56 (s, 1H).

EXAMPLE 252

2-(5-isoquinolinyl)-N-{4-[(trifluoromethyl)thio] benzyl}propanamide

The title compound was prepared using the procedure described in Example 222B using 4-[(trifluoromethyl)thio] benzylamine and 2-(5-isoquinolinyl)propanoic acid instead of 4-(trifluoromethoxy)benzylamine and 5-isoquinolinylacetic acid. MS (ESI+) m/z 391 (M+H)$^+$; MS (ESI−) m/z 389 (M−H)$^-$; $^1$H NMR (DMSO, 300 MHz) δ 1.57 (d, J 7.1, 3H), 4.33 (d, J 6.1, 2H), 4.65 (q, J 7.1, 1H), 7.33 (d, J 8.1, 1H), 7.65 (m, 2H), 7.76 (m, 1H), 7.98 (m, 2H), 8.19 (d, J 7.1, 1H), 8.42 (d, J 7.8, 1H), 8.61 (br s, 1H), 8.62 (d, J 6.8, 1H), 8.73 (d, J 6.8, 1H), 8.96 (t, J 5.8, 1H), 9.86 (s, 1H); Anal. Calcd for $C_{20}H_{17}F_3N_2OS$+2.1 HCl: C, 51.44; H, 4.12. Found: C, 51.35; H, 3.91.

EXAMPLE 253

N-(4-bromobenzyl)-2-(5-isoquinolinyl)propanamide

The title compound was prepared using the procedure described in Example 222B using 4-bromobenzylamine and 2-(5-isoquinolinyl)propanoic acid instead of 4-(trifluoromethoxy)benzylamine and 5-isoquinolinylacetic acid. MS (ESI+) m/z 371, 369 (M+H)$^+$; MS (ESI−) m/z 369, 367 (M−H)$^-$; $^1$H NMR (DMSO, 300 MHz) δ 1.57 (d, J 7.1, 3H), 4.23 (d, J 6.1, 2H), 4.63 (q, J 7.1, 1H), 7.14 (m, 2H), 7.47 (m, 2H), 7.76 (m, 1H), 7.98 (t, J 7.5, 1H), 8.17 (d, J 7.1, 1H), 8.43 (d, J 7.8, 1H), 8.69 (br s, 1H), 8.74 (d, J 6.8, 1H), 8.92 (t, J 5.8, 1H), 9.88 (s, 1H); Anal. Calcd for $C_{19}H_{17}BrN_2O$+1.4 HCl: C, 54.30; H, 4.41; N, 6.66. Found: C, 54.49; H, 4.28; N, 6.75.

EXAMPLE 254

N-(4-tert-butylbenzyl)-2-(5-isoquinolinyl) propanamide

The title compound was prepared using the procedure described in Example 222B using 4-(tert-butyl)benzylamine and 2-(5-isoquinolinyl)propanoic acid instead of 4-(trifluoromethoxy)benzylamine and 5-isoquinolinylacetic acid. MS (ESI+) m/z 347 (M+H)$^+$; MS (ESI−) m/z 345 (M−H)$^-$; $^1$H NMR (DMSO, 300 MHz) δ 1.56 (d, J 7.1, 3H), 4.22 (d, J 6.1, 2H), 4.57 (q, J 7.1, 1H), 7.10 (d, J 8.5, 2H), 7.29 (d, J 8.5, 2H), 7.98 (t, J 7.5, 1H), 8.13 (d, J 7.1, 1H), 8.34 (d, J 7.8, 1H), 8.56 (d, J 6.8, 1H), 8.69 (m, 2H), 9.78 (s, 1H); Anal. Calcd for $C_{23}H_{26}N_2O$+1.1 HCl: C, 71.46; H, 7.07; N, 7.25. Found: C, 71.13; H, 7.17; N, 7.02.

EXAMPLE 255

N-[3-fluoro-5-(trifluoromethyl)benzyl]-2-(5-isoquinolinyl)propanamide

The title compound was prepared using the procedure described in Example 222B using 3-fluoro-5-(trifluoromethyl)benzylamine and 2-(5-isoquinolinyl) propanoic acid instead of 4-(trifluoromethoxy)benzylamine and 5-isoquinolinylacetic acid. MS (ESI+) m/z 377 (M+H)$^+$; MS (ESI−) m/z 375 (M−H)$^-$; $^1$H NMR (DMSO, 300 MHz) δ 1.55 (d, J 7.1, 3H), 4.36 (m, 2H), 4.53 (q, J 7.1, 1H), 7.29 (m, 2H), 7.49 (d, J 8.7, 1H), 7.80 (t, J 7.8, 1H), 7.93 (d, J 6.5, 1H), 8.21 (d, J 8.1, 1H), 8.31 (d, J 6.4, 1H), 8.60 (d, J 6.2, 1H), 8.73 (t, J 5.8, 1H), 9.56 (s, 1H).

EXAMPLE 256

2-(5-isoquinolinyl)-N-[4-(trifluoromethoxy)benzyl] propanamide

The title compound was prepared using the procedure described in Example 222B using 2-(5-isoquinolinyl) propanoic acid instead of 5-isoquinolinylacetic acid. MS (ESI+) m/z 375 (M+H)$^+$; MS (ESI−) m/z 373 (M−H)$^-$; $^1$H NMR (DMSO, 300 MHz) δ 1.54 (d, J 7.1, 3H), 4.28 (d, J 6.1, 2H), 4.50 (q, J 7.1, 1H), 7.28 (q, J 8.5, 4H), 7.79 (t, J 7.8, 1H), 7.93 (d, J 7.2, 1H), 8.18 (d, J 8.1, 1H), 8.26 (d, J 6.2, 1H), 8.59 (d, J 6.8, 1H), 8.65 (t, J 5.8, 1H), 9.53 (s, 1H).

EXAMPLE 257

2-(5-isoquinolinyl)-N-[3-(trifluoromethoxy)benzyl] propanamide

The title compound was prepared using the procedure described in Example 222B using 3-(trifluoromethoxy) benzylamine and 2-(5-isoquinolinyl)propanoic acid instead of 4-(trifluoromethoxy)benzylamine and 5-isoquinolinylacetic acid. MS (ESI+) m/z 375 (M+H)$^+$; MS (ESI−) m/z 373 (M−H)$^-$; $^1$H NMR (DMSO, 300 MHz) δ 1.54 (d, J 7.1, 3H), 4.28 (d, J 6.1, 2H), 4.50 (q, J 7.1, 1H), 7.05 (s, 1H), 7.20 (m, 2H), 7.40 (m, 1H), 7.81 (t, J 7.8, 1H), 7.96 (d, J 7.2, 1H), 8.21 (d, J 8.1, 1H), 8.32 (d, J 6.2, 1H), 8.61 (d, J 6.8, 1H), 8.70 (t, J 5.8, 1H), 9.57 (s, 1H).

EXAMPLE 258

N-(2,4-dimethylbenzyl)-2-(5-isoquinolinyl) propanamide

The title compound was prepared using the procedure described in Example 222B using 2,4-dimethylbenzylamine and 2-(5-isoquinolinyl)propanoic acid instead of 4-(trifluoromethoxy)benzylamine and 5-isoquinolinylacetic acid. MS (ESI+) m/z 319 (M+H)$^+$; MS (ESI−) m/z 317 (M−H)$^−$; $^1$H NMR (DMSO, 300 MHz) δ 1.52 (d, J 7.1, 3H), 2.13 (s, 3H), 2.21 (s, 3H), 4.20 (m, 2H), 4.51 (q, J 7.1, 1H), 6.88 (d, J 7.5, 1H), 6.94 (s, 1H), 6.98 (d, J 7.5, 1H), 7.82 (t, J 7.8, 1H), 7.99 (d, J 6.5, 1H), 8.21 (d, J 8.1, 1H), 8.35 (d, J 6.4, 1H), 8.44 (t, J 5.8, 1H), 8.62 (d, J 6.2, 1H), 9.57 (s, 1H).

EXAMPLE 259

N-(2,5-dimethylbenzyl)-2-(5-isoquinolinyl)propanamide

The title compound was prepared using the procedure described in Example 222B using 2,5-dimethylbenzylamine and 2-(5-isoquinolinyl)propanoic acid instead of 4-(trifluoromethoxy)benzylamine and 5-isoquinolinylacetic acid. MS (ESI+) m/z 319 (M+H)$^+$; MS (ESI−) m/z 317 (M−H)$^−$; $^1$H NMR (DMSO, 300 MHz) δ 1.54 (d, J 7.1, 3H), 2.09 (s, 3H), 2.12 (s, 3H), 4.20 (m, 2H), 4.53 (q, J 7.1, 1H), 6.79 (s, 1H), 6.91 (d, J 7.8, 1H), 6.98 (d, J 7.8, 1H), 7.83 (t, J 7.8, 1H), 8.00 (d, J 6.5, 1H), 8.21 (d, J 8.1, 1H), 8.37 (d, J 6.4, 1H), 8.46 (t, J 5.8, 1H), 8.62 (d, J 6.2, 1H), 9.57 (s, 1H).

EXAMPLE 260

N-(2,3-dichlorobenzyl)-2-(5-isoquinolinyl)propanamide

The title compound was prepared using the procedure described in Example 222B using 2,3-dichlorobenzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^−$; $^1$H NMR (DMSO, 300 MHz) δ 1.54 (d, J 7.1, 3H), 4.20 (m, 2H), 4.53 (q, J 7.1, 1H), 7.17 (d, J 7.8, 1H), 7.26 (t, J 7.8, 1H), 7.52 (d, J 8.1, 1H), 7.78 (t, J 7.8, 1H), 7.91 (d, J 6.5, 1H), 8.16 (d, J 8.1, 1H), 8.24 (d, J 6.4, 1H), 8.59 (d, J 6.2, 1H), 8.66 (t, J 5.8, 1H), 9.50 (s, 1H).

EXAMPLE 261

N-(2,4-dichlorobenzyl)-2-(5-isoquinolinyl)propanamide

The title compound was prepared using the procedure described in Example 222B using 2,4-dichlorobenzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^−$; $^1$H NMR (DMSO, 300 MHz) δ 1.54 (d, J 7.1, 3H), 4.20 (m, 2H), 4.53 (q, J 7.1, 1H), 7.22 (d, J 8.4, 1H), 7.33 (m, 2H), 7.56 (s, 1H), 7.78 (t, J 7.8, 1H), 7.90 (d, J 6.5, 1H), 8.17 (d, J 8.1, 1H), 8.25 (d, J 6.4, 1H), 8.62 (m, 2H), 9.51 (s, 1H).

EXAMPLE 262

N-(2,5-dichlorobenzyl)-2-(5-isoquinolinyl)propanamide

The title compound was prepared using the procedure described in Example 222B using 2,5-dichlorobenzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^−$; $^1$H NMR (DMSO, 300 MHz) δ 1.54 (d, J 7.1, 3H), 4.20 (m, 2H), 4.53 (q, J 7.1, 1H), 7.06 (s, 1H), 7.32 (d, J 8.4, 1H), 7.44 (d, J 8.4, 1H), 7.51 (s, 1H), 7.78 (t, J 7.8, 1H), 7.90 (d, J 6.5, 1H), 8.16 (d, J 8.1, 1H), 8.26 (d, J 6.4, 1H), 8.60 (d, J 6.2, 1H), 8.65 (t, J 5.8, 1H), 9.49 (s, 1H).

EXAMPLE 263

N-(3,4-dichlorobenzyl)-2-(5-isoquinolinyl)propanamide

The title compound was prepared using the procedure described in Example 222B using 3,4-dichlorobenzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^−$; $^1$H NMR (DMSO, 300 MHz) δ 1.54 (d, J 7.1, 3H), 4.20 (m, 2H), 4.53 (q, J 7.1, 1H), 7.16 (d, J 8.4, 1H), 7.31 (s, 1H), 7.52 (d, J 8.4, 1H), 7.77 (t, J 7.8, 11H), 7.89 (d, J 6.5, 11H), 8.16 (d, J 8.1, 1H), 8.22 (d, J 6.4, 11H), 8.59 (d, J 6.2, 11H), 8.64 (t, J 5.8, 11H), 9.49 (s, 1H).

EXAMPLE 264

N-(3,5-dichlorobenzyl)-2-(5-isoquinolinyl)propanamide

The title compound was prepared using the procedure described in Example 222B using 3,5-dichlorobenzylamine and 2-(5-isoquinolinyl)propanoic acid instead of 4-(trifluoromethoxy)benzylamine and 5-isoquinolinylacetic acid. MS (ESI+) m/z 359 (M+H)$^+$; MS (ESI−) m/z 357 (M−H)$^−$; $^1$H NMR (DMSO, 300 MHz) δ 1.54 (d, J 7.1, 3H), 4.20 (m, 2H), 4.53 (q, J 7.1, 1H), 7.13 (s, 2H), 7.42 (s, 1H), 7.78 (t, J 7.8, 11H), 7.89 (d, J 6.5, 11H), 8.17 (d, J 8.1, 1H), 8.23 (d, J 6.4, 1H), 8.59 (d, J 6.2, 1H), 8.64 (t, J 5.8, 1H), 9.51 (s, 1H).

EXAMPLE 265

N-[4-(1-azepanyl)-3-fluorobenzyl]-2-(5-isoquinolinyl)acetamide

The title compound was prepared using the procedure described in Example 222B using 4-(1-azepanyl)-3-fluorobenzylamine instead of 4-(trifluoromethoxy)benzylamine. MS (ESI+) m/z 392 (M+H)$^+$; MS (ESI−) m/z 390 (M−H)$^−$; $^1$H NMR (DMSO, 300 MHz) δ 1.53 (m, 4H), 1.72 (m, 4H), 3.32 (m, 4H), 3.96 (s, 2H), 4.18 (d, J 6.1, 2H), 6.86 (m, 3H), 7.69 (m, 2H), 7.94 (d, J 7.5, 1H), 8.03 (d, J 7.1, 1H), 8.50 (d, J 7.8, 1H), 8.62 (t, J 5.8, 1H), 9.30 (s, 1H); Anal. Calcd for $C_{24}H_{26}FN_3O+0.3H_2O$: C, 72.63; H, 6.76; N, 10.59. Found: C, 72.78; H, 7.05; N, 10.80.

EXAMPLE 266

N-[4-(1-azepanyl)benzyl]-2-(5-isoquinolinyl)propanamide

The title compound was prepared using the procedure described in Example 222B using 4-(1-azepanyl)benzylamine and 2-(5-isoquinolinyl)propanoic acid instead of 4-(trifluoromethoxy)benzylamine and 5-isoquinolinylacetic acid. MS (ESI+) m/z 388 (M+H)$^+$; MS (ESI−) m/z 366 (M−H)$^−$; $^1$H NMR (DMSO, 300 MHz) δ 1.53 (m, 7H), 1.72 (m, 4H), 3.85 (s, 2H), 4.03 (q, J 7.1, 1H), 6.76 (m, 3H), 7.26 (m, 2H), 7.58 (m, 1H), 7.71 (m, 1H), 8.10 (m, 2H), 8.72 (t, J 5.8, 1H), 9.91 (s, 1H); Anal. Calcd for $C_{25}H_{29}N_3O+2.15\ HCl+2H_2O$: C, 59.82; H, 7.06. Found: C, 59.59; H, 7.28.

EXAMPLE 267

N-[4-(1-azepanyl)-3-fluorobenzyl]-2-(5-isoquinolinyl)propanamide

The title compound was prepared using the procedure described in Example 222B using 4-(1-azepanyl)-3- fluorobenzylamine and 2-(5-isoquinolinyl)propanoic acid instead of 4-(trifluoromethoxy)benzylamine and 5-isoquinolinylacetic acid. MS (ESI+) m/z 406 (M+H)⁺; MS (ESI−) m/z 404 (M−H)⁻; ¹H NMR (DMSO, 300 MHz) δ 1.53 (m, 7H), 1.72 (m, 4H), 3.32 (m, 4H), 3.65 (s, 2H), 4.18 (q, J 7.1, 1H), 6.86 (m, 3H), 7.58 (m, 2H), 7.74 (m, 1H), 8.13 (m, 2H), 8.52 (d, J 7.8, 1H), 9.30 (s, 1H); Anal. Calcd for $C_{25}H_{28}FN_3O+3.25$ HCl: C, 57.30; H, 6.01. Found: C, 57.26; H, 5.98.

EXAMPLE 268 ethyl 2-(5-isoquinolinyl)butanoate

The title compound was prepared using the procedure described in Example 248 using ethyl iodide instead of methyl iodide. MS (ESI+) m/z 244 (M+H)⁺; MS (ESI−) m/z 242 (M−H)—; ¹H NMR (DMSO, 300 MHz) δ 1.53 (d, J 7.1, 3H), 4.35 (d, J 6.1, 2H), 4.47 (q, J 7.1, 1H), 7.18 (m, 2H), 7.70 (m, 3H), 8.05 (m, 2H), 8.53 (d, J 6.1, 1H), 8.68 (t, J 6.8, 1H), 9.32 (s, 1H); Anal. Calcd for $C_{15}H_{17}NO_2+0.4H_2O$: C, 71.92; H, 7.16; N, 5.59. Found: C, 72.23; H, 7.32; N, 5.31.

EXAMPLE 269

N-[3-fluoro-4-(trifluoromethyl)benzyl]-2-(5-isoquinolinyl)butanamide

EXAMPLE 269A 2-(5-isoquinolinyl)butanoic acid

The title compound was prepared using the procedure described in Example 249A using ethyl 2-(5-isoquinolinyl)butanoate instead of ethyl 2-(5-isoquinolinyl)propanoate.

EXAMPLE 269B

N-[3-fluoro-4-(trifluoromethyl)benzyl]-2-(5-isoquinolinyl)butanamide

The title compound was prepared using the procedure described in Example 222B using 3-fluoro-4-(trifluoromethyl)benzylamine and 2-(5-isoquinolinyl)butanoic acid instead of 4-(trifluoromethoxy)benzylamine and 5-isoquinolinylacetic acid. MS (ESI+) m/z 391 (M+H)⁺; MS (ESI−) m/z 389 (M−H)⁻; ¹H NMR (DMSO, 300 MHz) δ 0.91 (t, J 7.5, 3H), 1.81 (m, 1H), 2.17 (m, 2H), 4.35 (m, 2H), 7.17 (m, 2H), 7.69 (t, J 7.8, 1H), 7.86 (t, J 7.8, 1H), 8.04 (d, J 7.1, 1H), 8.23 (d, J 8.1, 1H), 8.65 (d, J 6.8, 1H), 8.83 (t, J 6.8, 1H), 9.60 (s, 1H); Anal. Calcd for $C_{21}H_{18}F_4N_2O+1$ HCl: C, 54.77; H, 3.80; N, 5.55. Found: C, 54.62; H, 3.57; N, 5.50.

EXAMPLE 270

2-(5-isoquinolinyl)-N-[4-(trifluoromethyl)benzyl]butanamide

The title compound was prepared using the procedure described in Example 222B using 4-(trifluoromethyl)benzylamine and 2-(5-isoquinolinyl)butanoic acid instead of 4-(trifluoromethoxy)benzylamine and 5-isoquinolinylacetic acid. MS (ESI+) m/z 391 (M+H)⁺; MS (ESI−) m/z 371 (M−H)⁻; ¹H NMR (DMSO, 300 MHz) δ 0.91 (t, J 7.5, 3H), 1.91 (m, 1H), 2.19 (m, 4H), 4.38 (m, 2H), 7.38 (d, J 8.5, 2H), 7.64 (d, J 8.5, 2H), 7.96 (t, J 7.8, 1H), 8.20 (d, J 7.1, 1H), 8.39 (d, J 8.1, 1H), 8.72 (s, 1H), 9.02 (t, J 6.8, 1H), 9.81 (s, 1H), 10.12 (br s, 1H); Anal. Calcd for $C_{21}H_{19}F_3N_2O$: C, 67.73; H, 5.14; N, 7.52. Found: C, 67.46; H, 4.90; N, 7.90.

EXAMPLE 271

N-(4-bromobenzyl)-2-(5-isoquinolinyl)butanamide

The title compound was prepared using the procedure described in Example 222B using 4-bromobenzylamine and 2-(5-isoquinolinyl)butanoic acid instead of 4-(trifluoromethoxy)benzylamine and 5-isoquinolinylacetic acid. MS (ESI+) m/z 385, 383 (M+H)⁺; MS (ESI−) m/z 383, 381 (M−H)⁻; ¹H NMR (DMSO, 300 MHz) δ 0.91 (t, J 7.5, 3H), 1.81 (m, 1H), 2.19 (m, 1H), 3.39 (m, 1H), 4.22 (m, 2H), 7.13 (d, J 8.5, 2H), 7.44 (m, 3H), 7.57 (t, J 7.8, 1H), 8.00 (m, 1H), 8.21 (d, J 7.1, 1H), 8.41 (d, J 8.1, 1H), 8.72 (s, 1H), 8.93 (t, J 6.8, 1H), 9.81 (s, 1H), 10.16 (br s, 1H); Anal. Calcd for $C_{20}H_{19}BrN_2O$: C, 62.67; H, 5.00. Found: C, 62.52; H, 4.95.

EXAMPLE 272

2-(5-isoquinolinyl)-N-{4-[(trifluoromethyl)thio]benzyl}butanamide

The title compound was prepared using the procedure described in Example 222B using 4-[(trifluoromethyl)thio]benzylamine and 2-(5-isoquinolinyl)butanoic acid instead of 4-(trifluoromethoxy)benzylamine and 5-isoquinolinylacetic acid. MS (ESI+) m/z 405 (M+H)⁺; MS (ESI−) m/z 403 (M−H)⁻; ¹H NMR (DMSO, 300 MHz) δ 0.91 (t, J 7.5, 3H), 1.81 (m, 1H), 2.21 (m, 1H), 3.39 (m, 1H), 4.34 (m, 2H), 7.31 (m, 2H), 7.58 (m, 2H), 7.62 (d, J 7.8, 1H), 8.00 (m, 2H), 8.22 (d, J 7.1, 1H), 8.45 (m, 1H), 8.77 (m, 1H), 8.82 (m, 1H), 9.06 (t, J 6.8, 1H), 9.87 (s, 1H), 10.30 (br s, 1H); Anal. Calcd for $C_{21}H_{19}F_3N_2OS+0.65$ HCl: C, 58.91; H, 4.63; N, 6.54. Found: C, 59.24; H, 4.30; N, 6.60.

EXAMPLE 273

N-[4-(1-azepanyl)-3-fluorobenzyl]-2-(5-isoquinolinyl)butanamide

The title compound was prepared using the procedure described in Example 222B using 4-(1-azepanyl)-3-fluorobenzylamine and 2-(5-isoquinolinyl)butanoic acid instead of 4-(trifluoromethoxy)benzylamine and 5-isoquinolinylacetic acid. MS (ESI+) m/z 420 (M+H)⁺; MS (ESI−) m/z 418 (M−H)⁻; ¹H NMR (DMSO, 300 MHz) δ 0.90 (t, J 7.5, 3H), δ 1.55 (m, 4H), 1.76 (m, 6H), 2.20 (m, 1H), 3.34 (m, 5H), 4.18 (m, 2H), 6.81 (m, 1H), 7.62 (m, 1H), 8.00 (m, 2H), 8.27 (d, J 7.1, 1H), 8.45 (d, 1H), 8.77 (d, 1H), 8.82 (m, 1H), 9.90 (s, 1H), 10.18 (br s, 1H); Anal. Calcd for $C_{26}H_{30}FN_3O+0.45H_2O$: C, 73.02; H, 7.28. Found: C, 73.05; H, 7.20.

EXAMPLE 274 ethyl 2-(5-isoquinolinyl)-2-methylpropanoate

The title compound was prepared using the procedure described in Example 248 using ethyl 2-(5-isoquinolinyl)propanoate instead of ethyl 5-isoquinolinylacetate. MS (ESI+) m/z 244 (M+H)⁺; MS (ESI−) m/z 242 (M−H)⁻; ¹H NMR (DMSO, 300 MHz) rotamers δ 0.98, 1.08 (t, J 7.1, 3H), 1.67 (s, 6H), 4.58 (q, J 7.1, 1H), 7.53 (m, 1H), 7.82 (m, 1H), 7.97 (m, 1H), 8.05 (m, 1H), 8.55, 8.50 (d, J 6.1, 1H), 9.33 (s, 1H).

EXAMPLE 275

2-(5-isoquinolinyl)-2-methyl-N-{4-[(trifluoromethyl)thio]benzyl}propanamide

EXAMPLE 275A 2-(5-isoquinolinyl)-2-methylpropanoic acid

The title compound was prepared using the procedure described in Example 249A using ethyl 2-(5-isoquinolinyl)-2-methylpropanoate instead of ethyl 2-(5-isoquinolinyl)propanoate.

EXAMPLE 275B 2-(5-isoquinolinyl)-2-methyl-N-{4-[(trifluoromethyl)thio]benzyl}propanamide The title compound was prepared using the procedure described in Example 222B using 4-[(trifluoromethyl)thio]benzylamine and 2-(5-isoquinolinyl)-2-methylpropanoic acid instead of 4-(trifluoromethoxy)benzylamine and 5-isoquinolinylacetic acid. MS (ESI+) m/Z 405 (M+H)$^+$; MS (ESI−) m/z 403 (M−H)$^-$; $^1$H NMR (DMSO, 300 MHz) δ 1.57 (s, 3H), 1.64 (s, 3H), 4.33 (d, J 6.1, 2H), 6.57 (s, 1H), 7.18 (m, 1H), 7.33 (m, 1H), 7.52 (m, 2H), 7.82 (m, 1H), 8.11 (m, 1H), 8.36 (d, J 7.8, 1H), 8.57 (m, 1H), 9.42 (s, 1H), 10.08 (s, 1H); Anal. Calcd for $C_{21}H_{19}F_3N_2OS$+2 HCl: C, 52.84; H, 4.43. Found: C, 52.66; H, 4.39.

EXAMPLE 276 ethyl hydroxy(5-isoquinolinyl)acetate

The title compound was prepared using the procedure described in Example 248 using (S) camphorsulfonyloxaziridine (2 equivalents) instead of methyl iodide.

EXAMPLE 277

N-(4-tert-butylbenzyl)-2-hydroxy-2-(5-isoquinolinyl)acetamide

EXAMPLE 277A hydroxy(5-isoquinolinyl)acetic acid

The title compound was prepared using the procedure described in Example 249A using ethyl hydroxy(5-isoquinolinyl)acetate instead of ethyl 2-(5-isoquinolinyl)propanoate. MS (ESI+) m/z 204 (M+H)$^+$; MS (ESI−) m/z 202 (M−H)$^-$; $^1$H NMR (DMSO, 300 MHz) δ 4.97 (d, J 3.1, 1H), 5.34 (d, J 3.3, 1H), 7.55 (m, 1H), 7.68 (d, J 7.5, 1H), 7.90 (d, J 8.1, 1H), 8.21 (d, J 6.8, 1H), 8.40 (d, J 6.8, 1H), 9.22 (s, 1H); Anal. Calcd for $C_{11}H_9NO_3$+1.9 HCl: C, 51.96; H, 5.00. Found: C, 51.89; H, 5.25.

EXAMPLE 277B

N-(4-tert-butylbenzyl)-2-hydroxy-2-(5-isoquinolinyl)acetamide

The title compound was prepared using the procedure described in Example 222B using 4-(tert-butyl)benzylamine and hydroxy(5-isoquinolinyl)acetic acid instead of 4-(trifluoromethoxy)benzylamine and 5-isoquinolinylacetic acid. $[α]^{22}_D$ −47.2 (c 0.7, MeOH); MS (ESI+) m/z 349 (M+H)$^+$; MS (ESI−) m/z 347 (M−H)$^-$; $^1$H NMR (DMSO, 300 MHz) δ 1.26 (s, 9H), 3.69 (s, 1H), 4.27 (d, J 6.1, 2H), 5.62 (s, 1H), 6.52 (br s, 1H), 7.17 (d, J 8.1, 2H), 7.29 (m, 3H), 7.67 (t, J 8.1, 1H), 7.82 (d, J 7.1, 1H), 8.10 (m, 2H), 8.44 (d, J 5.8, 1H), 8.71 (t, J 6.1, 1H), 9.30 (s, 1H); Anal. Calcd for $C_{22}H_{24}N_2O_2$+0.25$H_2O$: C, 74.87; H, 7.00; N, 7.94. Found: C, 75.22; H, 7.40; N, 7.80.

EXAMPLE 278

N-(4-tert-butyl-3-fluorobenzyl)-2-hydroxy-2-(5-isoquinolinyl)acetamide

The title compound was prepared using the procedure described in Example 222B using 3-fluoro-4-(trifluoromethyl)benzylamine and hydroxy(5-isoquinolinyl)acetic acid instead of 4-(trifluoromethoxy)benzylamine and 5-isoquinolinylacetic acid. MS (ESI+) m/z 379 (M+H)$^+$; MS (ESI−) m/z 377 (M−H)$^-$; $^1$H NMR (DMSO, 300 MHz) δ 4.37 (d, J 6.1, 2H), 5.65 (d, 1H), 6.63 (d, 1H), 7.27 (m, 2H), 7.29 (m, 3H), 7.67 (m, 2H), 7.82 (d, J 7.1, 1H), 8.15 (m, 2H), 8.44 (d, J 5.8, 1H), 8.96 (t, J 6.1, 1H), 9.30 (s, 1H); Anal. Calcd for $C_{22}H_{24}N_2O_2$+0.25$H_2O$: C, 74.87; H, 7.00; N, 7.94. Found: C, 75.22; H, 7.40; N, 7.80.

EXAMPLE 279

4-tert-butyl 1-ethyl 2-(5-isoquinolinyl)succinate

The title compound was prepared using the procedure described in Example 248 using tert-butyl bromoacetate instead of methyl iodide. MS (ESI+) m/z 330 (M+H)$^+$; MS (ESI−) m/z 328 (M−H)$^-$; $^1$H NMR (DMSO, 300 MHz) δ 1.06 (t, J 7.1, 3H), 1.30 (s, 9H), 2.76 (dd, $J_1$ 16.7, $J_2$ 6.1, 1H), 3.14 (dd, J 9.5, $J_2$ 6.1, 1H), 4.12 (q, J 7.1, 1H), 4.76 (dd, $J_1$ 16.7, $J_2$ 9.5, 1H), 7.70 (m, 2H), 8.05 (m, 2H), 8.58 (d, J 6.1, 1H), 9.34 (s, 1H); Anal. Calcd for $C_{19}H_{23}NO_4$+1$H_2O$: C, 65.69; H, 7.25; N, 4.03. Found: C, 65.37; H, 6.91; N, 3.67.

EXAMPLE 280 tert-butyl 4-[(4-tert-butylbenzyl)amino]-3-(5-isoquinolinyl)-4-oxobutanoate

EXAMPLE 280A 4-tert-butoxy-2-(5-isoquinolinyl)-4-oxobutanoic acid

4-Tert-butyl 1-ethyl 2-(5-isoquinolinyl)succinate (1.00 g, 3.04 mmol) and LiOH (0.29 g) were stirred in MeOH:$H_2O$ (3:1, 20 mL) at room temperature for 5 hours. The solution was poured into aqueous $H_3PO_4$ (0.1M, 30 mL) and extracted with $CHCl_3$:IPA (3:1, 30 mL×3). The extracts were combined, dried ($MgSO_4$), filtered, and the filtrate was concentrated under reduced pressure to provide the title compound. MS (ESI+) m/z 302 (M+H)$^+$; MS (ESI−) m/z 300 (M−H)$^-$; $^1$H NMR (DMSO, 300 MHz) δ 1.28 (s, 9H), 2.74 (dd, $J_1$ 16.7, $J_2$ 6.1, 1H), 3.10 (dd, $J_1$ 9.5, $J_2$ 6.1, 1H), 4.68 (dd, $J_1$ 16.7, $J_2$ 9.5, 1H), 7.70 (m, 2H), 8.05 (m, 2H), 8.57 (d, J 6.1, 1H), 9.33 (s, 1H); Anal. Calcd for $C_{17}H_{19}NO_4$+1.25$H_2O$: C, 63.05; H, 6.69. Found: C, 63.27; H, 6.95.

EXAMPLE 280B tert-butyl 4-[(4-tert-butylbenzyl)amino]-3-(5-isoquinolinyl)-4-oxobutanoate The title compound was prepared using the procedure described in Example 222B using 4-(tert-butyl)benzylamine and 4-tert-butoxy-2-(5-isoquinolinyl)-4-oxobutanoic acid instead of 4-(trifluoromethoxy)benzylamine and 5-isoquinolinylacetic acid. MS (ESI+) m/z 447 (M+H)$^+$; $^1$H NMR (DMSO, 300 MHz) δ 1.23 (s, 9H), 1.25 (s, 9H), 2.71 (dd, 1H), 3.02 (dd, 1H), 4.22 (m, 2H), 4.71 (m, 1H), 6.57 (s, 1H), 7.08 (d, J 8.5, 2H), 7.24 (d, J 8.5, 2H), 7.67 (m, 1H), 7.78 (m, 1H), 8.03 (d, J 7.8, 1H), 8.13 (d, J 7.1, 1H), 8.55 (d, J 6.8, 1H), 8.63 (m, 1H), 9.31 (s, 1H); Anal. Calcd for $C_{28}H_{34}N_2O_3$+1 $CH_3CN$+0.8$H_2O$: C, 71.77; H, 7.75; N, 8.37. Found: C, 71.64; H, 7.38; N, 8.16.

EXAMPLE 281

2-[(4-tert-butylbenzyl)amino]-1-(5-isoquinolinyl)-2-oxoethyl acetate

The product from Example 277B (100 mg, 0.287 mmol) and DMAP (59 mg, 0.480 mmol) in $CH_2Cl_2$ (1 mL) was treated with acetic anhydride (38 μL). After stirring for 30 minutes, the mixture was treated with $CH_2Cl_2$ (5 mL) and the phases separated. The organic layer was washed with water (10 mL×3), dried ($Na_2SO_4$), filtered, and the filtrate was concentrated to provide the title compound. MS (ESI+) m/z 391 (M+H)$^+$; MS (ESI−) m/z 389 (M−H)$^−$; $^1$H NMR (DMSO, 300 MHz) δ 1.25 (s, 9H), 4.27 (dq, $J_1$ 14.9, $J_2$ 6.1, 2H), 6.56 (s, 1H), 7.09 (d, J 8.5, 2H), 7.28 (d, J 8.5, 2H), 7.72 (t, J 7.1, 1H), 7.90 (d, J 6.1, 1H), 8.07 (d, J 6.1, 1H), 8.17 (d, J 8.1, 1H), 8.53 (d, J 6.1, 1H), 8.86 (t, J 6.1, 1H), 9.35 (s, 1H); Anal. Calcd for $C_{24}H_{26}N_2O_3+0.8H_2O$: C, 71.19; H, 6.87; N, 6.92. Found: C, 70.87; H, 6.47; N, 6.92.

EXAMPLE 282

2-[(4-tert-butylbenzyl)amino]-1-(5-isoquinolinyl)-2-oxoethyl methanesulfonate

The product from Example 277B (1.00 g, 2.87 mmol) in pyridine (5 mL) was treated with methanesulfonyl chloride (5.56 μL, 7.17 mmol). After stirring for 30 minutes, the mixture was concentrated under reduced pressure and diluted with $CH_2Cl_2$ (50 mL). The organic layer was washed with water (50 mL×3), dried ($Na_2SO_4$), filtered, and the filtrate concentrated under reduce pressure to provide the title compound. MS (ESI+) m/z 427 (M+H)$^+$; MS (ESI−) m/z 425 (M−H)$^−$; $^1$H NMR (DMSO, 300 MHz) δ 1.27 (s, 9H), 2.37 (s, 3H), 4.27 (dq, $J_1$ 14.9, $J_2$ 6.1, 2H), 6.84 (s, 1H), 7.17 (d, J 8.5, 2H), 7.38 (d, J 8.5, 2H), 8.07 (m, 2H), 8.37 (d, J 8.1, 1H), 8.60 (d, J 6.1, 1H), 8.97 (m, 1H), 9.21 (t, J 6.1, 1H), 9.96 (s, 1H).

EXAMPLE 283

N-(4-tert-butylbenzyl)-2-(5-isoquinolinyl)-2-methoxyacetamide

The product from Example 277B (100 mg, 0.287 mmol) in THF (2 mL) was treated with NaH (95%, 8.7 mg, 0.344 mmol). After stirring at room temperature for 20 minutes, the mixture was treated with methyl iodide (1.2 eq, 21.4 μL) and stirred for 1 hour. The mixture was concentrated under reduced pressure and $CH_2Cl_2$ (10 mL) was added. The organic layer was washed with water (5 mL×3), dried ($Na_2SO_4$), filtered, and the filtrate concentrated under reduced pressure to provide the title compound. MS (ESI+) m/z 363 (M+H)$^+$; MS (ESI−) m/z 361 (M−H)$^−$; $^1$H NMR (DMSO, 300 MHz) rotamers δ 1.25 (s, 9H), 3.32 (s, 3H), 4.27 (d, J 6.1, 2H), 5.37 (s, 1H), 7.18 (d, J 8.5, 2H), 7.32 (d, J 8.5, 2H), 7.70 (t, J 7.1, 1H), 7.83 (d, J 6.1, 1H), 8.07 (m, 2H), 8.43 (d, J 6.1, 1H), 8.80 (t, J 6.1, 1H), 9.35 (s, 1H); Anal. Calcd for $C_{23}H_{26}N_2O_2+0.3H_2O$: C, 75.09; H, 7.29; N, 7.61. Found: C, 75.02; H, 7.34; N, 7.43.

EXAMPLE 284

N-(4-tert-butylbenzyl)-2-chloro-2-(5-isoquinolinyl)acetamide

The product from Example 182 (300 mg, 0.704 mmol) in toluene (10 mL) was treated with $Bu_4NCl$ (458 mg, 1.408 mmol) and heated at 100° C. for 12 hours. The mixture was concentrated under reduced pressure and diluted with $CH_2C_{12}$ (50 mL). The organic layer was washed with water (50 mL×3), dried ($Na_2SO_4$), filtered, and the filtrate concentrated under reduced pressure. MS (ESI+) m/z 367 (M+H)$^+$; MS (ESI−) m/z 365 (M−H)$^−$; $^1$H NMR (DMSO, 300 MHz) δ 1.26 (s, 9H), 4.11 (d, J 5.1, 2H), 6.59 (s, 1H), 7.16 (d, J 8.1, 2H), 7.36 (d, J 8.1, 2H), 7.97 (d, J 8.1, 2H), 8.30 (d, J 7.5, 1H), 8.48 (d, J 8.1, 1H), 8.56 (d, J 6.8, 1H), 8.73 (d, J 6.8, 1H), 8.97 (m, 1H), 9.18 (t, J 6.1, 1H), 9.81 (s, 1H); Anal. Calcd for $C_{22}H_{23}ClN_2O+1$ HCl+1.5 $CH_3OH$: C, 62.53; H, 6.70; N, 6.21. Found: C, 62.75; H, 6.87; N, 6.11.

EXAMPLE 285

N-5-isoquinolinyl-3-[4-(trifluoromethyl)phenyl]acrylamide

5-Aminoisoquinoline (0.50 g, 3.47 mmol) and 3-[4-(trifluoromethyl)phenyl]acrylic acid (3.47 mmol) were combined in a sealed tube and heated at 175° C. for 16 hours with stirring. The mixture was cooled to room temperature, diluted with MeOH, transferred to a flask, and concentrated under reduced pressure. The residue was triturated with ethyl acetate and filtered to provide the title compound. MS (ESI+) m/z 343 (M+H)$^+$; MS (ESI−) m/z 341 (M−H)$^−$; $^1$H NMR (DMSO, 300 MHz) rotamers δ 6.68 (d, J 15.9, 1H), 7.29 (d, J 15.9, 1H), 7.60 (d, J 15.9, 1H), 7.80 (m, 1H), 8.25 (d, J 6.8, 1H), 8.57 (d, J 5.8, 1H), 9.35 (s, 1H), 10.36 (s, 1H); Anal. Calcd for $C_{19}H_{13}F_3N_2O+2$ HCl+0.3$H_2O$: C, 54.25; H, 3.74; N, 6.66. Found: C, 53.90; H, 3.94; N, 7.20.

EXAMPLE 286

N-5-isoquinolinyl-3-[3-(trifluoromethyl)phenyl]acrylamide

The title compound was prepared using the procedure described in Example 285 using 3-[3-(trifluoromethyl)phenyl]acrylic acid instead of 3-[4-(trifluoromethyl)phenyl]acrylic acid. MS (ESI+) m/z 343 (M+H)$^+$; MS (ESI−) m/z 341 (M−H); $^1$H NMR (DMSO, 300 MHz) rotamers δ 6.72 (d, J 15.9, 1H), 6.87 (d, J 7.4, 1H), 7.23 (d, J 8.1, 1H), 7.36 (t, J 7.8, 1H), 7.70 (m, 2H), 7.93 (d, J 6.1, 11H), 8.10 (m, 2H), 8.35 (d, J 5.8, 1H), 9.09 (s, 1H); Anal. Calcd for $C_{19}H_{13}F_3N_2O+2.15$ HCl: C, 54.24; H, 3.63; N, 6.66. Found: C, 53.96; H, 3.93; N, 6.93.

EXAMPLE 287

3-(4-isopropylphenyl)-N-5-isoquinolinylacrylamide

The title compound was prepared using the procedure described in Example 285 using 3-(4-isopropylphenyl)acrylic acid instead of 3-[4-(trifluoromethyl)phenyl]acrylic acid. MS (ESI+) m/z 317 (M+H)$^+$; MS (ESI−) m/z 315 (M−H)$^−$; $^1$H NMR (DMSO, 300 MHz) δ 1.24 (d, J 6.8, 3H), 2.94 (sept, J 6.8, 1H), 7.10 (d, J 15.6, 1H), 7.35 (d, J 7.4, 2H), 7.61 (d, J 8.1, 2H), 7.63 (d, J 15.6, 1H), 7.84 (t, J 7.8, 1H), 8.12 (d, J 7.8, 1H), 8.26 (d, J 6.4, 1H), 8.35 (d, J 7.1, 1H), 8.64 (d, J 6.8, 1H), 9.56 (s, 1H), 10.35 (s, 1H); Anal. Calcd for $C_{21}H_{20}N_2O+0.35$ TFA: C, 73.15; H, 5.76; N, 7.86. Found: C, 73.02; H, 5.50; N, 7.88.

EXAMPLE 288

N-5-isoquinolinyl-2-phenylcyclopropanecarboxamide

The title compound was prepared using the procedure described in Example 285 using 2-phenylcyclopropanecarboxylic acid instead of 3-[4-(trifluoromethyl)phenyl]acrylic acid. MS (ESI+) m/z 289 (M+H)$^+$; MS (ESI−) m/z 287 (M−H)$^−$; $^1$H NMR (DMSO, 300 MHz) δ 1.46 (m, 1H), 1.56 (m, 1H), 2.46 (m, 2H), 7.24 (m, 3H), 7.32 (m, 2H), 7.82 (t, J 7.8, 1H), 8.10 (d, J 7.8, 1H), 8.28 (d, J 6.4, 1H), 8.62 (d, J 6.8, 1H), 9.58 (s, 1H), 10.46 (s, 1H); Anal. Calcd for $C_{19}H_{16}N_2O+0.65$ TFA: C, 67.27; H, 4.63; N, 7.73. Found: C, 67.27; H, 4.31; N, 7.52.

EXAMPLE 289

3-(3,4-dichlorophenyl)-N-5-isoquinolinylacrylamide

The title compound was prepared using the procedure described in Example 285 using 3-(3,4-dichlorophenyl) acrylic acid instead of 3-[4-(trifluoromethyl)phenyl]acrylic acid. MS (ESI+) m/z 344 (M+H)$^+$; MS (ESI−) m/z 342 (M−H)$^−$; $^1$H NMR (DMSO, 300 MHz) δ 7.20 (d, J 15.6, 1H), 7.67 (m, 3H), 7.84 (d, J 15.6, 1H), 7.97 (d, J 1.7, 1H), 8.10 (d, J 7.8, 1H), 8.22 (d, J 6.4, 1H), 8.35 (d, J 7.1, 1H), 8.64 (d, J 6.8, 1H), 9.53 (s, 1H), 10.37 (s, 1H); Anal. Calcd for $C_{18}H_{12}Cl_2N_2O$+0.75 TFA: C, 54.63; H, 3.00; N, 6.53. Found: C, 54.43; H, 2.92; N, 6.39.

EXAMPLE 290

3-(1,1'-biphenyl-4-yl)-N-5-isoquinolinylacrylamide

The title compound was prepared using the procedure described in Example 285 using 3-(1,1'-biphenyl-4-yl) acrylic acid instead of 3-[4-(trifluoromethyl)phenyl]acrylic acid. MS (ESI+) m/z 351 (M+H)$^+$; MS (ESI−) m/z 349 (M−H)$^−$; $^1$H NMR (DMSO, 300 MHz) δ 7.21 (d, J 15.6, 1H), 7.39–7.79 (m, 10H), 7.97 (d, J 7.8, 1H), 8.08 (d, J 6.4, 1H), 8.29 (d, J 7.1, 1H), 8.58 (d, J 6.8, 1H), 9.34 (s, 1H); Anal. Calcd for $C_{24}H_{18}N_2O$+0.85 HCl: C, 75.58; H, 4.98. Found: C, 75.69; H, 4.69.

EXAMPLE 291

3-(3-bromo-4-fluorophenyl)-N-5-isoquinolinylacrylamide

The title compound was prepared using the procedure described in Example 285 using 3-(3-bromo-4-fluorophenyl)acrylic acid instead of 3-[4-(trifluoromethyl) phenyl]acrylic acid. MS (ESI+) m/z 374, 372 (M+H)$^+$; MS (ESI−) m/z 372, 370 (M−H)$^−$; $^1$H NMR (DMSO, 300 MHz) δ 7.14 (d, J 15.6, 1H), 7.50 (t, J 8.8, 1H), 7.65 (d, J 15.6, 1H), 7.76 (m, 1H), 7.83 (t, J 7.8, 1H), 8.05 (dd, $J_1$ 6.8, $J_2$ 2.1, 1H), 8.11 (d, J 7.8, 1H), 8.24 (d, J 6.4, 1H), 8.36 (d, J 7.1, 1H), 8.64 (d, J 6.8, 1H), 9.55 (s, 1H), 10.35 (s, 1H); Anal. Calcd for $C_{18}H_{12}BrFN_2O$+1 TFA: C, 49.51; H, 2.70; N, 5.77. Found: C, 49.78; H, 2.71; N, 5.768.

EXAMPLE 292

3-(4-tert-butylphenyl)-N-5-isoquinolinylacrylamide

The title compound was prepared using the procedure described in Example 285 using 3-(4-tert-butylphenyl) acrylic acid instead of 3-[4-(trifluoromethyl)phenyl]acrylic acid. MS (ESI+) m/z 331 (M+H)$^+$; MS (ESI−) m/z 329 (M−H)$^−$; $^1$H NMR (DMSO, 300 MHz) δ 1.31 (s, 9H), 7.10 (d, J 15.6, 1H), 7.51 (d, J 8.5, 2H), 7.62 (d, J 8.5, 2H), 7.67 (d, J 15.6, 1H), 7.86 (t, J 8.2, 1H), 8.14 (d, J 6.1, 1H), 8.31 (d, J 8.2, 1H), 8.40 (d, J 6.1, 1H), 8.66 (d, J 6.1, 1H), 9.60 (s, 1H), 10.39 (s, 1H); Anal. Calcd for $C_{22}H_{22}N_2O$+1 TFA: C, 64.86; H, 5.22; N, 6.30. Found: C, 64.54; H, 5.13; N, 6.18.

EXAMPLE 293

3-[3-fluoro-4-(trifluoromethyl)phenyl]-N-5-isoquinolinylacrylamide

The title compound was prepared using the procedure described in Example 285 using 3-[3-fluoro-4-(trifluoromethyl)phenyl]acrylic acid instead of 3-[4-(trifluoromethyl)phenyl]acrylic acid. MS (ESI+) m/z 361 (M+H)$^+$; MS (ESI−) m/z 359 (M−H)—; $^1$H NMR (DMSO, 300 MHz) δ 7.30 (d, J 15.6, 1H), 7.72–7.85 (m, 4H), 7.91 (t, J 8.2, 1H), 8.13 (d, J 6.1, 1H), 8.24 (d, J 8.2, 1H), 8.35 (d, J 6.1, 1H), 8.65 (d, J 6.1, 1H), 9.56 (s, 1H), 10.50 (s, 1H); Anal. Calcd for $C_{19}H_{12}F_4N_2O$+0.8 TFA: C, 54.80; H, 2.86; N, 6.20. Found: C, 54.59; H, 2.82; N, 6.06.

EXAMPLE 294

N-(8-bromo-5-isoquinolinyl)-N'-(2,4-dichlorobenzyl)urea

EXAMPLE 294A

8-bromo-5-isoquinolinamine

6,8-dibromo-5-isoquinolinamine

5-Aminoisoquinoline (5.50 g, 38.1 mmol) and aluminium trichloride (15.1 g, 113 mmol) were combined and heated at 80° C. in a 3-necked flask equipped with a dropping funnel, stirrer bar, needle and sintered glass tube. The mixture was treated with bromine (3.04 g, 19.05 mmol) via the sintered glass funnel dropwise. After stirring at 80° C. for 2 hours, the suspension was treated with crushed ice in small portions and the solution was basified with concentrated sodium hydroxide solution. The aqueous layer was extracted with ethyl acetate (4×100 mL). The organic layers were combined, dried ($Na_2SO_4$), filtered, and the filtrate was concentrated under reduced pressure. The residue was purified by column chromatography (hexanes:ethyl acetate, 3:1) to provide the separate title compounds. Monobromo: MS (ESI+) m/z 225 (M+H)$^+$; MS (ESI−) m/z 223 (M−H)$^−$; $^1$H NMR (CDCl$_3$, 300 MHz) δ 4.22 (br s, 2H), 6.83 (d, J 8.1, 1H), 7.25 (s, 1H), 7.54 (d, J 5.8, 1H), 7.61 (d, J 8.1, 1H), 8.59 (d, J 5.8, 1H), 9.56 (s, 1H); Dibromo: MS (ESI+) m/z 303 (M+H)$^+$; MS (ESI−) m/z 301 (M−H)$^−$; $^1$H NMR (DMSO, 300 MHz) δ 6.41 (br s, 2H), 7.92 (s, 1H), 8.18 (d, J 6.1, 1H), 8.59 (d, J 6.1, 1H), 9.30 (s, 1H).

EXAMPLE 294B

N-(8-bromo-5-isoquinolinyl)-N'-(2,4-dichlorobenzyl)urea

8-Bromo-5-isoquinolinamine (120 mg, 0.52 mmol) in THF:toluene (5 mL, 1:4) was treated with 2,4-dichloro-1-(isocyanatomethyl)benzene (108 mg, 0.52 mmol) in THF (0.5 mL). After stirring for 16 hours at room temperature, the mixture was filtered and the filter cake was dried under reduced pressure to provide the title compound. MS (ESI+) m/z 426 (M+H)$^+$; MS (ESI−) m/z 424 (M−H)$^−$; $^1$H NMR (DMSO, 300 MHz) δ 4.42 (d, 5.8, 2H), 7.22 (t, J 5.8, 1H), 7.65 (m, 1H), 7.91 (d, J 8.5, 1H), 8.02 (d, J 6.1, 1H), 8.22 (d, J 8.5, 1H), 8.69 (d, J 5.8, 1H), 9.01 (s, 1H), 9.44 (s, 1H); Anal. Calcd for $C_{17}H_{12}BrCl_2N_3O$·HCl+0.25EtOH: C, 44.41; H, 3.14; N, 8.88. Found: C, 44.80; H, 2.76; N, 8.84.

EXAMPLE 295

N-(8-bromo-5-isoquinolinyl)-N'-(4-fluorobenzyl)urea

The title compound was prepard using the procedure described in Example 294B using 1-fluoro-4-(isocyanatomethyl)benzene instead of 2,4-dichloro-1-(isocyanatomethyl)benzene. MS (ESI+) m/z 376 (M+H)$^+$; MS (ESI−) m/z 374 (M−H)$^−$; $^1$H NMR (DMSO, 300 MHz) δ 4.35 (d, 5.8, 2H), 7.12 (m, 1H), 7.18 (m, 2H), 7.40 (m, 1H), 7.91 (d, J 8.5, 1H), 7.99 (d, J 6.1, 1H), 8.24 (d, J 8.5, 1H), 8.69 (d, J 5.8, 1H), 8.88 (s, 1H), 9.44 (s, 1H); Anal. Calcd for $C_{17}H_{13}BrFN_3O$: C, 54.56; H, 3.50; N, 11.23. Found: C, 54.61; H, 3.35; N, 11.14.

EXAMPLE 296

N-(8-bromo-5-isoquinolinyl)-N'-(3-fluorobenzyl) urea

The title compound was prepard using the procedure described in Example 294B using 1-fluoro-4-(isocyanatomethyl)benzene instead of 2,4-dichloro-1-(isocyanatomethyl)benzene. MS (ESI+) m/z 376 (M+H)$^+$; MS (ESI−) m/z 374 (M−H)$^-$; $^1$H NMR (DMSO, 300 MHz) δ 4.39 (d, 5.8, 2H), 7.09 (m, 1H), 7.17 (m, 2H), 7.40 (m, 1H), 7.91 (d, J 8.5, 1H), 8.01 (d, J 6.1, 1H), 8.23 (d, J 8.5, 1H), 8.69 (d, J 5.8, 1H), 8.93 (s, 1H), 9.44 (s, 1H); Anal. Calcd for $C_{17}H_{13}BrFN_3O$: C, 54.56; H, 3.50; N, 11.23. Found: C, 54.64; H, 3.33; N, 11.19.

EXAMPLE 297

N-[1-(4-chlorophenyl)-1-methylethyl]-N'-5-isoquinolinylurea

EXAMPLE 297A 2-(4-chlorophenyl)-2-methylpropanoyl chloride 2-(4-Chlorophenyl)-2-methylpropanoic acid (3.85 g, 19.4 mmol) in toluene (5 mL) and thionyl chloride (5.00 g, 3.1 mL) was heated at 80° C. for 2 hours. The mixture was cooled and concentrated under reduced pressure to provide the title compound.

EXAMPLE 297B 1-chloro-4-(1-isocyanato-1-methylethyl)benzene

The product from Example 297A (4.00 g, 19.4 mmol) in acetone (9 mL) at 0° C. ws treated with sodium azide (1.27 g) in water (9 mL) dropwise over 15 minutes. after stirring for 30 minutes at 0° C., the mixture was extracted with toluene (20 mL). The toluene solution was dried over MgSO$_4$, filtered, and the filtrate was heated to reflux for 1 hour. The cooled solution was concentrated under reduced pressure to provide the title compound.

EXAMPLE 297C

N-[1-(4-chlorophenyl)-1-methylethyl]-N'-5-isoquinolinylurea

The title compound was prepared using the procedure described in Example 60F using 1-chloro-4-(1-isocyanato-1-methylethyl)benzene and 5-isoquinolinamine instead of the product from Example 60E and 1-bromo-4-(isocyanatomethyl)benzene. MS (ESI+) m/z 355 (M+H)$^+$; MS (ESI−) m/z 353 (M−H)$^-$; $^1$H NMR (DMSO, 300 MHz) δ 1.63 (s, 6H), 7.23 (s, 1H), 7.37 (d, J 8.8, 2H), 7.47 (d, J 8.8, 2H), 7.73 (t, J 9.2, 1H), 7.93 (d, J 8.1, 1H), 8.25 (d, J 6.4, 1H), 8.39 (d, J 8.1, 1H), 8.67 (d, J 6.4, 1H), 8.87 (s, 1H), 9.58 (s, 1H); Anal. Calcd for $C_{19}H_{18}ClN_3O·HCl+0.25EtOH$: C, 60.40; H, 5.33; N, 10.54. Found: C, 60.82; H, 5.23; N, 10.45.

EXAMPLE 298

N-(4-bromo-3-methylbenzyl)-N'-5-isoquinolinylurea

The title compound was prepared using the procedure described in Example 61B using 4-bromo-3-methylbenzylamine instead of 4-cyanobenzyl alcohol. MS (ESI+) m/z 372, 370 (M+H)$^+$; MS (ESI−) m/z 370, 368 (M−H)$^-$; $^1$H NMR (DMSO, 300 MHz) δ 2.34 (s, 3H), 4.31 (s, 2H), 4.09 (s, 2H), 7.13 (d, J 7.2, 2H), 7.34 (s, 1H), 7.55 (m, 2H), 7.82 (d, J 7.9, 11H), 7.90 (m, 1H), 8.09 (d, 1H), 8.65 (m, 2H), 8.80 (d, J 6.4, 11H), 9.68 (s, 1H), 9.79 (s, 1H); Anal. Calcd for $C_{18}H_{16}BrN_3O+1.05$ HCl: C, 52.66; H, 4.86; N, 10.24. Found: C, 53.00; H, 4.27; N, 10.37.

EXAMPLE 299

N-[2-fluoro-4-(trifluoromethyl)benzyl]-N'-5-isoquinolinylurea

EXAMPLE 299A 2-fluoro-4-(trifluoromethyl)benzylamine

The title compound was prepared using the procedure described in Example 172B using 2-fluoro-4-(trifluoromethyl)benzonitrile instead of 4-(4-morpholinyl)benzonitrile. MS (ESI+) m/z 194 (M+H)$^+$; MS (ESI−) m/z 192 (M−H)$^-$; $^1$H NMR (DMSO, 300 MHz) δ 3.97 (s, 2H), 7.30 (m, 1H), 7.46 (m, 2H).

EXAMPLE 299B

N-[2-fluoro-4-(trifluoromethyl)benzyl]-N'-5-isoquinolinylurea

The title compound was prepared using the procedure described in Example 61B using 2-fluoro-4-(trifluoromethyl)benzylamine instead of 4-cyanobenzyl alcohol. MS (ESI+) m/z 364 (M+H)$^+$; MS (ESI−) m/z 362 (M−H)$^-$; $^1$H NMR (DMSO, 300 MHz) δ 4.51 (d, J 5.8, 2H), 7.65 (m, 4H), 7.90 (t, J 8.1, 1H), 8.09 (d, J 7.8, 1H), 8.59 (d, J 7.8, 1H), 8.71 (s, 2H), 9.66 (s, 1H), 9.76 (s, 1H); Anal. Calcd for $C_{18}H_{13}F_4N_3O+1$ HCl: C, 54.08; H, 3.53; N, 10.51. Found: C, 54.40; H, 3.60; N, 10.61.

EXAMPLE 300

N-(4-bromobenzyl)-N'-(3-hydroxy-5-isoquinolinyl) urea

EXAMPLE 300A 5-nitro-3-isoquinolinol

3-Hydroxyisoquinoline (1.09 g, 7.53 mmol) in concentrated H$_2$SO$_4$ (20 mL) at 0° C. was treated with NaNO$_3$ (0.71 g, 8.34 mmol) in concentrated H$_2$SO$_4$ (5 mL) dropwise over 15 minutes. After stirring for 90 minutes, the mixture was allowed to warm to room temperature, stir for 2 hours, poured over an ice-NH$_4$Cl mixture, and the pH was adjusted to 7–8 with 50% NaOH solution. The mixture was filtered and the filter cake dried to provide the title compound. Structure analysis determined a 2:1 mixture of the 5-nitro and 7-nitro isomers which were not separated. MS (ESI+) m/z 191 (M+H)$^+$; MS (ESI−) m/z 189 (M−H)$^-$; $^1$H NMR (DMSO, 300 MHz) δ 4.60 (s, 1H), 7.48 (t, J 8.0, 1H), 7.57 (s, 1H), 8.42 (d, J 8.0, 1H), 8.57 (d, J 7.7, 1H), 9.19 (s, 1H).

EXAMPLE 300B 5-nitro-3-isoquinolinyl acetate

5-Nitro-3-isoquinolinol (3.40 g, 17.9 mmol) in acetic anhydride (40 mL) was treated with acetic acid (5 mL) and pyridine (5 mL) and heated at 120° C. for 2 hours. The mixture was cooled to room temperature and concentrated under reduced pressure to provide the title compound which was used in the next step without further purification. MS (ESI+) m/z 233 (M+H)$^+$; MS (ESI−) m/z 231 (M−H)$^-$; $^1$H NMR (DMSO, 300 MHz) isomers δ 2.39 (s, 3H), 7.88 (m, 1H), 8.27 (m, 1H), 8.50 (m, 1H), 8.65, 8.74 (d, J 7.8, 1H), 9.47, 9.55 (s, 1H).

EXAMPLE 300C 5-amino-3-isoquinolinyl acetate

5-Nitro-3-isoquinolinyl acetate (50 mg, 0.21 mmol) in 1,4-dioxane (20 mL) was treated with Raney-nickel powder (85 mg) and exposed to a hydrogen atmosphere via a balloon for 16 hours. The mixture was filtered through a plug of Celite and the filtrate was concentrated under reduced pressure to provide the title compound which was used without further purification.

EXAMPLE 300D

N-(4-bromobenzyl)-N'-(3-hydroxy-5-isoquinolinyl) urea

5-Amino-3-isoquinolinyl acetate in toluene:THF (5:1, 5 mL) was treated with 1-bromo-4-(isocyanatomethyl) benzene (105 mg). After stirring for 1 hour, the mixture was concentrated under reduced pressure and the residue dissolved in MeOH (20 mL) and treated with K$_2$CO$_3$ (4 eq) and stirred for 16 hours. The mixture was concentrated under reduced pressure and partitioned between CH$_2$Cl$_2$ and water. The aqueous phase was separated and the pH was adjusted to approximately 6 with HCl. The acidified solution was filtered, and the filter cake was dried. The solid was purified by reverse-phase chromatography (using TFA as eluent) to provide the title compound. MS (ESI+) m/z 374, 372 (M+H)$^+$; MS (ESI−) m/z 372, 370 (M−H)$^-$; $^1$H NMR (DMSO, 300 MHz) δ 4.33 (d, J 5.8, 2H), 7.06 (m, 1H), 7.29 (m, 3H), 7.57 (m, 3H), 8.07 (d, J 7.8, 1H), 8.48 (s, 1H), 8.80 (s, 1H), 8.87 (s, 1H); Anal. Calcd for C$_{17}$H$_{14}$BrN$_3$O$_2$+0.2 TFA: C, 53.08; H, 3.42; N, 10.43. Found: C, 52.91; H, 3.62; N, 10.43.

EXAMPLE 301

N-5-isoquinolinyl-N'-{[5-(trifluoromethyl)-2-pyridinyl]methyl}urea

EXAMPLE 301A 5-(trifluoromethyl)-2-pyridinecarbonitrile

Copper (I) cyanide (14.1 g) and 2-bromo-5-trifluoromethylpyridine (3.00 g, 13.3 mmol) in dry DMSO (70 mL) were combined and heated at 180° C. for 2 hours, cooled, and poured into NH$_4$OH (3M). The mixture was then extracted with ethyl acetate (3×500 mL), washed with water (1×200 mL), dried (MgSO$_4$), filtered and the filtrate concentrated under reduced pressure to provide the title compound. $^1$H NMR (DMSO, 300 MHz) δ 8.22 (m, 1H), 8.42 (m, 1H), 9.01 (s, 1H).

EXAMPLE 301B

[5-(trifluoromethyl)-2-pyridinyl]methylamine

The title compound was prepared using the procedure described in Example 172B using 5-(trifluoromethyl)-2-pyridinecarbonitrile instead of 4-(4-morpholinyl) benzonitrile.

EXAMPLE 301C

N-5-isoquinolinyl-N'-{[5-(trifluoromethyl)-2-pyridinyl]methyl}urea

The title compound was prepared using the procedure described in Example 61B using [5-(trifluoromethyl)-2-pyridinyl]methylamine instead of 4-cyanobenzyl alcohol. $^1$H NMR (DMSO, 300 MHz) δ 4.51 (m, 2H), 7.97 (m, 2H), 8.12 (m, 1H), 8.47 (d, J 7.8, 1H), 8.72 (m, 3H), 9.13 (d, J 6.8, 1H), 9.78 (m, 2H), 10.80 (s, 1H); Anal. Calcd for C$_{17}$H$_{13}$F$_3$N$_4$O+0.8 HCl+0.7 CH$_3$OH: C, 53.43; H, 4.20; N, 14.08. Found: C, 53.41; H, 4.31; N, 14.11.

EXAMPLE 302

N-[3-bromo-4-(trifluoromethyl)benzyl]-N'-5-isoquinolinylurea

The title compound was prepared using the procedure described in Example 61B using 3-bromo-4-(trifluoromethyl)benzylamine instead of 4-cyanobenzyl alcohol. MS (ESI+) m/z 426, 424 (M+H)$^+$; MS (ESI−) m/z 424, 422 (M−H)$^-$; $^1$H NMR (DMSO, 300 MHz) δ 4.46 (d, J 5.8, 2H), 7.26 (t, J 6.1, 1H), 7.56 (d, J 8.8, 1H), 7.90 (m, 2H), 7.97 (d, J 8.1, 1H), 8.21 (d, J 6.4, 1H), 8.39 (d, J 8.8, 1H), 8.64 (d, J 6.4, 1H), 9.08 (s, 1H), 9.57 (s, 1H); Anal. Calcd for C$_{18}$H$_{13}$BrF$_3$N$_3$O+0.9 TFA: C, 45.14; H, 2.66; N, 7.98. Found: C, 45.18; H, 2.64; N, 7.86.

EXAMPLE 303

N-[2,4-bis(trifluoromethyl)benzyl]-N'-5-isoquinolinylurea

The title compound was prepared using the procedure described in Example 61B using 2,4-bis(trifluoromethyl) benzylamine instead of 4-cyanobenzyl alcohol. MS (ESI+) m/z 414 (M+H)$^+$; MS (ESI−) m/z 412 (M−H)$^-$; $^1$H NMR (DMSO, 300 MHz) rotamers δ 4.63 (d, J 5.8, 2H), 7.70–8.20 (m, 6H), 8.60 (m, 3H), 9.60 (m, 2H); Anal. Calcd for C$_{19}$H$_{13}$F$_6$N$_3$O+1 HCl: C, 50.74; H, 3.14; N, 9.34. Found: C, 50.88; H, 3.08; N, 9.10.

EXAMPLE 304

N-[2,3-difluoro-4-(trifluoromethyl)benzyl]-N'-5-isoquinolinylurea

The title compound was prepared using the procedure described in Example 61B using 2,3-difluoro-4-(trifluoromethyl)benzylamine instead of 4-cyanobenzyl alcohol. MS (ESI+) m/z 382 (M+H)$^+$; MS (ESI−) m/z 380 (M−H)$^-$; $^1$H NMR (DMSO, 300 MHz) rotamers δ 4.55 (d, J 5.8, 2H), 7.45 (m, 1H), 7.63 (t, J 6.1, 1H), 7.82 (m, 1H), 8.05 (d, J 8.1, 1H), 8.56 (m, 2H), 8.69 (d, J 6.4, 1H), 9.51 (s, 1H), 9.70 (s, 1H); Anal. Calcd for C$_{18}$H$_{12}$F$_5$N$_3$O+0.8 HCl: C, 52.67; H, 3.14; N, 10.24. Found: C, 52.53; H, 3.38; N, 10.22.

EXAMPLE 305

N-[2-chloro-4-(trifluoromethyl)benzyl]-N'-5-isoquinolinylurea

The title compound was prepared using the procedure described in Example 61B using 2-chloro-4-(trifluoromethyl)benzylamine instead of 4-cyanobenzyl alcohol. MS (ESI+) m/z 380 (M+H)$^+$; MS (ESI−) m/z 378 (M−H)$^-$; $^1$H NMR (DMSO, 300 MHz) δ 4.53 (d, J 5.8, 2H), 7.69 (m, 2H), 7.87 (m, 1H), 8.06 (d, J 8.1, 1H), 8.56 (d, J 7.8, 1H), 8.63 (d, J 6.8, 1H), 8.70 (d, J 6.8, 1H), 9.59 (s, 1H), 9.72 (s, 1H); Anal. Calcd for $C_{18}H_{13}ClF_3N_3O+1.3$ HCl: C, 50.61; H, 3.37; N, 9.84. Found: C, 50.60; H, 3.42; N, 9.61.

EXAMPLE 306

N-5-isoquinolinyl-N'-{1-methyl-1-[4-(trifluoromethyl)phenyl]ethyl}urea

The title compound was prepared using the procedure described in Example 61B using 2-[4-(trifluoromethyl)phenyl]-2-propanamine instead of 4-cyanobenzyl alcohol. MS (ESI+) m/z 374 (M+H)$^+$; MS (ESI–) m/z 372 (M–H)$^-$; $^1$H NMR (DMSO, 300 MHz) δ 1.67 (s, 6H), 7.67 (s, 4H), 7.82 (t, J 8.1, 1H), 8.02 (d, J 8.1, 1H), 8.54 (d, J 7.8, 1H), 8.72 (d, J 6.8, 1H), 8.87 (d, J 6.8, 1H), 9.65 (s, 1H), 9.77 (s, 1H); Anal. Calcd for $C_{20}H_{18}F_3N_3O+1$ HCl: C, 58.61; H, 4.67. Found: C, 58.62; H, 4.65.

EXAMPLE 307

N-[2-(4-bromophenyl)-2-hydroxyethyl]-N'-5-isoquinolinylurea

The title compound was prepared using the procedure described in Example 61B using 2-amino-1-(4-bromophenyl)ethanol instead of 4-cyanobenzyl alcohol. MS (ESI+) m/z 388, 386 (M+H)$^+$; MS (ESI–) m/z 386, 384(M–H)$^-$; $^1$H NMR (DMSO, 300 MHz) rotamers δ 3.27 (m, 1H), 3.42 (m, 1H), 4.70 (m, 1H), 6.82 (t, J 5.0, 2H), 7.38 (d, J 8.5, 1H), 7.56 (d, J 8.5, 1H), 7.81 (t, J 7.8, 1H), 7.98 (d, J 8.7, 1H), 8.29 (d, J 7.5, 1H), 8.50 (d, J 5.9, 1H), 8.67 (d, J 6.4, 1H), 9.01 (s, 1H), 9.64 (s, 1H); Anal. Calcd for $C_{18}H_{16}BrN_3O_2+2.35$ TFA: C, 41.68; H, 2.83; N, 6.42. Found: C, 41.69; H, 2.86; N, 6.43.

EXAMPLE 309 methyl 4-({[(1-naphthylmethyl)amino]carbonyl}amino)-1H-indazole-1-carboxylate

EXAMPLE 309A 4-nitro-1H-indazole

2-Methyl-3-nitroaniline (20 g) in acetic acid (~200 mL) was treated with NaNO$_2$ (20 g) in water (50 mL) at 4° C. (mechanical stirring). The reaction mixture was allowed to warm to room temperature and stir overnight. The solvent was removed under reduced pressure. The residue was treated with water (700 mL) and the mixture was filtered. The solid was dried at 45° C. in a vacuum oven overnight to provide the title compound. $^1$H NMR (DMSO-d$_6$) δ 13.91 (s, 1H), 8.55 (s, 1H), 8.18 (d, 1H), 8.10 (d, 1H), 7.61 (dd, 1H); MS (ESI) m/z 164 (M+H)$^+$.

EXAMPLE 309B methyl 4-nitro-1H-indazole-1-carboxylate

NaH (0.3 g, 12.5 mmol) in DMF (5 mL) was treated with 4-nitro-1H-indazole (1.33 g, 10 mmol) at 0° C. The reaction mixture was allowed to warm to room temperature and stir for 1 hour. The mixture was treated with methyl chloroformate (0.9 mL) and stirred at room temperature for 3 hours. The mixture was treated with water and filtered to provide the title compound as a solid. $^1$H NMR (300 MHz, DMSO-d$_6$) δ 4.1 9 (s, 3H), 7.9 (t, 1H), 8.38 (d, 1H), 8.62 (d, 1H), 8.85 (s, 1H).

EXAMPLE 309C methyl 4-amino-1H-indazole-1-carboxylate

Methyl 4-nitro-1H-indazole-1-carboxylate 1.66 g, 7.5 mmol) and 10% Pd/C were combined in ethanol (20 mL) and exposed to a hydrogen atmosphere. The reaction mixture was heated at 80° C. for 20 minutes, allowed to cool to room temperature, and filtered through Celite. The filtrate was evaporated to provide title compound. $^1$H NMR (300 MHz, DMSO-d$_6$) δ 6.1 (s, 2H), 6.41 (dd, 1H), 7.21 (m, 2H), 8.42 (s, 1H).

EXAMPLE 309D methyl 4-({[(2,5-dioxo-1-pyrrolidinyl)oxy]carbonyl}amino)-1H-indazole-1-carboxylate Methyl 4-amino-1H-indazole-1-carboxylate (1.9 g, 10 mmol) and 1-({[(2,5-dioxo-1-pyrrolidinyl)oxy]carbonyl}oxy)-2,5-pyrrolidinedione (2.8 g, 11 mmol) were combined in acetonitrile (100 mL), stirred for 48 hours at ambient temperature, and filtered. The filter cake was washed with acetonitrile (10 mL) and dried under reduced pressure at ambient temperature to provide the title compound.

EXAMPLE 309E methyl 4-({[(1-naphthylmethyl)amino]carbonyl}amino)-1H-indazole-1-carboxylate 1-Naphthylmethylamine (2.1 mmol) and diisopropylethylamine (2 mmol, 0.26 g) were combined in DMF (6 mL) and treated with methyl 4-({[(2,5-dioxo-1-pyrrolidinyl)oxy]carbonyl}amino)-1H-indazole-1-carboxylate (6.6 g, 2 mmol) at ambient temperature. After stirring for 30 minutes, the reaction mixture was diluted with water (6 ml) and filtered. The filter cake was washed with water:acetonitrile (1:1) and dried to provide the title compound. $^1$H NMR (DMSO-d$_6$) δ 4.02 (s, 3H); 4.81 (d, 2H); 6.85 (m, 1H); 7.42–7.64 (m, 5H); 7.67 (d, 1H); 7.87 (m, 2H); 7.97 (d, 1H); 8.15 (d, 1H); 8.38 (s, 1H); 8.99 (s, 1H).

EXAMPLE 310 methyl 4-({[(1,1'-biphenyl-3-ylmethyl)amino]carbonyl}amino)-1H-indazole-1-carboxylate The title compound was prepared using the procedure described in Example 309E except using 1,1'-biphenyl-3-ylmethylamine instead of 1-naphthylmethylamine. $^1$H NMR (DMSO-D$_6$) δ 4.02 (S, 3H); 4.43 (D, 2H); 6.89 (m, 1H); 7.36 (m, 2H); 7.42–7.51 (m, 4H); 7.56 (m, 1H), 7.60–7.72 (m, 4H); 7.82 (m, 1H); 8.42 (S, 1H); 9.04 (S, 1H).

EXAMPLE 311 methyl 4-({[(2-chlorobenzyl)amino]carbonyl}amino)-1H-indazole-1-carboxylate

The title compound was prepared using the procedure described in Example 309E except using 2-chlorobenzylamine instead of 1-naphthylmethylamine. $^1$H NMR (DMSO-D$_6$) δ 4.02 (S, 3H); 4.43 (D, 2H); 6.89 (m, 1H); 7.25–7.39 (m, 2H); 7.41–7.52 (m, 3H); 7.68 (D, 1H); 7.81 (D, 1H); 8.44 (S, 1H); 9.14 (S, 1H).

EXAMPLE 312 methyl 4-[({[2-fluoro-5-(trifluoromethyl)benzyl]amino}carbonyl)amino]-1H-indazole-1-carboxylate The title compound was prepared using the procedure described in Example 309E except using 2-chloro-5-

(trifluoromethyl)benzylamine instead of 1-naphthylmethylamine. NMR (6, DMSO-d$_6$) δ 4.02 (s, 3H); 4.471 (d, 2H); 6.97 (m, 1H); 7.41–7.52 (m, 2H); 7.69 (d, 1H); 7.71–7.80 (m, 3H); 7.97 (d, 1H); 8.42 (s, 1H); 9.14 (s, 1H).

EXAMPLE 313

N-1H-indazol-4-yl-N'-(1-naphthylmethyl)urea

Methyl 4-({[(1-naphthylmethyl)amino]carbonyl}amino)-1H-indazole-1-carboxylate in methanol was treated with 5M sodium hydroxide (8 equivalents) (prepared by dissolution of 1 gram of sodium hydroxide in 20 µL of methanol). After stirring for 30 minutes, the mixture was diluted with water (10 mL) and filtered. The filter cake was washed with water (10 mL), water:methanol (1:1), and dried under reduced pressure to provide the title compound. MS (M+H)$^+$ 317.

EXAMPLE 314

N-(1,1'-biphenyl-3-ylmethyl)-N'-1H-indazol-4-ylurea

The title compound was prepared using the procedure described in Example 313 except using methyl 4-({[(1,1'-biphenyl-3-ylmethyl)amino]carbonyl}amino)-1H-indazole-1-carboxylate instead of methyl 4-({[(1-naphthylmethyl)amino]carbonyl}amino)-1H-indazole-1-carboxylate. MS (M+H)$^+$ 343.

EXAMPLE 315

N-(2-chlorobenzyl)-N'-1H-indazol-4-ylurea

The title compound was prepared using the procedure described in Example 313 except using methyl 4-({[(2-chlorobenzyl)amino]carbonyl}amino)-1H-indazole-1-carboxylate instead of methyl 4-({[(1-naphthylmethyl)amino]carbonyl}amino)-1H-indazole-1-carboxylate. MS (M+H)$^+$ 301.

EXAMPLE 316

N-[2-fluoro-5-(trifluoromethyl)benzyl]-N'-1H-indazol-4-ylurea

The title compound was prepared using the procedure described in Example 313 except using methyl 4-[({[2-fluoro-5-(trifluoromethyl)benzyl]amino}carbonyl)amino]-1H-indazole-1-carboxylate instead of methyl 4-({[(1-naphthylmethyl)amino]carbonyl}amino)-1H-indazole-1-carboxylate. MS (M+H)$^+$ 354.

EXAMPLE 317

N-1H-indazol-4-yl-N'-(3-phenylpropyl)urea

Methyl 4-amino-1H-indazole-1-carboxylate (0.46 g, 2.4 mmol) and phosgene (20% in toluene, 2.4 ml, 4.8 mmol) were combined in toluene (80 ml) and heated at reflux for 3 hours. The mixture was allowed to cool to ambient temperature and the solvent was removed under reduced pressure. The residue was treated with diethyl ether (80 ml) and triethyl amine (2 ml) and then filtered. The filtrate was treated with 3-phenylpropylamine (2.4 mmol, 324 mg) and stirred for 16 hours at ambient temperature. The solvent was concentrated to half volume under reduced pressure and filtered. The filter cake was washed with diethyl ether:hexanes (1:1). The obtained solid in methanol (10 ml) was treated with a 5M solution of sodium hydroxide in methanol (4 ml, 20 mmol) and stirred for 30 minutes. The reaction mixture was diluted with water and extracted with ethyl acetate (2×25 mL). The organics were combined, washed with water (2×25 ml), brine, dried over Mg$_2$SO$_4$, filtered and the filtrate was concentrated under reduced pressure. The residue was treated with ethanolic HCl to provide the title compound as the HCl salt. $^1$H NMR (DMSO-d$_6$) δ 8.81 (s, 1H), 8.18 (s, 1H), 7.62 (d, 1H), 7.22 (m, 6H), 7.03 (d, 1H), 3.17 (t, 2H), 2.62 (t, 2H), 1.78 (m, 2H); MS (ESI) m/z 295 (M+H)$^+$.

EXAMPLE 318

N-[2-(2,4-dimethylphenyl)ethyl]-N'-1H-indazol-4-ylurea

The title compound was prepared using the procedure described in Example 317 except using 2-(2,4-dimethylphenyl)ethylamine instead of 3-phenylpropylamine. $^1$H NMR (DMSO-d$_6$) δ 8.80 (s, 1H), 8.16 (s, 1H), 7.63 (d, 1H), 7.18 (t, 1H), 7.05 (t, 2H), 6.88 (m, 2H), 3.30 (t, 2H), 2.74 (t, 2H), 2.25 (s, 3H), 2.22 (s, 3H); MS (ESI) m/z 309 (M+H)$^+$.

EXAMPLE 319

N-[2-(3,4-dichlorophenyl)ethyl]-N'-1H-indazol-4-ylurea

The title compound was prepared using the procedure described in Example 317 except using 2-(3,4-dichlorophenyl)ethylamine instead of 3-phenylpropylamine. $^1$H NMR (DMSO-d$_6$) δ 8.82 (s, 1H), 8.17 (s, 1H), 7.58 (m, 4H), 7.27 (dd, 1H), 7.18 (t, 1H), 7.03 (d, 2H), 6.58 (bs, 1H), 3.40 (t, 2H), 2.80 (t, 2H); MS (ESI) m/z 349 (M+H)$^+$.

EXAMPLE 320

N-1H-indazol-4-yl-N'-[2-(4-methylphenyl)ethyl]urea

The title compound was prepared using the procedure described in Example 317 except using 2-(4-methylphenyl)ethylamine instead of 3-phenylpropylamine. $^1$H NMR (DMSO-d$_6$) δ 8.77 (s, 1H), 8.20 (s, 1H), 7.62 (d, 1H), 7.28 (m, 2H), 7.15 (m, 5H), 3.38 (t, 2H), 2.73 (t, 2H); MS (ESI) m/z 395, (M+H)$^+$.

EXAMPLE 321

N-[4-azepan-1-yl-3-(trifluoromethyl)benzyl]-N'-1H-indazol-4-ylurea

The title compound was prepared using the procedure described in Example 317 except using 4-azepan-1-yl-3-(trifluoromethyl)benzylamine instead of 3-phenylpropylamine. $^1$H NMR (DMSO-d$_6$) δ 8.98 (s, 1H), 8.18 (s, 1H), 7.60 (m, 3H), 7.48 (d, 1H), 7.19 (t, 1H), 7.06, (d, 2H), 4.37 (d, 2H), 3.00 (m, 4H), 2.64 (s, 8H); MS (ESI) m/z 432, (M+H)$^+$.

EXAMPLE 322

N-[4-azepan-1-yl-2-(trifluoromethyl)benzyl]-N'-1H-indazol-4-ylurea

The title compound was prepared using the procedure described in Example 317 except using 4-azepan-1-yl-2-(trifluoromethyl)benzylamine instead of 3-phenylpropylamine. $^1$H NMR (DMSO-d$_6$) δ 9.00 (s, 1H), 8.19 (s, 1H), 7.64 (d, 1H), 7.41 (d, 1H), 7.19 (t, 1H), 7.03, (d, 1H), 6.91 (m, 4H), 4.37 (s, 2H), 3.43 (t, 4H), 1.71 (s, 4H), 1.43 (m, 4H); MS (ESI) m/z 432, (M+H)+.

EXAMPLE 323

N-[4-(2-azabicyclo[2.2.1]hept-2-yl)-2-(trifluoromethyl)benzyl]-N'-1H-indazol-4-ylurea The title compound was prepared using the procedure described in Example 317 except using 4-(2-azabicyclo[2.2.1]hept-2-yl)-2-(trifluoromethyl)benzylamine instead of 3-phenylpropylamine. $^1$H NMR (DMSO-d$_6$) δ 9.00 (s, 1H), 8.19 (s, 1H), 7.64 (d, 1H), 7.40 (d, 1H), 7.19 (t, 1H), 7.04 (d, 1H), 6.91 (bs, 1H), 6.80 (dd, 1H), 6.70 (d, 1H), 4.38 (s, 2H), 4.21 (s, 1H), 3.43 (m, 2H), 2.71 (d, 1H), 2.60 (s, 1H), 1.1.65 (m, 3H), 1.50 (m, 1H), 1.28 (m, 1H); MS (ESI) m/z 430, (M+H)+.

EXAMPLE 324

N-[4-(8-azabicyclo[3.2.1]oct-8-yl)-2-(trifluoromethyl)benzyl]-N'-1H-indazol-4-ylurea The title compound was prepared using the procedure described in Example 317 except using 4-(8-azabicyclo[3.2.1]oct-8-yl)-2-(trifluoromethyl)benzylamine instead of 3-phenylpropylamine. $^1$H NMR (DMSO-d$_6$) δ 9.02 (s, 1H), 8.20 (s, 1H), 7.63 (d, 1H), 7.44 (d, 1H), 7.19 (t, 1H), 7.05 (m, 2H), 7.00 (m, 2H), 4.38 (s, 2H), 4.23 (s, 2H), 2.01 (m, 2H), 1.80 (m, 5H), 1.41 (m, 1H), 1.26 (m, 2H); MS (ESI) m/z 444 (M+H)+.

EXAMPLE 325

N-[4-(8-azabicyclo[3.2.1]oct-8-yl)-3-fluorobenzyl]-N'-1H-indazol-4-ylurea

EXAMPLE 325A 4-(8-azabicyclo[3.2.1]oct-8-yl)-3-fluorobenzonitrile 3,4-Difluorobenzonitrile (1.75 g; 25.1 mmol), 8-azabicyclo[3.2.1]octane hydrochloride (2.1 g; 13.8 mmol), and diisopropylethylamine (3.2 g; 25.1 mmol), were combined in DMSO (30 mL) and heated at 120° C. overnight. The mixture was allowed to cool to ambient temperature, poured into brine (75 mL), and extracted with diethyl ether (2×50 mL). The organics were combined, dried over MgSO$_4$, filtered, and the filtrate was concentrated under reduced pressure. The residue was filtered through a pad of silica gel (ethyl acetate as eluent) to provide the title compound. $^1$H NMR (DMSO-d$_6$) δ 7.69 (dd, 1H), 7.42 (dd, 1H), 7.15 (t, 1H), 4.41 (s, 2H), 1.98 (m, 2H), 1.62–1.86 (m, 5H), 1.41 (m, 3H); MS (ESI) m/z 231, (M+H)+.

EXAMPLE 325B 4-(8-azabicyclo[3.2.1]oct-8-yl)-3-fluorobenzylamine

Lithium aluminum hydride (1.6 g; 43.2 mmol) in THF was treated with 4-(8-azabicyclo[3.2.1]oct-8-yl)-3-fluorobenzonitrile (2.48 g; 10.8 mmol) dropwise. After complete addition, the slurry was refluxed for 2 hours, allowed to cool to ambient temperature, and quenched with sodium sulfate decahydrate. The mixture was filtered and the filter cake was washed with THF (2×50 mL). The organics were combined and concentrated under reduced pressure. The residue was chromatographed (SiO$_2$; 5% methanol in methylene chloride) to provide the title compound. $^1$H NMR (DMSO-d$_6$) δ 7.03 (dd, 1H), 7.92 (dd, 1H), 7.85 (t, 1H), 4.21 (s, 2H), 3.60 (s, 2H), 1.93 (m, 2H), 1.77 (m, 5H), 1.42 (m, 1H), 1.32 (m, 2H); MS (ESI) m/z 235, (M+H)+.

N-[4-(8-azabicyclo[3.2.1]oct-8-yl)-3-fluorobenzyl]-N'-1H-indazol-4-ylurea

The title compound was prepared using the procedure described in Example 317 except using 4-(8-azabicyclo[3.2.1]oct-8-yl)-3-fluorobenzylamine instead of 3-phenylpropylamine. $^1$H NMR (DMSO-d$_6$) δ 9.00 (s, 1H), 8.20 (s, 1H), 7.64 (d, 1H), 7.18 (t, 1H), 7.03 (m, 5H), 4.24 (s, 2H), 4.17 (s, 2H), 1.95 (m, 2H), 1.80 (m, 6H), 1.41 (m, 2H); MS (ESI) m/z 394 (M+H)+.

EXAMPLE 326

N-(3-chloro-4-azepan-1-ylbenzyl)-N'-1H-indazol-4-ylurea

The title compound was prepared using the procedure described in Example 317 except using 3-chloro-4-azepan-1-ylbenzylamine instead of 3-phenylpropylamine. $^1$H NMR (DMSO-d$_6$) δ 8.90 (s, 1H), 8.19 (s, 1H), 7.62 (d, 1H), 7.36 (d, 1H), 7.20 (m, 4H), 7.03, (d, 1H), 6.98 (bs, 1H), 4.26 (s, 2H), 3.18 (m, 4H), 1.78 (m, 4H), 1.62 (m, 4H); MS (ESI) m/z 398, (M+H)+.

EXAMPLE 327

N-1H-indazol-4-yl-N'-{[6-(trifluoromethyl)-3-pyridinyl]methyl}urea

The title compound was prepared using the procedure described in Example 317 except using [6-(trifluoromethyl)-3-pyridinyl]methylamine instead of 3-phenylpropylamine. $^1$H NMR (DMSO-d$_6$) δ 9.09 (s, 1H), 8.78 (s, 1H), 8.20 (s, 1H), 8.03 (d, 1H), 7.90 (d, 1H), 7.60, (d, 1H), 7.22 (m, 2H), 7.05 (d, 1H), 4.49 (dd, 2H); MS (ESI) m/z 336 (M+H)+.

EXAMPLE 328

N-[(1S)-1-(4-bromophenyl)ethyl]-N'-1H-indazol-4-ylurea

The title compound was prepared using the procedure described in Example 317 except using (1S)-1-(4-bromophenyl)ethylamine instead of 3-phenylpropylamine. $^1$H NMR (DMSO-d$_6$) δ 8.82 (s, 1H), 8.16 (s, 1H), 7.57 (m, 3H), 7.35 (d, 2H), 7.17 (t, 1H), 7.03, (d, 2H), 4.82 (m, 1H), 1.41 (d, 3H); MS (ESI) m/z 336 (M+H)+.

EXAMPLE 329

N-(3-bromo-4-fluorobenzyl)-N'-1H-indazol-4-ylurea

The title compound was prepared using the procedure described in Example 317 except using 3-bromo-4-fluorobenzylamine instead of 3-phenylpropylamine. $^1$H NMR (DMSO-d$_6$) δ 9.02 (s, 1H), 8.20 (s, 1H), 7.63 (m, 2H), 7.38 (m, 2H), 7.19 (t, 1H), 7.14 (bs, 1H), 7.03, (d, 1H), 4.35 (m, 1H); MS (ESI) m/z 364, (M+H)+.

EXAMPLE 330

N-(2,4-dimethylbenzyl)-N'-1H-indazol-4-ylurea

The title compound was prepared using the procedure described in Example 317 except using 2,4-dimethylbenzylamine instead of 3-phenylpropylamine. $^1$H NMR (DMSO-(d$_6$) δ 8.88 (s, 1H), 8.17 (s, 1H), 7.63 (d, 2H), 7.19 (m, 2H), 7.01 (m, 4H), 6.83 (bs, 1H), 4.28 (s, 2H), 2.20 (s, 3H), 2.16 (s, 3H); MS (ESI) m/z 295 (M+H)$^+$.

EXAMPLE 331

N-(4-chlorobenzyl)-N'-1H-indazol-4-ylurea

The title compound was prepared using the procedure described in Example 317 except using 4-chlorobenzylamine instead of 3-phenylpropylamine. $^1$H NMR (DMSO-d$_6$) δ 8.96 (s, 1H), 8.18 (s, 1H), 7.62 (d, 1H), 7.39 (m, 4H), 7.19 (t, 1H), 7.06 (d, 2H), 4.36 (d, 2H); MS (ESI) m/z 301 (M+H)$^+$.

EXAMPLE 332

N-[3-fluoro-4-(trifluoromethyl)benzyl]-N'-1H-indazol-4-ylurea

The title compound was prepared using the procedure described in Example 317 except using 3-fluoro-4-(trifluoromethyl)benzylamine instead of 3-phenylpropylamine. $^1$H NMR (DMSO-d$_6$) δ 9.17 (s, 1H), 8.22 (s, 1H), 7.77 (t, 1H), 7.60 (d, 1H), 7.41 (m, 2H), 7.28 (bs, 1H), 7.19 (t, 2H), 7.05 (d, 1H), 4.47 (d, 2H); MS (ESI) m/z 353, (M+H)$^+$.

EXAMPLE 333

N-1H-indazol-4-yl-N'-(4-methylbenzyl)urea

The title compound was prepared using the procedure described in Example 317 except using 4-methylbenzylamine instead of 3-phenylpropylamine. $^1$H NMR (DMSO-d$_6$) δ 9.02 (s, 1H), 8.21 (s, 1H), 7.64 (d, 1H), 7.19 (m, 6H), 7.05 (d, 1H), 4.30 (s, 1H); MS (ESI) m/z 281, (M+H)$^+$.

EXAMPLE 334

N-1H-indazol-4-yl-N'-[3-(trifluoromethoxy)benzyl]urea

The title compound was prepared using the procedure described in Example 317 except using 3-(trifluoromethoxy)benzylamine instead of 3-phenylpropylamine. $^1$H NMR (DMSO-d$_6$) δ 9.07 (s, 1H), 8.22 (s, 1H), 7.48 (t, 1H), 7.39 (d, 1H), 7.32 (s, 1H), 7.20 (m, 3H), 7.03 (d, 1H), 4.20 (s, 1H); MS (ESI) m/z 351 (M+H)$^+$.

EXAMPLE 335

N-(3-chloro-4-fluorobenzyl)-N'-1H-indazol-4-ylurea

The title compound was prepared using the procedure described in Example 317 except using 3-chloro-4-fluorobenzylamine instead of 3-phenylpropylamine. $^1$H NMR (DMSO-d$_6$) δ 9.20 (s, 1H), 8.29 (s, 1H), 7.63 (d, 1H), 7.35 (dd, 1H), 7.38 (m, 3H), 7.20 (t, 1H), 7.03 (d, 1H), 4.38 (s, 1H); MS (ESI) m/z 353, (M+H)$^+$.

EXAMPLE 336

N-(3,4-dimethylbenzyl)-N'-1H-indazol-4-ylurea

The title compound was prepared using the procedure described in Example 317 except using 3,4-dimethylbenzylamine instead of 3-phenylpropylamine. $^1$H NMR (DMSO-(d$_6$); 9.00 (s, 1H), 8.21 (s, 1H), 7.64 (d, 1H), 7.20 (t, 1H), 7.07 (m, 5H), 4.23 (s, 3H), 2.21 (s, 3H), 1.98 (s, 3H); MS (ESI) m/z 295, (M+H)$^+$.

EXAMPLE 337

N-[3-fluoro-5-(trifluoromethyl)benzyl]-N'-1H-indazol-4-ylurea

The title compound was prepared using the procedure described in Example 317 except using 3-fluoro-5-(trifluoromethyl)benzylamine instead of 3-phenylpropylamine. $^1$H NMR (DMSO-d$_6$) δ 9.25 (s, 1H), 8.30 (s, 1H), 7.57 (m, 5H), 7.43 (bs, 1H), 7.20 (t, 1H), 7.05 (d, 1H), 4.42 (s, 2H); MS (ESI) m/z 351 (M–H)—.

EXAMPLE 338

N-(2-chloro-4-azepan-1-ylbenzyl)-N'-1H-indazol-4-yl urea

The title compound was prepared using the procedure described in Example 317 except using 2-chloro-4-azepan-1-ylbenzylamine instead of 3-phenylpropylamine. $^1$H NMR (DMSO-d$_6$) δ 9.00 (s, 1H), 8.20 (s, 1H), 7.63 (d, 1H), 7.23 (d, 1H), 7.19 (t, 1H), 7.03 (d, 1H), 6.98 (bs, 1H), 6.64 (m, 3H), 4.25 (s, 2H), 3.42 (m, 4H), 1.70 (m, 4H), 1.43 (m, 4H); MS (ESI) m/z 398 (M+H)$^+$.

EXAMPLE 339

N-(2,3-dichlorobenzyl)-N'-1H-indazol-4-ylurea

The title compound was prepared using the procedure described in Example 317 except using 2,3-dichlorobenzylamine instead of 3-phenylpropylamine. $^1$H NMR (DMSO-(d$_6$) δ 9.06 (s, 1H), 8.18 (s, 1H), 7.61 (d, 1H), 7.58 (d, 1H), 7.40 (m, 2H), 7.19 (m, 1H), 7.12 (t, 1H), 7.06 (d, 1H), 4.25 (s, 2H), 4.23 (d, 2H); MS (ESI) m/z 336 (M+H)$^+$.

EXAMPLE 340

N-1H-indazol-4-yl-N'-{4-[(trifluoromethyl)thio]benzyl}urea

The title compound was prepared using the procedure described in Example 317 except using 4-[(trifluoromethyl)thio]benzylamine instead of 3-phenylpropylamine. $^1$H NMR (DMSO-d$_6$) δ 9.06 (s, 1H), 8.21 (s, 1H), 7.71 (d, 2H), 7.62 (d, 1H), 7.50 (d, 2H), 7.18 (m, 2H), 7.05 (d, 1H), 4.21 (s, 2H); MS (ESI) m/z 367 (M+H)$^+$.

EXAMPLE 341

N-1H-indazol-4-yl-N'-[3-(trifluoromethyl)benzyl]urea

The title compound was prepared using the procedure described in Example 317 except using 3-(trifluoromethyl)benzylamine instead of 3-phenylpropylamine. $^1$H NMR (DMSO-d$_6$) δ 9.17 (s, 1H), 8.24 (s, 1H), 7.63 (m, 6H), 7.30 (bs, 1H), 7.19 (t, 1H), 7.16 (d, 1H), 4.43 (s, 1H), 4.21; MS (ESI) m/z 335 (M+H)$^+$.

EXAMPLE 342

N-(3,5-difluoro-4-azepan-1-ylbenzyl)-N'-1H-indazol-4-ylurea

EXAMPLE 342A 3,5-difluoro-4-azepan-1-ylbenzonitrile

The title compound was prepared using the procedure described in Example 325A except using 3,4,5- trifluorobenzonitrile and azepane instead of 3,4-difluorobenzonitrile and 8-aza-bicyclo[3.2.1]octane hydrochloride. $^1$H NMR (DMSO-d$_6$) δ 7.62 (d, 2H), 3.39 (m, 4H), 1.73 (m, 4H), 1.61 (m, 4H); MS (ESI) m/z 237 (M+H)$^+$.

EXAMPLE 342B 3,5-difluoro-4-azepan-1-ylbenzylamine

The title compound was prepared using the procedure described in Example 325B except using 3,5-difluoro-4-azepan-1-ylbenzonitrile instead of 4-(8-azabicyclo[3.2.1]oct-8-yl)-3-fluorobenzonitrile. $^1$H NMR (DMSO-d$_6$) δ 6.97 (d, 2H), 3.62 (s, 2H), 3.27 (m, 4H), 1.63 (m, 8H); MS (ESI) m/z 241 (M+H)$^+$.

EXAMPLE 342C

N-(3,5-difluoro-4-azepan-1-ylbenzyl)-N'-1H-indazol-4-ylurea

The title compound was prepared using the procedure described in Example 317 except using 3,5-difluoro-4-azepan-1-ylbenzylamine instead of 3-phenylpropylamine. $^1$H NMR (DMSO-d$_6$) δ 9.00 (s, 1H), 8.20 (s, 1H), 7.62 (d, 1H), 7.20 (t, 1H), 7.06 (d, 2H), 6.98 (d, 2H), 4.26 (s, 2H), 3.18 (m, 4H), 1.62 (m, 8H); MS (ESI) m/z 400 (M+H)$^+$.

EXAMPLE 343

N-[4-(8-azabicyclo[3.2.1]oct-8-yl)-3,5-difluorobenzyl]-N'-1H-indazol-4-ylurea

EXAMPLE 343A 4-(8-azabicyclo[3.2.1]oct-8-yl)-3,5-difluorobenzonitrile

The title compound was prepared using the procedure described in Example 325A except using 3,4,5-trifluorobenzonitrile instead of 3,4-difluorobenzonitrile. $^1$H NMR (DMSO-d$_6$) δ 7.58 (dd, 2H), 4.34 (s, 2H), 1.95 (m, 2H), 1.78 (m, 5H), 1.46 (m, 3H); MS (ESI) m/z 249 (M+H)$^+$.

EXAMPLE 343B 4-(8-azabicyclo[3.2.1]oct-8-yl)-3,5-difluorobenzylamine

The title compound was prepared using the procedure described in Example 325B except using 4-(8-azabicyclo[3.2.1]oct-8-yl)-3,5-difluorobenzonitrile instead of 4-(8-azabicyclo[3.2.1]oct-8-yl)-3-fluorobenzonitrile. $^1$H NMR (DMSO-d$_6$) δ 6.97 (d, 2H), 4.00 (s, 2H), 3.59 (m, 2H), 1.91 (m, 2H), 1.76 (m, 5H), 1.42 (m, 3H); MS (ESI) m/z 253 (M+H)$^+$.

EXAMPLE 343C

N-[4-(8-azabicyclo[3.2.1]oct-8-yl)-3,5-difluorobenzyl]-N'-1H-indazol-4-ylurea

The title compound was prepared using the procedure described in Example 317 except using 4-(8-azabicyclo[3.2.1]oct-8-yl)-3,5-difluorobenzylamine instead of 3-phenylpropylamine. $^1$H NMR (DMSO-d$_6$) δ 8.98 (s, 1H), 8.20 (s, 1H), 7.62 (d, 1H), 7.19 (t, 1H), 7.06 (d, 2H), 6.93 (d, 2H), 4.23 (s, 2H), 4.06 (s, 2H), 1.91 (m, 2H), 1.74 (m, 5H), 1.41 (m, 3H); MS (ESI) m/z 412, (M+H)$^+$.

EXAMPLE 344

N-(4-chlorobenzyl)-N'-(1-methyl-1H-indazol-4-yl)urea

EXAMPLE 344A 1-methyl-4-nitro-1H-indazole

A suspension of NaH (1.1 g, 32.2 mmol; 60% dispersion in mineral oil) in DMF (40 mL) was treated with 4-nitro-1H-indazole (5 g, 30.6 mmol) in DMF (40 mL) at 0° C. After stirring for 30 minutes, the mixture was treated with methyl iodide (4.6 g, 32.18 mmol) in DMF (20 ml) drop wise. The mixture was allowed to gradually warm to ambient temperature and stir overnight. The mixture was poured into water (250 ml) and extracted with ethyl acetate (2×100 mL). The organics were combined, washed with water, brine, dried over Na$_2$SO$_4$, filtered, and the filtrate was concentrated under reduced pressure. The residue was chromatographed (SiO$_2$, ethyl acetate/hexanes) to provide the title compound. $^1$H NMR (DMSO-d$_6$) δ 8.50 (s, 1H), 8.24 (d, 1H), 8.19 (d, 1H), 7.65 (t, 1H).

EXAMPLE 344B 1-methyl-1H-indazol-4-amine

1-Methyl-4-nitro-1H-indazole (6.1 g; 35.4 mmol) and 10% Pd/carbon (500 mg) were combined in ethanol and hydrogenated in a Parr apparatus at 60 PSI hydrogen at 50° C. for 1 hour. The mixture was allowed to cool to ambient temperature, filtered through Celite, and concentrated under reduced pressure to provide the title compound. $^1$H NMR (DMSO-d$_6$) δ 8.02 (s, 1H), 7.02 (t, 1H), 6.62 (d, 1H), 6.14 (d, 1H), 5.75 (s, 2H), 3.90 (s, 2H).

EXAMPLE 344C

N-(4-chlorobenzyl)-N'-(1-methyl-1H-indazol-4-yl)urea

1-Methyl-1H-indazol-4-amine (1.00 g, 6.8 mmol) in toluene (225 mL) was treated with phosgene (20% in toluene, 7 ml, 13.2 mmol). The mixture was heated at reflux for 3 hours, cooled, and the solvent removed under reduced pressure. The residue was taken in diethyl ether (100 ml) and triethyl amine (6 ml), and filtered. The filtrate was treated with 4-chlorobenzylamine (963 mg, 6.8 mmol). After stirring at ambient temperature for 16 hours, the solvent was reduced to half volume under reduced pressure, filtered, and the filter cake washed with diethyl ether:hexanes (1:1) to provide the title compound. The title compound was treated with HCl/ethanol and evaporated to dryness to provide the hydrochloride. $^1$H NMR (DMSO-d$_6$) δ 9.25 (s, 1H), 8.25 (s, 1H), 7.68 (d, 1H), 7.39 (m, 5H), 7.24 (t, 1H), 7.13 (d, 1H), 4.34 (s, 2H), 3.99 (s, 3H); MS (ESI) m/z 315 (M+H)$^+$.

EXAMPLE 345 methyl 4-[({[4-(8-azabicyclo[3.2.1]oct-8-yl)-2-chlorobenzyl]amino}carbonyl)amino]-1-carboxylate

EXAMPLE 345A 8-azabicyclo[3.2.1]octane

8-Methyl-8-azabicyclo[3.2.1]octane in dichloroethane (400 mL) was treated with 1-chloroethylchloroformate (29.3 g, 205 mmol) in dichloroethane (75 mL) dropwise via addition funnel at 0° C. After complete addition, the mixture was heated at reflux for four hours. The mixture was allowed to cool to ambient temperature and was concentrated under reduced pressure. The residue was filtered through a silica gel plug eluting with 1:1 ethyl ether:hexane and the filtrate was concentrated under reduced pressure. The residue was taken up in 250 mL methanol, heated at reflux for 1 hour, allowed to cool to ambient temperature, and concentrated under reduced pressure. The residue was triturated with diethyl ether and filtered. The filter cake was washed with diethyl ether and dried under reduced pressure at 60° C. to provide the title compound as a solid. $^1$H NMR (300 MHz, DMSO-d$_6$) δ 8.90 (bs, 2H), 3.87 (m, 2H), 2.02–1.76 (m, 6H), 1.74–1.40 (m, 4H); MS (DCI) 112 (M+H)$^+$.

EXAMPLE 345B 4-(8-azabicyclo[3.2.1]oct-8-yl)-2-chlorobenzonitrile

2-Chloro-4-fluorobenzonitrile (0.97 g, 6.2 mmol), 8-azabicyclo[3.2.1]octane hydrochloride (0.92 g, 6.2 mmol), and N,N-diisopropylethylamine (1.6 g, 12 mmol) were combined in DMSO (15 mL) and heated at 120° C. for 16 hours. The mixture was allowed to cool to ambient temperature and partitioned between diethyl ether and saturated NaHCO$_3$ solution. The aqueous phase was separated and extracted with diethyl ether. The organic layers were combined, washed with water, brine, dried (Na$_2$SO$_4$), filtered, and the filtrate was concentrated under reduced pressure to provide the title compound which was used in the next step without further purification.

EXAMPLE 345C 4-(8-azabicyclo[3.2.1]oct-8-yl)-2-chlorobenzylamine 4-(8-Azabicyclo[3.2.1]oct-8-yl)-2-chlorobenzonitrile in THF (50 mL) was treated with solid LAH (0.47 g, 12 mmol) at 0° C. portionwise. The mixture was heated at reflux for 1 hour, allowed to cool to 0° C., and quenched by addition of (Na$_2$SO$_4$ 10H$_2$O). The mixture was stirred for 30 minutes, filtered, and the filtrate concentrated under reduced pressure. The residue was purified by flash chromatography eluting with 5% to 10% MeOH/CH$_2$Cl$_2$ to provide the title compound. $^1$H NMR (300 MHz, DMSO-d$_6$) δ 7.27 (d, 1H, J=8.6 Hz), 6.74 (d, 1H, J=2.4 Hz), 6.70 (dd, 1H, J=8.6, 2.4 Hz), 4.16 (bs, 2H), 3.65 (s, 2H), 2.05 (bs, 2H), 1.97 (m, 2H), 1.88–1.65 (m, 5H), 1.40 (m, 1H), 1.23 (m, 2H); MS (ESI) 234 (M−NH$_2$)$^+$.

EXAMPLE 345D methyl 4-[({[4-(8-azabicyclo[3.2.1]oct-8-yl)-2-chlorobenzyl]amino}carbonyl)amino]-1-carboxylate A suspension of methyl 4-amino-1H-indazole-1-carboxylate (554 mg, 2.90 mmol) in toluene (100 mL) was treated with phosgene in toluene (2.90 mL, approx. 20% w/w) via syringe. The mixture was heated at reflux for 3.5 hours, allowed to cool to ambient temperature, and concentrated under reduced pressure. The residue was taken up in diethyl ether and concentrated under reduced pressure. The residue was again taken up in diethyl ether (100 mL) and treated with triethylamine (3 mL). After stirring for 10 minutes, the mixture was filtered. The filtrate was treated with 4-(8-azabicyclo[3.2.1]oct-8-yl)-2-chlorobenzylamine (484 mg, 1.93 mmol) in THF (10 mL). After stirring for 2 hours, the mixture was concentrated under reduced pressure. The residue was purified by flash chromatography eluting with 2% to 5% MeOH/CH$_2$Cl$_2$ to provide the title compound as a solid. $^1$H NMR (300 MHz, DMSO-d$_6$) δ 9.00 (s, 1H), 8.41 (s, 1H), 7.85 (d, 1H, J=7.8 Hz), 7.68 (d, 1H, J=8.5 Hz), 7.48 (t, 1H, J=8.1 Hz), 7.25 (d, 1H, J=8.5 Hz), 6.82 (d, 1H, J=2.4 Hz), 6.73 (dd, 1H, J=8.5, 2.4 Hz), 6.68 (t, 1H, J=5.4 Hz), 4.30 (d, 2H, J=5.4 Hz), 4.19 (m, 2H), 4.03 (s, 3H), 2.05–1.65 (m, 7H), 1.40 (m, 1H), 1.25 (m, 2H); MS (ESI) 468 (M+H)$^+$.

EXAMPLE 346

N-[4-(8-azabicyclo[3.2.1]oct-8-yl)-2-chlorobenzyl]-N'-1H-indazol-4-ylurea

Methyl 4-[({[4-(8-azabicyclo[3.2.1]oct-8-yl)-2-chlorobenzyl]amino}carbonyl)amino]-1H-indazole-1-carboxylate (803 mg, 1.72 mmol) in methanol (40 mL) was treated with 1.2N NaOH in MeOH (20 mL). After stirring for 30 minutes, the mixture was concentrated under reduced pressure. The residue was partitioned between ethyl acetate and saturated NaHCO$_3$ solution. The separated aqueous phase was extracted with ethyl acetate. The organic layers were combined, washed with brine, dried (Na$_2$SO$_4$), filtered, and the filtrate was concentrated under reduced pressure. The residue was purified by flash chromatography (7% to 10% MeOH/CH$_2$Cl$_2$) to provide the title compound as a solid. The obtained solid was treated with ethanolic HCl followed by precipitation with diethyl ether to provide the hydrochloride salt. $^1$H NMR (300 MHz, DMSO-d$_6$) δ 8.91 (s, 1H), 8.16 (s, 1H), 7.65 (d, 1H, J=7.5 Hz), 7.27 (d, 1H, J=8.5 Hz), 7.19 (t, 1H, J=8.1 Hz), 7.05 (d, 1H, J=8.5 Hz), 6.87 (m, 2H), 6.79 (m, 1H), 4.29 (m, 2H), 4.21 (m, 2H), 2.05–1.65 (m, 7H), 1.40 (m, 1H), 1.26 (m, 2H); MS (ESI) 410 (M+H)$^+$; Anal. Calcd for C$_{22}$H$_{24}$ClN$_5$O.1.6HCl: C, 56.43; H, 5.51; N, 14.96. Found: C, 56.30; H, 5.29; N, 14.81.

EXAMPLE 347 methyl 4-[({[4-(8-azabicyclo[3.2.1]oct-8-yl)-3-(trifluoromethyl)benzyl]amino}carbonyl)amino]-1H-indazole-1-carboxylate

EXAMPLE 347A 4-(8-azabicyclo[3.2.1]oct-8-yl)-3-(trifluoromethyl)benzonitrile 4-Fluoro-3-(trifluoromethyl)benzonitrile (1.35 g, 7.14 mmol), 8-aza-bicyclo[3.2.1]octane hydrochloride (1.26 g, 8.57 mmol), and N,N-diisopropylethylamine (1.79 g, 13.8 mmol) were combined in DMSO (15 mL) and heated at 120° C. for 24 hours. The mixture was allowed to cool to ambient temperature and partitioned between diethyl ether and saturated NaHCO$_3$ solution. The separated aqueous phase was extracted with diethyl ether and the combined organic layers were washed with water, brine, dried (Na$_2$SO$_4$), filtered, and the filtrate was concentrated under reduced pressure to provide the title compound which was used in the next step without further purification.

EXAMPLE 347B 4-(8-azabicyclo[3.2.1]oct-8-yl)-3-(trifluoromethyl)benzylamine 4-(8-Azabicyclo[3.2.1]oct-8-yl)-3-(trifluoromethyl)benzonitrile in THF (50 mL) was treated with solid LAH (0.68 g, 18 mmol) at 0° C. portionwise. The mixture was heated at reflux 1 hour, allowed to cool to 0° C., and quenched by addition of (Na$_2$SO$_4$ 10H$_2$O). The mixture was stirred 30 minutes, filtered, and the filtrate was concentrated under reduced pressure. The residue was purified by flash chromatography eluting with 5% to 10% MeOH/CH$_2$Cl$_2$ to provide the title compound. $^1$H NMR (300 MHz, DMSO-d$_6$) δ 7.57 (d, 1H, J=2.0 Hz), 7.42 (dd, 1H, J=8.1, 2.0 Hz), 7.08 (d, 1H, J=8.4 Hz), 3.658 (m, 4H), 2.15 (bs, 2H), 1.92 (m, 2H), 1.88–1.55 (m, 5H), 1.48 (m, 3H); MS (ESI) 268 (M−NH$_2$)$^+$.

EXAMPLE 347C methyl 4-[({[4-(8-azabicyclo[3.2.1]oct-8-yl)-3-(trifluoromethyl)benzyl]amino}carbonyl)amino]-1H-indazole-1-carboxylate Methyl 4-amino-1H-indazole-1-carboxylate (1.72 g, 9.00 mmol) in toluene (300 mL) was treated with phosgene in toluene (9.00 mL, approx. 20% w/w) via syringe. The mixture was heated at reflux for 3.5 hours, allowed to cool to ambient temperature, and concentrated under reduced pressure. The residue was taken up in diethyl ether and concentrated under reduced pressure. The residue was again taken up in diethyl ether (325 mL) followed by addition of triethylamine (10 mL). The mixture was stirred briefly and then filtered. An aliquot of the filtrate (150 mL, 4.14 mmol) was treated with 4-(8-azabicyclo[3.2.1]oct-8-yl)-3-(trifluoromethyl)benzylamine (1.03 g, 3.62 mmol) in THF (10 mL). After stirring for 2 hours, the mixture was concentrated under reduced pressure to approximately 30 mL and filtered. The filter cake was washed with diethyl ether-:hexane (1:1) and dried under reduced pressure to provide the title compound. $^1$H NMR (300 MHz, DMSO-d$_6$) δ 9.07 (s, 1H), 8.43 (s, 1H), 7.80 (d, 1H, J=7.8 Hz), 7.69 (d, 1H, J=8.1 Hz), 7.58 (t, 1H, J=2.0 Hz), 7.47 (m, 2H), 7.14 (d, 1H, J=8.1 Hz), 6.86 (t, 1H, J=5.8 Hz), 4.32 (d, 2H, J=5.8 Hz), 4.03 (s, 3H), 3.72 (m, 2H), 1.93 (m, 2H), 1.88–1.55 (m, 5H), 1.49 (m, 3H); MS (ESI) 502 (M+H)$^+$.

EXAMPLE 348

N-[4-(8-azabicyclo[3.2.1]oct-8-yl)-3-(trifluoromethyl)benzyl]-N'-1H-indazol-4-ylurea A suspension of methyl 4-[({[4-(8-azabicyclo[3.2.1]oct-8-yl)-3-(trifluoromethyl)benzyl]amino}carbonyl)amino]-1H-indazole-1-carboxylate (1.65 g, 3.29 mmol) in methanol (30 mL) was treated with 1.2 N NaOH in MeOH (10 mL). The mixture was stirred for 30 minutes and concentrated under reduced pressure. The residue was partitioned between ethyl acetate and saturated NaHCO$_3$ solution. The separated aqueous phase was extracted with ethyl acetate and the combined organic layers were washed with brine, dried (Na$_2$SO$_4$), filtered, and the filtrate was concentrated under reduced pressure. The residue was purified by flash chromatography (7% to 10% MeOH/CH$_2$Cl$_2$) to provide the title compound as a solid. The obtained solid was treated with ethanolic HCl followed by precipitation with diethyl ether to provide the hydrochloride salt. $^1$H NMR (300 MHz, DMSO-d$_6$) δ 8.99 (s, 1H), 8.19 (s, 1H), 7.62 (d, 1H, J=7.5 Hz), 7.57 (d, 1H, J=2.0 Hz), 7.46 (dd, 1H, J=8.5, 2.0 Hz), 7.19 (t, 1H, J=8.1 Hz), 7.10 (m, 3H), 4.31 (m, 2H), 3.72 (m, 2H), 1.93 (m, 2H), 1.87–1.56 (m, 5H), 1.48 (m, 3H); MS (ESI) 444 (M+H)$^+$; Anal. Calcd for C$_{23}$H$_{24}$F$_3$N$_5$O.1.6HCl: C, 55.05; H, 5.14; N, 13.96. Found: C, 54.95; H, 4.66; N, 13.53.

EXAMPLE 349

N-[4-(8-azabicyclo[3.2.1]oct-8-yl)-3-chlorobenzyl]-N'-1H-indazol-4-ylurea

EXAMPLE 349A 4-(8-azabicyclo[3.2.1]oct-8-yl)-3-chlorobenzonitrile

The title compound was prepared using the procedure described in Example 347A except using 4-fluoro-3-chlorobenzonitrile instead of 4-fluoro-3-(trifluoromethyl)benzonitrile.

EXAMPLE 349B 4-(8-azabicyclo[3.2.1]oct-8-yl)-3-chlorobenzylamine

The title compound was prepared using the procedure described in Example 347B except using 4-(8-azabicyclo[3.2.1]oct-8-yl)-3-chlorobenzonitrile instead of 4-(8-azabicyclo[3.2.1]oct-8-yl)-3-(trifluoromethyl)benzonitrile.

EXAMPLE 349C

N-[4-(8-azabicyclo[3.2.1]oct-8-yl)-3-chlorobenzyl]-N'-1H-indazol-4-ylurea

The title compound was prepared using the procedure described in Example 317 except using 4-(8-azabicyclo[3.2.1]oct-8-yl)-3-chlorobenzylamine instead of 3-phenylpropylamine. $^1$H NMR (300 MHz, DMSO-d$_6$) δ 8.84 (s, 1H), 8.13 (s, 1H), 7.62 (d, 1H, J=7.5 Hz), 7.35 (d, 1H, J=2.0 Hz), 7.16 (m, 2H), 7.03 (m, 2H), 6.91 (m, 1H), 4.25 (d, 2H, J=4.4 Hz), 3.91 (m, 2H), 1.84 (m, 4H), 1.67 (m, 3H), 1.50 (m, 3H); MS (ESI) 410 (M+H)$^+$; Anal. Calcd for C$_{22}$H$_{24}$ClN$_5$O.0.8HCl: C, 60.18; H, 5.69; N, 15.95. Found: C, 60.09; H, 5.37; N, 15.64.

EXAMPLE 350

N-[4-(8-azabicyclo[3.2.1]oct-8-yl)benzyl]-N'-1H-indazol-4-ylurea

EXAMPLE 350A 4-(8-azabicyclo[3.2.1]oct-8-yl)benzonitrile

The title compound was prepared using the procedure described in Example 347A except using 4-fluorobenzonitrile instead of 4-fluoro-3-(trifluoromethyl)benzonitrile.

EXAMPLE 350B 4-(8-azabicyclo[3.2.1]oct-8-yl)benzylamine

The title compound was prepared using the procedure described in Example 347B except using 4-(8-azabicyclo[3.2.1]oct-8-yl)benzonitrile instead of 4-(8-azabicyclo[3.2.1]oct-8-yl)-3-(trifluoromethyl)benzonitrile.

EXAMPLE 350C

N-[4-(8-azabicyclo[3.2.1]oct-8-yl)benzyl]-N'-1H-indazol-4-ylurea

The title compound was prepared using the procedure described in Example 317 except using 4-(8-azabicyclo[3.2.1]oct-8-yl)benzylamine instead of 3-phenylpropylamine. $^1$H NMR (300 MHz, DMSO-d$_6$) δ 8.85 (m, 1H), 8.15 (s, 1H), 7.65 (d, 1H, J=7.8 Hz), 7.25 (m, 2H), 7.19 (t, 1H, J=8.0 Hz), 7.05 (d, 1H, J=8.1 Hz), 6.87 (m, 2H), 4.26 (m, 4H), 2.10–1.65 (m, 7H), 1.60–1.15 (m, 3H); MS (ESI) 376 (M+H)$^+$; Anal. Calcd for C$_{22}$H$_{25}$N$_5$O.1.1HCl: C, 63.58; H, 6.33; N, 16.85. Found: C, 63.36; H, 6.05; N, 16.57.

EXAMPLE 351

N-(4-tert-butylbenzyl)-N'-(1-methyl-1H-indazol-4-yl)urea 4-tert-Butylbenzylamine (0.46 mL, 2.62 mmol) in toluene (8 mL) was treated with 20% phosgene solution (1.4 mL) and refluxed for 3 hours. The mixture was allowed to cool to ambient temperature and concentrated under reduced pressure. The residue was then taken up in toluene (10 mL) and treated with diisopropylamine (3 mL) and 1-methyl-1H-indazol-4-amine (prepared as described in J. Med. Chem. 45:742 (2002); 200 mg, 1.36 mmol). The reaction mixture was heated at 80° C. for 3 hours, allowed to cool to ambient temperature, and concentrated under reduced pressure. The residue was purified by flash chromatography (98:2 $CH_2Cl_2$:$CH_3OH$ to 95:5 $CH_2Cl_2$:$CH_3OH$, eluant gradient) to provide the title compound. The corresponding hydrochloride salt was prepared with methanolic HCl. $^1H$ NMR (300 MHz, $d_6$-DMSO) δ 8.72 (s, 1H), 8.03 (d, J=0.7 Hz, 1H), 7.66 (dd, J=7.8 Hz, 0.6 Hz, 1H), 7.37 (m, 2H), 7.27 (m, 2H), 7.24 (m, 1H), 7.13 (m, 1H), 6.74 (m, 1H), 4.30 (d, J=5.8 Hz, 2H), 3.99 (s, 3H), 1.27 (s, 9H); MS (ESI$^+$) m/z 337 (M+H)$^+$.

EXAMPLE 352

N-[3-fluoro-4-(trifluoromethyl)benzyl]-N'-(1-methyl-1H-indazol-4-yl)urea

The title compound was prepared using the procedure described in Example 351 except using 3-fluoro-4-(trifluoromethyl)benzylamine instead of 4-tert-butylbenzylamine. NMR (300 MHz, $d_6$-DMSO) δ 8.92 (s, 1H), 8.08 (d, J=1.1 Hz, 1H), 7.77 (t, J=8.0 Hz, 1H), 7.62 (dd, J=7.3 Hz, 0.7 Hz, 1H), 7.41 (m, 1H), 7.25 (m, 1H), 7.15 (m, 1H), 6.98 (t, J=6.1 Hz, 1H), 4.45 (d, J=6.1 Hz, 2H), 4.00 (s, 3H); MS (ESI$^+$) m/z 367 (M+H)$^+$.

EXAMPLE 353

N-[4-chloro-3-(trifluoromethyl)benzyl]-N'-(1-methyl-1H-indazol-4-yl)urea

The title compound was prepared using the procedure described in Example 351 except using 4-chloro-3-(trifluoromethyl)benzylamine instead of 4-tert-butylbenzylamine. $^1H$ NMR (300 MHz, $d_6$-DMSO) δ 8.89 (s, 1H), 8.06 (d, J=1.0 Hz, 1H), 7.82 (s, 1H), 7.60–7.70 (m, 3H), 7.22 (m, 1H), 7.17 (m, 1H), 6.92 (m, 1H), 4.42 (d, J=5.8 Hz, 2H), 3.99 (s, 3H); MS (ESI$^+$) m/z 383/385 (M+H, $^{35}Cl/^{37}Cl$)$^+$.

EXAMPLE 354

N-(1-methyl-1H-indazol-4-yl)-4-[4-(trifluoromethyl)-2-pyridinyl]-1-piperazinecarboxamide 1-Methyl-1H-indazol-4-amine (560 mg, 3.81 mmol) in toluene (20 mL) was treated with 20% phosgene solution (2.5 mL) and refluxed overnight. The mixture was allowed to cool to ambient temperature and was concentrated under reduced pressure. The residue was taken up in THF (20 mL) and treated with diisopropylamine (5 mL) and 1-[4-(trifluoromethyl)-2-pyridinyl]piperazine (450 mg, 1.95 mmol). The mixture was refluxed overnight, allowed to cool to ambient temperature, and concentrated under reduced pressure. The residue was purified by flash chromatography (97:3 $CH_2Cl_2$:$CH_3OH$ to 95:5 $CH_2Cl_2$:$CH_3OH$) to provide the title compound. The corresponding hydrochloride salt was prepared by treatment with methanolic HCl. $^1H$ NMR (300 MHz, $d_6$-DMSO) δ 8.78 (s, 1H), 8.44 (m, 1H), 8.07 (d, J=1.0 Hz, 1H), 7.83 (m, 1H), 7.19–7.31 (m, 3H), 7.02 (d, 9.2 Hz, 1H), 4.00 (s, 3H), 3.74 (m, 4H), 3.63 (m, 4H); MS (ESI$^+$) m/z 405 (M+H)$^+$.

EXAMPLE 355

N-(3,4-dichlorobenzyl)-N'-(1-methyl-1H-indazol-4-yl)urea

1-Methyl-1H-indazol-4-amine (390 mg, 2.65 mmol) and 3,4-dichlorobenzyl isocyanate (0.39 mL, 2.65 mmol) were combined in toluene (20 mL) and heated overnight at 80° C. The mixture was allowed to cool to ambient temperature, filtered, and the filter cake was allowed to air-dry to provide the title compound. The corresponding hydrochloride salt was prepared by treatment with methanolic HCl. $^1H$ NMR (300 MHz, $d_6$-DMSO) δ 8.86 (s, 1H), 8.06 (d, J=1.0 Hz, 1H), 7.59–7.64 (m, 3H), 7.33 (m, 1H), 7.25 (m, 1H), 7.15 (m, 1H), 6.91 (t, J=6.0 Hz), 4.35 (d, J=5.8 Hz, 2H), 3.99 (s, 3H); MS (ESI$^+$) m/z 349/351 (M+H, $^{35}Cl/^{37}Cl$)$^+$.

EXAMPLE 356

N-(2,4-dichlorobenzyl)-N'-(1-methyl-1H-indazol-4-yl)urea

1-Methyl-1H-indazol-4-amine (310 mg, 2.1 mmol) and 2,4-dichlorobenzyl isocyanate (0.3 mL, 2.06 mmol) were combined in toluene (10 mL) and heated for 2 hours at 80° C. The mixture was then allowed to cool to ambient temperature, filtered, and the filter cake was allowed to air-dry to provide the title compound. The corresponding hydrochloride salt was prepared by treatment with methanolic HCl. $^1H$ NMR (300 MHz, $d_6$-DMSO) δ 9.22 (s, 1H), 8.21 (d, J=1.0 Hz, 1H), 7.62–7.67 (m, 2H), 7.43–7.46 (m, 2H), 7.21–7.27 (m, 2H), 7.12 (m, 1H), 4.40 (d, J=5.5 Hz, 2H), 3.99 (s, 3H); MS (ESI$^+$) m/z 349/351 (M+H, $^{35}Cl/^{37}Cl$)$^+$.

EXAMPLE 357

N-(4-ethylbenzyl)-N'-(1-methyl-1H-indazol-4-yl)urea

The title compound was prepared using the procedure described in Example 354 except using 4-ethylbenzylamine instead of 1-[4-(trifluoromethyl)-2-pyridinyl]piperazine. $^1H$ NMR (300 MHz, $d_6$-DMSO) δ 8.73 (s, 1H), 8.03 (d, 1H, J=0.7 Hz), 7.66 (d, J=7.4 Hz, 1H), 7.12–7.28 (m, 6H), 6.75 (t, J=5.8 Hz, 1H), 3.99 (s, 3H), 2.59 (q, J=7.6 Hz, 2H), 1.16 (t, J=7.5 Hz, 3H); MS (ESI$^+$) m/z 309 (M+H)$^+$.

EXAMPLE 358

N-(2-chlorobenzyl)-N'-(1-methyl-1H-indazol-4-yl)urea

The title compound was prepared using the procedure described in Example 355 except using 2-chlorobenzyl isocyanate instead of 3,4-dichlorobenzyl isocyanate. $^1H$ NMR (300 MHz, $d_6$-DMSO) δ 8.88 (s, 1H), 8.06 (d, J=0.7 Hz, 1H), 7.65 (dd, J=7.4 Hz, 0.7 Hz, 1H), 7.44–7.49 (m, 2H), 7.28–7.39 (m, 2H), 7.25 (m, 1H), 7.14 (m, 1H), 6.87 (t, J=6.0 Hz, 1H), 4.43 (d, J=6.1 Hz, 2H), 4.00 (s, 3H); MS (ESI$^+$) m/z 315/317 (M+H, $^{35}Cl/^{37}C$)$^+$.

EXAMPLE 359

N-(4-fluorobenzyl)-N'-(1-methyl-1H-indazol-4-yl)urea

The title compound was prepared using the procedure described in Example 355 except using 4-fluorobenzyl isocyanate instead of 3,4-dichlorobenzyl isocyanate. $^1H$ NMR (300 MHz, $d_6$-DMSO) δ 8.78 (s, 1H), 8.05 (d, J=1.0 Hz, 1H), 7.65 (m, 1H), 7.36–7.41 (m, 2H), 7.12–7.28 (m, 4H), 6.82 (t, J=5.9 Hz, 1H), 4.33 (d, J=5.8 Hz, 2H), 3.99 (s, 3H); MS (ESI$^+$) m/z 299 (M+H)$^+$.

EXAMPLE 360

N-(2-fluorobenzyl)-N'-(1-methyl-1H-indazol-4-yl)urea

The title compound was prepared using the procedure described in Example 355 except using 2-fluorobenzyl isocyanate instead of 3,4-dichlorobenzyl isocyanate. $^1$H NMR (300 MHz, d$_6$-DMSO) δ 8.83 (s, 1H), 8.06 (d, J=1.0 Hz, 1H), 7.65 (m, 1H), 7.40 (m, 1H), 7.05–7.28 (m, 4H), 6.89 (t, J=5.9 Hz, 1H), 4.37 (d, J=5.8 Hz, 2H), 3.99 (s, 3H); MS (ESI$^+$) m/z 299 (M+H)$^+$.

EXAMPLE 361

N-[1-(4-bromophenyl)ethyl]-N'-(1-methyl-1H-indazol-4-yl)urea

The title compound was prepared using the procedure described in Example 355 except using 1-bromo-4-(1-isocyanatoethyl)benzene instead of 3,4-dichlorobenzyl isocyanate. $^1$H NMR (300 MHz, d$_6$-DMSO) δ 8.66 (s, 1H), 8.02 (s, 1H), 7.61 (d, J=7.4 Hz, 1H), 7.54 (m, 2H), 7.33 (m, 2H), 7.23 (m, 1H), 7.12 (d, J=8.5 Hz, 1H), 6.85 (d, J=7.4 Hz, 1H), 4.83 (quintet, J=7.0 Hz, 1H), 3.99 (s, 3H), 1.42 (d, J=6.8 Hz, 3H); MS (ESI$^+$) m/z 373/375 (M+H, $^{79}$Br/$^{81}$Br)$^+$.

EXAMPLE 362

N-(1-methyl-1H-indazol-4-yl)-N'-{4-[(trifluoromethyl)thio]benzyl}urea

The title compound was prepared using the procedure described in Example 355 except using 4-[(trifluoromethyl)thio]benzylamine instead of 4-tert-butylbenzylamine. $^1$H NMR (300 MHz, d$_6$-DMSO) δ 8.86 (s, 1H), 8.06 (d, J=0.7 Hz, 1H), 7.70 (d, J=8.2 Hz, 2H), 7.65 (d, J=7.5 Hz, 1H), 7.50 (d, J=8.2 Hz, 2H), 7.13–7.28 (m, 3H), 6.92 (t, J=5.9 Hz, 1H), 4.43 (d, J=6.1 Hz, 2H), 4.00 (s, 3H); MS (ESI$^+$) m/z 381 (M+H)$^+$.

EXAMPLE 363

N-(4-tert-butylbenzyl)-N'-(7-methyl-1H-indazol-4-yl)urea

EXAMPLE 363A 2,2,2-trichloro-N-(7-methyl-1H-indazol-4-yl)acetamide

7-Methyl-1H-indazol-4-amine (J. Chem. Soc. 1955, 2412; 550 mg, 3.74 mmol) and triethylamine (1.6 mL, 11.5 mmol) were combined in CH$_2$Cl$_2$ (22 mL) and treated with trichloroacetyl chloride (0.54 mL, 4.84 mmol) dropwise at 0° C. The mixture was allowed to gradually warm to ambient temperature and stir overnight. The mixture was concentrated and the residue was purified by flash chromatography (98:2, CH$_2$C$_{12}$:CH$_3$OH), to provide the title compound.

EXAMPLE 363B

N-(4-tert-butylbenzyl)-N'-(7-methyl-1H-indazol-4-yl)urea 2,2,2-Trichloro-N-(7-methyl-1H-indazol-4-yl)acetamide (72 mg, 0.25 mmol), 4-tert-butylbenzylamine (55 mg, 0.34 mmol), and 1,8-diazabicyclo[5.4.0]undec-7-ene (DBU) (0.09 mL, 0.60 mmol) were combined in CH$_3$CN (6 mL) and refluxed overnight. The mixture was allowed to cool to ambient temperature and was concentrated under reduced pressure. The residue was taken up in ethyl acetate and washed twice with saturated aqueous NH$_4$Cl solution. The organic layer was dried (Na$_2$SO$_4$), filtered, and the filtrate was concentrated under reduced pressure. The residue was triturated with ethyl acetate to provide the title compound.

The corresponding hydrochloride salt was prepared with methanolic HCl. $^1$H NMR (300 MHz, d$_6$-DMSO) δ 12.90 (br s, 1H), 7.94 (d, J=1.3 Hz, 1H), 7.91 (s, 1H), 7.47 (m, 2H), 7.37 (m, 2H), 7.25 (m, 2H), 6.84 (t, J=5.8 Hz, 1H), 4.26 (d, J=5.7 Hz, 2H), 2.35 (s, 3H), 1.27 (s, 9H); MS (ESI$^+$) m/z 337 (M+H)$^+$.

EXAMPLE 364

N-(7-methyl-1H-indazol-4-yl)-N'-[4-(trifluoromethyl)benzyl]urea

The title compound was prepared using the procedure described in Example 363B except using 4-(trifluoromethyl)benzylamine instead of 4-tert-butylbenzylamine. $^1$H NMR (300 MHz, d$_6$-DMSO) δ 12.93 (s, 1H), 8.01 (s, 1H), 7.95 (d, J=1.4 Hz, 1H), 7.72 (d, J=8.2 Hz, 2H), 7.53 (d, J=8.2 Hz, 2H), 7.43 (m, 2H), 6.96 (m, 1H), 4.40 (d, J=5.8 Hz, 2H), 2.36 (s, 3H); MS (ESI$^+$) m/z 349 (M+H)$^+$.

EXAMPLE 365

N-(7-methyl-1H-indazol-4-yl)-N'-{4-[(trifluoromethyl)thio]benzyl}urea

The title compound was prepared using the procedure described in Example 363B except using 4-[(trifluoromethyl)thio]benzylamine instead of 4-tert-butylbenzylamine. $^1$H NMR (300 MHz, d$_6$-DMSO) δ 12.93 (s, 1H), 8.01 (s, 1H), 7.95 (d, J=1.4 Hz, 1H), 7.70 (d, J=8.1 Hz, 2H), 7.43–7.49 (m, 4H), 6.94 (m, 1H), 4.37 (d, J=6.1 Hz, 2H), 2.36 (s, 3H); MS (ESI$^+$) m/z 381 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

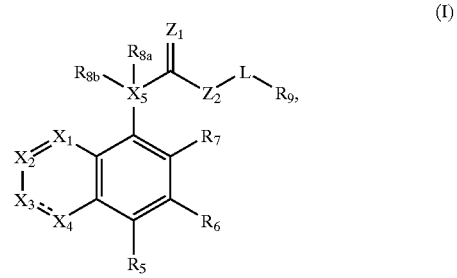

of a pharmaceutically acceptable salt or prodrug thereof, wherein

- - - is absent or is a single bond;

X$_1$ is CR$_1$;

X$_2$ is selected from the group consisting of N and NR$_2$;

X$_3$ is selected from the group consisting of N and NR$_3$;

X$_4$ is a bond;

X$_5$ is N;

Z$_1$ is O;

L is selected from the group consisting of alkenylene, alkylene, alkynylene, cycloalkylene,

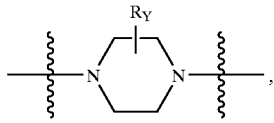

—(CH$_2$)$_m$O(CH$_2$)$_n$—, and N(R$_y$), wherein the left end of —(CH$_2$)$_m$O(CH$_2$)$_n$— is attached to Z$_2$ and the right end is attached to R$_9$;

m and n are each independently 1–6;

R$_y$ is selected from the group consisting of hydrogen and alkyl;

R$_1$, R$_3$, R$_5$, R$_6$, and R$_7$ are each independently selected from the group consisting of hydrogen, alkenyl, alkoxy, alkoxyalkyl, alkoxycarbonyl, alkoxycarbonylalkyl, alkyl, alkylcarbonyl, alkylcarbonylalkyl, alkylcarbonyloxy, carboxy, cyano, cyanoalkyl, cycloalkyl, cycloalkylalkyl, haloalkoxy, haloalkyl, haloalkylthio, halogen, hydroxy, hydroxyalkyl, —S(O)$_2$ OR$_A$, —S(O)$_2$RB, —NZ$_A$Z$_B$, (Z$_A$Z$_B$N)alkyl-, (Z$_A$Z$_B$N)carbonyl-, (Z$_A$Z$_B$N)carbonylalkyl-, and (Z$_A$Z$_B$N)sulfonyl-, wherein Z$_A$ and Z$_B$ are each independently selected from the group consisting of hydrogen, alkyl, alkylcarbonyl, formyl, aryl, and arylalkyl;

R$_2$ is independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, carboxy, carboxyalkyl, cyano, cyanoalkyl, cycloalkyl, cycloalkylalkyl, haloalkoxy, haloalkyl, haloalkylthio, halogen, hydroxy, hydroxyalkyl, —NR$_A$S(O)$_2$R$_B$, —S(O)$_2$OR$_A$, S(O)$_2$RB, NZ$_A$Z$_B$, (Z$_A$Z$_B$N)alkyl, (Z$_A$Z$_B$N)carbonyl, (Z$_A$Z$_B$N)carbonylalkyl, and (Z$_A$Z$_B$N)sulfonyl;

R$_A$ is selected from the group consisting of hydrogen and alkyl;

R$_B$ is selected from the group consisting of alkyl, aryl, and arylalkyl;

R$_{8a}$ is selected from the group consisting of hydrogen and alkyl;

R$_{8b}$ is absent when X$_5$ is N; and

R$_9$ is selected from the group consisting of hydrogen, aryl, cycloalkyl, and heterocyclyl; with the proviso that variables X$_2$ and X$_3$ are not simultaneously NR$_2$ and NR$_3$.

2. The compound according to claim 1 wherein

- - - is absent;

X$_2$ is N;

X$_3$ is NR$_3$;

R$_{8b}$ is absent;

L is alkylene; and

R$_9$ is aryl.

3. The compound according to claim 2 wherein

R$_1$, R$_5$, R$_6$ and R$_7$ are each hydrogen; and

R$_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —NZ$_C$Z$_D$; and Z$_C$ and Z$_D$ are independently selected from the group consisting of hydrogen and alkyl.

4. The compound according to claim 3 selected from the group consisting of

N-(3,4-dichlorobenzyl)-N'-1H-indazol-4-ylurea;

N-1H-indazol-4-yl-N'-[4-(1-piperidinyl)benzyl]urea;

N-[3-fluoro-4-(1-piperidinyl)benzyl]-N'-1H-indazol-4-ylurea;

N-1H-indazol-4-yl-N'-[4-(1-pyrrolidinyl)benzyl]urea;

N-[3-fluoro-4-(1-pyrrolidinyl)benzyl]-N'-1H-indazol-4-ylurea;

N-[4-(1-azepanyl)benzyl]-N'-1H-indazol-4-ylurea;

N-[4-(1-azepanyl)-3-fluorobenzyl]-N'-1H-indazol-4-ylurea;

N-(1-methyl-1H-indazol-4-yl)-N'-[4-(1-piperidinyl) benzyl]urea;

N-[3-fluoro-4-(1-piperidinyl)benzyl]-N'-(1-methyl-1H-indazol-4-yl)urea;

N-(1-methyl-1H-indazol-4-yl)-N'-[4-(1-pyrrolidinyl) benzyl]urea;

N-[3-fluoro-4-(1-pyrrolidinyl)benzyl]-N'-(1-methyl-1H-indazol-4-yl)urea;

N-[4-(1-azepanyl)benzyl]-N'-(1-methyl-1H-indazol-4-yl) urea;

N-[4-(1-azepanyl)-3-fluorobenzyl]-N'-(1-methyl-1H-indazol-4-yl)urea;

methyl 4-({[(1-naphthylmethyl)amino]carbonyl}amino)-1H-indazole-1-carboxylate;

methyl 4-({[(1,1'-biphenyl-3-ylmethyl)amino]carbonyl}amino)-1H-indazole-1-carboxylate;

methyl 4-({[(2-chlorobenzyl)amino]carbonyl}amino)-1H-indazole-1-carboxylate;

methyl 4-[({[2-fluoro-5-(trifluoromethyl)benzyl]amino}carbonyl)amino]-1H-indazole-1-carboxylate;

N-(1,1'-biphenyl-3-ylmethyl)-N'-1H-indazol-4-ylurea;

N-(2-chlorobenzyl)-N'-1H-indazol-4-ylurea;

N-[2-fluoro-5-(trifluoromethyl)benzyl]-N'-1H-indazol-4-ylurea;

N-[2-(2,4-dimethylphenyl)ethyl]-N'-1H-indazol-4-ylurea;

N-[2-(3,4-dichlorophenyl)ethyl]-N'-1H-indazol-4-ylurea;

N-1H-indazol-4-yl-N'-[2-(4-methylphenyl)ethyl]urea;

N-[4-azepan-1-yl-3-(trifluoromethyl)benzyl]-N'-1H-indazol-4-ylurea;

N-[4-azepan-1-yl-2-(trifluoromethyl)benzyl]-N'-1H-indazol-4-ylurea;

N-[4-(2-azabicyclo[2.2.1]hept-2-yl)-2-(trifluoromethyl) benzyl]-N'-1H-indazol-4-ylurea;

N-[4-(8-azabicyclo[3.2.1]oct-8-yl)-2-(trifluoromethyl) benzyl]-N'-1H-indazol-4-ylurea;

N-[4-(8-azabicyclo[3.2.1]oct-8-yl)-3-fluorobenzyl]-N'-1H-indazol-4-ylurea;

N-(3-chloro-4-azepan-1-ylbenzyl)-N'-1H-indazol-4-ylurea;

N-[(1S)-1-(4-bromophenyl)ethyl]-N'-1H-indazol-4-ylurea;

N-(3-bromo-4-fluorobenzyl)-N'-1H-indazol-4-ylurea;

N-(2,4-dimethylbenzyl)-N'-1H-indazol-4-ylurea;
N-(4-chlorobenzyl)-N'-1H-indazol-4-ylurea;
N-[3-fluoro-4-(trifluoromethyl)benzyl]-N'-1H-indazol-4-ylurea;
N-1H-indazol-4-yl-N'-(4-methylbenzyl)urea;
N-1H-indazol-4-yl-N'-[3-(trifluoromethoxy)benzyl]urea;
N-(3-chloro-4-fluorobenzyl)-N'-1H-indazol-4-ylurea;
N-(3,4-dimethylbenzyl)-N'-1H-indazol-4-ylurea;
N-[3-fluoro-5-(trifluoromethyl)benzyl]-N'-1H-indazol-4-ylurea;
N-(2-chloro-4-azepan-1-ylbenzyl)-N'-1H-indazol-4-ylurea;
N-(2,3-dichlorobenzyl)-N'-1H-indazol-4-ylurea;
N-1H-indazol-4-yl-N'-{4-[(trifluoromethyl)thio]benzyl}urea;
N-1H-indazol-4-yl-N'-[3-(trifluoromethyl)benzyl]urea;
N-(3,5-difluoro-4-azepan-1-ylbenzyl)-N'-1H-indazol-4-ylurea;
N-[4-(8-azabicyclo[3.2.1]oct-8-yl)-3,5-difluorobenzyl]-N'-1H-indazol-4-ylurea;
N-(4-chlorobenzyl)-N'-(1-methyl-1H-indazol-4-yl)urea;
N-[4-(8-azabicyclo[3.2.1]oct-8-yl)-2-chlorobenzyl]-N'-1H-indazol-4-ylurea;
methyl 4-[({[4-(8-azabicyclo[3.2.1]oct-8-yl)-3-(trifluoromethyl)benzyl]amino}carbonyl)amino]-1H-indazole-1-carboxylate;
N-[4-(8-azabicyclo[3.2.1]oct-8-yl)-3-chlorobenzyl]-N'-1H-indazol-4-ylurea;
N-[4-(8-azabicyclo[3.2.1]oct-8-yl)benzyl]-N'-1H-indazol-4-ylurea;
N-(4-tert-butylbenzyl)-N'-(1-methyl-1H-indazol-4-yl)urea;
N-[3-fluoro-4-(trifluoromethyl)benzyl]-N'-(1-methyl-1H-indazol-4-yl)urea;
N-[4-chloro-3-(trifluoromethyl)benzyl]-N'-(1-methyl-1H-indazol-4-yl)urea;
N-(3,4-dichlorobenzyl)-N'-(1-methyl-1H-indazol-4-yl)urea;
N-(2,4-dichlorobenzyl)-N'-(1-methyl-1H-indazol-4-yl)urea;
N-(4-ethylbenzyl)-N'-(1-methyl-1H-indazol-4-yl)urea;
N-(2-chlorobenzyl)-N'-(1-methyl-1H-indazol-4-yl)urea;
N-(4-fluorobenzyl)-N'-(1-methyl-1H-indazol-4-yl)urea;
N-(2-fluorobenzyl)-N'-(1-methyl-1H-indazol-4-yl)urea;
N-[1-(4-bromophenyl)ethyl]-N'-(1-methyl-1H-indazol-4-yl)urea; and
N-(1-methyl-1H-indazol-4-yl)-N'-{4-[(trifluoromethyl)thio]benzyl}urea.

5. The compound according to claim 2 wherein
$R_{8a}$, $R_1$, $R_5$, $R_6$ and $R_7$ are each hydrogen;
L is alkylene wherein the alkylene is —$CH_2$—;
$R_9$ is aryl wherein said aryl is phenyl substituted with 2 substituents independently selected from the group consisting of (8-azabicyclo[3.2.1]oct-8-yl), trifluoromethyl, and —Cl; and
$R_3$ is selected from the group consisting of hydrogen and alkoxycarbonyl.

6. The compound according to claim 2 wherein
$R_{8a}$, $R_1$, $R_5$, $R_6$ and $R_7$ are each hydrogen;
L is alkylene wherein the alkylene is —$CH_2$—;
$R_9$ is aryl wherein said aryl is 4-(8-azabicyclo[3.2.1]oct-8-yl)-3-(trifluoromethyl)phenyl; and
$R_3$ is selected from the group consisting of hydrogen and alkoxycarbonyl.

7. The compound according to claim 2 wherein
$R_{8a}$, $R_1$, $R_5$, $R_6$ and $R_7$ are each hydrogen;
L is alkylene wherein die alkylene is —$CH_2$—;
$R_9$ is aryl wherein said aryl is 2-chloro-4-(8-azabicyclo[3.2.1]oct-8-yl)phenyl; and
$R_3$ is selected from the group consisting of hydrogen and alkoxycarbonyl.

8. The compound according to claim 5 selected from the group consisting of
N-[4-(8-azabicyclo[3.2.1]oct-8-yl)-2-chlorobenzyl]-N'-1H-indazol-4-ylurea; and
N-[4-(8-azabicyclo[3.2.1]oct-8-yl)-3-(trifluoromethyl)benzyl]-N'-1H-indazol-4-ylurea.

9. The compound according to claim 2 wherein
$R_1$, $R_6$ and $R_7$ are each hydrogen;
$R_5$ is alkyl; and
$R_9$ is aryl wherein said aryl is phenyl optionally substituted with 1, 2, or 3 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

10. The compound according to claim 9 selected from the group consisting of
N-(4-tert-butylbenzyl)-N'-(7-methyl-1H-indazol-4-yl)urea;
N-(7-methyl-1H-indazol-4-yl)-N'-[4-(trifluoromethyl)benzyl]urea; and
N-(7-methyl-1H-indazol-4-yl)-N'-{4-[(trifluoromethyl)thio]benzyl}urea.

11. The compound according to claim 2 wherein
$R_5$, $R_6$ and $R_7$ are each hydrogen;
$R_9$ is aryl wherein said aryl is selected from the group consisting of naphthyl and phenyl.

12. The compound according to claim 11 selected from the group consisting of
N-1H-indazol-4-yl-N'-(1-naphthylmethyl)urea; and
N-1H-indazol-4-yl-N'-(3-phenylpropyl)urea.

13. The compound according to claim 2 wherein
$R_1$, $R_5$, $R_6$ and $R_7$ are each hydrogen; and
$R_9$ is heterocycle wherein said heterocycle is pyridinyl optionally substituted with 1 or 2 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$.

14. The compound according to claim 13 that is N-1H-indazol-4-yl-N'-{[6-(trifluoromethyl)-3-pyridinyl]methyl}urea.

15. The compound according to claim 2 wherein L is

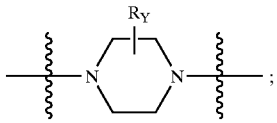

and
$R_9$ is heterocycle.

16. The compound according to claim 2 wherein $R_1$, $R_5$, $R_6$ and $R_7$ are each hydrogen;
L is

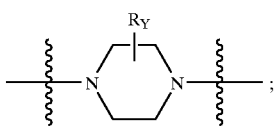

$R_9$ is heterocycyl wherein said heterocycyl is pyridinyl optionally substituted with 1 or 2 substituents independently selected from the group consisting of alkoxy, alkyl, alkylsulfonyl, 2-azabicyclo[2.2.1]hept-2-yl, 8-azabicyclo[3.2.1]oct-8-yl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

17. The compound according to claim 16 that is N-(1-methyl-1H-indazol-4-yl)-4-[4-(trifluoromethyl)-2-pyridinyl]-1-piperazinecarboxamide.

18. A pharmaceutical composition comprising a therapeutically effective amount of a compound of formula (I) as defined in claim 1, or a pharmaceutically acceptable salt thereof, and a pharmaceutically acceptable carrier.

19. A method of treating a disorder wherein the disorder is ameliorated by inhibiting vanilloid receptor subtype 1 (VR1) receptor, and wherein the disorder is selected from the group comprising pain, bladder overactivity, urinary incontinence and inflammatory thermal liyperalgesia in a host mammal in need of such treatment comprising administering a therapeutically effective amount of a compound of formula (I) as defined in claim 1, or a pharmaceutically acceptable salt thereof.

20. A method of treating bladder overactivity in a host mammal in need of such treatment comprising administering a therapeutically effective amount of a compound of formula (I) as defined in claim 1, or a pharmaceutically acceptable salt thereof.

21. A method of treating urinau incontinence in a host mammal in need of such treatment comprising administering a therapeutically effective amount of a compound of formula (I) as defined in claim 1, or a pharmaceutically acceptable salt thereof.

22. A method of treating pain in a host mammal in need of such treatment comprising administering a therapeutically effective amount of a compound of formula (I) as defined in claim 1, or a pharmaceutically acceptable salt thereof.

23. A method of treating inflammatory thermal hyperalgesia in a host mammal in need of such treatment comprising administering a therapeutically effective amount of a compound of formula (I) as defined in claim 1, or a pharmaceutically acceptable salt thereof.

* * * * *

UNITED STATES PATENT AND TRADEMARK OFFICE
CERTIFICATE OF CORRECTION

PATENT NO. : 6,933,311 B2
APPLICATION NO. : 10/634678
DATED : August 23, 2005
INVENTOR(S) : Lee Chih-Hung et al.

It is certified that error appears in the above-identified patent and that said Letters Patent is hereby corrected as shown below:

Col. 144, line 68 insert -- $Z_2$ is NH --
Col. 145, line 54, replace "$X_2$ is N" with -- $X_2$ is NH --.

Col. 148, line 48
  replace "$R_5$, $R_6$ and $R_7$ are each hydrogen:"
  with --$R_1$, $R_5$, $R_6$ and $R_7$ are each hydrogen:--.

Col. 150, line 10
  replace "incontinence and inflammatory thermal liyperalgesia in a "
  with --incontinence and inflammatory thermal hyperalgesia in a --.

Col. 150, line 21
  replace "A method of treating urinau incontinence in a host"
  with --A method of treating urinary incontinence in a host--.

Signed and Sealed this

Fourth Day of September, 2007

JON W. DUDAS
*Director of the United States Patent and Trademark Office*